(12) United States Patent
Serber et al.

(10) Patent No.: US 10,336,998 B2
(45) Date of Patent: Jul. 2, 2019

(54) MICROBIAL STRAIN IMPROVEMENT BY A HTP GENOMIC ENGINEERING PLATFORM

(71) Applicant: Zymergen Inc., Emeryville, CA (US)

(72) Inventors: Zach Serber, Sausalito, CA (US); Erik Jedediah Dean, Lafayette, CA (US); Shawn Manchester, Oakland, CA (US); Katherine Gora, Oakland, CA (US); Michael Flashman, Eureka, CA (US); Erin Shellman, Seattle, WA (US); Aaron Kimball, San Francisco, CA (US); Shawn Szyjka, Martinez, CA (US); Barbara Frewen, Alameda, CA (US); Thomas Treynor, Berkeley, CA (US); Kenneth S. Bruno, Walnut Creek, CA (US)

(73) Assignee: Zymergen Inc., Emeryville, CA (US)

( * ) Notice: Subject to any disclaimer, the term of this patent is extended or adjusted under 35 U.S.C. 154(b) by 0 days.

(21) Appl. No.: 15/923,527

(22) Filed: Mar. 16, 2018

(65) Prior Publication Data

US 2018/0216099 A1 Aug. 2, 2018

Related U.S. Application Data

(63) Continuation of application No. 15/396,230, filed on Dec. 30, 2016, now Pat. No. 9,988,624, which is a continuation of application No. PCT/US2016/065465, filed on Dec. 7, 2016, which is a continuation-in-part of application No. 15/140,296, filed on Apr. 27, 2016.

(60) Provisional application No. 62/368,786, filed on Jul. 29, 2016, provisional application No. 62/264,232, filed on Dec. 7, 2015.

(51) Int. Cl.

| | | |
|---|---|---|
| *C12N 15/10* | (2006.01) | |
| *C12N 15/77* | (2006.01) | |
| *C12N 15/80* | (2006.01) | |
| *G16B 20/00* | (2019.01) | |
| *G16B 5/00* | (2019.01) | |
| *G01N 35/00* | (2006.01) | |

(52) U.S. Cl.
CPC ..... *C12N 15/1058* (2013.01); *C12N 15/1079* (2013.01); *C12N 15/77* (2013.01); *C12N 15/80* (2013.01); *G01N 35/00871* (2013.01); *G16B 5/00* (2019.02); *G16B 20/00* (2019.02)

(58) Field of Classification Search
None
See application file for complete search history.

(56) References Cited

U.S. PATENT DOCUMENTS

| | | | |
|---|---|---|---|
| 4,435,504 A | 3/1984 | Zuk et al. | |
| 4,489,160 A | 12/1984 | Katsumata et al. | |
| 4,601,893 A | 7/1986 | Cardinal | |
| 4,855,240 A | 8/1989 | Rosenstein et al. | |
| 4,980,298 A | 12/1990 | Blake et al. | |
| 5,158,891 A | 10/1992 | Takeda et al. | |
| 5,275,940 A | 1/1994 | Kino et al. | |
| 5,516,670 A | 5/1996 | Kuehnle et al. | |
| 5,591,645 A | 1/1997 | Rosenstein | |
| 5,605,793 A | 2/1997 | Stemmer | |
| 5,753,477 A | 5/1998 | Chan | |
| 5,756,345 A | 5/1998 | Camakaris et al. | |
| 5,770,409 A | 6/1998 | Pfefferle et al. | |
| 5,811,238 A | 9/1998 | Stemmer et al. | |
| 5,827,698 A | 10/1998 | Kikuchi et al. | |
| 5,830,721 A | 11/1998 | Stemmer et al. | |
| 5,834,252 A | 11/1998 | Stemmer et al. | |
| 5,837,458 A | 11/1998 | Minshull et al. | |
| 5,928,905 A | 7/1999 | Stemmer et al. | |
| 5,990,350 A | 11/1999 | Stevens et al. | |
| 6,040,439 A | 3/2000 | Hayakawa et al. | |
| 6,060,296 A | 5/2000 | Hoekstra | |
| 6,090,592 A | 7/2000 | Adams et al. | |
| 6,117,679 A | 9/2000 | Stemmer et al. | |
| 6,136,565 A | 10/2000 | Best et al. | |
| 6,174,673 B1 | 1/2001 | Short et al. | |
| 6,251,674 B1 | 6/2001 | Tobin et al. | |
| 6,287,862 B1 | 9/2001 | delCardayre et al. | |

(Continued)

FOREIGN PATENT DOCUMENTS

| | | |
|---|---|---|
| CN | 101434910 A | 5/2009 |
| CN | 101628296 A | 1/2010 |

(Continued)

OTHER PUBLICATIONS

Chandran et al. TinkerCell: modular CAD tool for synthetic biology Journal of Biological Engineering vol. 3, article 19 (Year: 2009).*
Lewis et al. Constraining the metabolic genotype-phenotype relationship using a phylogeny of in silico methods Nature Reviews Microbiology vol. 10 pp. 291-305 (Year: 2012).*
Askenazi, M., et al., "Integrating transcriptional and metabolite profiles to direct the engineering of lovastatin-producing fungal strains." Nat. Biotechnol. (2003); 21: 150-156.
Choi, J.H. et al., "Enhanced production of insulin-like growth factor I fusion protein in *Escherichia coli* by coexpression of the downregulated genes identified by transcriptome profiling." Appl. Environ. Microbiol. (2003); 69(8): 4737-4742.

(Continued)

*Primary Examiner* — John S Brusca
(74) *Attorney, Agent, or Firm* — Cooley LLP

(57) ABSTRACT

The present disclosure provides a HTP microbial genomic engineering platform that is computationally driven and integrates molecular biology, automation, and advanced machine learning protocols. This integrative platform utilizes a suite of HTP molecular tool sets to create HTP genetic design libraries, which are derived from, inter alia, scientific insight and iterative pattern recognition. The HTP genomic engineering platform described herein is microbial strain host agnostic and therefore can be implemented across taxa. Furthermore, the disclosed platform can be implemented to modulate or improve any microbial host parameter of interest.

19 Claims, 53 Drawing Sheets

Specification includes a Sequence Listing.

(56) References Cited

U.S. PATENT DOCUMENTS

| | | |
|---|---|---|
| 6,300,070 B1 | 10/2001 | Boles et al. |
| 6,326,204 B1 | 12/2001 | delCardayre et al. |
| 6,335,160 B1 | 1/2002 | Patten et al. |
| 6,335,198 B1 | 1/2002 | delCardayre et al. |
| 6,352,859 B1 | 3/2002 | delCardayre et al. |
| 6,358,709 B1 | 3/2002 | Short et al. |
| 6,379,964 B1 | 4/2002 | delCardayre et al. |
| 6,479,258 B1 | 11/2002 | Short |
| 6,528,311 B1 | 3/2003 | delCardayre et al. |
| 6,586,214 B1 | 7/2003 | Dunican et al. |
| 6,605,449 B1 | 8/2003 | Short |
| 6,713,279 B1 | 3/2004 | Short |
| 6,716,631 B1 | 4/2004 | delCardayre et al. |
| 6,759,195 B1 | 7/2004 | Bentley et al. |
| 6,759,218 B2 | 7/2004 | Mockel et al. |
| 7,033,781 B1 | 4/2006 | Short |
| 7,115,400 B1 | 10/2006 | Adessi et al. |
| 7,118,904 B2 | 10/2006 | Mockel et al. |
| 7,127,379 B2 | 10/2006 | Palsson et al. |
| 7,138,266 B2 | 11/2006 | Debabov et al. |
| 7,148,054 B2 | 12/2006 | delCardayre et al. |
| 7,507,574 B2 | 3/2009 | Bill et al. |
| 7,510,854 B2 | 3/2009 | Pompejus et al. |
| 7,629,170 B2 | 12/2009 | delCardayre et al. |
| 7,711,490 B2 | 5/2010 | Maranas et al. |
| 7,826,975 B2 | 11/2010 | Maranas et al. |
| 7,842,485 B2 | 11/2010 | Gill et al. |
| 7,846,688 B2 | 12/2010 | Gill et al. |
| 7,987,056 B2 | 7/2011 | Gill et al. |
| 8,076,138 B2 | 12/2011 | delCardayre et al. |
| 8,108,152 B2 | 1/2012 | Maranas et al. |
| 8,110,360 B2 | 2/2012 | Serber et al. |
| 8,221,982 B2 | 7/2012 | Serber et al. |
| 8,332,160 B1 | 12/2012 | Platt et al. |
| 8,349,587 B2 | 1/2013 | Fischer et al. |
| 8,377,681 B2 | 2/2013 | delCardayre et al. |
| 8,467,975 B2 | 6/2013 | Gill et al. |
| 8,476,041 B2 | 7/2013 | Cervin et al. |
| 8,530,203 B2 | 9/2013 | Ikeda et al. |
| 8,546,136 B2 | 10/2013 | Serber et al. |
| 8,685,737 B2 | 4/2014 | Serber et al. |
| 8,697,359 B1 | 4/2014 | Zhang |
| 8,741,603 B2 | 6/2014 | Han et al. |
| 8,771,945 B1 | 7/2014 | Zhang |
| 8,795,965 B2 | 8/2014 | Zhang |
| 8,865,406 B2 | 10/2014 | Zhang et al. |
| 8,871,445 B2 | 10/2014 | Cong et al. |
| 8,883,464 B2 | 11/2014 | Lynch et al. |
| 8,889,356 B2 | 11/2014 | Zhang |
| 8,889,418 B2 | 11/2014 | Zhang et al. |
| 8,895,308 B1 | 11/2014 | Zhang et al. |
| 8,906,616 B2 | 12/2014 | Zhang et al. |
| 8,932,814 B2 | 1/2015 | Cong et al. |
| 8,945,839 B2 | 2/2015 | Zhang |
| 8,993,233 B2 | 3/2015 | Zhang et al. |
| 8,999,641 B2 | 4/2015 | Zhang et al. |
| 9,388,419 B2 | 7/2016 | Lynch et al. |
| 9,428,778 B2 | 8/2016 | Lynch et al. |
| 9,506,067 B2 | 11/2016 | Vroom et al. |
| 9,506,167 B2 | 11/2016 | Shetty et al. |
| 9,580,719 B2 | 2/2017 | Retallack et al. |
| 9,637,739 B2 | 5/2017 | Siksnys et al. |
| 9,677,090 B2 | 6/2017 | Donohue et al. |
| 9,688,972 B2 | 6/2017 | May et al. |
| 9,701,971 B2 | 7/2017 | Serber et al. |
| 9,738,687 B2 | 8/2017 | Guay et al. |
| 9,745,562 B2 | 8/2017 | Donohue et al. |
| 9,752,176 B2 | 9/2017 | Kung et al. |
| 9,771,795 B2 | 9/2017 | Knight et al. |
| 9,790,490 B2 | 10/2017 | Zhang et al. |
| 9,816,081 B1 | 11/2017 | Donohue et al. |
| 9,822,372 B2 | 11/2017 | Zhang et al. |
| 9,840,713 B2 | 12/2017 | Zhang |
| 9,902,980 B2 | 2/2018 | Fischer et al. |
| 9,988,624 B2 | 6/2018 | Serber et al. |
| 10,047,358 B1 | 8/2018 | Serber et al. |
| 2002/0169562 A1 | 11/2002 | Stephanopoulos et al. |
| 2002/0197605 A1 | 12/2002 | Nakagawa et al. |
| 2003/0027175 A1 | 2/2003 | Stephanopoulos et al. |
| 2004/0077090 A1 | 4/2004 | Short |
| 2004/0101963 A1 | 5/2004 | Bibb et al. |
| 2005/0054106 A1 | 3/2005 | Ow et al. |
| 2005/0124010 A1 | 6/2005 | Short et al. |
| 2006/0019301 A1 | 1/2006 | Hansen et al. |
| 2006/0084098 A1 | 4/2006 | Gill et al. |
| 2006/0269975 A1 | 11/2006 | Pompejus et al. |
| 2006/0286574 A1 | 12/2006 | Romesberg et al. |
| 2007/0166792 A1 | 1/2007 | Olson et al. |
| 2007/0042474 A1 | 2/2007 | Pompejus et al. |
| 2007/0059768 A1 | 3/2007 | Gill et al. |
| 2007/0118916 A1 | 5/2007 | Puzio et al. |
| 2007/0122890 A1 | 5/2007 | Park et al. |
| 2007/0218533 A1 | 9/2007 | Gill et al. |
| 2007/0274972 A1 | 11/2007 | Muller et al. |
| 2007/0292918 A1 | 12/2007 | Stelman et al. |
| 2008/0103060 A1 | 5/2008 | Gill et al. |
| 2008/0243397 A1* | 10/2008 | Peccoud ............... G06F 19/18 702/20 |
| 2009/0221442 A1 | 9/2009 | Dower et al. |
| 2009/0253174 A1 | 10/2009 | Serber et al. |
| 2009/0280529 A1 | 11/2009 | Berg et al. |
| 2009/0325248 A1 | 12/2009 | Marx et al. |
| 2010/0048938 A1 | 2/2010 | Berg et al. |
| 2010/0105865 A1 | 4/2010 | Telford et al. |
| 2010/0124768 A1 | 5/2010 | Serber et al. |
| 2010/0136633 A1 | 6/2010 | Serber et al. |
| 2010/0137143 A1 | 6/2010 | Rothberg et al. |
| 2010/0210017 A1 | 8/2010 | Gill et al. |
| 2010/0216648 A1 | 8/2010 | Stahler et al. |
| 2010/0304982 A1 | 12/2010 | Hinz et al. |
| 2010/0317115 A1 | 12/2010 | Gill et al. |
| 2011/0054654 A1 | 3/2011 | Phillips et al. |
| 2011/0136688 A1 | 6/2011 | Scholl et al. |
| 2011/0172127 A1 | 7/2011 | Jacobsen et al. |
| 2011/0223638 A1 | 9/2011 | Wiedenheft et al. |
| 2011/0223671 A1 | 9/2011 | Yoder et al. |
| 2011/0244575 A1 | 10/2011 | Lipscomb et al. |
| 2011/0277179 A1 | 11/2011 | Puzio et al. |
| 2012/0070870 A1 | 3/2012 | Way et al. |
| 2012/0077681 A1 | 3/2012 | Gill et al. |
| 2012/0245056 A1 | 9/2012 | Serber et al. |
| 2012/0252681 A1 | 10/2012 | Del Cardayre et al. |
| 2012/0264902 A1 | 10/2012 | Lipscomb et al. |
| 2012/0277120 A1 | 11/2012 | Del Cardayre et al. |
| 2013/0071893 A1 | 3/2013 | Lynch et al. |
| 2013/0078709 A1 | 3/2013 | Franklin et al. |
| 2013/0122541 A1 | 5/2013 | Lynch et al. |
| 2013/0149742 A1 | 6/2013 | Bower et al. |
| 2013/0217132 A1 | 8/2013 | Gill et al. |
| 2013/0252240 A1 | 9/2013 | Cutler et al. |
| 2014/0045231 A1 | 2/2014 | Lynch et al. |
| 2014/0068797 A1 | 3/2014 | Doudna et al. |
| 2014/0172318 A1 | 6/2014 | Fisher et al. |
| 2014/0180660 A1* | 6/2014 | Clancy ............... G06F 19/16 703/11 |
| 2014/0186942 A1 | 7/2014 | Serber et al. |
| 2014/0295457 A1 | 10/2014 | Broenstrup et al. |
| 2014/0356921 A1 | 12/2014 | Deng et al. |
| 2015/0031100 A1 | 1/2015 | Gill et al. |
| 2015/0056651 A1 | 2/2015 | Lynch et al. |
| 2015/0056684 A1 | 2/2015 | Lipscomb et al. |
| 2015/0132263 A1 | 5/2015 | Liu et al. |
| 2015/0140626 A1 | 5/2015 | Song et al. |
| 2015/0211013 A1 | 7/2015 | Emalfarb et al. |
| 2015/0275224 A1 | 10/2015 | Basra et al. |
| 2015/0284810 A1 | 10/2015 | Knight et al. |
| 2015/0284811 A1 | 10/2015 | Knight et al. |
| 2015/0299742 A1 | 10/2015 | Gill et al. |
| 2015/0315599 A1 | 11/2015 | Shetty et al. |
| 2015/0344916 A1 | 12/2015 | Lynch et al. |
| 2015/0368639 A1 | 12/2015 | Gill et al. |
| 2015/0376628 A1 | 12/2015 | Schoenherr et al. |
| 2016/0046961 A1 | 2/2016 | Jinek et al. |
| 2016/0060653 A1 | 3/2016 | Doudna et al. |

(56) References Cited

U.S. PATENT DOCUMENTS

| | | |
|---|---|---|
| 2016/0060654 A1 | 3/2016 | Doudna et al. |
| 2016/0068864 A1 | 3/2016 | Doudna et al. |
| 2016/0130608 A1 | 5/2016 | Doudna et al. |
| 2016/0130609 A1 | 5/2016 | Doudna et al. |
| 2016/0138008 A1 | 5/2016 | Doudna et al. |
| 2016/0283651 A1 | 9/2016 | Knight et al. |
| 2016/0290132 A1 | 10/2016 | Knight et al. |
| 2016/0304905 A1 | 10/2016 | Hansen et al. |
| 2017/0009283 A1 | 1/2017 | Gill et al. |
| 2017/0051310 A1 | 2/2017 | Doudna et al. |
| 2017/0051312 A1 | 2/2017 | Jinek et al. |
| 2017/0067046 A1 | 3/2017 | Gill et al. |
| 2017/0073695 A1 | 3/2017 | Verruto et al. |
| 2017/0074889 A1 | 3/2017 | Shetty et al. |
| 2017/0114377 A1 | 4/2017 | Lynch et al. |
| 2017/0139078 A1 | 5/2017 | Knight et al. |
| 2017/0147742 A1* | 5/2017 | Jayaraman .............. G06F 19/12 |
| 2017/0159045 A1 | 6/2017 | Serber et al. |
| 2017/0173086 A1 | 6/2017 | Boyle et al. |
| 2017/0240886 A1 | 8/2017 | Oleinikov |
| 2017/0240922 A1 | 8/2017 | Gill et al. |
| 2017/0240923 A1 | 8/2017 | Serber et al. |
| 2017/0316353 A1 | 11/2017 | Frewen et al. |
| 2017/0321198 A1 | 11/2017 | Severinov et al. |
| 2017/0321226 A1 | 11/2017 | Gill et al. |
| 2017/0342132 A1 | 11/2017 | Fraser et al. |
| 2017/0369870 A1 | 12/2017 | Gill et al. |
| 2017/0370213 A1 | 12/2017 | Knight et al. |
| 2018/0023120 A1 | 1/2018 | Kung et al. |
| 2018/0216100 A1 | 8/2018 | Serber et al. |
| 2018/0216101 A1 | 8/2018 | Serber et al. |

FOREIGN PATENT DOCUMENTS

| | | |
|---|---|---|
| DE | 19548222 A1 | 6/1997 |
| DE | 19831609 A1 | 4/1999 |
| DE | 19947791 A1 | 4/2001 |
| DE | 19950409 A1 | 4/2001 |
| DE | 19959328 A1 | 6/2001 |
| EP | 0131171 A1 | 1/1985 |
| EP | 0238023 A2 | 9/1987 |
| EP | 0197335 B1 | 2/1991 |
| EP | 0472869 A2 | 3/1992 |
| EP | 0356739 B1 | 12/1995 |
| EP | 0635574 B1 | 4/2003 |
| EP | 0972081 B1 | 6/2007 |
| EP | 1546312 B1 | 7/2014 |
| JP | 01-225487 A | 9/1989 |
| KR | 1020080042823 A | 5/2008 |
| WO | WO 1991/006628 A1 | 5/1991 |
| WO | WO 1995/022625 A1 | 8/1995 |
| WO | WO 1996/015246 A1 | 5/1996 |
| WO | WO 1996/033207 A1 | 10/1996 |
| WO | WO 1996/034112 A1 | 10/1996 |
| WO | WO 1998/031837 A1 | 7/1998 |
| WO | WO 2000/004190 A1 | 1/2000 |
| WO | WO 2000/004920 A2 | 2/2000 |
| WO | WO 2000/020555 A2 | 4/2000 |
| WO | WO 2001/012791 A1 | 2/2001 |
| WO | WO 2002/029032 A2 | 4/2002 |
| WO | WO 2003/014330 A2 | 2/2003 |
| WO | WO 2003/040373 A2 | 5/2003 |
| WO | WO 2004/054381 A1 | 7/2004 |
| WO | WO 2004/069996 A2 | 8/2004 |
| WO | WO 2005/006875 A2 | 1/2005 |
| WO | WO 2005/021772 A1 | 3/2005 |
| WO | WO 2006/069711 A1 | 7/2006 |
| WO | WO 2007/012078 A1 | 1/2007 |
| WO | WO 2007/015178 A2 | 2/2007 |
| WO | WO 2007/141580 A2 | 12/2007 |
| WO | WO 2009/043803 A2 | 4/2009 |
| WO | WO 2009/126623 A2 | 10/2009 |
| WO | WO 2010/059763 A2 | 5/2010 |
| WO | WO 2010/075424 A2 | 7/2010 |
| WO | WO 2011/154147 A1 | 12/2011 |
| WO | WO 2012/082720 A2 | 6/2012 |
| WO | WO 2012/142591 A2 | 10/2012 |
| WO | WO 2012/149470 A1 | 11/2012 |
| WO | WO 2012/164565 A1 | 12/2012 |
| WO | WO 2013/066848 A1 | 5/2013 |
| WO | WO 2013/142578 A1 | 9/2013 |
| WO | WO 2014/011800 A1 | 1/2014 |
| WO | WO 2014/019527 A1 | 2/2014 |
| WO | WO 2014/089436 A1 | 6/2014 |
| WO | WO 2014/102782 A1 | 7/2014 |
| WO | WO 2015/070193 A1 | 5/2015 |
| WO | WO 2015/123339 A1 | 8/2015 |
| WO | WO 2015/148680 A1 | 10/2015 |
| WO | WO 2015/175793 A1 | 11/2015 |
| WO | WO 2006/028063 A1 | 3/2016 |
| WO | WO 2016/073690 A1 | 5/2016 |
| WO | WO 2016/196319 A1 | 12/2016 |
| WO | WO 2017/037304 A2 | 3/2017 |
| WO | WO 2017/100376 A2 | 6/2017 |
| WO | WO 2017/100377 A1 | 6/2017 |
| WO | WO 2017/189784 A1 | 11/2017 |
| WO | WO 2017/215790 A1 | 12/2017 |
| WO | WO 2017/223538 A1 | 12/2017 |
| WO | WO 2018/005655 A2 | 1/2018 |
| WO | WO 2018/005793 A1 | 1/2018 |
| WO | WO 2018/009372 A1 | 1/2018 |
| WO | WO 2018/013990 A1 | 1/2018 |
| WO | WO 2018/022972 A1 | 2/2018 |
| WO | WO 2018/071672 A1 | 4/2018 |

OTHER PUBLICATIONS

Dauner, M., et al., "Intracellular carbon fluxes in riboflavin-producing Bacillus subtilis during growth on two-carbon substrate mixtures." Appl. Environ. Microbiol. (2002); 68(4): 1760-1771.

Duarte, N.C., et al., "Reconstruction and validation of *Saccharomyces scerevisiae* iND750, a fully compartmentalized genome-scale metabolic model." Genome Res. (2004); 14: 1298-1309.

Edwards, J.S. and Palsson, B.O., "Systems properties of the Haemophilus influenzae Rd metabolic genotype." J. Biol. Chem. (1999); 274(25): 17410-17416.

Edwards, J.S. and Palsson, B.O., "The *Escherichia coli* MG1655 in silico metabolic genotype: its definition, characteristics, and capabilities." Proc. Natl. Acad. Sci. U. S. A. (2000); 97(10): 5528-5533.

Fischer, S., et al., "The art of CHO cell engineering: A comprehensive retrospect and future perspectives." Biotechnology Advances (2015); 33: 1878-1896.

Förster, J., et al., "Genome-scale reconstruction of the *Saccharomyces cerevisiae* metabolic network." Genome Res. (2003); 13: 244-253.

Han, M.J. et al., "Engineering *Escherichia coli* for increased production of serine-rich proteins based on proteome profiling." Appl. Environ. Microbiol. (2003); 69(10): 5772-5781.

Han, M.J. et al., "Proteome analysis of metabolically engineered *Escherichia coli* cells producing poly(3-hydroxybutyrate)." J. Bacteriol. (2001); 183(1): 301-308.

Hong, S.H., et al., "The genome sequence of the capnophilic rumen bacterium Mannheimia succiniciproducens." Nat. Biotechnol. (2004); 22: 1275-1281.

Kabir, M.M. and Shimizu, K., "Fermentation characteristics and protein expression patterns in a recombinant *Escherichia coli* mutant lacking phosphoglucose isomerase for poly(3-hydroxybutyrate) production." Appl. Microbiol. Biotechnol. (2003); 62: 244-255.

Krämer, O., et al., "Methods in mammalian cell line engineering: from random mutagenesis to sequence-specific approaches." Appl Microbiol Biotechnol (2010); 88: 425-436.

Krömer, J.O., et al., "In-depth profiling of lysine-producing Corynebacterium glutamicum by combined analysis of the transcriptome, metabolome, and fluxome." J. Bacteriol. (2004); 186(6): 1769-1784.

Kuo, Chih-Chung, et al., "The emerging role of systems biology for engineering protein production in CHO cells." Current Opinion in Biotechnology (2018); 51: 64-69.

(56) References Cited

OTHER PUBLICATIONS

Lee, et al., "A Highly Characterized Yeast Toolkit for Modular, Multipart Assembly." ACS Synthetic Biology (2015); 4(9): 975-986 (Published Apr. 14, 2015).
Lee, J.H., et al., "Global analyses of transcriptomes and proteomes of a parent strain and an L-threonine-overproducing mutant strain." J. Bacteriol. (2003); 185(18): 5442-5451.
Lee, Sang Yup, et al., "Systems biotechnology for strain improvement." TRENDS in Biotechnology (2005); 23(7): 349-358.
Ohnishi, J. et al., "Efficient 40 degrees C fermentation of L-lysine by a new Corynebacterium glutamicum mutant developed by genome breeding." Appl. Microbiol. Biotechnol. (2003); 62: 69-75.
Price, N.D., et al., "Genome-scale models of microbial cells: evaluating the consequences of constraints." Nat. Rev. Microbiol. (2004); 2: 886-897.
Reed, J.L., et al., "An expanded genome-scale model of *Escherichia coli* K-12 (iJR904 GSM/GPR)." Genome Biol. (2003); 4, R54.
Rückert, C., et al., "Genome-wide analysis of the L-methionine biosynthetic pathway in Corynebacterium glutamicum by targeted gene deletion and homologous complementation." J. Biotechnol. (2003); 104: 213-228.
Schilling, C.H., et al., "Genome-scale metabolic model of Helicobacter pylori 26695." J. Bacteriol. (2002); 184(16): 4582-4593.
Snitkin and Segre, "Epistatic Interaction Maps Relative to Multiple Metabolic Phenotypes." PLoS Genet (2011); 7(2): e1001294.
Stephanopoulos, G., "Exploiting biological complexity for strain improvement through systems biology." Nat. Biotechnol. (2004); 22: 1261-1267.
Third Party Observation filed in connection with International Application No. PCT/US2016/065465, dated Apr. 6, 2018, 12 pages.
Tummala, S.B. et al., "Transcriptional analysis of productconcentration driven changes in cellular programs of recombinant Clostridium acetobutylicum strains." Biotechnol. Bioeng. (2003); 84, 842-854.
WIPO Communication dated Apr. 10, 2018 to Applicant, Zymergen Inc. in connection with International Application No. PCT/US2016/065465, advising of third party observation filed Apr. 6, 2018.
Wittmann, C. and Heinzle, E., "Modeling and experimental design for metabolic flux analysis of lysine-producing Corynebacteria by mass spectrometry." Metab. Eng. (2001); 3: 173-191.
Yoon, S.H., et al., "Combined transcriptome and proteome analysis of *Escherichia coli* during high Cell density culture." Biotechnol. Bioeng. (2003); 81: 753-767.
"Designing a Million Genomes: Machine Learning, Automation and Biotech.", Strata + Hadoop World, Make Data Work conference, London, UK, May 5, 2015; https://youtu.be/658kvYgrJBE, Published on Oct. 7, 2015, Business-focused talk at Strata UK 2015 by Aaron Kimball, CTO of Zymergen Inc.
"The Data-Driven future of biotechnology." https://www.youtube.com/watch?v=IYmgJUHcG9g&feature=youtu.be&t=915, Strata + Hadoop World, NY Sep. 28-Oct. 1, 2015, Published on Nov. 15, 2015, Technical talk at Strata NY 2015 by Aaron Kimball, CTO of Zymergen Inc. about Zymergen's technology.
Adrio, Jose-Luis et al., "Recombinant organisms for production of industrial products", Bioengineered Bugs, 2010, pp. 116-131, vol. 1, No. 2.
Almeida, Elionor R.P., et al. "Transgenic expression of two marker genes under the control of an Arabidopsis rbcS promoter: Sequences encoding the Rubisco transit peptide increase expression levels." Molecular and General Genetics MGG (1989); 218.1: 78-86.
Alper et al., "Construction of lycopene-overproducing *E. coli* strains by combining systematic and combinatorial gene knockout targets." Nature Biotechnology (2005); 23: 612-616.
Anonymous: "ABI 3900 High Throughput DNA Synthesizer", Mar. 1, 2001 (Mar. 1, 2001), URL:https://assets.thermofisher.com/TFS-Assets/LSG/manuals/cms_095580.pdf [retrieved on Jan. 2, 2018], 144 pages.
Aslanidis, Charalampos, et al. "Ligation-independent cloning of PCR products (LIC-PCR)." Nucleic Acids Research (1990); 18.20: 6069-6074.
Azhayev, Alex V., et al. "Amide group assisted 3'-dephosphorylation of oligonucleotides synthesized on universal A-supports." Tetrahedron (2001); 57.23: 4977-4986.
Barcellos, Fernando Gomes, et al. "Genetic analysis of Aspergillus nidulans unstable transformants obtained by the biolistic process." Canadian Journal of Microbiology (1998); 44.12: 1137-1141.
Bartley, Bryan, et al. "Synthetic biology open language (SBOL) version 2.0. 0." Journal of Integrative Bioinformatics (JIB) (2015); 12(2): 902-991.
Becker, Daniel M., and Guarente, Leonard. "[12] High-efficiency transformation of yeast by electroporation." Methods in Enzymology (1991); 194: 182-187.
Bentley, David R., et al. "Accurate whole human genome sequencing using reversible terminator chemistry." Nature (2008); 456.7218: 53-59.
Bernard, Philippe, et al. "The F plasmid CcdB protein induces efficient ATP-dependent DNA cleavage by gyrase." Journal of Molecular Biology (1993); 234.3: 534-541.
Bilitchenko, Al., "Eugene—a domain specific language for specifying and constraining synthetic biological parts, devices, and systems." PloS ONE (2011); 6.4: e18882 (and Supplemental Data).
Bilitchenko, et al. "Eugene—a domain specific language for specifying and constraining synthetic biological parts, devices, and systems." PloS One (2011); 6.4: e18882.
Boyd, J., et al. "Analysis of the diphtheria tox promoter by site-directed mutagenesis." Journal of Bacteriology (1988);170.12: 5949-5952.
Buchholz et al., "Platform Engineering of Corynebacterium glutamicum with Reduced Pyruvate Dehydrogenase Complex Activity for Improved Production of L-Lysine, L-Valine, and 2-Ketoisovalerate." Applied and Environmental Microbiology (2013); 79(18): 5566-5575.
Chakraborty, B. N., and Kapoor, M., "Transformation of filamentous fungi by electroporation." Nucleic Acids Research (1990); 18.22: 6737.
Chen et al., "DeviceEditor visual biological CAD canvas." Journal of Biological Engineering (2012); 6:1, pp. 1-12.
Christiansen, Solveig K., et al. "Biolistic transformation of the obligate plant pathogenic fungus, *Erysiphe graminis* f. sp. hordei." Current Genetics (1995); 29.1: 100-102.
Christie, Peter J., and Gordon, Jay E. "The Agrobacterium ti plasmids." Microbiology Spectrum (2014); 2.6.
Costanzo, Michael, et al. "The genetic landscape of a cell." Science (2010); 327 (5964): 425-431.
Cramer, Paula, et al. "Functional association between promoter structure and transcript alternative splicing." Proceedings of the National Academy of Sciences (1997); 94.21: 11456-11460.
Crameri, A., et al. "Improved green fluorescent protein by molecular evolution using." Nat. Biotechnol (1996); 14.3: 315-319.
Crameri, Andreas, et al. "DNA shuffling of a family of genes from diverse species accelerates directed evolution." Nature (1998); 391.6664: 288-291.
Crameri, Andreas, et al. "Molecular evolution of an arsenate detoxification pathway by DNA shuffling." Nature Biotechnology (1997); 15.5: 436-438.
Crameri, Andreas, et al. "Construction and evolution of antibody-phage libraries by DMA shuffling." Nature Medicine (1996); 2.1: 100-102.
Czar, Michael J., et al. "Gene synthesis demystified." Trends in Biotechnology (2009); 27.2: 63-72.
Dahl, et al., "Multi-task Neural Networks for QSAR Predictions" Dept. of Computer Science, Univ. of Toronto, Jun. 2014, 21 pages (arXiv:1406.1231 [stat.ML]).
Dalphin, Mark E., et al. "TransTerm: A database of translational signals." Nucleic Acids Research (1996); 24.1: 216-218.
Damha, Masad J., et al. "An improved procedure for derivatization of controlled-pore glass beads for solid-phase oligonucleotide synthesis." Nucleic Acids Research (1990); 18.13 : 3813-3821.
Database EMBL [Online], "DNA fragment having promoter function." XP002767746, retrieved from EBI accession No. EM PAT:DD324094, Sep. 20, 2006.
Database Geneseq [Online] "Corynebacterium glutamicum DNA gyrase subunit B DNA, Seq ID: 123." XP002767747, retrieved from EBI accession No. GSN: AEM36105. Mar. 8, 2007.

(56) References Cited

OTHER PUBLICATIONS

Database Geneseq [Online] "Corynebacterium glutamicum DNA gyrase subunit B DNA, Seq ID: 123." XP002770467, retrieved from EBI accession No. GSN:AEM36105, Mar. 8, 2007.
Drmanac, Radoje, et al. "Human genome sequencing using unchained base reads on self-assembling DNA nanoarrays." Science (2010); 327.5961: 78-81.
Dunican, L.K. and Shivnan, E. "High frequency transformation of whole cells of amino acid producing coryneform bacteria using high voltage electroporation." Nature Biotechnology (1989); 7.10: 1067-1070.
Durand, Roger, et al. "Transient expression of the β-glucuronidase gene after biolistic transformation of the anaerobic fungus Neocallimastix frontalis." Current Genetics (1997); 31.2: 158-161.
Eid, John, et al. "Real-time DNA sequencing from single polymerase molecules." Science (2009); 323.5910: 133-138.
Eikmanns, Bernhard J. "Identification, sequence analysis, and expression of a Corynebacterium glutamicum gene cluster encoding the three glycolytic enzymes glyceraldehyde-3-phosphate dehydrogenase, 3-phosphoglycerate kinase, and triosephosphate isomerase." Journal of Bacteriology (1992); 174.19: 6076-6086.
Eikmanns, Bernhard J., et al. "A family of Corynebacterium glutamicum/ Escherichia coli shuttle vectors for cloning, controlled gene expression, and promoter probing." Gene (1991); 102.1: 93-98.
Engler, Carola, et al. "A one pot, one step, precision cloning method with high throughput capability." PloS One (2008); 3.11: e3647.
Fitzpatrick, R., et al. "Construction and characterization of recA mutant strains of Corynebacterium glutamicum and Brevibacterium lactofermentum." Applied Microbiology and Biotechnology (1994); 42.4: 575-580.
Fox, Richard J., et al. "Improving catalytic function by ProSAR-driven enzyme evolution." Nature Biotechnology (2007); 25.3: 338-344.
Frewen, B., et al., "A Detailed, flexible model for sharing DNA concepts." IWBDA 2015, 7th International Workshop on Bio-Design Automation, University of Washington, pp. 66-67, Aug. 19-21, 2015 (Presentation and Poster), 86 pages.
Gardner et al., "Production of Citric Acid by Mutants of Aspergillus niger." J. Gen. Microbial (1956); 14: 228-237.
GenBank Accession No. CP010451.1 (Jan. 20, 2015), Corynebacterium glutamicum strain B253 DNA, complete genome, downloaded Jan. 12, 2018, 10 pages, https://www.ncbi.nlm.nih.gov/nuccore/748809780?sat=21&satkey=31610401.
Gibson, Daniel G., et al. "Enzymatic assembly of DNA molecules up to several hundred kilobases." Nature Methods (2009); 6.5: 343-345.
Goosen, Theo, et al. "Transformation of Aspergillus niger using the homologous orotidine-5'-phosphate-decarboxylase gene." Current Genetics (1987); 11.6: 499-503.
GPU-Based Deep Learning Inference: A Performance and Power Analysis, NVidia Whitepaper, Nov. 2015, 12 pages.
Greger, Ingo H., et al. "Balancing transcriptional interference and initiation on the GAL7 promoter of Saccharomyces cerevisiae." Proceedings of the National Academy of Sciences (2000); 97.15: 8415-8420.
Guerrero, Carmen, et al. "Directed mutagenesis of a regulatory palindromic sequence upstream from the Brevibacterium lactofermentum tryptophan operon." Gene (1994); 138.1: 35-41.
Haynes, Jill A., and Britz, Margaret L. "The effect of growth conditions of Corynebacterium glutamicum on the transformation frequency obtained by electroporation." Microbiology (1990); 136.2: 255-263.
Hermann, Thomas, et al. "Proteome analysis of Corynebacterium glutamicum." Electrophoresis (2001); 22.9: 1712-1723.
Hillson, N.J., "j5 DNA Assembly Design Automation Software." ACS Synthetic Biology (2011); 1: 14-21.
Hong, Jiong, et al. "Cloning and functional expression of thermostable β-glucosidase gene from Thermoascus aurantiacus." Applied Microbiology and Biotechnology (2007); 73.6: 1331-1339.

Hui, A., et al. "Mutagenesis of the three bases preceding the start codon of the beta-galactosidase mRNA and its effect on translation in *Escherichia coli*." The EMBO Journal (1984); 3.3: 623-629.
Ikeda et al., "A genome-based approach to create a minimally mutated Corynebacterium glutamicum strain for efficient L-lysine production." J. Ind. Microbial. Biotechnol. (2006); 33(7): 610-615.
International Search Report, PCT Application No. PCT/US2016/065464, 10 pages, dated Jun. 26, 2017.
International Application No. PCT/US2016/065465, Invitation to Pay Additional Fees, dated Feb. 23, 2017, 5 pages.
International Application No. PCT/US2016/065465, International Search Report and Written Opinion, dated Apr. 21, 2017, 22 pages.
International Application No. PCT/US2017/029725, International Search Report and Written Opinion, dated Sep. 8, 2017, 10 pages.
Ito, Hisao, et al. "Transformation of intact yeast cells treated with alkali cations." Journal of Bacteriology (1983); 153.1: 163-168.
J5 DeviceEditor manual excerpt from https://j5.jbei.org/index.php/Main_Page_downloadedcontent available Apr. 19, 2016, 45 pages.
Jäger, W., et al. "Expression of the Bacillus subtilis sacB gene leads to sucrose sensitivity in the gram-positive bacterium Corynebacterium glutamicum but not in Streptomyces lividans." Journal of Bacteriology (1992);174.16: 5462-5465.
Jensen, Peter Ruhdal and Hammer, Karin. "Artificial promoters for metabolic optimization." Biotechnology and Bioengineering (1998); 58.2-3: 191-195.
Jones, Jonathan DG, et al. "High level expression of introduced chimaeric genes in regenerated transformed plants." The EMBO Journal (1985); 4.10: 2411.
Jungwirth, Britta, et al. "Triple transcriptional control of the resuscitation promoting factor 2 (rpf2) gene of Corynebacterium glutamicum by the regulators of acetate metabolism RamA and RamB and the cAMP-dependent regulator GlxR." FEMS Microbiology Letters (2008); 281.2: 190-197.
Kadonaga, James T. "Regulation of RNA polymerase II transcription by sequence-specific DNA binding factors." Cell (2004); 116.2: 247-257.
Kashyap, Hirak, et al. "Big data analytics in bioinformatics: A machine learning perspective." Journal of Latex Class Files (2014);13(9): 20 pages.
Khanna, N.C., et al. "Identification of the template binding polypeptide in the pea chlcroplast transcriptional complex." Nucleic Acids Research (1992); 20.1: 69-74.
Khudyakov, Yu E., et al. "Effect of structure of the initiator codon on translation in *E. coli*." FEBS Letters (1998); 232.2: 369-371.
Kikuchi, Yoshimi, et al. "Functional analysis of the twin-arginine translocation pathway in Corynebacterium glutamicum ATCC 13869." Applied and environmental microbiology (2006); 72.11: 7183-7192.
Kim, Jae Bum, et al. "Polony multiplex analysis of gene expression (PMAGE) in mouse hypertrophic cardiomyopathy." Science (2007); 316.5830: 1481-1484.
Kimball, A., "The Data-Driven Future of Biotechnology." Zymergen, Machine learning, automation, and biotech, Strata + Hadoop World, Make Data Work conference, Presentation, London, UK, May 5, 2015, 49 pages http://cdn.oreillystatic.com/en/assets/1/event/132/The%20data-driven%20future%20of%20biotechnology%20Presentation.pdf.
Kirchner, Oliver and Tauch, Andreas. "Tools for genetic engineering in the amino acid-producing bacterium Corynebacteriumglutamicum." Journal of Biotechnology (2003); 104.1: 287-299.
Kotera, Ippei, et al. "A high-throughput and single-tube recombination of crude PCR products using a DNA polymerase inhibitor and type IIS restriction enzyme." Journal of Biotechnology (2008); 137.1: 1-7.
Kozlov, Igor A., et al. "Significant improvement of quality for long oligonucleotides by using controlled pore glass with large pores." Nucleosides, Nucleotides and Nucleic Acids (2005); 24.5-7: 1037-1041.
Labarre, Jean, et al. "Gene replacement, integration, and amplification at the gdhA locus of Corynebacterium glutamicum." Journal of Bacteriology (1993); 175.4: 1001-1007.

(56) References Cited

OTHER PUBLICATIONS

Lee, Joo-Young, et al. "Adaptive evolution of Corynebacterium glutamicum resistant to oxidative stress and its global gene expression profiling." Biotechnology Letters (2013); 35.5: 709-717.

Leng, Xiaoyan, et al. "Classification using functional data analysis for temporal gene expression data." Bioinformatics (2006); 22.1: 68-76.

Libbrecht, Maxwell W., et al. "Machine learning applications in genetics and genomics." Nature Reviews Genetics (2015); 16.6: 321-332.

Lindroth, Peter, and Mopper, Kenneth. "High performance liquid chromatographic determination of subpicomole amounts of amino acids by precolumn fluorescence derivatization withoff-phthaldialdehyde." Anal. Chem (1979); 51.11: 1667-1674.

Liu, et al., "Developing a high-throughput screening method for threonine overproduction based on an artificial promoter." Microbial Cell Factories (2015); 14: 121, 11 pages.

Makrides, Savvas C. "Strategies for achieving high-level expression of genes in *Escherichia coli*." Microbiological Reviews (1996); 60.3: 512-538.

Malumbres, Marcos, et al. "Codon preference in corynebacteria." Gene (1993); 134.1: 15-24.

Margulies, Marcel, et al. "Genome sequencing in microfabricated high-density picolitre reactors." Nature (2005); 437.7057: 376-380.

Martin, J. F., et al. "Cloning Systems in Amino Acid-Producing Corynebacteria." Nature Biotechnology (1987); 5.2: 137-146.

Menkel et al., "Influence of increased aspartate availability on lysine formation by a recombinant strain of Corynebacterium glutamicum and utilization of fumarate." Appl. Environ. Microbiol. (1989); 55(3): 684-688.

Mockel, Bettina, et al. "Functional and structural analyses of threonine dehydratase from Corynebacterium glutamicum." Journal of Bacteriology (1992);174.24: 8065-8072.

Mockel, Bettina, et al. "Threonine dehydratases of Corynebacterium glutamicum with altered allosteric control: their generation and biochemical and structural analysis." Molecular Microbiology (1994); 13.5: 833-842.

Moore, Jeffrey C., et al. "Strategies for the in vitro evolution of protein function: enzyme evolution by random recombination of improved sequences." Journal of Molecular Biology (1997); 272.3: 336-347.

Murray, Elizabeth E. et al. "Codon usage in plant genes." Nucleic Acids Research (1989); 17.2: 477-498.

Nakashima, Nobutaka, et al. "Bacterial cellular engineering by genome editing and gene silencing." International Journal of Molecular Sciences (2014); 15.2: 2773-2793.

Neumann, Susanne, and Quiñones, Ariel. "Discoordinate gene expression of gyrA and gyrB in response to DNA gyrase inhibition in *Escherichia coli*." Journal of Basic Microbiology (1997); 37.1: 53-69.

Ohnishi et al., "A novel methodology employing Corynebacterium glutamicum genome information to generate a new L-lysine-producing mutant." Appl. Microbial Biotechnol (2002); 58(2): 217-223.

Paek, Se-Hwan, et al. "Development of rapid one-step immunochromatographic assay." Methods (2000); 22.1: 53-60.

Parry, Neil J., et al. "Biochemical characterization and mechanism of action of a thermostable β-glucosidase purified from Thermoascus aurantiacus." Biochemical Journal (2001); 353.1: 117-127.

Pátek, Miroslav, et al. "Promoters from Corynebacterium glutamicum: cloning, molecular analysis and search for a consensus motif." Microbiology (1996); 142.5: 1297-1309.

Peters-Wendisch, Petra G., et al. "Pyruvate carboxylase from Corynebacterium glutamicum: characterization, expression and inactivation of the pyc gene." Microbiology (1998); 144.4: 915-927.

Pfeifer-Sancar, Katharina, et al. "Comprehensive analysis of the Corynebacterium glutamicum transcriptome using an improved RNAseq technique." BMC Genomics (2013):14.1: 888, 23 pages.

Prompramote, Supawan, et al. "Machine learning in bioinformatics." Bioinformatics Technologies. Springer Berlin Heidelberg (2005); pp. 117-153.

Qiu, Zhihao, et al. "The *Escherichia coli* polB Locus Is Identical to dinA, the Structural Gene for DNA Polymerase II Characterization of Pol II Purified From a polB Mutant." Journal of Biological Chemistry (1997); 272.13: 8611-8617.

Rastegari, Hilda et al., "Improvement in the Production of L-Lysine by Over-expression of Aspartokinase (ASK) in C. glutamicum ATCC-21799", Tropical Journal of Pharmaceutical Research, Feb. 2013, pp. 51-56, vol. 12, No. 1.

Reddy, Prasad, et al. "Translational efficiency of the *Escherichia coli* adenylate cyclase gene: mutating the UUG initiation codon to GUG or AUG results in increased gene expression." Proceedings of the National Academy of Sciences (1985); 82.17: 5656-5660.

Reimer, et al., "High-Throughput Screening of a Corynebacterium glutamicum Mutant Library on Genomic and Metabolic Level." PLoS ONE (2014); 9(2): e86799, 12 pages.

Reinscheid, Dieter J., et al. "Stable expression of hom-1-thrB in Corynebacterium glutamicum and its effect on the carbon flux to threonine and related amino acids." Applied and Environmental Microbiology (1994); 60.1: 126-132.

Rey, Daniel Alexander, et al. "The putative transcriptional repressor McbR, member of the TetR-family, is involved in the regulation of the metabolic network directing the synthesis of sulfur containing amino acids in Corynebacterium glutamicum." Journal of Biotechnology (2003); 103.1: 51-65.

Reyrat, Jean-Marc, et al. "Counterselectable markers: untapped tools for bacterial genetics and pathogenesis." Infection and Immunity (1998); 66.9: 4011-4017.

Ricciardelli, Carmela, et al. "Development and characterization of primary cultures of smooth muscle cells from the fibromuscular stroma of the guinea pig prostate." In Vitro Cellular & Developmental Biology (1989); 25.11: 1016-1024.

Sahm, Hermann, et al. "d-Pantothenate Synthesis in Corynebacterium glutamicum and Use of panBC and Genes Encoding I-Valine Synthesis ford-Pantothenate Overproduction." Applied and Environmental Microbiology (1999); 65.5: 1973-1979.

Sasaki, et al. "Simultaneous utilization of D-cellobiose, D-glucose, and D-xylose by recombinant Corynebacterium glutamicum under oxygen-deprived conditions." Applied Microbiology and Biotechnology (2008); 81.4: 691-699.

Schäfer, A., et al. "Increased fertility of Corynebacterium glutamicum recipients in intergeneric matings with *Escherichia coli* after stress exposure." Applied and Environmental Microbiology (1994); 60.2: 756-759.

Schäfer, Andreas, et al. "Small mobilizable multi-purpose cloning vectors derived from the *Escherichia coli* plasmids pK18 and pK19: selection of defined deletions in the chromosome of Corynebacterium glutamicum." Gene (1994); 145.1: 69-73.

Schrumpf, Barbel, et al. "A functionally split pathway for lysine synthesis in Corynebacterium glutamicium." Journal of Bacteriology (1991); 173.14: 4510-4516.

Schwarzer, Astrid, and Pühler, Alfred. "Manipuiation of Corynebacterium glutamicum by Gene Disruption and Replacement." Nature Biotechnology (1991); 9.1: 84-87.

Serwold-Davis, Theresa M., et al. "Localization of an origin of replication in Corynebacterium diphtheriae broad host range plasmid pNG2 that also functions in *Escherichia coli*." FEMS Microbiology Letters (1990) 66.1-3: 119-123.

Shevade, Shirish Krishnaj, et al. "A simple and efficient algorithm for gene selection using sparse logistic regression." Bioinformatics (2003); 19.17: 2246-2253.

Shuman, Stewart. "Novel approach to molecular cloning and polynucleotide synthesis using vaccinia DNA topoisomerase." Journal of Biological Chemistry (1994); 269.51: 32678-32684.

Sierzchala, Agnieszka B., et al. "Solid-phase oligodeoxynucleotide synthesis: a two-step cycle using peroxy anion deprotection." Journal of the American Chemical Society (2003); 125.44: 13427-13441.

Simon, R., et al. "A broad host range mobilization system for in vivo genetic engineering: transposon mutagenesis in gram negative bacteria." Nature Biotechnology (1983); 1.9: 784-791.

(56) References Cited

OTHER PUBLICATIONS

Sonnen, Hans, et al. "Characterization of pGA1, a new plasmid from Corynebacterium glutamicum LP-6." Gene (1991); 107.1: 69-74.
Spackman, Darrel H., et al. "Automatic recording apparatus for use in the chromatography of amino acids." Analytical Chemistry (1958); 30: 1190-1206.
Spratt, Brian G., et al. "Kanamycin-resistant vectors that are analogues of plasmids pUC8, pUC9, pEMBL8 and pEMBL9." Gene (1986); 41.2: 337-342.
Stansen, Corinna, et al. "Characterization of a Corynebacterium glutamicum lactate utilization operon induced during temperature-triggered glutamate production." Applied and environmental microbiology (2005); 71.10: 5920-5928.
Stemmer, Willem P. "DNA shuffling by random fragmentation and reassembly: In vitro recombination for molecular evolution." Proceedings of the National Academy of Sciences (1994); 91.22: 10747-10751.
Stemmer, Willem P.C., "Searching Sequence Space" Nature Biotechnology (1995); 13: 549-553.
Stemmer, Willem P.C., et al. "Single-step assembly of a gene and entire plasmid from large numbers of oligodeoxyribonucleotides." Gene (1995); 164.1: 49-53.
Stemmer, Willem P.C. "Rapid evolution of a protein in vitro by DNA shuffling." Nature (1994); 370.6488: 389-391.
Stemmer, Willem P.C. "The evolution of molecular computation." Science (1995); 270.5241: 1510-1511.
Stenström, C. Magnus, et al. "Cooperative effects by the initiation codon and its flanking regions on translation initiation." Gene (2001); 273.2: 259-265.
Student. "The probable error of a mean." Biometrika (1908); 6(1): 1-25.
Su, Shin-San, et al. "*Escherichia coli* mutS-encoded protein binds to mismatched DNA base pairs." Proceedings of the National Academy of Sciences (1986); 83.14: 5057-5061.
Suda, Masako, et al. "Transcriptional regulation of Corynebacterium glutamicum methionine biosynthesis genes in response to methionine supplementation under oxygen deprivation." Applied Microbiology and Biotechnology (2008); 81.3: 505.
Sugimoto, Masakazu, et al. "Sequence analysis of functional regions of homoserine dehydrogenase genes from L-lysine and L-threonine-producing mutants of Brevibacterium lactofermentum." Bioscience, Biotechnology, and Biochemistry (1997); 61.10: 1760-1762.
Tauch, Andreas, et al. "Corynebacterium glutamicum DNA is subjected to methylation-restriction in *Escherichia coli*." FEMS Microbiology Letters (1994); 123.3: 343-347.
Tauch, Andreas, et al. "Plasmids in Corynebacterium glutamicum and their molecular classification by comparative genomics." Journal of Biotechnology (2003);104.1: 27-40.
Tear, Crystal Jing Ying, et al. "Excision of Unstable Artificial Gene-Specific Inverted Repeats Mediates Scar-Free Gene Deletions in *Escherichia coli*." Applied Biochemistry and Biotechnology (2015); 175.4: 1858-1867.
Thierbach, Georg, et al. "Transformation of spheroplasts and protoplasts of Corynebacterium glutamicum." Applied Microbiology and Biotechnology (1998); 29.4: 356-362.
Third-Party Submission filed with the U.S. Patent and Trademark Office on Dec. 7, 2017, in connection with U.S. Appl. No. 15/396,230, 14 pages.
Tian, Jingdong, et al. "Advancing high-throughput gene synthesis technology." Molecular BioSystems (2009); 5.7: 714-722.
Tsuchiya, Makoto, and Morinaga, Yasushi. "Genetic control systems of *Escherichia coli* can confer inducible expression of cloned genes in coryneform bacteria." Nature Biotechnology (1998); 6.4: 428-430.
Trikka et al., "Iterative carotenogenic screens identify combinations of yeast gene deletions that enhance sclareol production." Microbial Cell Factories (2015); 14:60 (Published on line Apr. 24, 2015), 19 pages.

Vašicová, Pavla, et al. "Analysis of the Corynebacterium glutamicum dapA promoter." Journal of Bacteriology (1999);181.19: 6188-6191.
Voskuil, Martin I., et al. "The-16 region of Bacillus subtilis and other gram-positive bacterial promoters." Nucleic Acids Research (1998); 26.15: 3584-3590.
Wagner, Robert, et al. "Mutation detection using immobilized mismatch binding protein (MutS)." Nucleic Acids Research (1995); 23.19: 3944-3948.
Wang, Junping, et al. "An improved recombineering approach by adding RecA to λ red recombination." Molecular Biotechnology (2006); 32.1: 43-53.
Wang et al., "Programming cells by multiplex genome engineering and accelerated evolution." Nature (2009); 460: 894-898.
Weber, Ernst, et al. "Assembly of designer TAL effectors by Golden Gate cloning." PloS One (2011); 6.5: e19722.
West, Steven and Proudfoot, Nicholas J. "Transcriptional termination enhances protein expression in human cells." Molecular Cell (2009); 33.3: 354-364.
West, Steven, et al. "Molecular dissection of mammalian RNA polymerase II transcriptional termination." Molecular Cell (2008); 29.5: 600-610.
Wilson, Erin H., et al., "Genotype specification language." ACS Synthetic Biology (2016); 5.6: 471-478.
Written Opinion, PCT Application No. PCT/US2016/065464, 6 pages, dated Jun. 26, 2017.
Yelton, M. Melanie, et al. "Transformation of Aspergillus nidulans by using a trpC plasmid." Proceedings of the National Academy of Sciences (1984); 81.5: 1470-1474.
Zhang, Ji-Hu, et al. "Directed evolution of a fucosidase from a galactosidase by DNA shuffling and screening." Proceedings of the National Academy of Sciences (1997); 94.9: 4504-4509.
Beal, et al., "An End-to-End Workflow for Engineering of Biological Networks from High-Level Specifications." ACS Synth. Biol. (2012); 1 (8): 317-331. Publication Date (Web): Jul. 10, 2012.
GenBank CP001663.1, "Mycobacterium smegmatis str. MC2 155, complete genome." Jan. 31, 2014 (Jan. 31, 2014) [retrieved on Oct. 30, 2017, https://www.ncbi.nlm.nih.gov/nuccore/CP001663.1] genomic sequence nucleotide 4269453-4267996, 2 pages.
International Application No. PCT/US2014/064911, International Preliminary Report on Patentability, dated May 17, 2016, 7 pages.
International Application No. PCT/US2014/064911, International Search Report and Written Opinion, dated Mar. 25, 2015, 9 pages.
International Application No. PCT/US2016/034723, International Preliminary Report on Patentability, dated Dec. 5, 2017, 9 pages.
International Application No. PCT/US2016/034723, International Search Report and Written Opinion, dated Oct. 24, 2016, 13 pages.
International Application No. PCT/US2016/065465, International Preliminary Report on Patentability, dated May 17, 2016, 7 pages.
International Application No. PCT/US2017/039452, International Search Report and Written Opinion, dated Sep. 29, 2017, 24 pages.
International Application No. PCT/US2017/039772, International Search Report and Written Opinion, dated Jan. 8, 2018, 18 pages.
International Application No. PCT/US2017/039997, International Search Report and Written Opinion, dated Nov. 9, 2017, 13 pages.
International Application No. PCT/US2017/042245, International Search Report and Written Opinion, dated Oct. 2, 2017, 11 pages.
International Application No. PCT/US2017/069086, International Search Report and Written Opinion, dated May 14, 2018, 18 pages.
Isojärvi, J., et al., "Draft Genome Sequence of Calothrix Strain 336/3, a Novel H2-Producing Cyanobacterium Isolated from a Finnish Lake." Genome Announcements (2015); 3 (1): 1-2, e01474-14.
Li, et al., "C-Brick: A New Standard for Assembly of Biological Parts Using Cpf1." ACS Synth. Biol. (2016); 5 (12): 1383-1388.
Pedersen and Phillips, "Towards programming languages for genetic engineering of living cells." J.R. Soc. Interface (2009); 6 (Suppl 4): S437-S450. Published online Apr. 15, 2009.
Third-Party Submission filed with the U.S. Patent and Trademark Office on May 1, 2018, in connection with U.S. Appl. No. 15/140,296, 63 pages.
Zetsche, et al., "Cpf1 Is a Single RNA-Guided Endonuclease of a Class 2 CRISPR-Cas System." Cell (2015); 163 (2): 759-771.

(56) References Cited

OTHER PUBLICATIONS

Rytter, et al., "Synthetic promoter libraries for Corynebacterium glutamicum." Applied Microbiology and Biotechnology (2014); 98 (6): 2617-2623.
International Application No. PCT/US2016/065464, International Preliminary Report on Patentability, dated Jun. 12, 2018, 7 pages.
International Application No. PCT/US2016/065465, International Preliminary Report on Patentability, dated Jun. 12, 2018, 11 pages.
Extended European Search Report for European Patent Application No. 16873805.2, dated Feb. 18, 2019, 12 pages.
International Application No. PCT/US2017/029725, International Preliminary Report on Patentability, dated Oct. 30, 2018, 7 pages.

\* cited by examiner

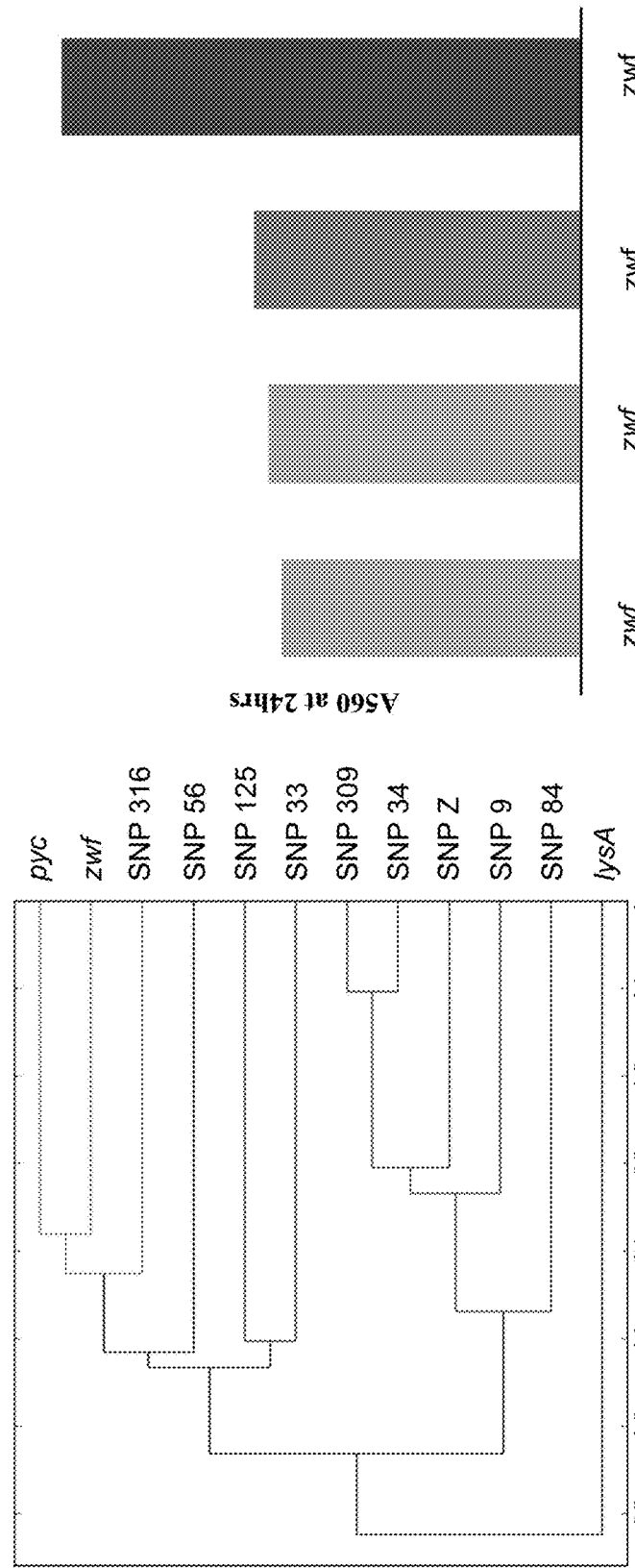
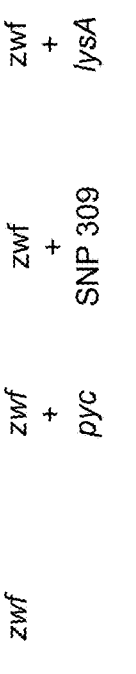
Fig. 16
Figure 16 A
Figure 16 B

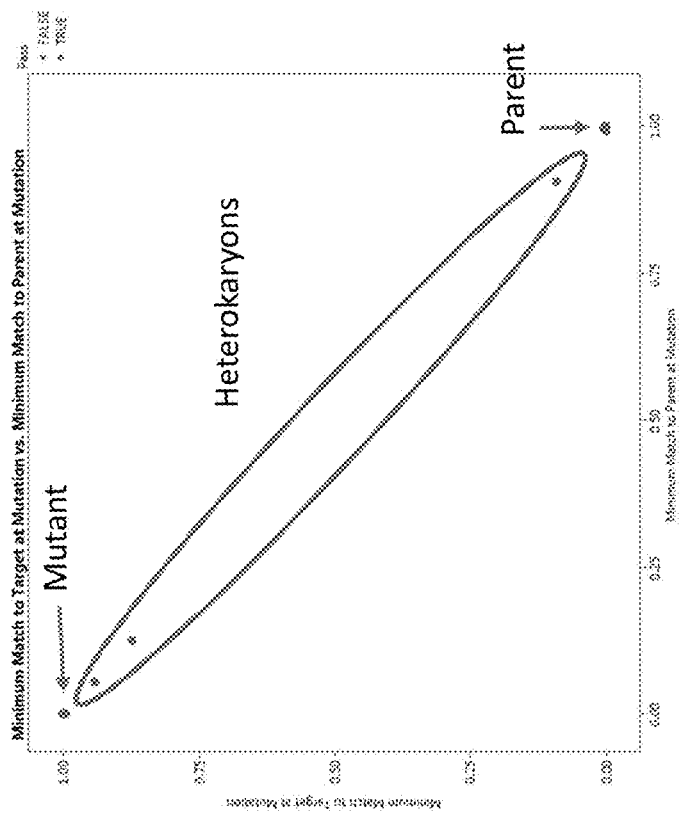
Figure 43 B
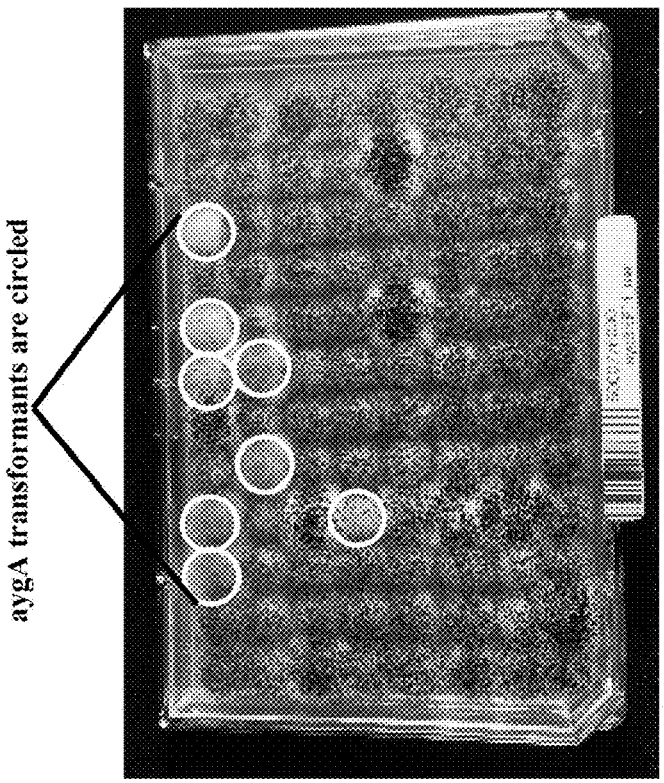
Figure 43 A
Fig. 43

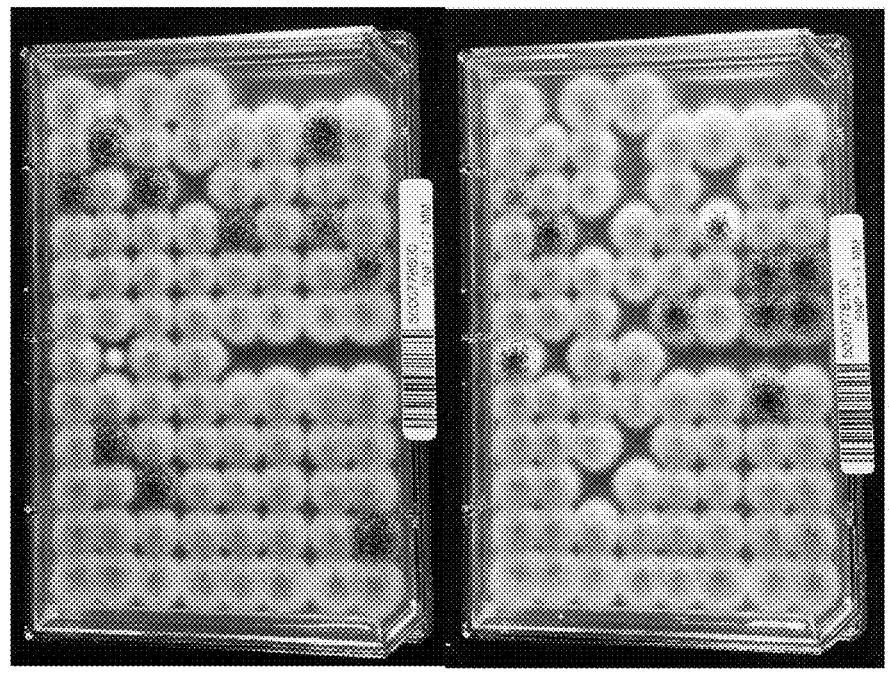
Figure 44 B
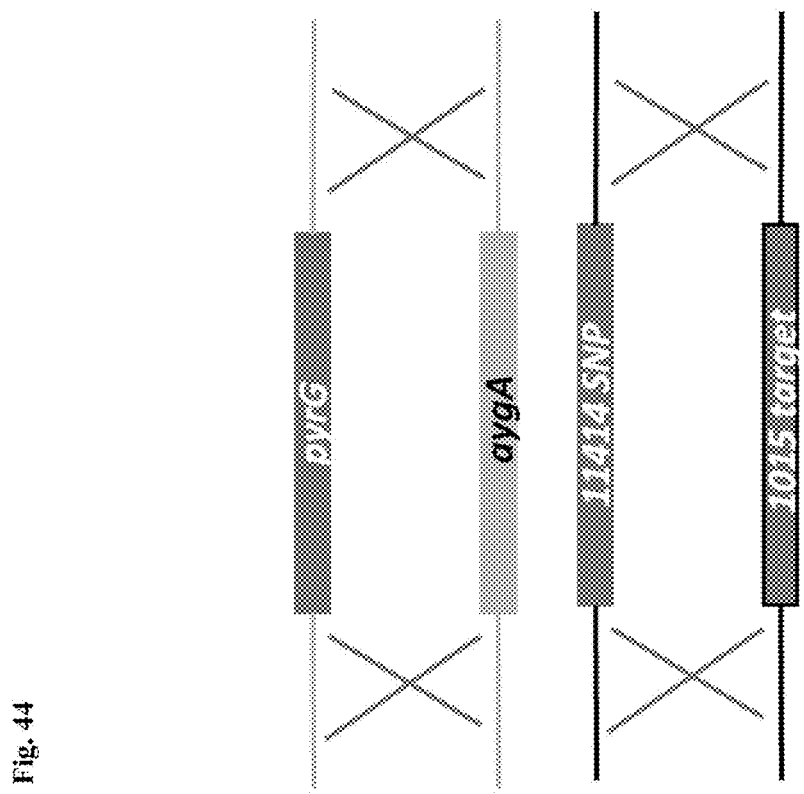
Figure 44 A
Fig. 44

SEQUENCE LISTING

```
<160> NUMBER OF SEQ ID NOS: 16

<210> SEQ ID NO 1
<211> LENGTH: 97
<212> TYPE: DNA
<213> ORGANISM: Unknown
<220> FEATURE:
<223> OTHER INFORMATION: Expression promoter derived from Pcg0007_lib_39

<400> SEQUENCE: 1
tgccgtttct cgcgttgtgt gtggtactac gtggggacct aagcgtgtat tatggaaacg      60
tctgtatcgg ataagtagcg aggagtgttc gttaaaa                              97

<210> SEQ ID NO 2
<211> LENGTH: 97
<212> TYPE: DNA
<213> ORGANISM: Unknown
<220> FEATURE:
<223> OTHER INFORMATION: Expression promoter derived from Pcg0007

<400> SEQUENCE: 2
tgccgtttct cgcgttgtgt gtggtactac gtggggacct aagcgtgtaa gatggaaacg      60
tctgtatcgg ataagtagcg aggagtgttc gttaaaa                              97
```

```
<210> SEQ ID NO 3
<211> LENGTH: 93
<212> TYPE: DNA
<213> ORGANISM: Unknown
<220> FEATURE:
<223> OTHER INFORMATION: Expression promoter derived from Pcg1860

<400> SEQUENCE: 3
cttagctttg acctgcacaa atagttgcaa attgtcccac atacacataa agtagcttgc     60
gtatttaaaa ttatgaacct aagggggttta gca                                93

<210> SEQ ID NO 4
<211> LENGTH: 98
<212> TYPE: DNA
<213> ORGANISM: Unknown
<220> FEATURE:
<223> OTHER INFORMATION: Expression promoter derived from Pcg0755

<400> SEQUENCE: 4
aataaattta taccacacag tctattgcaa tagaccaagc tgttcagtag ggtgcatggg     60
agaagaattt cctaataaaa actcttaagg acctccaa                            98

<210> SEQ ID NO 5
<211> LENGTH: 97
<212> TYPE: DNA
<213> ORGANISM: Unknown
<220> FEATURE:
<223> OTHER INFORMATION: Expression promoter derived from Pcg0007_265

<400> SEQUENCE: 5
tgccgtttct cgcgttgtgt gtggtactac gtggggacct aagcgtgtac gctggaaacg     60
tctgtatcgg ataagtagcg aggagtgttc gttaaaa                             97

<210> SEQ ID NO 6
<211> LENGTH: 86
<212> TYPE: DNA
<213> ORGANISM: Unknown
<220> FEATURE:
<223> OTHER INFORMATION: Expression promoter derived from Pcg3381

<400> SEQUENCE: 6
cgccggataa atgaattgat tattttaggc tcccagggat taagtctagg gtggaatgca     60
gaaatatttc ctacggaagg tccgtt                                         86

<210> SEQ ID NO 7
<211> LENGTH: 97
<212> TYPE: DNA
<213> ORGANISM: Unknown
<220> FEATURE:
<223> OTHER INFORMATION: Expression promoter derived from Pcg0007_119

<400> SEQUENCE: 7
tgccgtttct cgcgttgtgt gtggtactac gtggggacct aagcgtgttg catggaaacg     60
tctgtatcgg ataagtagcg aggagtgttc gttaaaa                             97

<210> SEQ ID NO 8
<211> LENGTH: 87
<212> TYPE: DNA
<213> ORGANISM: Unknown
<220> FEATURE:
<223> OTHER INFORMATION: Expression promoter derived from Pcg3121

<400> SEQUENCE: 8
```
gtggctaaaa cttttggaaa cttaagttac ctttaatcgg aaacttattg aattcgggtg    60
aggcaactgc aactctggac ttaaagc    87

<210> SEQ ID NO 9
<211> LENGTH: 25
<212> TYPE: DNA
<213> ORGANISM: Unknown
<220> FEATURE:
<223> OTHER INFORMATION: cg0001 Terminator

<400> SEQUENCE: 9
gacccatctt cggatgggtc ttttt    25

<210> SEQ ID NO 10
<211> LENGTH: 30
<212> TYPE: DNA
<213> ORGANISM: Unknown
<220> FEATURE:
<223> OTHER INFORMATION: cg0007 Terminator

<400> SEQUENCE: 10
cccgcccctg gaattctggg ggcgggtttt    30

<210> SEQ ID NO 11
<211> LENGTH: 24
<212> TYPE: DNA
<213> ORGANISM: Unknown
<220> FEATURE:
<223> OTHER INFORMATION: cg0371 Terminator

<400> SEQUENCE: 11
ccggtaactt ttgtaagttg ccgg    24

<210> SEQ ID NO 12
<211> LENGTH: 27
<212> TYPE: DNA
<213> ORGANISM: Unknown
<220> FEATURE:
<223> OTHER INFORMATION: cg0480 Terminator

<400> SEQUENCE: 12
cccctcagaa gcgattctga ggggttt    27

<210> SEQ ID NO 13
<211> LENGTH: 28
<212> TYPE: DNA
<213> ORGANISM: Unknown
<220> FEATURE:
<223> OTHER INFORMATION: cg0494 Terminator

<400> SEQUENCE: 13
gcaccgcctt tcggggcggt gctttttt    28

<210> SEQ ID NO 14
<211> LENGTH: 28
<212> TYPE: DNA
<213> ORGANISM: Unknown
<220> FEATURE:
<223> OTHER INFORMATION: cg0564 Terminator

<400> SEQUENCE: 14
ggccccatgc tttgcatggg gtctttt    28

<210> SEQ ID NO 15
<211> LENGTH: 30

```
<212> TYPE: DNA
<213> ORGANISM: Unknown
<220> FEATURE:
<223> OTHER INFORMATION: cg0610 Terminator

<400> SEQUENCE: 15
gcacttacct taactggtag gtgcttttt                                    30

<210> SEQ ID NO 16
<211> LENGTH: 24
<212> TYPE: DNA
<213> ORGANISM: Unknown
<220> FEATURE:
<223> OTHER INFORMATION: cg0695 Terminator

<400> SEQUENCE: 16
acccggtcac cagaccgggt cttt                                          24
```

MICROBIAL STRAIN IMPROVEMENT BY A HTP GENOMIC ENGINEERING PLATFORM

CROSS-REFERENCE TO RELATED APPLICATIONS

This Application is a Continuation Application of U.S. application Ser. No. 15/396,230, filed on Dec. 30, 2016, now issued as U.S. Pat. No. 9,988,624, which is a Continuation U.S. Utility Application under 35 U.S.C. § 111, claiming the benefit of priority to International Application No. PCT/US2016/065465, filed on Dec. 7, 2016, which claims the benefit of priority to U.S. Provisional Application No. 62/264,232, filed on Dec. 7, 2015, U.S. Nonprovisional application Ser. No. 15/140,296, filed on Apr. 27, 2016, and U.S. Provisional Application No. 62/368,786, filed on Jul. 29, 2016, each of which are hereby incorporated by reference in their entirety, including all descriptions, references, figures, and claims for all purposes.

FIELD

The present disclosure is directed to high-throughput (HTP) microbial genomic engineering. The disclosed HTP genomic engineering platform is computationally driven and integrates molecular biology, automation, and advanced machine learning protocols. This integrative platform utilizes a suite of HTP molecular tool sets to create HTP genetic design libraries, which are derived from, inter alia, scientific insight and iterative pattern recognition.

STATEMENT REGARDING SEQUENCE LISTING

The Sequence Listing associated with this application is provided in text format in lieu of a paper copy, and is hereby incorporated by reference into the specification. The name of the text file containing the Sequence Listing is ZYMR_001_02US_SeqList_ST25.txt. The text file is ≈5 KB, was created on Feb. 23, 2018, and is being submitted electronically via EFS-Web.

BACKGROUND

Humans have been harnessing the power of microbial cellular biosynthetic pathways for millennia to produce products of interest, the oldest examples of which include alcohol, vinegar, cheese, and yogurt. These products are still in large demand today and have also been accompanied by an ever increasing repertoire of products producible by microbes. The advent of genetic engineering technology has enabled scientists to design and program novel biosynthetic pathways into a variety of organisms to produce a broad range of industrial, medical, and consumer products. Indeed, microbial cellular cultures are now used to produce products ranging from small molecules, antibiotics, vaccines, insecticides, enzymes, fuels, and industrial chemicals.

Given the large number of products produced by modern industrial microbes, it comes as no surprise that engineers are under tremendous pressure to improve the speed and efficiency by which a given microorganism is able to produce a target product.

A variety of approaches have been used to improve the economy of biologically-based industrial processes by "improving" the microorganism involved. For example, many pharmaceutical and chemical industries rely on microbial strain improvement programs in which the parent strains of a microbial culture are continuously mutated through exposure to chemicals or UV radiation and are subsequently screened for performance increases, such as in productivity, yield and titer. This mutagenesis process is extensively repeated until a strain demonstrates a suitable increase in product performance. The subsequent "improved" strain is then utilized in commercial production.

As alluded to above, identification of improved industrial microbial strains through mutagenesis is time consuming and inefficient. The process, by its very nature, is haphazard and relies upon one stumbling upon a mutation that has a desirable outcome on product output.

Not only are traditional microbial strain improvement programs inefficient, but the process can also lead to industrial strains with a high degree of detrimental mutagenic load. The accumulation of mutations in industrial strains subjected to these types of programs can become significant and may lead to an eventual stagnation in the rate of performance improvement.

Thus, there is a great need in the art for new methods of engineering industrial microbes, which do not suffer from the aforementioned drawbacks inherent with traditional strain improvement programs and greatly accelerate the process of discovering and consolidating beneficial mutations.

Further, there is an urgent need for a method by which to "rehabilitate" industrial strains that have been developed by the antiquated and deleterious processes currently employed in the field of microbial strain improvement.

SUMMARY OF THE DISCLOSURE

The present disclosure provides a high-throughput (HTP) microbial genomic engineering platform that does not suffer from the myriad of problems associated with traditional microbial strain improvement programs.

Further, the HTP platform taught herein is able to rehabilitate industrial microbes that have accumulated non-beneficial mutations through decades of random mutagenesis-based strain improvement programs.

The disclosed HTP genomic engineering platform is computationally driven and integrates molecular biology, automation, and advanced machine learning protocols. This integrative platform utilizes a suite of HTP molecular tool sets to create HTP genetic design libraries, which are derived from, inter alia, scientific insight and iterative pattern recognition.

The taught HTP genetic design libraries function as drivers of the genomic engineering process, by providing libraries of particular genomic alterations for testing in a microbe. The microbes engineered utilizing a particular library, or combination of libraries, are efficiently screened in a HTP manner for a resultant outcome, e.g. production of a product of interest. This process of utilizing the HTP genetic design libraries to define particular genomic alterations for testing in a microbe and then subsequently screening host microbial genomes harboring the alterations is implemented in an efficient and iterative manner. In some aspects, the iterative cycle or "rounds" of genomic engineering campaigns can be at least 1, 2, 3, 4, 5, 6, 7, 8, 9, 10, 20, 30, 40, 50, 60, 70, 80, 90, 100, or more iterations/cycles/rounds.

Thus, in some aspects, the present disclosure teaches methods of conducting at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 125, 150, 175, 200, 225, 250, 275, 300, 325, 350, 375, 400, 425, 450, 475, 500, 525, 550, 575, 600, 625, 650, 675, 700, 725, 750, 775, 800, 825, 850, 875, 900, 925, 950, 975, 1000 or more "rounds" of HTP genetic engineering (e.g., rounds of SNP swap, PRO swap, STOP swap, or combinations thereof).

In some embodiments the present disclosure teaches a linear approach, in which each subsequent HTP genetic engineering round is based on genetic variation identified in the previous round of genetic engineering. In other embodiments the present disclosure teaches a non-linear approach, in which each subsequent HTP genetic engineering round is based on genetic variation identified in any previous round of genetic engineering, including previously conducted analysis, and separate HTP genetic engineering branches.

The data from these iterative cycles enables large scale data analytics and pattern recognition, which is utilized by the integrative platform to inform subsequent rounds of HTP genetic design library implementation. Consequently, the HTP genetic design libraries utilized in the taught platform are highly dynamic tools that benefit from large scale data pattern recognition algorithms and become more informative through each iterative round of microbial engineering.

In some embodiments, the genetic design libraries of the present disclosure comprise at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 125, 150, 175, 200, 225, 250, 275, 300, 325, 350, 375, 400, 425, 450, 475, 500, 525, 550, 575, 600, 625, 650, 675, 700, 725, 750, 775, 800, 825, 850, 875, 900, 925, 950, 975, 1000 or more individual genetic changes (e.g., at least X number of promoter:gene combinations in the PRO swap library).

In some embodiments, the present disclosure provides illustrative examples and text describing application of HTP strain improvement methods to microbial strains. In some embodiments, the strain improvement methods of the present disclosure are applicable to any host cell.

In some embodiments, the present disclosure teaches a high-throughput (HTP) method of genomic engineering to evolve a microbe to acquire a desired phenotype, comprising: a) perturbing the genomes of an initial plurality of microbes having the same microbial strain background, to thereby create an initial HTP genetic design microbial strain library comprising individual microbial strains with unique genetic variations; b) screening and selecting individual microbial strains of the initial HTP genetic design microbial strain library for the desired phenotype; c) providing a subsequent plurality of microbes that each comprise a unique combination of genetic variation, said genetic variation selected from the genetic variation present in at least two individual microbial strains screened in the preceding step, to thereby create a subsequent HTP genetic design microbial strain library; d) screening and selecting individual microbial strains of the subsequent HTP genetic design microbial strain library for the desired phenotype; e) repeating steps c)-d) one or more times, in a linear or non-linear fashion, until a microbe has acquired the desired phenotype, wherein each subsequent iteration creates a new HTP genetic design microbial strain library comprising individual microbial strains harboring unique genetic variations that are a combination of genetic variation selected from amongst at least two individual microbial strains of a preceding HTP genetic design microbial strain library.

In some embodiments, the present disclosure teaches that the initial HTP genetic design microbial strain library is at least one selected from the group consisting of a promoter swap microbial strain library, SNP swap microbial strain library, start/stop codon microbial strain library, optimized sequence microbial strain library, a terminator swap microbial strain library, or any combination thereof.

In some embodiments, the present disclosure teaches methods of making a subsequent plurality of microbes that each comprise a unique combination of genetic variations, wherein each of the combined genetic variations is derived from the initial HTP genetic design microbial strain library or the HTP genetic design microbial strain library of the preceding step.

In some embodiments, the combination of genetic variations in the subsequent plurality of microbes will comprise a subset of all the possible combinations of the genetic variations in the initial HTP genetic design microbial strain library or the HTP genetic design microbial strain library of the preceding step.

In some embodiments, the present disclosure teaches that the subsequent HTP genetic design microbial strain library is a full combinatorial microbial strain library derived from the genetic variations in the initial HTP genetic design microbial strain library or the HTP genetic design microbial strain library of the preceding step.

For example, if the prior HTP genetic design microbial strain library only had genetic variations A, B, C, and D, then a partial combinatorial of said variations could include a subsequent HTP genetic design microbial strain library comprising three microbes each comprising either the AB, AC, or AD unique combinations of genetic variations (order in which the mutations are represented is unimportant). A full combinatorial microbial strain library derived from the genetic variations of the HTP genetic design library of the preceding step would include six microbes, each comprising either AB, AC, AD, BC, BD, or CD unique combinations of genetic variations.

In some embodiments, the methods of the present disclosure teach perturbing the genome utilizing at least one method selected from the group consisting of: random mutagenesis, targeted sequence insertions, targeted sequence deletions, targeted sequence replacements, or any combination thereof.

In some embodiments of the presently disclosed methods, the initial plurality of microbes comprise unique genetic variations derived from an industrial production strain microbe.

In some embodiments of the presently disclosed methods, the initial plurality of microbes comprise industrial production strain microbes denoted $S_1Gen_1$ and any number of subsequent microbial generations derived therefrom denoted $S_nGen_n$.

In some embodiments, the present disclosure teaches a method for generating a SNP swap microbial strain library, comprising the steps of: a) providing a reference microbial strain and a second microbial strain, wherein the second microbial strain comprises a plurality of identified genetic variations selected from single nucleotide polymorphisms, DNA insertions, and DNA deletions, which are not present in the reference microbial strain; b) perturbing the genome of either the reference microbial strain, or the second microbial strain, to thereby create an initial SNP swap microbial strain library comprising a plurality of individual microbial strains with unique genetic variations found within each strain of said plurality of individual microbial strains, wherein each of said unique genetic variations corresponds to a single genetic variation selected from the plurality of identified genetic variations between the reference microbial strain and the second microbial strain.

In some embodiments of SNP swap library, the genome of the reference microbial strain is perturbed to add one or more of the identified single nucleotide polymorphisms, DNA insertions, or DNA deletions, which are found in the second microbial strain.

In some embodiments of SNP swap library methods of the present disclosure, the genome of the second microbial strain is perturbed to remove one or more of the identified single nucleotide polymorphisms, DNA insertions, or DNA deletions, which are not found in the reference microbial strain.

In some embodiments, the genetic variations of the SNP swap library will comprise a subset of all the genetic variations identified between the reference microbial strain and the second microbial strain.

In some embodiments, the genetic variations of the SNP swap library will comprise all of the identified genetic variations identified between the reference microbial strain and the second microbial strain.

In some embodiments, the present disclosure teaches a method for rehabilitating and improving the phenotypic performance of an industrial microbial strain, comprising the steps of: a) providing a parental lineage microbial strain and an industrial microbial strain derived therefrom, wherein the industrial microbial strain comprises a plurality of identified genetic variations selected from single nucleotide polymorphisms, DNA insertions, and DNA deletions, not present in the parental lineage microbial strain; b) perturbing the genome of either the parental lineage microbial strain, or the industrial microbial strain, to thereby create an initial SNP swap microbial strain library comprising a plurality of individual microbial strains with unique genetic variations found within each strain of said plurality of individual microbial strains, wherein each of said unique genetic variations corresponds to a single genetic variation selected from the plurality of identified genetic variations between the parental lineage microbial strain and the industrial microbial strain; c) screening and selecting individual microbial strains of the initial SNP swap microbial strain library for phenotype performance improvements over a reference microbial strain, thereby identifying unique genetic variations that confer said microbial strains with phenotype performance improvements; d) providing a subsequent plurality of microbes that each comprise a unique combination of genetic variation, said genetic variation selected from the genetic variation present in at least two individual microbial strains screened in the preceding step, to thereby create a subsequent SNP swap microbial strain library; e) screening and selecting individual microbial strains of the subsequent SNP swap microbial strain library for phenotype performance improvements over the reference microbial strain, thereby identifying unique combinations of genetic variation that confer said microbial strains with additional phenotype performance improvements; and f) repeating steps d)-e) one or more times, in a linear or non-linear fashion, until a microbial strain exhibits a desired level of improved phenotype performance compared to the phenotype performance of the industrial microbial strain, wherein each subsequent iteration creates a new SNP swap microbial strain library comprising individual microbial strains harboring unique genetic variations that are a combination of genetic variation selected from amongst at least two individual microbial strains of a preceding SNP swap microbial strain library.

In some embodiments the present disclosure teaches methods for rehabilitating and improving the phenotypic performance of an industrial microbial strain, wherein the genome of the parental lineage microbial strain is perturbed to add one or more of the identified single nucleotide polymorphisms, DNA insertions, or DNA deletions, which are found in the industrial microbial strain.

In some embodiments the present disclosure teaches methods for rehabilitating and improving the phenotypic performance of an industrial microbial strain, wherein the genome of the industrial microbial strain is perturbed to remove one or more of the identified single nucleotide polymorphisms, DNA insertions, or DNA deletions, which are not found in the parental lineage microbial strain.

In some embodiments, the present disclosure teaches a method for generating a promoter swap microbial strain library, said method comprising the steps of: a) providing a plurality of target genes endogenous to a base microbial strain, and a promoter ladder, wherein said promoter ladder comprises a plurality of promoters exhibiting different expression profiles in the base microbial strain; b) engineering the genome of the base microbial strain, to thereby create an initial promoter swap microbial strain library comprising a plurality of individual microbial strains with unique genetic variations found within each strain of said plurality of individual microbial strains, wherein each of said unique genetic variations comprises one of the promoters from the promoter ladder operably linked to one of the target genes endogenous to the base microbial strain.

In some embodiments, the present disclosure teaches a promoter swap method of genomic engineering to evolve a microbe to acquire a desired phenotype, said method comprising the steps of: a) providing a plurality of target genes endogenous to a base microbial strain, and a promoter ladder, wherein said promoter ladder comprises a plurality of promoters exhibiting different expression profiles in the base microbial strain; b) engineering the genome of the base microbial strain, to thereby create an initial promoter swap microbial strain library comprising a plurality of individual microbial strains with unique genetic variations found within each strain of said plurality of individual microbial strains, wherein each of said unique genetic variations comprises one of the promoters from the promoter ladder operably linked to one of the target genes endogenous to the base microbial strain; c) screening and selecting individual microbial strains of the initial promoter swap microbial strain library for the desired phenotype; d) providing a subsequent plurality of microbes that each comprise a unique combination of genetic variation, said genetic variation selected from the genetic variation present in at least two individual microbial strains screened in the preceding step, to thereby create a subsequent promoter swap microbial strain library; e) screening and selecting individual microbial strains of the subsequent promoter swap microbial strain library for the desired phenotype; f) repeating steps d)-e) one or more times, in a linear or non-linear fashion, until a microbe has acquired the desired phenotype, wherein each subsequent iteration creates a new promoter swap microbial strain library comprising individual microbial strains harboring unique genetic variations that are a combination of genetic variation selected from amongst at least two individual microbial strains of a preceding promoter swap microbial strain library.

In some embodiments, the present disclosure teaches a method for generating a terminator swap microbial strain library, said method comprising the steps of: a) providing a plurality of target genes endogenous to a base microbial strain, and a terminator ladder, wherein said terminator ladder comprises a plurality of terminators exhibiting different expression profiles in the base microbial strain; b) engineering the genome of the base microbial strain, to thereby create an initial terminator swap microbial strain library comprising a plurality of individual microbial strains with unique genetic variations found within each strain of said plurality of individual microbial strains, wherein each of said unique genetic variations comprises one of the target genes endogenous to the base microbial strain operably linked to one or more of the terminators from the terminator ladder.

In some embodiments, the present disclosure teaches a terminator swap method of genomic engineering to evolve a microbe to acquire a desired phenotype, said method comprising the steps of: a) providing a plurality of target genes endogenous to a base microbial strain, and a terminator ladder, wherein said terminator ladder comprises a plurality of terminators exhibiting different expression profiles in the base microbial strain; b) engineering the genome of the base microbial strain, to thereby create an initial terminator swap microbial strain library comprising a plurality of individual microbial strains with unique genetic variations found within each strain of said plurality of individual microbial strains, wherein each of said unique genetic variations comprises one of the target genes endogenous to the base microbial strain operably linked to one or more of the terminators from the terminator ladder; c) screening and selecting individual microbial strains of the initial terminator swap microbial strain library for the desired phenotype; d) providing a subsequent plurality of microbes that each comprise a unique combination of genetic variation, said genetic variation selected from the genetic variation present in at least two individual microbial strains screened in the preceding step, to thereby create a subsequent terminator swap microbial strain library; e) screening and selecting individual microbial strains of the subsequent terminator swap microbial strain library for the desired phenotype; f) repeating steps d)-e) one or more times, in a linear or non-linear fashion, until a microbe has acquired the desired phenotype, wherein each subsequent iteration creates a new terminator swap microbial strain library comprising individual microbial strains harboring unique genetic variations that are a combination of genetic variation selected from amongst at least two individual microbial strains of a preceding terminator swap microbial strain library.

In some embodiments, the present disclosure teaches iteratively improving the design of candidate microbial strains by (a) accessing a predictive model populated with a training set comprising (1) inputs representing genetic changes to one or more background microbial strains and (2) corresponding performance measures; (b) applying test inputs to the predictive model that represent genetic changes, the test inputs corresponding to candidate microbial strains incorporating those genetic changes; (c) predicting phenotypic performance of the candidate microbial strains based at least in part upon the predictive model; (d) selecting a first subset of the candidate microbial strains based at least in part upon their predicted performance; (e) obtaining measured phenotypic performance of the first subset of the candidate microbial strains; (f) obtaining a selection of a second subset of the candidate microbial strains based at least in part upon their measured phenotypic performance; (g) adding to the training set of the predictive model (1) inputs corresponding to the selected second subset of candidate microbial strains, along with (2) corresponding measured performance of the selected second subset of candidate microbial strains; and (h) repeating (b)-(g) until measured phenotypic performance of at least one candidate microbial strain satisfies a performance metric. In some cases, during a first application of test inputs to the predictive model, the genetic changes represented by the test inputs comprise genetic changes to the one or more background microbial strains; and during subsequent applications of test inputs, the genetic changes represented by the test inputs comprise genetic changes to candidate microbial strains within a previously selected second subset of candidate microbial strains.

In some embodiments, selection of the first subset may be based on epistatic effects. This may be achieved by: during a first selection of the first subset: determining degrees of dissimilarity between performance measures of the one or more background microbial strains in response to application of a plurality of respective inputs representing genetic changes to the one or more background microbial strains; and selecting for inclusion in the first subset at least two candidate microbial strains based at least in part upon the degrees of dissimilarity in the performance measures of the one or more background microbial strains in response to application of genetic changes incorporated into the at least two candidate microbial strains.

In some embodiments, the present invention teaches applying epistatic effects in the iterative improvement of candidate microbial strains, the method comprising: obtaining data representing measured performance in response to corresponding genetic changes made to at least one microbial background strain; obtaining a selection of at least two genetic changes based at least in part upon a degree of dissimilarity between the corresponding responsive performance measures of the at least two genetic changes, wherein the degree of dissimilarity relates to the degree to which the at least two genetic changes affect their corresponding responsive performance measures through different biological pathways; and designing genetic changes to a microbial background strain that include the selected genetic changes. In some cases, the microbial background strain for which the at least two selected genetic changes are designed is the same as the at least one microbial background strain for which data representing measured responsive performance was obtained.

In some embodiments, the present disclosure teaches HTP strain improvement methods utilizing only a single type of genetic microbial library. For example, in some embodiments, the present disclosure teaches HTP strain improvement methods utilizing only SNP swap libraries. In other embodiments, the present disclosure teaches HTP strain improvement methods utilizing only PRO swap libraries. In some embodiments, the present disclosure teaches HTP strain improvement methods utilizing only STOP swap libraries. In some embodiments, the present disclosure teaches HTP strain improvement methods utilizing only Start/Stop Codon swap libraries.

In other embodiments, the present disclosure teaches HTP strain improvement methods utilizing two or more types of genetic microbial libraries. For example, in some embodiments, the present disclosure teaches HTP strain improvement methods combining SNP swap and PRO swap libraries. In some embodiments, the present disclosure teaches HTP strain improvement methods combining SNP swap and STOP swap libraries. In some embodiments, the present disclosure teaches HTP strain improvement methods combining PRO swap and STOP swap libraries.

In other embodiments, the present disclosure teaches HTP strain improvement methods utilizing multiple types of genetic microbial libraries. In some embodiments the genetic microbial libraries are combined to produce combination mutations (e.g., promoter/terminator combination ladders applied to one or more genes). In yet other embodiments, the HTP strain improvement methods of the present disclosure can be combined with one or more traditional strain improvement methods.

In some embodiments, the HTP strain improvement methods of the present disclosure result in an improved host cell. That is, the present disclosure teaches methods of improving one or more host cell properties. In some embodiments the improved host cell property is selected from the group consisting of volumetric productivity, specific productivity, yield or titre, of a product of interest produced by the host cell. In some embodiments the improved host cell property is volumetric productivity. In some embodiments the improved host cell property is specific productivity. In some embodiments the improved host cell property is yield.

In some embodiments, the HTP strain improvement methods of the present disclosure result in a host cell that exhibits a 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, 150%, 200%, 250%, 300% or more of an improvement in at least one host cell property over a control host cell that is not subjected to the HTP strain improvements methods (e.g, an X % improvement in yield or productivity of a biomolecule of interest, incorporating any ranges and subranges therebetween). In some embodiments, the HIT strain improvement methods of the present disclosure are selected from the group consisting of SNP swap, PRO swap, STOP swap, and combinations thereof.

Thus, in some embodiments, the SNP swap methods of the present disclosure result in a host cell that exhibits a 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, 150%, 200%, 250%, 300% or more of an improvement in at least one host cell property over a control host cell that is not subjected to the SNP swap methods (e.g, an X % improvement in yield or productivity of a biomolecule of interest, incorporating any ranges and subranges therebetween).

Thus, in some embodiments, the PRO swap methods of the present disclosure result in a host cell that exhibits a 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, 150%, 200%, 250%, 300% or more of an improvement in at least one host cell property over a control host cell that is not subjected to the PRO swap methods (e.g, an X % improvement in yield or productivity of a biomolecule of interest, incorporating any ranges and subranges therebetween).

BRIEF DESCRIPTION OF THE FIGURES

FIG. 6A depicts the steps for building DNA fragments, cloning said DNA fragments into vectors, transforming said vectors into host strains, and looping out selection sequences through counter selection. FIG. 6B depicts the steps for high-throughput culturing, screening, and evaluation of selected host strains. This figure also depicts the optional steps of culturing, screening, and evaluating selected strains in culture tanks.

FIG. 16A-B depicts the results of an epistasis mapping experiment. Combination of SNPs and PRO swaps with low functional similarities yields improved strain performance. FIG. 16A depicts a dendrogram clustered by functional similarity of all the SNPs/PRO swaps. FIG. 16B depicts host strain performance of consolidated SNPs as measured by product yield. Greater cluster distance correlates with improved consolidation performance of the host strain.

FIG. 17A depicts the relationship among the strains of this experiment. Strain A is the wild-type host strain. Strain B is an intermediate engineered strain. Strain C is the industrial production strain. FIG. 17B is a graph identifying the number of unique and shared SNPs in each strain.

FIG. 43A-B depicts the results of A. niger transformation and validation according to the methods of the present disclosure. FIG. 43A—is a picture of a 96-well media plate of A. niger transformants. Transformed cultures comprise a mutation in the aygA, which causes the cells to appear lighter yellow instead of black (transformed wells are circled in white). FIG. 43B—depicts the results of next generation sequencing of transformed A. niger mutants. The X-axis represents the target DNA's sequence identity with the untransformed parent strain. The Y-axis represents the target DNA's sequence identity with the expected mutation. Data points towards the bottom right of the chart exhibit high similarity with the parent strain, and low similarity with the expected transformed sequences. Data points towards the top left of the chart exhibit high similarity to expected transformed sequences and low identity with parent strain. Data points in the middle likely represent heterokaryons with multiple nuclei.

FIG. 44A-B illustrates a SNP swap implementation in A. Niger. FIG. 44A—illustrates the designed genetic edits for each SNP of the SNP swap. The figure further illustrates the cotransformation in which the pyrG gene is introduced into the locus for the aygA wild type gene. FIG. 44B—are two pictures of the 96-well media plates for screening the A. niger transformants. Light yellow colonies represent transformants in which the aygA gene has been successfully disrupted.

DETAILED DESCRIPTION

Definitions

Figure 1:
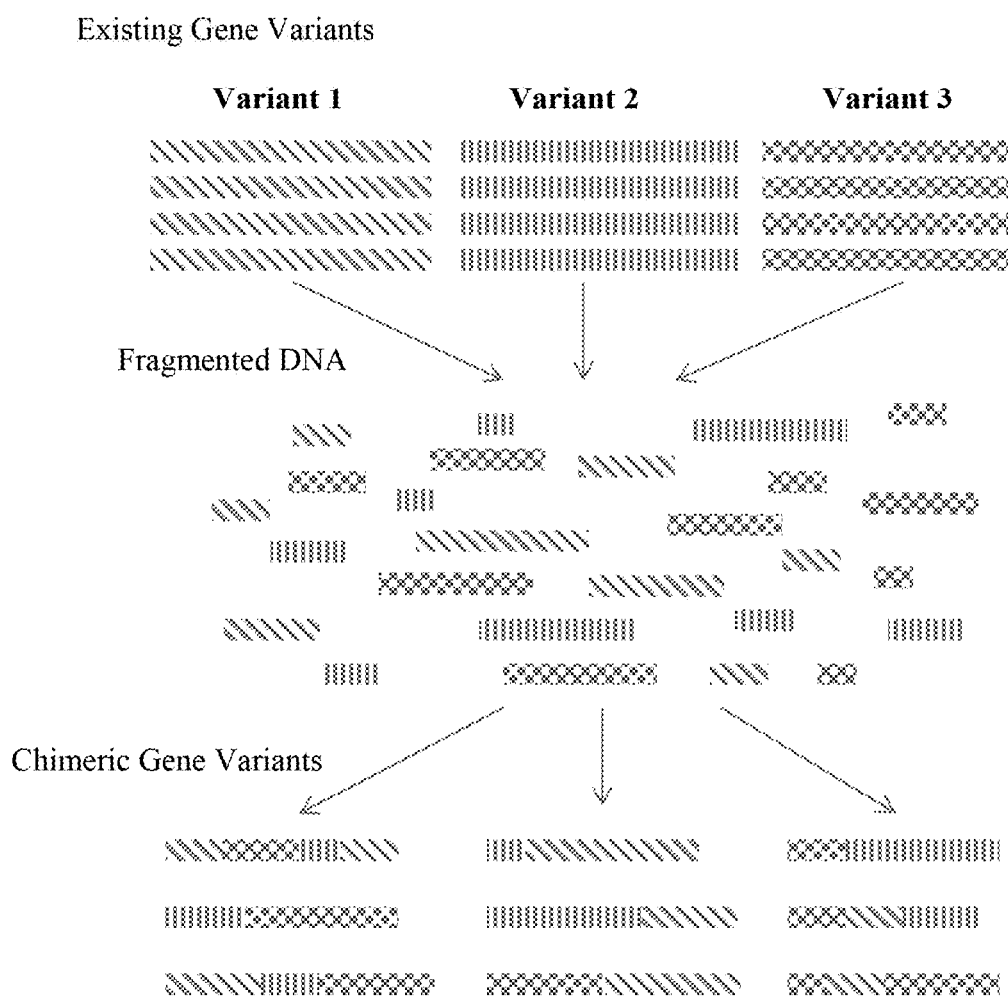
FIG. 1 depicts a DNA recombination method of the present disclosure for increasing variation in diversity pools. DNA sections, such as genome regions from related species, can be cut via physical or enzymatic/chemical means. The cut DNA regions are melted and allowed to reanneal, such that overlapping genetic regions prime polymerase extension reactions. Subsequent melting/extension reactions are carried out until products are reassembled into chimeric DNA, comprising elements from one or more starting sequences.

While the following terms are believed to be well understood by one of ordinary skill in the art, the following definitions are set forth to facilitate explanation of the presently disclosed subject matter.

The term "a" or "an" refers to one or more of that entity, i.e. can refer to a plural referents. As such, the terms "a" or "an", "one or more" and "at least one" are used interchangeably herein. In addition, reference to "an element" by the indefinite article "a" or "an" does not exclude the possibility that more than one of the elements is present, unless the context clearly requires that there is one and only one of the elements.

As used herein the terms "cellular organism" "microorganism" or "microbe" should be taken broadly. These terms are used interchangeably and include, but are not limited to, the two prokaryotic domains, Bacteria and Archaea, as well as certain eukaryotic fungi and protists. In some embodiments, the disclosure refers to the "microorganisms" or "cellular organisms" or "microbes" of lists/tables and figures present in the disclosure. This characterization can refer to not only the identified taxonomic genera of the tables and figures, but also the identified taxonomic species, as well as the various novel and newly identified or designed strains of any organism in said tables or figures. The same characterization holds true for the recitation of these terms in other parts of the Specification, such as in the Examples.

The term "prokaryotes" is art recognized and refers to cells which contain no nucleus or other cell organelles. The prokaryotes are generally classified in one of two domains, the Bacteria and the Archaea. The definitive difference between organisms of the Archaea and Bacteria domains is based on fundamental differences in the nucleotide base sequence in the 16S ribosomal RNA.

The term "Archaea" refers to a categorization of organisms of the division Mendosicutes, typically found in unusual environments and distinguished from the rest of the prokaryotes by several criteria, including the number of ribosomal proteins and the lack of muramic acid in cell walls. On the basis of ssrRNA analysis, the Archaea consist of two phylogenetically-distinct groups: Crenarchaeota and Euryarchaeota. On the basis of their physiology, the Archaea can be organized into three types: methanogens (prokaryotes that produce methane); extreme halophiles (prokaryotes that live at very high concentrations of salt (NaCl); and extreme (hyper) *thermophilus* (prokaryotes that live at very high temperatures). Besides the unifying archaeal features that distinguish them from Bacteria (i.e., no murein in cell wall, ester-linked membrane lipids, etc.), these prokaryotes exhibit unique structural or biochemical attributes which adapt them to their particular habitats. The Crenarchaeota consists mainly of hyperthermophilic sulfur-dependent prokaryotes and the Euryarchaeota contains the methanogens and extreme halophiles.

"Bacteria" or "eubacteria" refers to a domain of prokaryotic organisms. Bacteria include at least 11 distinct groups as follows: (1) Gram-positive (gram+) bacteria, of which there are two major subdivisions: (1) high G+C group (*Actinomycetes, Mycobacteria, Micrococcus*, others) (2) low G+C group (*Bacillus, Clostridia, Lactobacillus, Staphylococci, Streptococci, Mycoplasmas*); (2) Proteobacteria, e.g., Purple photosynthetic+non-photosynthetic Gram-negative bacteria (includes most "common" Gram-negative bacteria); (3) Cyanobacteria, e.g., oxygenic phototrophs; (4) Spirochetes and related species; (5) Planctomyces; (6) *Bacteroides, Flavobacteria*; (7) *Chlamydia*; (8) Green sulfur bacteria; (9) Green non-sulfur bacteria (also anaerobic phototrophs); (10) Radioresistant micrococci and relatives; (11) *Thermotoga* and *Thermosipho thermophiles*.

A "eukaryote" is any organism whose cells contain a nucleus and other organelles enclosed within membranes. Eukaryotes belong to the taxon Eukarya or Eukaryota. The defining feature that sets eukaryotic cells apart from prokaryotic cells (the aforementioned Bacteria and Archaea) is that they have membrane-bound organelles, especially the nucleus, which contains the genetic material, and is enclosed by the nuclear envelope.

The terms "genetically modified host cell," "recombinant host cell," and "recombinant strain" are used interchangeably herein and refer to host cells that have been genetically modified by the cloning and transformation methods of the present disclosure. Thus, the terms include a host cell (e.g., bacteria, yeast cell, fungal cell, CHO, human cell, etc.) that has been genetically altered, modified, or engineered, such that it exhibits an altered, modified, or different genotype and/or phenotype (e.g., when the genetic modification affects coding nucleic acid sequences of the microorganism), as compared to the naturally-occurring organism from which it was derived. It is understood that in some embodiments, the terms refer not only to the particular recombinant host cell in question, but also to the progeny or potential progeny of such a host cell The term "wild-type microorganism" or "wild-type host cell" describes a cell that occurs in nature, i.e. a cell that has not been genetically modified.

The term "genetically engineered" may refer to any manipulation of a host cell's genome (e.g. by insertion, deletion, mutation, or replacement of nucleic acids).

The term "control" or "control host cell" refers to an appropriate comparator host cell for determining the effect of a genetic modification or experimental treatment. In some embodiments, the control host cell is a wild type cell. In other embodiments, a control host cell is genetically identical to the genetically modified host cell, save for the genetic modification(s) differentiating the treatment host cell. In some embodiments, the present disclosure teaches the use of parent strains as control host cells (e.g., the $S_1$ strain that was used as the basis for the strain improvement program). In other embodiments, a host cell may be a genetically identical cell that lacks a specific promoter or SNP being tested in the treatment host cell.

As used herein, the term "allele(s)" means any of one or more alternative forms of a gene, all of which alleles relate to at least one trait or characteristic. In a diploid cell, the two alleles of a given gene occupy corresponding loci on a pair of homologous chromosomes.

As used herein, the term "locus" (loci plural) means a specific place or places or a site on a chromosome where for example a gene or genetic marker is found.

As used herein, the term "genetically linked" refers to two or more traits that are co-inherited at a high rate during breeding such that they are difficult to separate through crossing.

A "recombination" or "recombination event" as used herein refers to a chromosomal crossing over or independent assortment.

As used herein, the term "phenotype" refers to the observable characteristics of an individual cell, cell culture, organism, or group of organisms which results from the interaction between that individual's genetic makeup (i.e., genotype) and the environment.

As used herein, the term "chimeric" or "recombinant" when describing a nucleic acid sequence or a protein sequence refers to a nucleic acid, or a protein sequence, that links at least two heterologous polynucleotides, or two heterologous polypeptides, into a single macromolecule, or that re-arranges one or more elements of at least one natural nucleic acid or protein sequence. For example, the term "recombinant" can refer to an artificial combination of two otherwise separated segments of sequence, e.g., by chemical synthesis or by the manipulation of isolated segments of nucleic acids by genetic engineering techniques.

As used herein, a "synthetic nucleotide sequence" or "synthetic polynucleotide sequence" is a nucleotide sequence that is not known to occur in nature or that is not naturally occurring. Generally, such a synthetic nucleotide sequence will comprise at least one nucleotide difference when compared to any other naturally occurring nucleotide sequence.

As used herein, the term "nucleic acid" refers to a polymeric form of nucleotides of any length, either ribonucleotides or deoxyribonucleotides, or analogs thereof. This term refers to the primary structure of the molecule, and thus includes double- and single-stranded DNA, as well as double- and single-stranded RNA. It also includes modified nucleic acids such as methylated and/or capped nucleic acids, nucleic acids containing modified bases, backbone modifications, and the like. The terms "nucleic acid" and "nucleotide sequence" are used interchangeably.

As used herein, the term "gene" refers to any segment of DNA associated with a biological function. Thus, genes include, but are not limited to, coding sequences and/or the regulatory sequences required for their expression. Genes can also include non-expressed DNA segments that, for example, form recognition sequences for other proteins. Genes can be obtained from a variety of sources, including cloning from a source of interest or synthesizing from known or predicted sequence information, and may include sequences designed to have desired parameters.

As used herein, the term "homologous" or "homologue" or "ortholog" is known in the art and refers to related sequences that share a common ancestor or family member and are determined based on the degree of sequence identity. The terms "homology," "homologous," "substantially similar" and "corresponding substantially" are used interchangeably herein. They refer to nucleic acid fragments wherein changes in one or more nucleotide bases do not affect the ability of the nucleic acid fragment to mediate gene expression or produce a certain phenotype. These terms also refer to modifications of the nucleic acid fragments of the instant disclosure such as deletion or insertion of one or more nucleotides that do not substantially alter the functional properties of the resulting nucleic acid fragment relative to the initial, unmodified fragment. It is therefore understood, as those skilled in the art will appreciate, that the disclosure encompasses more than the specific exemplary sequences. These terms describe the relationship between a gene found in one species, subspecies, variety, cultivar or strain and the corresponding or equivalent gene in another species, subspecies, variety, cultivar or strain. For purposes of this disclosure homologous sequences are compared. "Homologous sequences" or "homologues" or "orthologs" are thought, believed, or known to be functionally related. A functional relationship may be indicated in any one of a number of ways, including, but not limited to: (a) degree of sequence identity and/or (b) the same or similar biological function. Preferably, both (a) and (b) are indicated. Homology can be determined using software programs readily available in the art, such as those discussed in Current Protocols in Molecular Biology (F. M. Ausubel et al., eds., 1987) Supplement 30, section 7.718, Table 7.71. Some alignment programs are MacVector (Oxford Molecular Ltd, Oxford, U.K.), ALIGN Plus (Scientific and Educational Software, Pa.) and AlignX (Vector NTI, Invitrogen, Carlsbad, Calif.). Another alignment program is Sequencher (Gene Codes, Ann Arbor, Mich.), using default parameters.

As used herein, the term "endogenous" or "endogenous gene," refers to the naturally occurring gene, in the location in which it is naturally found within the host cell genome. In the context of the present disclosure, operably linking a heterologous promoter to an endogenous gene means genetically inserting a heterologous promoter sequence in front of an existing gene, in the location where that gene is naturally present. An endogenous gene as described herein can include alleles of naturally occurring genes that have been mutated according to any of the methods of the present disclosure.

As used herein, the term "exogenous" is used interchangeably with the term "heterologous," and refers to a substance coming from some source other than its native source. For example, the terms "exogenous protein," or "exogenous gene" refer to a protein or gene from a non-native source or location, and that have been artificially supplied to a biological system.

As used herein, the term "nucleotide change" refers to, e.g., nucleotide substitution, deletion, and/or insertion, as is well understood in the art. For example, mutations contain alterations that produce silent substitutions, additions, or deletions, but do not alter the properties or activities of the encoded protein or how the proteins are made.

As used herein, the term "protein modification" refers to, e.g., amino acid substitution, amino acid modification, deletion, and/or insertion, as is well understood in the art.

As used herein, the term "at least a portion" or "fragment" of a nucleic acid or polypeptide means a portion having the minimal size characteristics of such sequences, or any larger fragment of the full length molecule, up to and including the full length molecule. A fragment of a polynucleotide of the disclosure may encode a biologically active portion of a genetic regulatory element. A biologically active portion of a genetic regulatory element can be prepared by isolating a portion of one of the polynucleotides of the disclosure that comprises the genetic regulatory element and assessing activity as described herein. Similarly, a portion of a polypeptide may be 4 amino acids, 5 amino acids, 6 amino acids, 7 amino acids, and so on, going up to the full length polypeptide. The length of the portion to be used will depend on the particular application. A portion of a nucleic acid useful as a hybridization probe may be as short as 12 nucleotides; in some embodiments, it is 20 nucleotides. A portion of a polypeptide useful as an epitope may be as short as 4 amino acids. A portion of a polypeptide that performs the function of the full-length polypeptide would generally be longer than 4 amino acids.

Variant polynucleotides also encompass sequences derived from a mutagenic and recombinogenic procedure such as DNA shuffling. Strategies for such DNA shuffling are known in the art. See, for example, Stemmer (1994) PNAS 91:10747-10751; Stemmer (1994) Nature 370:389-391; Crameri et al. (1997) Nature Biotech. 15:436-438; Moore et al. (1997) J. Mol. Biol. 272:336-347; Zhang et al. (1997) PNAS 94:4504-4509; Crameri et al. (1998) Nature 391:288-291; and U.S. Pat. Nos. 5,605,793 and 5,837,458.

For PCR amplifications of the polynucleotides disclosed herein, oligonucleotide primers can be designed for use in PCR reactions to amplify corresponding DNA sequences from cDNA or genomic DNA extracted from any organism of interest. Methods for designing PCR primers and PCR cloning are generally known in the art and are disclosed in Sambrook et al. (2001) Molecular Cloning: A Laboratory Manual ($3^{rd}$ ed., Cold Spring Harbor Laboratory Press, Plainview, N.Y.). See also Innis et al., eds. (1990) PCR Protocols: A Guide to Methods and Applications (Academic Press, New York); Innis and Gelfand, eds. (1995) PCR Strategies (Academic Press, New York); and Innis and Gelfand, eds. (1999) PCR Methods Manual (Academic Press, New York). Known methods of PCR include, but are not limited to, methods using paired primers, nested primers, single specific primers, degenerate primers, gene-specific primers, vector-specific primers, partially-mismatched primers, and the like.

The term "primer" as used herein refers to an oligonucleotide which is capable of annealing to the amplification target allowing a DNA polymerase to attach, thereby serving as a point of initiation of DNA synthesis when placed under conditions in which synthesis of primer extension product is induced, i.e., in the presence of nucleotides and an agent for polymerization such as DNA polymerase and at a suitable temperature and pH. The (amplification) primer is preferably single stranded for maximum efficiency in amplification. Preferably, the primer is an oligodeoxyribonucleotide. The primer must be sufficiently long to prime the synthesis of extension products in the presence of the agent for polymerization. The exact lengths of the primers will depend on many factors, including temperature and composition (A/T vs. G/C content) of primer. A pair of bi-directional primers consists of one forward and one reverse primer as commonly used in the art of DNA amplification such as in PCR amplification.

As used herein, "promoter" refers to a DNA sequence capable of controlling the expression of a coding sequence or functional RNA. In some embodiments, the promoter sequence consists of proximal and more distal upstream elements, the latter elements often referred to as enhancers. Accordingly, an "enhancer" is a DNA sequence that can stimulate promoter activity, and may be an innate element of the promoter or a heterologous element inserted to enhance the level or tissue specificity of a promoter. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. It is further recognized that since in most cases the exact boundaries of regulatory sequences have not been completely defined, DNA fragments of some variation may have identical promoter activity.

As used herein, the phrases "recombinant construct", "expression construct", "chimeric construct", "construct", and "recombinant DNA construct" are used interchangeably herein. A recombinant construct comprises an artificial combination of nucleic acid fragments, e.g., regulatory and coding sequences that are not found together in nature. For example, a chimeric construct may comprise regulatory sequences and coding sequences that are derived from different sources, or regulatory sequences and coding sequences derived from the same source, but arranged in a manner different than that found in nature. Such construct may be used by itself or may be used in conjunction with a vector. If a vector is used then the choice of vector is dependent upon the method that will be used to transform host cells as is well known to those skilled in the art. For example, a plasmid vector can be used. The skilled artisan is well aware of the genetic elements that must be present on the vector in order to successfully transform, select and propagate host cells comprising any of the isolated nucleic acid fragments of the disclosure. The skilled artisan will also recognize that different independent transformation events will result in different levels and patterns of expression (Jones et al., (1985) EMBO J. 4:2411-2418; De Almeida et al., (1989) Mol. Gen. Genetics 218:78-86), and thus that multiple events must be screened in order to obtain lines displaying the desired expression level and pattern. Such screening may be accomplished by Southern analysis of DNA, Northern analysis of mRNA expression, immunoblotting analysis of protein expression, or phenotypic analysis, among others. Vectors can be plasmids, viruses, bacteriophages, pro-viruses, phagemids, transposons, artificial chromosomes, and the like, that replicate autonomously or can integrate into a chromosome of a host cell. A vector can also be a naked RNA polynucleotide, a naked DNA polynucleotide, a polynucleotide composed of both DNA and RNA within the same strand, a poly-lysine-conjugated DNA or RNA, a peptide-conjugated DNA or RNA, a liposome-conjugated DNA, or the like, that is not autonomously replicating. As used herein, the term "expression" refers to the production of a functional end-product e.g., an mRNA or a protein (precursor or mature).

"Operably linked" means in this context the sequential arrangement of the promoter polynucleotide according to the disclosure with a further oligo- or polynucleotide, resulting in transcription of said further polynucleotide.

The term "product of interest" or "biomolecule" as used herein refers to any product produced by microbes from feedstock. In some cases, the product of interest may be a small molecule, enzyme, peptide, amino acid, organic acid, synthetic compound, fuel, alcohol, etc. For example, the product of interest or biomolecule may be any primary or secondary extracellular metabolite. The primary metabolite may be, inter alia, ethanol, citric acid, lactic acid, glutamic acid, glutamate, lysine, threonine, tryptophan and other amino acids, vitamins, polysaccharides, etc. The secondary metabolite may be, inter alia, an antibiotic compound like penicillin, or an immunosuppressant like cyclosporin A, a plant hormone like gibberellin, a statin drug like lovastatin, a fungicide like griseofulvin, etc. The product of interest or biomolecule may also be any intracellular component produced by a microbe, such as: a microbial enzyme, including: catalase, amylase, protease, pectinase, glucose isomerase, cellulase, hemicellulase, lipase, lactase, streptokinase, and many others. The intracellular component may also include recombinant proteins, such as: insulin, hepatitis B vaccine, interferon, granulocyte colony-stimulating factor, streptokinase and others.

The term "carbon source" generally refers to a substance suitable to be used as a source of carbon for cell growth. Carbon sources include, but are not limited to, biomass hydrolysates, starch, sucrose, cellulose, hemicellulose, xylose, and lignin, as well as monomeric components of these substrates. Carbon sources can comprise various organic compounds in various forms, including, but not limited to polymers, carbohydrates, acids, alcohols, aldehydes, ketones, amino acids, peptides, etc. These include, for example, various monosaccharides such as glucose, dextrose (D-glucose), maltose, oligosaccharides, polysaccharides, saturated or unsaturated fatty acids, succinate, lactate, acetate, ethanol, etc., or mixtures thereof. Photosynthetic organisms can additionally produce a carbon source as a product of photosynthesis. In some embodiments, carbon sources may be selected from biomass hydrolysates and glucose.

The term "feedstock" is defined as a raw material or mixture of raw materials supplied to a microorganism or fermentation process from which other products can be made. For example, a carbon source, such as biomass or the carbon compounds derived from biomass are a feedstock for a microorganism that produces a product of interest (e.g. small molecule, peptide, synthetic compound, fuel, alcohol, etc.) in a fermentation process. However, a feedstock may contain nutrients other than a carbon source.

The term "volumetric productivity" or "production rate" is defined as the amount of product formed per volume of medium per unit of time. Volumetric productivity can be reported in gram per liter per hour (g/L/h).

The term "specific productivity" is defined as the rate of formation of the product. Specific productivity is herein further defined as the specific productivity in gram product per gram of cell dry weight (CDW) per hour (g/g CDW/h). Using the relation of CDW to $OD_{600}$ for the given microorganism specific productivity can also be expressed as gram product per liter culture medium per optical density of the culture broth at 600 nm (OD) per hour (g/L/h/OD).

The term "yield" is defined as the amount of product obtained per unit weight of raw material and may be expressed as g product per g substrate (g/g). Yield may be expressed as a percentage of the theoretical yield. "Theoretical yield" is defined as the maximum amount of product that can be generated per a given amount of substrate as dictated by the stoichiometry of the metabolic pathway used to make the product.

The term "titre" or "titer" is defined as the strength of a solution or the concentration of a substance in solution. For example, the titre of a product of interest (e.g. small molecule, peptide, synthetic compound, fuel, alcohol, etc.) in a fermentation broth is described as g of product of interest in solution per liter of fermentation broth (g/L).

The term "total titer" is defined as the sum of all product of interest produced in a process, including but not limited to the product of interest in solution, the product of interest in gas phase if applicable, and any product of interest removed from the process and recovered relative to the initial volume in the process or the operating volume in the process As used herein, the term "HTP genetic design library" or "library" refers to collections of genetic perturbations according to the present disclosure. In some embodiments, the libraries of the present invention may manifest as i) a collection of sequence information in a database or other computer file, ii) a collection of genetic constructs encoding for the aforementioned series of genetic elements, or iii) host cell strains comprising said genetic elements. In some embodiments, the libraries of the present disclosure may refer to collections of individual elements (e.g., collections of promoters for PRO swap libraries, or collections of terminators for STOP swap libraries). In other embodiments, the libraries of the present disclosure may also refer to combinations of genetic elements, such as combinations of promoter::genes, gene:terminator, or even promoter:gene: terminators. In some embodiments, the libraries of the present disclosure further comprise meta data associated with the effects of applying each member of the library in host organisms. For example, a library as used herein can include a collection of promoter::gene sequence combinations, together with the resulting effect of those combinations on one or more phenotypes in a particular species, thus improving the future predictive value of using said combination in future promoter swaps.

As used herein, the term "SNP" refers to Small Nuclear Polymorphism(s). In some embodiments, SNPs of the present disclosure should be construed broadly, and include single nucleotide polymorphisms, sequence insertions, deletions, inversions, and other sequence replacements. As used herein, the term "non-synonymous" or non-synonymous SNPs" refers to mutations that lead to coding changes in host cell proteins A "high-throughput (HTP)" method of genomic engineering may involve the utilization of at least one piece of automated equipment (e.g. a liquid handler or plate handler machine) to carry out at least one step of said method.

Traditional Methods of Strain Improvement

Traditional approaches to strain improvement can be broadly categorized into two types of approaches: directed strain engineering, and random mutagenesis.

Directed engineering methods of strain improvement involve the planned perturbation of a handful of genetic elements of a specific organism. These approaches are typically focused on modulating specific biosynthetic or developmental programs, and rely on prior knowledge of the genetic and metabolic factors affecting said pathways. In its simplest embodiments, directed engineering involves the transfer of a characterized trait (e.g., gene, promoter, or other genetic element capable of producing a measurable phenotype) from one organism to another organism of the same, or different species.

Random approaches to strain engineering involve the random mutagenesis of parent strains, coupled with extensive screening designed to identify performance improvements. Approaches to generating these random mutations include exposure to ultraviolet radiation, or mutagenic chemicals such as Ethyl methanesulfonate. Though random and largely unpredictable, this traditional approach to strain improvement had several advantages compared to more directed genetic manipulations. First, many industrial organisms were (and remain) poorly characterized in terms of their genetic and metabolic repertoires, rendering alternative directed improvement approaches difficult, if not impossible.

Second, even in relatively well characterized systems, genotypic changes that result in industrial performance improvements are difficult to predict, and sometimes only manifest themselves as epistatic phenotypes requiring cumulative mutations in many genes of known and unknown function.

Additionally, for many years, the genetic tools required for making directed genomic mutations in a given industrial organism were unavailable, or very slow and/or difficult to use.

The extended application of the traditional strain improvement programs, however, yield progressively reduced gains in a given strain lineage, and ultimately lead to exhausted possibilities for further strain efficiencies. Beneficial random mutations are relatively rare events, and require large screening pools and high mutation rates. This inevitably results in the inadvertent accumulation of many neutral and/or detrimental (or partly detrimental) mutations in "improved" strains, which ultimately create a drag on future efficiency gains.

Another limitation of traditional cumulative improvement approaches is that little to no information is known about any particular mutation's effect on any strain metric. This fundamentally limits a researcher's ability to combine and consolidate beneficial mutations, or to remove neutral or detrimental mutagenic "baggage."

Other approaches and technologies exist to randomly recombine mutations between strains within a mutagenic lineage. For example, some formats and examples for iterative sequence recombination, sometimes referred to as DNA shuffling, evolution, or molecular breeding, have been described in U.S. patent application Ser. No. 08/198,431, filed Feb. 17, 1994, Serial No. PCT/US95/02126, filed, Feb. 17, 1995, Ser. No. 08/425,684, filed Apr. 18, 1995, Ser. No. 08/537,874, filed Oct. 30, 1995, Ser. No. 08/564,955, filed Nov. 30, 1995, Ser. No. 08/621,859, filed. Mar. 25, 1996, Ser. No. 08/621,430, filed Mar. 25, 1996, Serial No. PCT/US96/05480, filed Apr. 18, 1996, Ser. No. 08/650,400, filed May 20, 1996, Ser. No. 08/675,502, filed Jul. 3, 1996, Ser. No. 08/721,824, filed Sep. 27, 1996, and Ser. No. 08/722, 660 filed Sep. 27, 1996; Stemmer, Science 270:1510 (1995); Stemmer et al., Gene 164:49-53 (1995); Stemmer, Bio/Technology 13:549-553 (1995); Stemmer, Proc. Natl. Acad. Sci. U.S.A. 91:10747-10751 (1994); Stemmer, Nature 370: 389-391 (1994); Crameri et al., Nature Medicine 2(1):1-3 (1996); Crameri et al., Nature Biotechnology 14:315-319 (1996), each of which is incorporated herein by reference in its entirety for all purposes.

These include techniques such as protoplast fusion and whole genome shuffling that facilitate genomic recombination across mutated strains. For some industrial microorganisms such as yeast and filamentous fungi, natural mating cycles can also be exploited for pairwise genomic recombination. In this way, detrimental mutations can be removed by 'back-crossing' mutants with parental strains and beneficial mutations consolidated. Moreover, beneficial mutations from two different strain lineages can potentially be combined, which creates additional improvement possibilities over what might be available from mutating a single strain lineage on its own. However, these approaches are subject to many limitations that are circumvented using the methods of the present disclosure.

For example, traditional recombinant approaches as described above are slow and rely on a relatively small number of random recombination crossover events to swap mutations, and are therefore limited in the number of combinations that can be attempted in any given cycle, or time period. In addition, although the natural recombination events in the prior art are essentially random, they are also subject to genome positional bias.

Most importantly, the traditional approaches also provide little information about the influence of individual mutations and due to the random distribution of recombined mutations many specific combinations cannot be generated and evaluated.

To overcome many of the aforementioned problems associated with traditional strain improvement programs, the present disclosure sets forth a unique HTP genomic engineering platform that is computationally driven and integrates molecular biology, automation, data analytics, and machine learning protocols. This integrative platform utilizes a suite of HTP molecular tool sets that are used to construct HTP genetic design libraries. These genetic design libraries will be elaborated upon below.

The taught HTP platform and its unique microbial genetic design libraries fundamentally shift the paradigm of microbial strain development and evolution. For example, traditional mutagenesis-based methods of developing an industrial microbial strain will eventually lead to microbes burdened with a heavy mutagenic load that has been accumulated over years of random mutagenesis.

The ability to solve this issue (i.e. remove the genetic baggage accumulated by these microbes) has eluded microbial researchers for decades. However, utilizing the HTP platform disclosed herein, these industrial strains can be "rehabilitated," and the genetic mutations that are deleterious can be identified and removed. Congruently, the genetic mutations that are identified as beneficial can be kept, and in some cases improved upon. The resulting microbial strains demonstrate superior phenotypic traits (e.g., improved production of a compound of interest), as compared to their parental strains.

Furthermore, the HTP platform taught herein is able to identify, characterize, and quantify the effect that individual mutations have on microbial strain performance. This information, i.e. what effect does a given genetic change x have on host cell phenotype y (e.g., production of a compound or product of interest), is able to be generated and then stored in the microbial HTP genetic design libraries discussed below. That is, sequence information for each genetic permutation, and its effect on the host cell phenotype are stored in one or more databases, and are available for subsequent analysis (e.g., epistasis mapping, as discussed below). The present disclosure also teaches methods of physically saving/storing valuable genetic permutations in the form of genetic insertion constructs, or in the form of one or more host cell organisms containing said genetic permutation (e.g., see libraries discussed below.)

When one couples these HTP genetic design libraries into an iterative process that is integrated with a sophisticated data analytics and machine learning process a dramatically different methodology for improving host cells emerges. The taught platform is therefore fundamentally different from the previously discussed traditional methods of developing host cell strains. The taught HTP platform does not suffer from many of the drawbacks associated with the previous methods. These and other advantages will become apparent with reference to the HTP molecular tool sets and the derived genetic design libraries discussed below.

Genetic Design & Microbial Engineering: A Systematic Combinatorial Approach to Strain Improvement Utilizing a Suite of HTP Molecular Tools and HTP Genetic Design Libraries As aforementioned, the present disclosure provides a novel HTP platform and genetic design strategy for engineering microbial organisms through iterative systematic introduction and removal of genetic changes across strains. The platform is supported by a suite of molecular tools, which enable the creation of HTP genetic design libraries and allow for the efficient implementation of genetic alterations into a given host strain.

The HTP genetic design libraries of the disclosure serve as sources of possible genetic alterations that may be introduced into a particular microbial strain background. In this way, the HTP genetic design libraries are repositories of genetic diversity, or collections of genetic perturbations, which can be applied to the initial or further engineering of a given microbial strain. Techniques for programming genetic designs for implementation to host strains are described in pending U.S. patent application Ser. No. 15/140,296, entitled "Microbial Strain Design System and Methods for Improved Large Scale Production of Engineered Nucleotide Sequences," incorporated by reference in its entirety herein.

The HTP molecular tool sets utilized in this platform may include, inter alia: (1) Promoter swaps (PRO Swap), (2) SNP swaps, (3) Start/Stop codon exchanges, (4) STOP swaps, and (5) Sequence optimization. The HTP methods of the present disclosure also teach methods for directing the consolidation/combinatorial use of HTP tool sets, including (6) Epistasis mapping protocols. As aforementioned, this suite of molecular tools, either in isolation or combination, enables the creation of HTP genetic design host cell libraries.

As will be demonstrated, utilization of the aforementioned HTP genetic design libraries in the context of the taught HTP microbial engineering platform enables the identification and consolidation of beneficial "causative" mutations or gene sections and also the identification and removal of passive or detrimental mutations or gene sections. This new approach allows rapid improvements in strain performance that could not be achieved by traditional random mutagenesis or directed genetic engineering. The removal of genetic burden or consolidation of beneficial changes into a strain with no genetic burden also provides a new, robust starting point for additional random mutagenesis that may enable further improvements.

In some embodiments, the present disclosure teaches that as orthogonal beneficial changes are identified across various, discrete branches of a mutagenic strain lineage, they can also be rapidly consolidated into better performing strains. These mutations can also be consolidated into strains that are not part of mutagenic lineages, such as strains with improvements gained by directed genetic engineering.

In some embodiments, the present disclosure differs from known strain improvement approaches in that it analyzes the genome-wide combinatorial effect of mutations across multiple disparate genomic regions, including expressed and non-expressed genetic elements, and uses gathered information (e.g., experimental results) to predict mutation combinations expected to produce strain enhancements.

In some embodiments, the present disclosure teaches: i) industrial microorganisms, and other host cells amenable to improvement via the disclosed inventions, ii) generating diversity pools for downstream analysis, iii) methods and hardware for high-throughput screening and sequencing of large variant pools, iv) methods and hardware for machine learning computational analysis and prediction of synergistic effects of genome-wide mutations, and v) methods for high-throughput strain engineering.

The following molecular tools and libraries are discussed in terms of illustrative microbial examples. Persons having skill in the art will recognize that the HTP molecular tools of the present disclosure are compatible with any host cell, including eukaryotic cellular, and higher life forms.

Each of the identified HTP molecular tool sets—which enable the creation of the various HTP genetic design libraries utilized in the microbial engineering platform—will now be discussed.

1. Promoter Swaps: A Molecular Tool for the Derivation of Promoter Swap Microbial Strain Libraries In some embodiments, the present disclosure teaches methods of selecting promoters with optimal expression properties to produce beneficial effects on overall-host strain phenotype (e.g., yield or productivity).

For example, in some embodiments, the present disclosure teaches methods of identifying one or more promoters and/or generating variants of one or more promoters within a host cell, which exhibit a range of expression strengths (e.g. promoter ladders discussed infra), or superior regulatory properties (e.g., tighter regulatory control for selected genes). A particular combination of these identified and/or generated promoters can be grouped together as a promoter ladder, which is explained in more detail below.

The promoter ladder in question is then associated with a given gene of interest. Thus, if one has promoters $P_1$-$P_8$ (representing eight promoters that have been identified and/or generated to exhibit a range of expression strengths) and associates the promoter ladder with a single gene of interest in a microbe (i.e. genetically engineer a microbe with a given promoter operably linked to a given target gene), then the effect of each combination of the eight promoters can be ascertained by characterizing each of the engineered strains resulting from each combinatorial effort, given that the engineered microbes have an otherwise identical genetic background except the particular promoter(s) associated with the target gene.

The resultant microbes that are engineered via this process form HTP genetic design libraries.

The HTP genetic design library can refer to the actual physical microbial strain collection that is formed via this process, with each member strain being representative of a given promoter operably linked to a particular target gene, in an otherwise identical genetic background, said library being termed a "promoter swap microbial strain library."

Furthermore, the HTP genetic design library can refer to the collection of genetic perturbations—in this case a given promoter x operably linked to a given gene y—said collection being termed a "promoter swap library."

Further, one can utilize the same promoter ladder comprising promoters $P_1$-$P_8$ to engineer microbes, wherein each of the 8 promoters is operably linked to 10 different gene targets. The result of this procedure would be 80 microbes that are otherwise assumed genetically identical, except for the particular promoters operably linked to a target gene of interest. These 80 microbes could be appropriately screened and characterized and give rise to another HTP genetic design library. The characterization of the microbial strains in the HTP genetic design library produces information and data that can be stored in any data storage construct, including a relational database, an object-oriented database or a highly distributed NoSQL database. This data/information could be, for example, a given promoter's (e.g. $P_1$-$P_8$) effect when operably linked to a given gene target. This data/information can also be the broader set of combinatorial effects that result from operably linking two or more of promoters $P_1$-$P_8$ to a given gene target.

The aforementioned examples of eight promoters and 10 target genes is merely illustrative, as the concept can be applied with any given number of promoters that have been grouped together based upon exhibition of a range of expression strengths and any given number of target genes. Persons having skill in the art will also recognize the ability to operably link two or more promoters in front of any gene target. Thus, in some embodiments, the present disclosure teaches promoter swap libraries in which 1, 2, 3 or more promoters from a promoter ladder are operably linked to one or more genes.

In summary, utilizing various promoters to drive expression of various genes in an organism is a powerful tool to optimize a trait of interest. The molecular tool of promoter swapping, developed by the inventors, uses a ladder of promoter sequences that have been demonstrated to vary expression of at least one locus under at least one condition. This ladder is then systematically applied to a group of genes in the organism using high-throughput genome engineering. This group of genes is determined to have a high likelihood of impacting the trait of interest based on any one of a number of methods. These could include selection based on known function, or impact on the trait of interest, or algorithmic selection based on previously determined beneficial genetic diversity. In some embodiments, the selection of genes can include all the genes in a given host. In other embodiments, the selection of genes can be a subset of all genes in a given host, chosen randomly.

The resultant HTP genetic design microbial strain library of organisms containing a promoter sequence linked to a gene is then assessed for performance in a high-throughput screening model, and promoter-gene linkages which lead to increased performance are determined and the information stored in a database. The collection of genetic perturbations (i.e. given promoter x operably linked to a given gene y) form a "promoter swap library," which can be utilized as a source of potential genetic alterations to be utilized in microbial engineering processing. Over time, as a greater set of genetic perturbations is implemented against a greater diversity of host cell backgrounds, each library becomes more powerful as a corpus of experimentally confirmed data that can be used to more precisely and predictably design targeted changes against any background of interest.

Transcription levels of genes in an organism are a key point of control for affecting organism behavior. Transcription is tightly coupled to translation (protein expression), and which proteins are expressed in what quantities determines organism behavior. Cells express thousands of different types of proteins, and these proteins interact in numerous complex ways to create function. By varying the expression levels of a set of proteins systematically, function can be altered in ways that, because of complexity, are difficult to predict. Some alterations may increase performance, and so, coupled to a mechanism for assessing performance, this technique allows for the generation of organisms with improved function.

In the context of a small molecule synthesis pathway, enzymes interact through their small molecule substrates and products in a linear or branched chain, starting with a substrate and ending with a small molecule of interest. Because these interactions are sequentially linked, this system exhibits distributed control, and increasing the expression of one enzyme can only increase pathway flux until another enzyme becomes rate limiting.

Metabolic Control Analysis (MCA) is a method for determining, from experimental data and first principles, which enzyme or enzymes are rate limiting. MCA is limited however, because it requires extensive experimentation after each expression level change to determine the new rate limiting enzyme. Promoter swapping is advantageous in this context, because through the application of a promoter ladder to each enzyme in a pathway, the limiting enzyme is found, and the same thing can be done in subsequent rounds to find new enzymes that become rate limiting. Further, because the read-out on function is better production of the small molecule of interest, the experiment to determine which enzyme is limiting is the same as the engineering to increase production, thus shortening development time. In some embodiments the present disclosure teaches the application of PRO swap to genes encoding individual subunits of multi-unit enzymes. In yet other embodiments, the present disclosure teaches methods of applying PRO swap techniques to genes responsible for regulating individual enzymes, or whole biosynthetic pathways.

In some embodiments, the promoter swap tool of the present disclosure can is used to identify optimum expression of a selected gene target. In some embodiments, the goal of the promoter swap may be to increase expression of a target gene to reduce bottlenecks in a metabolic or genetic pathway. In other embodiments, the goal o the promoter swap may be to reduce the expression of the target gene to avoid unnecessary energy expenditures in the host cell, when expression of said target gene is not required.

In the context of other cellular systems like transcription, transport, or signaling, various rational methods can be used to try and find out, a priori, which proteins are targets for expression change and what that change should be. These rational methods reduce the number of perturbations that must be tested to find one that improves performance, but they do so at significant cost. Gene deletion studies identify proteins whose presence is critical for a particular function, and important genes can then be over-expressed. Due to the complexity of protein interactions, this is often ineffective at increasing performance. Different types of models have been developed that attempt to describe, from first principles, transcription or signaling behavior as a function of protein levels in the cell. These models often suggest targets where expression changes might lead to different or improved function. The assumptions that underlie these models are simplistic and the parameters difficult to measure, so the predictions they make are often incorrect, especially for non-model organisms. With both gene deletion and modeling, the experiments required to determine how to affect a certain gene are different than the subsequent work to make the change that improves performance. Promoter swapping sidesteps these challenges, because the constructed strain that highlights the importance of a particular perturbation is also, already, the improved strain.

Thus, in particular embodiments, promoter swapping is a multi-step process comprising:

1. Selecting a set of "x" promoters to act as a "ladder." Ideally these promoters have been shown to lead to highly variable expression across multiple genomic loci, but the only requirement is that they perturb gene expression in some way.

2. Selecting a set of "n" genes to target. This set can be every open reading frame (ORF) in a genome, or a subset of ORFs. The subset can be chosen using annotations on ORFs related to function, by relation to previously demonstrated beneficial perturbations (previous promoter swaps or previous SNP swaps), by algorithmic selection based on epistatic interactions between previously generated perturbations, other selection criteria based on hypotheses regarding beneficial ORF to target, or through random selection. In other embodiments, the "n" targeted genes can comprise non-protein coding genes, including non-coding RNAs.

Figure 21:
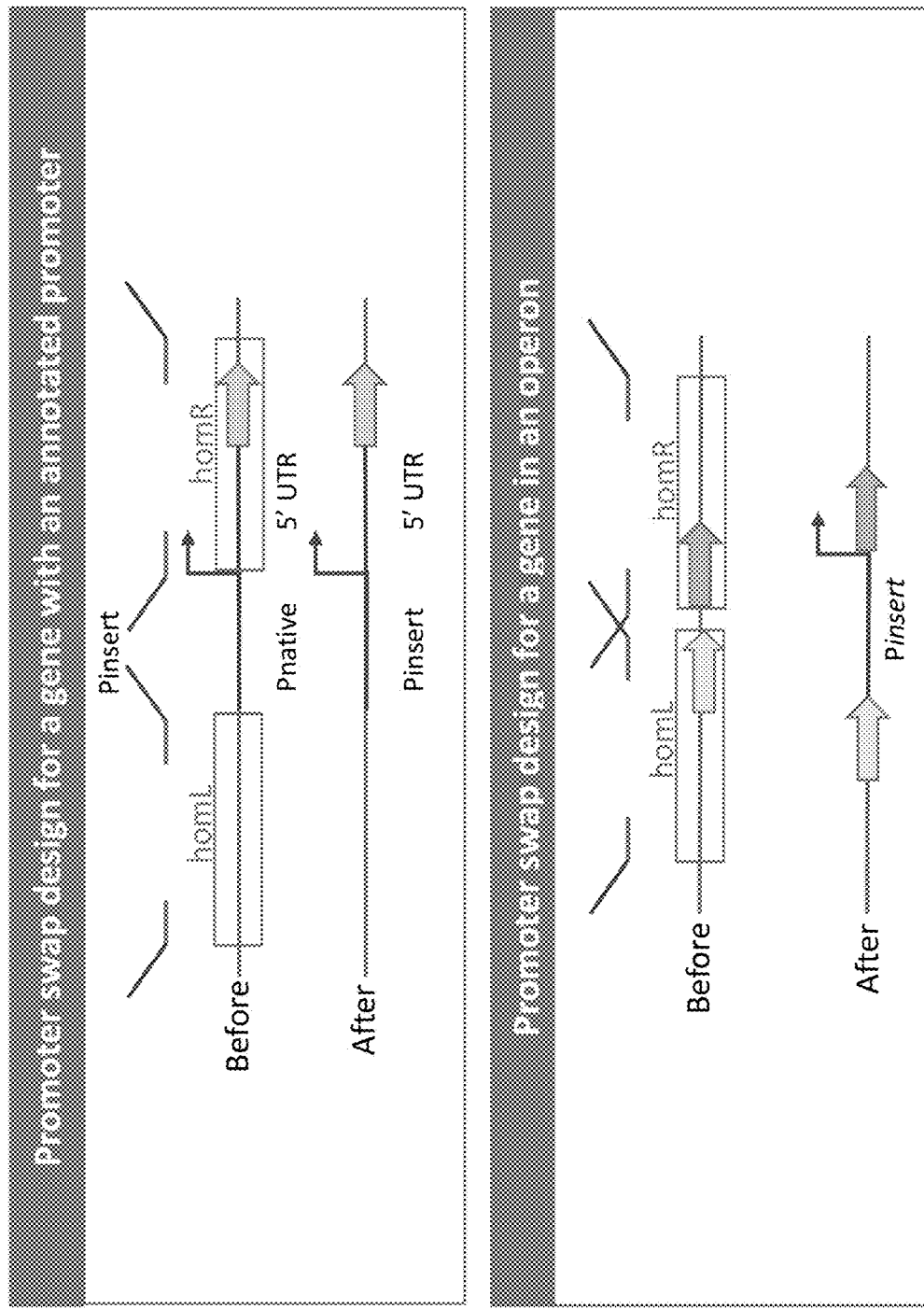
FIG. 21 illustrates that promoter swapping genetic outcomes depend on the particular gene being targeted.

3. High-throughput strain engineering to rapidly- and in some embodiments, in parallel-carry out the following genetic modifications: When a native promoter exists in front of target gene n and its sequence is known, replace the native promoter with each of the x promoters in the ladder. When the native promoter does not exist, or its sequence is unknown, insert each of the x promoters in the ladder in front of gene n (see e.g., FIG. 21). In this way a "library" (also referred to as a HTP genetic design library) of strains is constructed, wherein each member of the library is an instance of x promoter operably linked to n target, in an otherwise identical genetic context. As previously described combinations of promoters can be inserted, extending the range of combinatorial possibilities upon which the library is constructed.

4. High-throughput screening of the library of strains in a context where their performance against one or more metrics is indicative of the performance that is being optimized.

Figure 20:
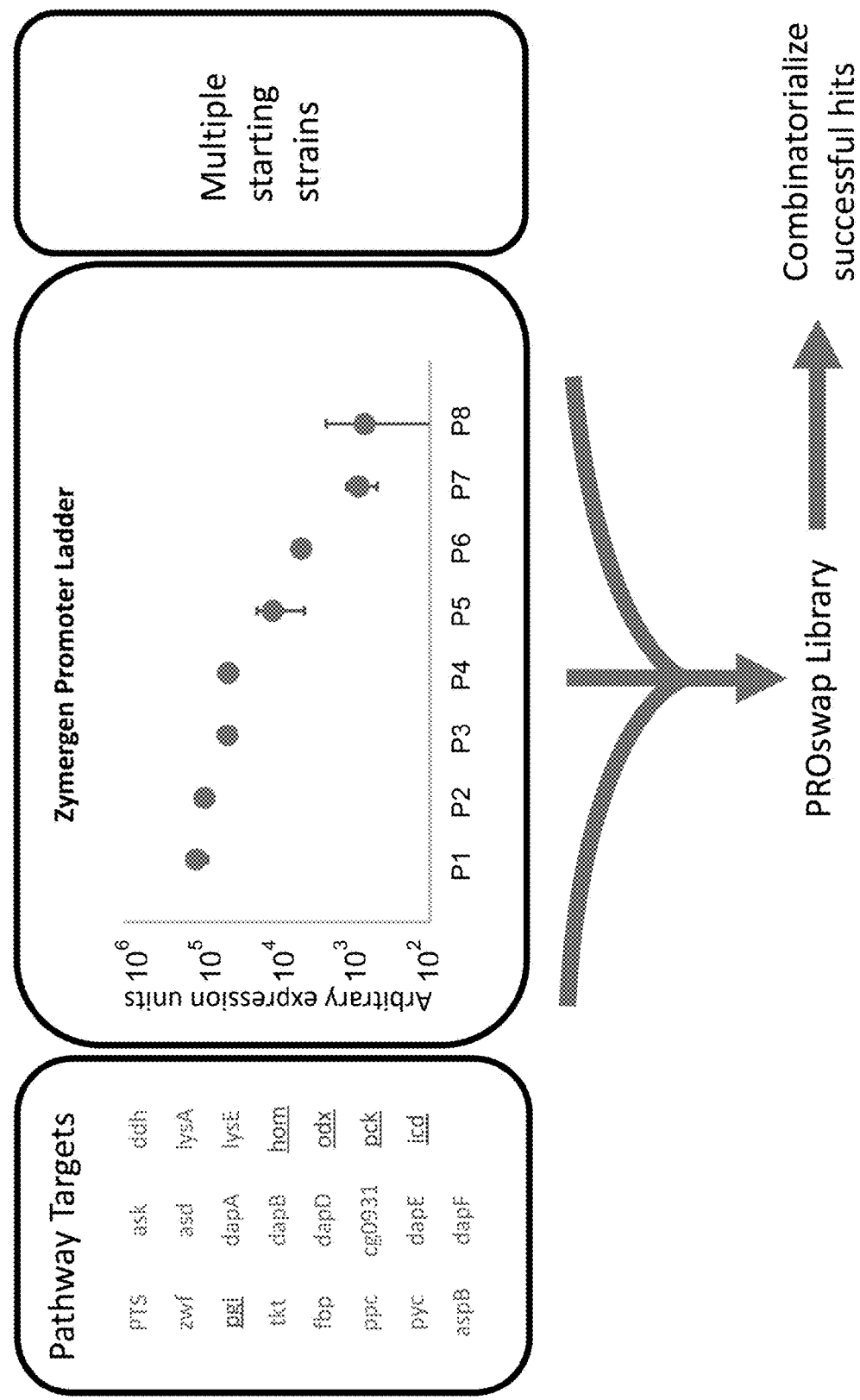
FIG. 20 illustrates an exemplary promoter library that is being utilized to conduct a promoter swap process for the identified gene targets. Promoters utilized in the PRO swap (i.e. promoter swap) process are $P_1$-$P_8$, the sequences and identity of which can be found in Table 1.

This foundational process can be extended to provide further improvements in strain performance by, inter alia: (1) Consolidating multiple beneficial perturbations into a single strain background, either one at a time in an interactive process, or as multiple changes in a single step. Multiple perturbations can be either a specific set of defined changes or a partly randomized, combinatorial library of changes. For example, if the set of targets is every gene in a pathway, then sequential regeneration of the library of perturbations into an improved member or members of the previous library of strains can optimize the expression level of each gene in a pathway regardless of which genes are rate limiting at any given iteration; (2) Feeding the performance data resulting from the individual and combinatorial generation of the library into an algorithm that uses that data to predict an optimum set of perturbations based on the interaction of each perturbation; and (3) Implementing a combination of the above two approaches (see FIG. 20).

The molecular tool, or technique, discussed above is characterized as promoter swapping, but is not limited to promoters and can include other sequence changes that systematically vary the expression level of a set of targets. Other methods for varying the expression level of a set of genes could include: a) a ladder of ribosome binding sites (or Kozak sequences in eukaryotes); b) replacing the start codon of each target with each of the other start codons (i.e start/stop codon exchanges discussed infra); c) attachment of various mRNA stabilizing or destabilizing sequences to the 5' or 3' end, or at any other location, of a transcript, d) attachment of various protein stabilizing or destabilizing sequences at any location in the protein.

The approach is exemplified in the present disclosure with industrial microorganisms, but is applicable to any organism where desired traits can be identified in a population of genetic mutants. For example, this could be used for improving the performance of CHO cells, yeast, insect cells, algae, as well as multi-cellular organisms, such as plants.

2. SNP Swaps: A Molecular Tool for the Derivation of SNP Swap Microbial Strain Libraries In certain embodiments, SNP swapping is not a random mutagenic approach to improving a microbial strain, but rather involves the systematic introduction or removal of individual Small Nuclear Polymorphism nucleotide mutations (i.e. SNPs) (hence the name "SNP swapping") across strains.

The resultant microbes that are engineered via this process form HTP genetic design libraries.

The HTP genetic design library can refer to the actual physical microbial strain collection that is formed via this process, with each member strain being representative of the presence or absence of a given SNP, in an otherwise identical genetic background, said library being termed a "SNP swap microbial strain library."

Furthermore, the HTP genetic design library can refer to the collection of genetic perturbations—in this case a given SNP being present or a given SNP being absent—said collection being termed a "SNP swap library."

In some embodiments, SNP swapping involves the reconstruction of host organisms with optimal combinations of target SNP "building blocks" with identified beneficial performance effects. Thus, in some embodiments, SNP swapping involves consolidating multiple beneficial mutations into a single strain background, either one at a time in an iterative process, or as multiple changes in a single step. Multiple changes can be either a specific set of defined changes or a partly randomized, combinatorial library of mutations.

In other embodiments, SNP swapping also involves removing multiple mutations identified as detrimental from a strain, either one at a time in an iterative process, or as multiple changes in a single step. Multiple changes can be either a specific set of defined changes or a partly randomized, combinatorial library of mutations. In some embodiments, the SNP swapping methods of the present disclosure include both the addition of beneficial SNPs, and removing detrimental and/or neutral mutations.

SNP swapping is a powerful tool to identify and exploit both beneficial and detrimental mutations in a lineage of strains subjected to mutagenesis and selection for an improved trait of interest. SNP swapping utilizes high-throughput genome engineering techniques to systematically determine the influence of individual mutations in a mutagenic lineage. Genome sequences are determined for strains across one or more generations of a mutagenic lineage with known performance improvements. High-throughput genome engineering is then used systematically to recapitulate mutations from improved strains in earlier lineage strains, and/or revert mutations in later strains to earlier strain sequences. The performance of these strains is then evaluated and the contribution of each individual mutation on the improved phenotype of interest can be determined. As aforementioned, the microbial strains that result from this process are analyzed/characterized and form the basis for the SNP swap genetic design libraries that can inform microbial strain improvement across host strains.

Removal of detrimental mutations can provide immediate performance improvements, and consolidation of beneficial mutations in a strain background not subject to mutagenic burden can rapidly and greatly improve strain performance. The various microbial strains produced via the SNP swapping process form the HTP genetic design SNP swapping libraries, which are microbial strains comprising the various added/deleted/or consolidated SNPs, but with otherwise identical genetic backgrounds.

As discussed previously, random mutagenesis and subsequent screening for performance improvements is a commonly used technique for industrial strain improvement, and many strains currently used for large scale manufacturing have been developed using this process iteratively over a period of many years, sometimes decades. Random approaches to generating genomic mutations such as exposure to UV radiation or chemical mutagens such as ethyl methanesulfonate were a preferred method for industrial strain improvements because: 1) industrial organisms may be poorly characterized genetically or metabolically, rendering target selection for directed improvement approaches difficult or impossible; 2) even in relatively well characterized systems, changes that result in industrial performance improvements are difficult to predict and may require perturbation of genes that have no known function, and 3) genetic tools for making directed genomic mutations in a given industrial organism may not be available or very slow and/or difficult to use.

However, despite the aforementioned benefits of this process, there are also a number of known disadvantages. Beneficial mutations are relatively rare events, and in order to find these mutations with a fixed screening capacity, mutations rates must be sufficiently high. This often results in unwanted neutral and partly detrimental mutations being incorporated into strains along with beneficial changes. Over time this 'mutagenic burden' builds up, resulting in strains with deficiencies in overall robustness and key traits such as growth rates. Eventually 'mutagenic burden' renders further improvements in performance through random mutagenesis increasingly difficult or impossible to obtain. Without suitable tools, it is impossible to consolidate beneficial mutations found in discrete and parallel branches of strain lineages.

SNP swapping is an approach to overcome these limitations by systematically recapitulating or reverting some or all mutations observed when comparing strains within a mutagenic lineage. In this way, both beneficial ('causative') mutations can be identified and consolidated, and/or detrimental mutations can be identified and removed. This allows rapid improvements in strain performance that could not be achieved by further random mutagenesis or targeted genetic engineering.

Removal of genetic burden or consolidation of beneficial changes into a strain with no genetic burden also provides a new, robust starting point for additional random mutagenesis that may enable further improvements.

In addition, as orthogonal beneficial changes are identified across various, discrete branches of a mutagenic strain lineage, they can be rapidly consolidated into better performing strains. These mutations can also be consolidated into strains that are not part of mutagenic lineages, such as strains with improvements gained by directed genetic engineering.

Other approaches and technologies exist to randomly recombine mutations between strains within a mutagenic lineage. These include techniques such as protoplast fusion and whole genome shuffling that facilitate genomic recombination across mutated strains. For some industrial microorganisms such as yeast and filamentous fungi, natural mating cycles can also be exploited for pairwise genomic recombination. In this way, detrimental mutations can be removed by 'back-crossing' mutants with parental strains and beneficial mutations consolidated. However, these approaches are subject to many limitations that are circumvented using the SNP swapping methods of the present disclosure.

For example, as these approaches rely on a relatively small number of random recombination crossover events to swap mutations, it may take many cycles of recombination and screening to optimize strain performance. In addition, although natural recombination events are essentially random, they are also subject to genome positional bias and some mutations may be difficult to address. These approaches also provide little information about the influence of individual mutations without additional genome sequencing and analysis. SNP swapping overcomes these fundamental limitations as it is not a random approach, but rather the systematic introduction or removal of individual mutations across strains.

In some embodiments, the present disclosure teaches methods for identifying the SNP sequence diversity present among the organisms of a diversity pool. A diversity pool can be a given number n of microbes utilized for analysis, with said microbes' genomes representing the "diversity pool."

In particular aspects, a diversity pool may be an original parent strain ($S_1$) with a "baseline" or "reference" genetic sequence at a particular time point ($S_1Gen_1$) and then any number of subsequent offspring strains ($S_{2-n}$) that were derived/developed from said $S_1$ strain and that have a different genome ($S_{2-n}Gen_{2-n}$), in relation to the baseline genome of $S_1$.

For example, in some embodiments, the present disclosure teaches sequencing the microbial genomes in a diversity pool to identify the SNPs present in each strain. In one embodiment, the strains of the diversity pool are historical microbial production strains. Thus, a diversity pool of the present disclosure can include for example, an industrial reference strain, and one or more mutated industrial strains produced via traditional strain improvement programs.

In some embodiments, the SNPs within a diversity pool are determined with reference to a "reference strain." In some embodiments, the reference strain is a wild-type strain. In other embodiments, the reference strain is an original industrial strain prior to being subjected to any mutagenesis. The reference strain can be defined by the practitioner and does not have to be an original wild-type strain or original industrial strain. The base strain is merely representative of what will be considered the "base," "reference" or original genetic background, by which subsequent strains that were derived, or were developed from said reference strain, are to be compared.

Once all SNPS in the diversity pool are identified, the present disclosure teaches methods of SNP swapping and screening methods to delineate (i.e. quantify and characterize) the effects (e.g. creation of a phenotype of interest) of SNPs individually and/or in groups.

In some embodiments, the SNP swapping methods of the present disclosure comprise the step of introducing one or more SNPs identified in a mutated strain (e.g., a strain from amongst $S_{2-n}Gen_{2-n}$) to a reference strain ($S_1Gen_1$) or wild-type strain ("wave up").

In other embodiments, the SNP swapping methods of the present disclosure comprise the step of removing one or more SNPs identified in a mutated strain (e.g., a strain from amongst $S_{2-n}Gen_{2-n}$) ("wave down").

In some embodiments, each generated strain comprising one or more SNP changes (either introducing or removing) is cultured and analyzed under one or more criteria of the present disclosure (e.g., production of a chemical or product of interest). Data from each of the analyzed host strains is associated, or correlated, with the particular SNP, or group of SNPs present in the host strain, and is recorded for future use. Thus, the present disclosure enables the creation of large and highly annotated HTP genetic design microbial strain libraries that are able to identify the effect of a given SNP on any number of microbial genetic or phenotypic traits of interest. The information stored in these HTP genetic design libraries informs the machine learning algorithms of the HTP genomic engineering platform and directs future iterations of the process, which ultimately leads to evolved microbial organisms that possess highly desirable properties/traits.

3. Start/Stop Codon Exchanges: A Molecular Tool for the Derivation of Start/Stop Codon Microbial Strain Libraries In some embodiments, the present disclosure teaches methods of swapping start and stop codon variants. For example, typical stop codons for *S. cerevisiae* and mammals are TAA (UAA) and TGA (UGA), respectively. The typical stop codon for monocotyledonous plants is TGA (UGA), whereas insects and *E. coli* commonly use TAA (UAA) as the stop codon (Dalphin et al. (1996) Nucl. Acids Res. 24: 216-218). In other embodiments, the present disclosure teaches use of the TAG (UAG) stop codons.

The present disclosure similarly teaches swapping start codons. In some embodiments, the present disclosure teaches use of the ATG (AUG) start codon utilized by most organisms (especially eukaryotes). In some embodiments, the present disclosure teaches that prokaryotes use ATG (AUG) the most, followed by GTG (GUG) and TTG (UUG).

In other embodiments, the present invention teaches replacing ATG start codons with TTG. In some embodiments, the present invention teaches replacing ATG start codons with GTG. In some embodiments, the present invention teaches replacing GTG start codons with ATG. In some embodiments, the present invention teaches replacing GTG start codons with TTG. In some embodiments, the present invention teaches replacing TTG start codons with ATG. In some embodiments, the present invention teaches replacing TTG start codons with GTG.

In other embodiments, the present invention teaches replacing TAA stop codons with TAG. In some embodiments, the present invention teaches replacing TAA stop codons with TGA. In some embodiments, the present invention teaches replacing TGA stop codons with TAA. In some embodiments, the present invention teaches replacing TGA stop codons with TAG. In some embodiments, the present invention teaches replacing TAG stop codons with TAA. In some embodiments, the present invention teaches replacing TAG stop codons with TGA.

4. Stop Swap: A Molecular Tool for the Derivation of Optimized Sequence Microbial Strain Libraries In some embodiments, the present disclosure teaches methods of improving host cell productivity through the optimization of cellular gene transcription. Gene transcription is the result of several distinct biological phenomena, including transcriptional initiation (RNAp recruitment and transcriptional complex formation), elongation (strand synthesis/extension), and transcriptional termination (RNAp detachment and termination). Although much attention has been devoted to the control of gene expression through the transcriptional modulation of genes (e.g., by changing promoters, or inducing regulatory transcription factors), comparatively few efforts have been made towards the modulation of transcription via the modulation of gene terminator sequences.

The most obvious way that transcription impacts on gene expression levels is through the rate of Pol II initiation, which can be modulated by combinations of promoter or enhancer strength and trans-activating factors (Kadonaga, J T. 2004 "Regulation of RNA polymerase II transcription by sequence-specific DNA binding factors" Cell. 2004 Jan. 23; 116(2):247-57). In eukaryotes, elongation rate may also determine gene expression patterns by influencing alternative splicing (Cramer P. et al., 1997 "Functional association between promoter structure and transcript alternative splicing." Proc Natl Acad Sci USA. 1997 Oct. 14; 94(21):11456-60). Failed termination on a gene can impair the expression of downstream genes by reducing the accessibility of the promoter to Pol II (Greger I H. et al., 2000 "Balancing transcriptional interference and initiation on the GAL7 promoter of *Saccharomyces cerevisiae*." Proc Natl Acad Sci USA. 2000 Jul. 18; 97(15):8415-20). This process, known as transcriptional interference, is particularly relevant in lower eukaryotes, as they often have closely spaced genes.

Termination sequences can also affect the expression of the genes to which the sequences belong. For example, studies show that inefficient transcriptional termination in eukaryotes results in an accumulation of unspliced pre-mRNA (see West, S., and Proudfoot, N. J., 2009 "Transcriptional Termination Enhances Protein Expression in Human Cells" Mol Cell. 2009 Feb. 13; 33(3-9); 354-364). Other studies have also shown that 3' end processing, can be delayed by inefficient termination (West, S et al., 2008 "Molecular dissection of mammalian RNA polymerase II transcriptional termination." Mol Cell. 2008 Mar. 14; 29(5): 600-10.). Transcriptional termination can also affect mRNA stability by releasing transcripts from sites of synthesis.

Termination of Transcription Mechanism in Eukaryotes

Transcriptional termination in eukaryotes operates through terminator signals that are recognized by protein factors associated with the RNA polymerase II. In some embodiments, the cleavage and polyadenylation specificity factor (CPSF) and cleavage stimulation factor (CstF) transfer from the carboxyl terminal domain of RNA polymerase II to the poly-A signal. In some embodiments, the CPSF and CstF factors also recruit other proteins to the termination site, which then cleave the transcript and free the mRNA from the transcription complex. Termination also triggers polyadenylation of mRNA transcripts. Illustrative examples of validated eukaryotic termination factors, and their conserved structures are discussed in later portions of this document.

Termination of Transcription in Prokaryotes

In prokaryotes, two principal mechanisms, termed Rho-independent and Rho-dependent termination, mediate transcriptional termination. Rho-independent termination signals do not require an extrinsic transcription-termination factor, as formation of a stem-loop structure in the RNA transcribed from these sequences along with a series of Uridine (U) residues promotes release of the RNA chain from the transcription complex. Rho-dependent termination, on the other hand, requires a transcription-termination factor called Rho and cis-acting elements on the mRNA. The initial binding site for Rho, the Rho utilization (rut) site, is an extended (~70 nucleotides, sometimes 80-100 nucleotides) single-stranded region characterized by a high cytidine/low guanosine content and relatively little secondary structure in the RNA being synthesized, upstream of the actual terminator sequence. When a polymerase pause site is encountered, termination occurs, and the transcript is released by Rho's helicase activity.

Terminator Swapping (STOP Swap)

In some embodiments, the present disclosure teaches methods of selecting termination sequences ("terminators") with optimal expression properties to produce beneficial effects on overall-host strain productivity.

For example, in some embodiments, the present disclosure teaches methods of identifying one or more terminators and/or generating variants of one or more terminators within a host cell, which exhibit a range of expression strengths (e.g. terminator ladders discussed infra). A particular combination of these identified and/or generated terminators can be grouped together as a terminator ladder, which is explained in more detail below.

The terminator ladder in question is then associated with a given gene of interest. Thus, if one has terminators $T_1$-$T_8$ (representing eight terminators that have been identified and/or generated to exhibit a range of expression strengths when combined with one or more promoters) and associates the terminator ladder with a single gene of interest in a host cell (i.e. genetically engineer a host cell with a given terminator operably linked to the 3' end of to a given target gene), then the effect of each combination of the terminators can be ascertained by characterizing each of the engineered strains resulting from each combinatorial effort, given that the engineered host cells have an otherwise identical genetic background except the particular promoter(s) associated with the target gene. The resultant host cells that are engineered via this process form HTP genetic design libraries.

The HTP genetic design library can refer to the actual physical microbial strain collection that is formed via this process, with each member strain being representative of a given terminator operably linked to a particular target gene, in an otherwise identical genetic background, said library being termed a "terminator swap microbial strain library" or "STOP swap microbial strain library."

Furthermore, the HTP genetic design library can refer to the collection of genetic perturbations—in this case a given terminator x operably linked to a given gene y—said collection being termed a "terminator swap library" or "STOP swap library."

Further, one can utilize the same terminator ladder comprising promoters $T_1$-$T_8$ to engineer microbes, wherein each of the eight terminators is operably linked to 10 different gene targets. The result of this procedure would be 80 host cell strains that are otherwise assumed genetically identical, except for the particular terminators operably linked to a target gene of interest. These 80 host cell strains could be appropriately screened and characterized and give rise to another HTP genetic design library. The characterization of the microbial strains in the HTP genetic design library produces information and data that can be stored in any database, including without limitation, a relational database, an object-oriented database or a highly distributed NoSQL database. This data/information could include, for example, a given terminators' (e.g., $T_1$-$T_8$) effect when operably linked to a given gene target. This data/information can also be the broader set of combinatorial effects that result from operably linking two or more of promoters $T_1$-$T_8$ to a given gene target.

The aforementioned examples of eight terminators and 10 target genes is merely illustrative, as the concept can be applied with any given number of promoters that have been grouped together based upon exhibition of a range of expression strengths and any given number of target genes.

In summary, utilizing various terminators to modulate expression of various genes in an organism is a powerful tool to optimize a trait of interest. The molecular tool of terminator swapping, developed by the inventors, uses a ladder of terminator sequences that have been demonstrated to vary expression of at least one locus under at least one condition. This ladder is then systematically applied to a group of genes in the organism using high-throughput genome engineering. This group of genes is determined to have a high likelihood of impacting the trait of interest based on any one of a number of methods. These could include selection based on known function, or impact on the trait of interest, or algorithmic selection based on previously determined beneficial genetic diversity.

The resultant HTP genetic design microbial library of organisms containing a terminator sequence linked to a gene is then assessed for performance in a high-throughput screening model, and promoter-gene linkages which lead to increased performance are determined and the information stored in a database. The collection of genetic perturbations (i.e. given terminator x linked to a given gene y) form a "terminator swap library," which can be utilized as a source of potential genetic alterations to be utilized in microbial engineering processing. Over time, as a greater set of genetic perturbations is implemented against a greater diversity of microbial backgrounds, each library becomes more powerful as a corpus of experimentally confirmed data that can be used to more precisely and predictably design targeted changes against any background of interest. That is in some embodiments, the present disclosures teaches introduction of one or more genetic changes into a host cell based on previous experimental results embedded within the meta data associated with any of the genetic design libraries of the invention.

Thus, in particular embodiments, terminator swapping is a multi-step process comprising:

1. Selecting a set of "x" terminators to act as a "ladder." Ideally these terminators have been shown to lead to highly variable expression across multiple genomic loci, but the only requirement is that they perturb gene expression in some way.

2. Selecting a set of "n" genes to target. This set can be every ORF in a genome, or a subset of ORFs. The subset can be chosen using annotations on ORFs related to function, by relation to previously demonstrated beneficial perturbations (previous promoter swaps, STOP swaps, or SNP swaps), by algorithmic selection based on epistatic interactions between previously generated perturbations, other selection criteria based on hypotheses regarding beneficial ORF to target, or through random selection. In other embodiments, the "n" targeted genes can comprise non-protein coding genes, including non-coding RNAs.

3. High-throughput strain engineering to rapidly and in parallel carry out the following genetic modifications: When a native terminator exists at the 3' end of target gene n and its sequence is known, replace the native terminator with each of the x terminators in the ladder. When the native terminator does not exist, or its sequence is unknown, insert each of the x terminators in the ladder after the gene stop codon.

In this way a "library" (also referred to as a HTP genetic design library) of strains is constructed, wherein each member of the library is an instance of x terminator linked to n target, in an otherwise identical genetic context. As previously described, combinations of terminators can be inserted, extending the range of combinatorial possibilities upon which the library is constructed.

4. High-throughput screening of the library of strains in a context where their performance against one or more metrics is indicative of the performance that is being optimized.

This foundational process can be extended to provide further improvements in strain performance by, inter alia: (1) Consolidating multiple beneficial perturbations into a single strain background, either one at a time in an interactive process, or as multiple changes in a single step. Multiple perturbations can be either a specific set of defined changes or a partly randomized, combinatorial library of changes. For example, if the set of targets is every gene in a pathway, then sequential regeneration of the library of perturbations into an improved member or members of the previous library of strains can optimize the expression level of each gene in a pathway regardless of which genes are rate limiting at any given iteration; (2) Feeding the performance data resulting from the individual and combinatorial generation of the library into an algorithm that uses that data to predict an optimum set of perturbations based on the interaction of each perturbation; and (3) Implementing a combination of the above two approaches.

The approach is exemplified in the present disclosure with industrial microorganisms, but is applicable to any organism where desired traits can be identified in a population of genetic mutants. For example, this could be used for improving the performance of CHO cells, yeast, insect cells, algae, as well as multi-cellular organisms, such as plants.

5. Sequence Optimization: A Molecular Tool for the Derivation of Optimized Sequence Microbial Strain Libraries In one embodiment, the methods of the provided disclosure comprise codon optimizing one or more genes expressed by the host organism. Methods for optimizing codons to improve expression in various hosts are known in the art and are described in the literature (see U.S. Pat. App. Pub. No. 2007/0292918, incorporated herein by reference in its entirety). Optimized coding sequences containing codons preferred by a particular prokaryotic or eukaryotic host (see also, Murray et al. (1989) Nucl. Acids Res. 17:477-508) can be prepared, for example, to increase the rate of translation or to produce recombinant RNA transcripts having desirable properties, such as a longer half-life, as compared with transcripts produced from a non-optimized sequence.

Protein expression is governed by a host of factors including those that affect transcription, mRNA processing, and stability and initiation of translation. Optimization can thus address any of a number of sequence features of any particular gene. As a specific example, a rare codon induced translational pause can result in reduced protein expression. A rare codon induced translational pause includes the presence of codons in the polynucleotide of interest that are rarely used in the host organism may have a negative effect on protein translation due to their scarcity in the available tRNA pool.

Alternate translational initiation also can result in reduced heterologous protein expression. Alternate translational initiation can include a synthetic polynucleotide sequence inadvertently containing motifs capable of functioning as a ribosome binding site (RBS). These sites can result in initiating translation of a truncated protein from a gene-internal site. One method of reducing the possibility of producing a truncated protein, which can be difficult to remove during purification, includes eliminating putative internal RBS sequences from an optimized polynucleotide sequence.

Repeat-induced polymerase slippage can result in reduced heterologous protein expression. Repeat-induced polymerase slippage involves nucleotide sequence repeats that have been shown to cause slippage or stuttering of DNA polymerase which can result in frameshift mutations. Such repeats can also cause slippage of RNA polymerase. In an organism with a high G+C content bias, there can be a higher degree of repeats composed of G or C nucleotide repeats. Therefore, one method of reducing the possibility of inducing RNA polymerase slippage, includes altering extended repeats of G or C nucleotides.

Interfering secondary structures also can result in reduced heterologous protein expression. Secondary structures can sequester the RBS sequence or initiation codon and have been correlated to a reduction in protein expression. Stem-loop structures can also be involved in transcriptional pausing and attenuation. An optimized polynucleotide sequence can contain minimal secondary structures in the RBS and gene coding regions of the nucleotide sequence to allow for improved transcription and translation.

For example, the optimization process can begin by identifying the desired amino acid sequence to be expressed by the host. From the amino acid sequence a candidate polynucleotide or DNA sequence can be designed. During the design of the synthetic DNA sequence, the frequency of codon usage can be compared to the codon usage of the host expression organism and rare host codons can be removed from the synthetic sequence. Additionally, the synthetic candidate DNA sequence can be modified in order to remove undesirable enzyme restriction sites and add or remove any desired signal sequences, linkers or untranslated regions. The synthetic DNA sequence can be analyzed for the presence of secondary structure that may interfere with the translation process, such as G/C repeats and stem-loop structures.

6. Epistasis Mapping—a Predictive Analytical Tool Enabling Beneficial Genetic Consolidations In some embodiments, the present disclosure teaches epistasis mapping methods for predicting and combining beneficial genetic alterations into a host cell. The genetic alterations may be created by any of the aforementioned HTP molecular tool sets (e.g., promoter swaps, SNP swaps, start/stop codon exchanges, sequence optimization) and the effect of those genetic alterations would be known from the characterization of the derived HTP genetic design microbial strain libraries. Thus, as used herein, the term epistasis mapping includes methods of identifying combinations of genetic alterations (e.g., beneficial SNPs or beneficial promoter/target gene associations) that are likely to yield increases in host performance.

In embodiments, the epistasis mapping methods of the present disclosure are based on the idea that the combination of beneficial mutations from two different functional groups is more likely to improve host performance, as compared to a combination of mutations from the same functional group. See, e.g., Costanzo, The Genetic Landscape of a Cell, Science, Vol. 327, Issue 5964, Jan. 22, 2010, pp. 425-431 (incorporated by reference herein in its entirety).

Mutations from the same functional group are more likely to operate by the same mechanism, and are thus more likely to exhibit negative or neutral epistasis on overall host performance. In contrast, mutations from different functional groups are more likely to operate by independent mechanisms, which can lead to improved host performance and in some instances synergistic effects. For example, referring to FIG. 19, lysA and zwf are genes that operate in different pathways to achieve the production of lysine. Based upon the dissimilarity in the individual performance of those genes, genetic changes using those genes should result in additive consolidation effects. This was borne out in the actual measurement of the consolidated effects of the combination of lysA and zwf, as shown in FIG. 16B and Examples 6.

Thus, in some embodiments, the present disclosure teaches methods of analyzing SNP mutations to identify SNPs predicted to belong to different functional groups. In some embodiments, SNP functional group similarity is determined by computing the cosine similarity of mutation interaction profiles (similar to a correlation coefficient, see FIG. 16A). The present disclosure also illustrates comparing SNPs via a mutation similarity matrix (see FIG. 15) or dendrogram (see FIG. 16A).

Thus, the epistasis mapping procedure provides a method for grouping and/or ranking a diversity of genetic mutations applied in one or more genetic backgrounds for the purposes of efficient and effective consolidations of said mutations into one or more genetic backgrounds.

In aspects, consolidation is performed with the objective of creating novel strains which are optimized for the production of target biomolecules. Through the taught epistasis mapping procedure, it is possible to identify functional groupings of mutations, and such functional groupings enable a consolidation strategy that minimizes undesirable epistatic effects.

As previously explained, the optimization of microbes for use in industrial fermentation is an important and difficult problem, with broad implications for the economy, society, and the natural world. Traditionally, microbial engineering has been performed through a slow and uncertain process of random mutagenesis. Such approaches leverage the natural evolutionary capacity of cells to adapt to artificially imposed selection pressure. Such approaches are also limited by the rarity of beneficial mutations, the ruggedness of the underlying fitness landscape, and more generally underutilize the state of the art in cellular and molecular biology.

Modern approaches leverage new understanding of cellular function at the mechanistic level and new molecular biology tools to perform targeted genetic manipulations to specific phenotypic ends. In practice, such rational approaches are confounded by the underlying complexity of biology. Causal mechanisms are poorly understood, particularly when attempting to combine two or more changes that each has an observed beneficial effect. Sometimes such consolidations of genetic changes yield positive outcomes (measured by increases in desired phenotypic activity), although the net positive outcome may be lower than expected and in some cases higher than expected. In other instances, such combinations produce either net neutral effect or a net negative effect. This phenomenon is referred to as epistasis, and is one of the fundamental challenges to microbial engineering (and genetic engineering generally).

As aforementioned, the present HTP genomic engineering platform solves many of the problems associated with traditional microbial engineering approaches. The present HTP platform uses automation technologies to perform hundreds or thousands of genetic mutations at once. In particular aspects, unlike the rational approaches described above, the disclosed HTP platform enables the parallel construction of thousands of mutants to more effectively explore large subsets of the relevant genomic space, as disclosed in U.S. application Ser. No. 15/140,296, entitled Microbial Strain Design System And Methods For Improved Large-Scale Production Of Engineered Nucleotide Sequences, incorporated by reference herein in its entirety. By trying "everything," the present HTP platform sidesteps the difficulties induced by our limited biological understanding.

However, at the same time, the present HTP platform faces the problem of being fundamentally limited by the combinatorial explosive size of genomic space, and the effectiveness of computational techniques to interpret the generated data sets given the complexity of genetic interactions. Techniques are needed to explore subsets of vast combinatorial spaces in ways that maximize non-random selection of combinations that yield desired outcomes.

Somewhat similar HTP approaches have proved effective in the case of enzyme optimization. In this niche problem, a genomic sequence of interest (on the order of 1000 bases), encodes a protein chain with some complicated physical configuration. The precise configuration is determined by the collective electromagnetic interactions between its constituent atomic components. This combination of short genomic sequence and physically constrained folding problem lends itself specifically to greedy optimization strategies. That is, it is possible to individually mutate the sequence at every residue and shuffle the resulting mutants to effectively sample local sequence space at a resolution compatible with the Sequence Activity Response modeling.

However, for full genomic optimizations for biomolecules, such residue-centric approaches are insufficient for some important reasons. First, because of the exponential increase in relevant sequence space associated with genomic optimizations for biomolecules. Second, because of the added complexity of regulation, expression, and metabolic interactions in biomolecule synthesis. The present inventors have solved these problems via the taught epistasis mapping procedure.

The taught method for modeling epistatic interactions, between a collection of mutations for the purposes of more efficient and effective consolidation of said mutations into one or more genetic backgrounds, is groundbreaking and highly needed in the art.

When describing the epistasis mapping procedure, the terms "more efficient" and "more effective" refers to the avoidance of undesirable epistatic interactions among consolidation strains with respect to particular phenotypic objectives.

As the process has been generally elaborated upon above, a more specific workflow example will now be described.

First, one begins with a library of M mutations and one or more genetic backgrounds (e.g., parent bacterial strains). Neither the choice of library nor the choice of genetic backgrounds is specific to the method described here. But in a particular implementation, a library of mutations may include exclusively, or in combination: SNP swap libraries, Promoter swap libraries, or any other mutation library described herein.

In one implementation, only a single genetic background is provided. In this case, a collection of distinct genetic backgrounds (microbial mutants) will first be generated from this single background. This may be achieved by applying the primary library of mutations (or some subset thereof) to the given background for example, application of a HTP genetic design library of particular SNPs or a HTP genetic design library of particular promoters to the given genetic background, to create a population (perhaps 100's or 1,000's) of microbial mutants with an identical genetic background except for the particular genetic alteration from the given HTP genetic design library incorporated therein. As detailed below, this embodiment can lead to a combinatorial library or pairwise library.

In another implementation, a collection of distinct known genetic backgrounds may simply be given. As detailed below, this embodiment can lead to a subset of a combinatorial library.

In a particular implementation, the number of genetic backgrounds and genetic diversity between these backgrounds (measured in number of mutations or sequence edit distance or the like) is determined to maximize the effectiveness of this method.

A genetic background may be a natural, native or wild-type strain or a mutated, engineered strain. N distinct background strains may be represented by a vector b. In one example, the background b may represent engineered backgrounds formed by applying N primary mutations $m_0=(m_1, m_2, \ldots m_N)$ to a wild-type background strain $b_0$ to form the N mutated background strains $b=m_0 b_0=(m_1 b_0, m_2 b_0, \ldots m_N b_0)$, where $m_i b_0$ represents the application of mutation $m_i$ to background strain $b_0$.

In either case (i.e. a single provided genetic background or a collection of genetic backgrounds), the result is a collection of N genetically distinct backgrounds. Relevant phenotypes are measured for each background.

Second, each mutation in a collection of M mutations $m_1$ is applied to each background within the collection of N background strains b to form a collection of M×N mutants. In the implementation where the N backgrounds were themselves obtained by applying the primary set of mutations $m_0$ (as described above), the resulting set of mutants will sometimes be referred to as a combinatorial library or a pairwise library. In another implementation, in which a collection of known backgrounds has been provided explicitly, the resulting set of mutants may be referred to as a subset of a combinatorial library. Similar to generation of engineered background vectors, in embodiments, the input interface 202 receives the mutation vector $m_1$ and the background vector b, and a specified operation such as cross product.

Continuing with the engineered background example above, forming the M×N combinatorial library may be represented by the matrix formed by $m_1 \times m_0 b_0$, the cross product of $m_1$ applied to the N backgrounds of $b=m_0 b_0$, where each mutation in $m_1$ is applied to each background strain within b. Each ith row of the resulting M×N matrix represents the application of the ith mutation within $m_1$ to all the strains within background collection b. In one embodiment, $m_1=m_0$ and the matrix represents the pairwise application of the same mutations to starting strain $b_0$. In that case, the matrix is symmetric about its diagonal (M=N), and the diagonal may be ignored in any analysis since it represents the application of the same mutation twice.

In embodiments, forming the M×N matrix may be achieved by inputting into the input interface 202 the compound expression $m_1 \times m_0 b_0$. The component vectors of the expression may be input directly with their elements explicitly specified, via one or more DNA specifications, or as calls to the library 206 to enable retrieval of the vectors during interpretation by interpreter 204. As described in U.S. patent application Ser. No. 15/140,296, entitled "Microbial Strain Design System and Methods for Improved Large Scale Production of Engineered Nucleotide Sequences," via the interpreter 204, execution engine 207, order placement engine 208, and factory 210, the LIMS system 200 generates the microbial strains specified by the input expression.

Figure 42:
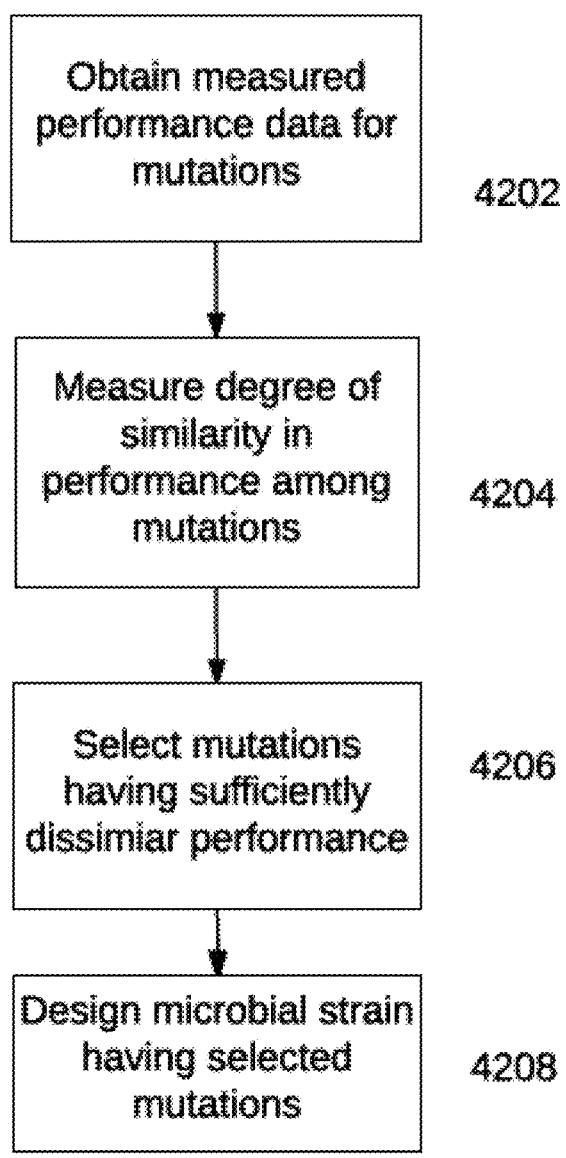
FIG. 42 is a flowchart illustrating the consideration of epistatic effects in the selection of mutations for the design of a microbial strain, according to embodiments of the disclosure.

Third, with reference to FIG. 42, the analysis equipment 214 measures phenotypic responses for each mutant within the M×N combinatorial library matrix (4202). As such, the collection of responses can be construed as an M×N Response Matrix R. Each element of R may be represented as $r_{ij}=y(m_i, m_j)$, where y represents the response (performance) of background strain $b_j$ within engineered collection b as mutated by mutation $m_i$. For simplicity, and practicality, we assume pairwise mutations where $m_1=m_0$. Where, as here, the set of mutations represents a pairwise mutation library, the resulting matrix may also be referred to as a gene interaction matrix or, more particularly, as a mutation interaction matrix.

Those skilled in the art will recognize that, in some embodiments, operations related to epistatic effects and predictive strain design may be performed entirely through automated means of the LIMS system 200, e.g., by the analysis equipment 214, or by human implementation, or through a combination of automated and manual means. When an operation is not fully automated, the elements of the LIMS system 200, e.g., analysis equipment 214, may, for example, receive the results of the human performance of the operations rather than generate results through its own operational capabilities. As described elsewhere herein, components of the LIMS system 200, such as the analysis equipment 214, may be implemented wholly or partially by one or more computer systems. In some embodiments, in particular where operations related to predictive strain design are performed by a combination of automated and manual means, the analysis equipment 214 may include not only computer hardware, software or firmware (or a combination thereof), but also equipment operated by a human operator such as that listed in Table 5 below, e.g., the equipment listed under the category of "Evaluate performance."

Fourth, the analysis equipment 212 normalizes the response matrix. Normalization consists of a manual and/or, in this embodiment, automated processes of adjusting measured response values for the purpose of removing bias and/or isolating the relevant portions of the effect specific to this method. With respect to FIG. 42, the first step 4202 may include obtaining normalized measured data. In general, in the claims directed to predictive strain design and epistasis mapping, the terms "performance measure" or "measured performance" or the like may be used to describe a metric that reflects measured data, whether raw or processed in some manner, e.g., normalized data. In a particular implementation, normalization may be performed by subtracting a previously measured background response from the measured response value. In that implementation, the resulting response elements may be formed as $r_{ij}=y(m_i, m_j)-y(m_j)$, where $y(m_j)$ is the response of the engineered background strain $b_j$ within engineered collection b caused by application of primary mutation $m_j$ to parent strain $b_0$. Note that each row of the normalized response matrix is treated as a response profile for its corresponding mutation. That is, the ith row describes the relative effect of the corresponding mutation $m_i$ applied to all the background strains $b_j$ for $j=1$ to N.

With respect to the example of pairwise mutations, the combined performance/response of strains resulting from two mutations may be greater than, less than, or equal to the performance/response of the strain to each of the mutations individually. This effect is known as "epistasis," and may, in some embodiments, be represented as $e_{ij}=y(m_i, m_j)-(y(m_i)+y(m_j))$. Variations of this mathematical representation are possible, and may depend upon, for example, how the individual changes biologically interact. As noted above, mutations from the same functional group are more likely to operate by the same mechanism, and are thus more likely to exhibit negative or neutral epistasis on overall host performance. In contrast, mutations from different functional groups are more likely to operate by independent mechanisms, which can lead to improved host performance by reducing redundant mutative effects, for example. Thus, mutations that yield dissimilar responses are more likely to combine in an additive manner than mutations that yield similar responses. This leads to the computation of similarity in the next step.

Figure 15:
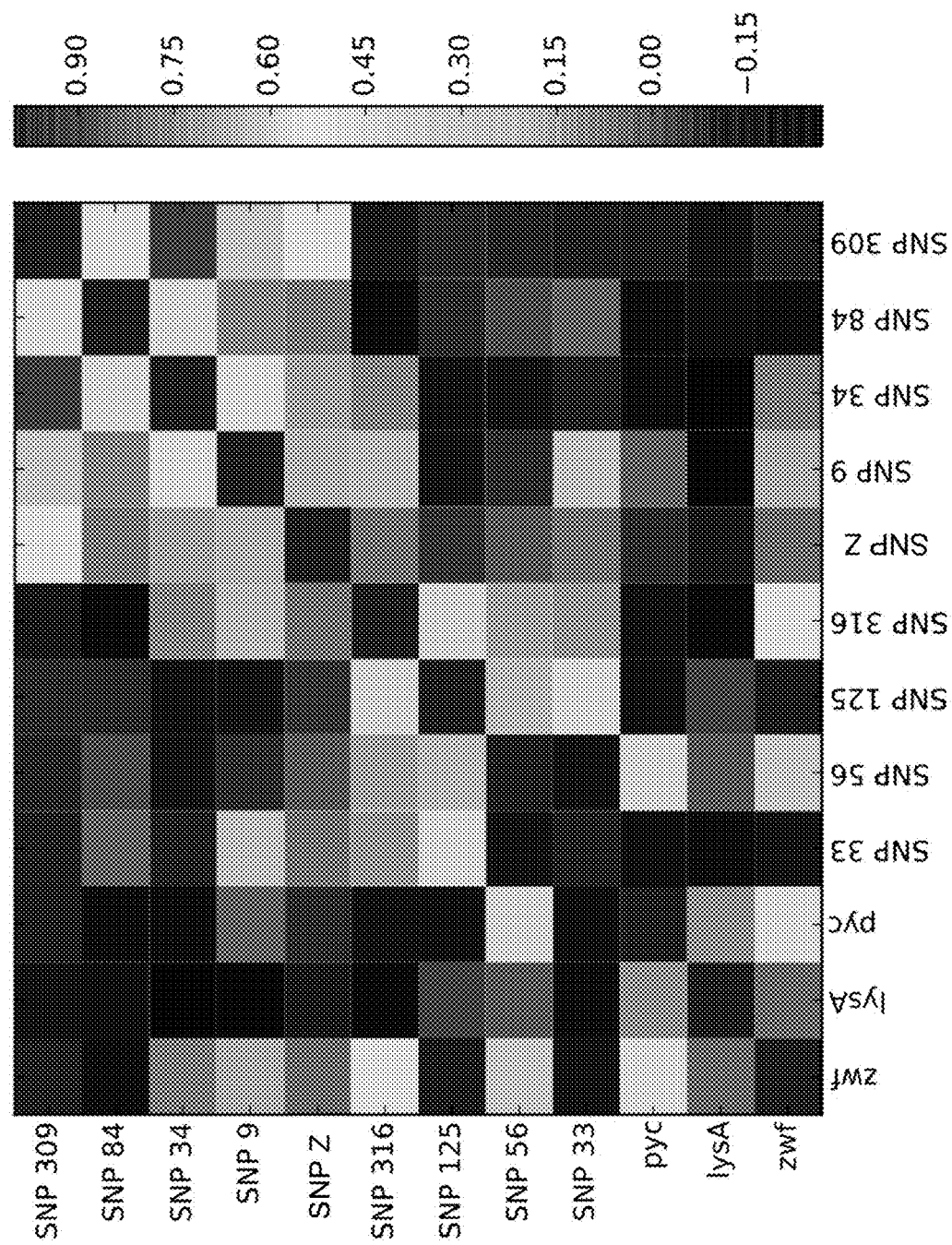
FIG. 15 is a similarity matrix computed using the correlation measure. The matrix is a representation of the functional similarity between SNP variants. The consolidation of SNPs with low functional similarity is expected to have a higher likelihood of improving strain performance, as opposed to the consolidation of SNPs with higher functional similarity.

Fifth, the analysis equipment 214 measures the similarity among the responses—in the pairwise mutation example, the similarity between the effects of the ith mutation and jth (e.g., primary) mutation within the response matrix (4204). Recall that the ith row of R represents the performance effects of the ith mutation $m_i$ on the N background strains, each of which may be itself the result of engineered mutations as described above. Thus, the similarity between the effects of the ith and jth mutations may be represented by the similarity $s_{ij}$ between the ith and jth rows, $\rho_i$ and $\rho_j$, respectively, to form a similarity matrix S, an example of which is illustrated in FIG. 15. Similarity may be measured using many known techniques, such as cross-correlation or absolute cosine similarity, e.g., $s_{ij}=abs(cos(\rho_i, \rho_j))$.

As an alternative or supplement to a metric like cosine similarity, response profiles may be clustered to determine degree of similarity. Clustering may be performed by use of a distance-based clustering algorithms (e.g. k-mean, hierarchical agglomerative, etc.) in conjunction with suitable distance measure (e.g. Euclidean, Hamming, etc). Alternatively, clustering may be performed using similarity based clustering algorithms (e.g. spectral, min-cut, etc.) with a suitable similarity measure (e.g. cosine, correlation, etc). Of course, distance measures may be mapped to similarity measures and vice-versa via any number of standard functional operations (e.g., the exponential function). In one implementation, hierarchical agglomerative clustering may be used in conjunction absolute cosine similarity. (See FIG. 16A).

As an example of clustering, let C be a clustering of mutations $m_i$ into k distinct clusters. Let C be the cluster membership matrix, where $c_{ij}$ is the degree to which mutation i belongs to cluster j, a value between 0 and 1. The cluster-based similarity between mutations i and j is then given by $C_i \times C_j$ (the dot product of the ith and jth rows of C). In general, the cluster-based similarity matrix is given by $CC^T$ (that is, C times C-transpose). In the case of hard-clustering (a mutation belongs to exactly one cluster), the similarity between two mutations is 1 if they belong to the same cluster and 0 if not.

As is described in Costanzo, The Genetic Landscape of a Cell, Science, Vol. 327, Issue 5964, Jan. 22, 2010, pp. 425-431 (incorporated by reference herein in its entirety), such a clustering of mutation response profiles relates to an approximate mapping of a cell's underlying functional organization. That is, mutations that cluster together tend to be related by an underlying biological process or metabolic pathway. Such mutations are referred to herein as a "functional group." The key observation of this method is that if two mutations operate by the same biological process or pathway, then observed effects (and notably observed benefits) may be redundant. Conversely, if two mutations operate by distant mechanism, then it is less likely that beneficial effects will be redundant.

Sixth, based on the epistatic effect, the analysis equipment 214 selects pairs of mutations that lead to dissimilar responses, e.g., their cosine similarity metric falls below a similarity threshold, or their responses fall within sufficiently separated clusters, (e.g., in FIG. 15 and FIG. 16A) as shown in FIG. 42 (4206). Based on their dissimilarity, the selected pairs of mutations should consolidate into background strains better than similar pairs.

Based upon the selected pairs of mutations that lead to sufficiently dissimilar responses, the LIMS system (e.g., all of or some combination of interpreter 204, execution engine 207, order placer 208, and factory 210) may be used to design microbial strains having those selected mutations (4208). In embodiments, as described below and elsewhere herein, epistatic effects may be built into, or used in conjunction with the predictive model to weight or filter strain selection.

It is assumed that it is possible to estimate the performance (a.k.a. score) of a hypothetical strain obtained by consolidating a collection of mutations from the library into a particular background via some preferred predictive model. A representative predictive model utilized in the taught methods is provided in the below section entitled "Predictive Strain Design" that is found in the larger section of: "Computational Analysis and Prediction of Effects of Genome-Wide Genetic Design Criteria."

When employing a predictive strain design technique such as linear regression, the analysis equipment 214 may restrict the model to mutations having low similarity measures by, e.g., filtering the regression results to keep only sufficiently dissimilar mutations. Alternatively, the predictive model may be weighted with the similarity matrix. For example, some embodiments may employ a weighted least squares regression using the similarity matrix to characterize the interdependencies of the proposed mutations. As an example, weighting may be performed by applying the "kernel" trick to the regression model. (To the extent that the "kernel trick" is general to many machine learning modeling approaches, this re-weighting strategy is not restricted to linear regression.)

Such methods are known to one skilled in the art. In embodiments, the kernel is a matrix having elements $1-w*s_{ij}$ where 1 is an element of the identity matrix, and w is a real value between 0 and 1. When w=0, this reduces to a standard regression model. In practice, the value of w will be tied to the accuracy ($r^2$ value or root mean square error (RMSE)) of the predictive model when evaluated against the pairwise combinatorial constructs and their associate effects $y(m_i, m_j)$. In one simple implementation, w is defined as $w=1-r^2$. In this case, when the model is fully predictive, $w=1-r^2=0$ and consolidation is based solely on the predictive model and epistatic mapping procedure plays no role. On the other hand, when the predictive model is not predictive at all, $w=1-r^2=1$ and consolidation is based solely on the epistatic mapping procedure. During each iteration, the accuracy can be assessed to determine whether model performance is improving.

It should be clear that the epistatic mapping procedure described herein does not depend on which model is used by the analysis equipment 214. Given such a predictive model, it is possible to score and rank all hypothetical strains accessible to the mutation library via combinatorial consolidation.

In some embodiments, to account for epistatic effects, the dissimilar mutation response profiles may be used by the analysis equipment 214 to augment the score and rank associated with each hypothetical strain from the predictive model. This procedure may be thought of broadly as a re-weighting of scores, so as to favor candidate strains with dissimilar response profiles (e.g., strains drawn from a diversity of clusters). In one simple implementation, a strain may have its score reduced by the number of constituent mutations that do not satisfy the dissimilarity threshold or that are drawn from the same cluster (with suitable weighting). In a particular implementation, a hypothetical strain's performance estimate may be reduced by the sum of terms in the similarity matrix associated with all pairs of constituent mutations associated with the hypothetical strain (again with suitable weighting). Hypothetical strains may be re-ranked using these augmented scores. In practice, such re-weighting calculations may be performed in conjunction with the initial scoring estimation.

The result is a collection of hypothetical strains with score and rank augmented to more effectively avoid confounding epistatic interactions. Hypothetical strains may be constructed at this time, or they may be passed to another computational method for subsequent analysis or use.

Those skilled in the art will recognize that epistasis mapping and iterative predictive strain design as described herein are not limited to employing only pairwise mutations, but may be expanded to the simultaneous application of many more mutations to a background strain. In another embodiment, additional mutations may be applied sequentially to strains that have already been mutated using mutations selected according to the predictive methods described herein. In another embodiment, epistatic effects are imputed by applying the same genetic mutation to a number of strain backgrounds that differ slightly from each other, and noting any significant differences in positive response profiles among the modified strain backgrounds.

Organisms Amenable to Genetic Design

The disclosed HTP genomic engineering platform is exemplified with industrial microbial cell cultures (e.g., *Corynebacterium* and *A. niger*), but is applicable to any host cell organism where desired traits can be identified in a population of genetic mutants.

Thus, as used herein, the term "microorganism" should be taken broadly. It includes, but is not limited to, the two prokaryotic domains, Bacteria and Archaea, as well as certain eukaryotic fungi and protists. However, in certain aspects, "higher" eukaryotic organisms such as insects, plants, and animals can be utilized in the methods taught herein.

The present disclosure provides working examples for both prokaryotic (Examples 1-9) and eukaryotic (Example 10-11) host cells Suitable host cells include, but are not limited to: bacterial cells, algal cells, plant cells, fungal cells, insect cells, and mammalian cells. In one illustrative embodiment, suitable host cells include *E. coli* (e.g., SHuffle™ competent *E. coli* available from New England BioLabs in Ipswich, Mass.).

Other suitable host organisms of the present disclosure include microorganisms of the genus *Corynebacterium*. In some embodiments, preferred *Corynebacterium* strains/species include: *C. efficiens*, with the deposited type strain being DSM44549, *C. glutamicum*, with the deposited type strain being ATCC13032, and *C. ammoniagenes*, with the deposited type strain being ATCC6871. In some embodiments the preferred host of the present disclosure is *C. glutamicum*.

Suitable host strains of the genus *Corynebacterium*, in particular of the species *Corynebacterium glutamicum*, are in particular the known wild-type strains: *Corynebacterium glutamicum* ATCC13032, *Corynebacterium acetoglutamicum* ATCC15806, *Corynebacterium acetoacidophilum* ATCC13870, *Corynebacterium melassecola* ATCC17965, *Corynebacterium thermoaminogenes* FERM BP-1539, *Brevibacterium flavum* ATCC14067, *Brevibacterium lactofermentum* ATCC13869, and *Brevibacterium divaricatum* ATCC14020; and L-amino acid-producing mutants, or strains, prepared therefrom, such as, for example, the L-lysine-producing strains: *Corynebacterium glutamicum* FERM-P 1709, *Brevibacterium flavum* FERM-P 1708, *Brevibacterium lactofermentum* FERM-P 1712, *Corynebacterium glutamicum* FERM-P 6463, *Corynebacterium glutamicum* FERM-P 6464, *Corynebacterium glutamicum* DM58-1, *Corynebacterium glutamicum* DG52-5, *Corynebacterium glutamicum* DSM5714, and *Corynebacterium glutamicum* DSM12866.

The term "*Micrococcus glutamicus*" has also been in use for *C. glutamicum*. Some representatives of the species *C. efficiens* have also been referred to as *C. thermoaminogenes* in the prior art, such as the strain FERM BP-1539, for example.

In some embodiments, the host cell of the present disclosure is a eukaryotic cell. Suitable eukaryotic host cells include, but are not limited to: fungal cells, algal cells, insect cells, animal cells, and plant cells. Suitable fungal host cells include, but are not limited to: Ascomycota, Basidiomycota,

*Deuteromycota, Zygomycota, Fungi imperfecti*. Certain preferred fungal host cells include yeast cells and filamentous fungal cells. Suitable filamentous fungi host cells include, for example, any filamentous forms of the subdivision *Eumycotina* and *Oomycota*. (see, e.g., Hawksworth et al., In Ainsworth and Bisby's Dictionary of The Fungi, 8th edition, 1995, CAB International, University Press, Cambridge, UK, which is incorporated herein by reference). Filamentous fungi are characterized by a vegetative mycelium with a cell wall composed of chitin, cellulose and other complex polysaccharides. The filamentous fungi host cells are morphologically distinct from yeast.

In certain illustrative, but non-limiting embodiments, the filamentous fungal host cell may be a cell of a species of: *Achlya, Acremonium, Aspergillus, Aureobasidium, Bjerkandera, Ceriporiopsis, Cephalosporium, Chrysosporium, Cochliobolus, Corynascus, Cryphonectria, Cryptococcus, Coprinus, Coriolus, Diplodia, Endothis, Fusarium, Gibberella, Gliocladium, Humicola, Hypocrea, Myceliophthora* (e.g., *Myceliophthora thermophila*), *Mucor, Neurospora, Penicillium, Podospora, Phlebia, Piromyces, Pyricularia, Rhizomucor, Rhizopus, Schizophyllum, Scytalidium, Sporotrichum, Talaromyces, Thermoascus, Thielavia, Tramates, Tolypocladium, Trichoderma, Verticillium, Volvariella,* or teleomorphs, or anamorphs, and synonyms or taxonomic equivalents thereof. In one embodiment, the filamentous fungus is selected from the group consisting of *A. nidulans, A. oryzae, A. sojae,* and *Aspergilli* of the *A. niger* Group. In an embodiment, the filamentous fungus is *Aspergillus niger*.

In another embodiment, specific mutants of the fungal species are used for the methods and systems provided herein. In one embodiment, specific mutants of the fungal species are used which are suitable for the high-throughput and/or automated methods and systems provided herein. Examples of such mutants can be strains that protoplast very well; strains that produce mainly or, more preferably, only protoplasts with a single nucleus; strains that regenerate efficiently in microtiter plates, strains that regenerate faster and/or strains that take up polynucleotide (e.g., DNA) molecules efficiently, strains that produce cultures of low viscosity such as, for example, cells that produce hyphae in culture that are not so entangled as to prevent isolation of single clones and/or raise the viscosity of the culture, strains that have reduced random integration (e.g., disabled non-homologous end joining pathway) or combinations thereof.

In yet another embodiment, a specific mutant strain for use in the methods and systems provided herein can be strains lacking a selectable marker gene such as, for example, uridine-requiring mutant strains. These mutant strains can be either deficient in orotidine 5 phosphate decarboxylase (OMPD) or orotate p-ribosyl transferase (OPRT) encoded by the pyrG or pyrE gene, respectively (T. Goosen et al., Curr Genet. 1987, 11:499 503; J. Begueret et al., Gene. 1984 32:487 92.

In one embodiment, specific mutant strains for use in the methods and systems provided herein are strains that possess a compact cellular morphology characterized by shorter hyphae and a more yeast-like appearance.

Suitable yeast host cells include, but are not limited to: *Candida, Hansenula, Saccharomyces, Schizosaccharomyces, Pichia, Kluyveromyces,* and *Yarrowia*. In some embodiments, the yeast cell is *Hansenula polymorpha, Saccharomyces cerevisiae, Saccharomyces carlsbergensis, Saccharomyces diastaticus, Saccharomyces norbensis, Saccharomyces kluyveri, Schizosaccharomyces pombe, Pichia pastoris, Pichia finlandica, Pichia trehalophila, Pichia kodamae, Pichia membranaefaciens, Pichia opuntiae, Pichia thermotolerans, Pichia salictaria, Pichia quercuum, Pichia pijperi, Pichia stipitis, Pichia methanolica, Pichia angusta, Kluyveromyces lactis, Candida albicans,* or *Yarrowia lipolytica.*

In certain embodiments, the host cell is an algal cell such as, *Chlamydomonas* (e.g., *C. Reinhardtii*) and *Phormidium* (P. sp. ATCC29409).

In other embodiments, the host cell is a prokaryotic cell. Suitable prokaryotic cells include gram positive, gram negative, and gram-variable bacterial cells. The host cell may be a species of, but not limited to: *Agrobacterium, Alicyclobacillus, Anabaena, Anacystis, Acinetobacter, Acidothermus, Arthrobacter, Azobacter, Bacillus, Bifidobacterium, Brevibacterium, Butyrivibrio, Buchnera, Campestris, Camplyobacter, Clostridium, Corynebacterium, Chromatium, Coprococcus, Escherichia, Enterococcus, Enterobacter, Erwinia, Fusobacterium, Faecalibacterium, Francisella, Flavobacterium, Geobacillus, Haemophilus, Helicobacter, Klebsiella, Lactobacillus, Lactococcus, Ilyobacter, Micrococcus, Microbacterium, Mesorhizobium, Methylobacterium, Methylobacterium, Mycobacterium, Neisseria, Pantoea, Pseudomonas, Prochlorococcus, Rhodobacter, Rhodopseudomonas, Rhodopseudomonas, Roseburia, Rhodospirillum, Rhodococcus, Scenedesmus, Streptomyces, Streptococcus, Synecoccus, Saccharomonospora, Saccharopolyspora, Staphylococcus, Serratia, Salmonella, Shigella, Thermoanaerobacterium, Tropheryma, Tularensis, Temecula, Thermosynechococcus, Thermococcus, Ureaplasma, Xanthomonas, Xylella, Yersinia,* and *Zymomonas*. In some embodiments, the host cell is *Corynebacterium glutamicum*.

In some embodiments, the bacterial host strain is an industrial strain. Numerous bacterial industrial strains are known and suitable in the methods and compositions described herein.

In some embodiments, the bacterial host cell is of the *Agrobacterium* species (e.g., *A. radiobacter, A. rhizogenes, A. rubi*), the *Arthrobacter* species (e.g., *A. aurescens, A. citreus, A. globformis, A. hydrocarboglutamicus, A. mysorens, A. nicotianae, A. paraffineus, A. protophonniae, A. roseoparaffinus, A. sulfureus, A. ureafaciens*), the *Bacillus* species (e.g., *B. thuringiensis, B. anthracis, B. megaterium, B. subtilis, B. lentus, B. circulars, B. pumilus, B. lautus, B. coagulans, B. brevis, B. firmus, B. alkaophius, B. licheniformis, B. clausii, B. stearothermophilus, B. halodurans* and *B. amyloliquefaciens*. In particular embodiments, the host cell will be an industrial *Bacillus* strain including but not limited to *B. subtilis, B. pumilus, B. licheniformis, B. megaterium, B. clausii, B. stearothermophilus* and *B. amyloliquefaciens*. In some embodiments, the host cell will be an industrial *Clostridium* species (e.g., *C. acetobutylicum, C. tetani* E88, *C. lituseburense, C. saccharobutylicum, C. perfringens, C. beijerinckii*). In some embodiments, the host cell will be an industrial *Corynebacterium* species (e.g., *C. glutamicum, C. acetoacidophilum*). In some embodiments, the host cell will be an industrial *Escherichia* species (e.g., *E. coli*). In some embodiments, the host cell will be an industrial *Erwinia* species (e.g., *E. uredovora, E. carotovora, E. ananas, E. herbicola, E. punctata, E. terreus*). In some embodiments, the host cell will be an industrial *Pantoea* species (e.g., *P. citrea, P. agglomerans*). In some embodiments, the host cell will be an industrial *Pseudomonas* species, (e.g., *P. putida, P. aeruginosa, P. mevalonii*). In some embodiments, the host cell will be an industrial *Streptococcus* species (e.g., *S. equisimiles, S. pyogenes, S. uberis*). In some embodiments, the host cell will be an industrial *Streptomyces* species (e.g., *S. ambofaciens, S.*

*achromogenes, S. avermitilis, S. coelicolor, S. aureofaciens, S. aureus, S. fungicidicus, S. griseus, S. lividans*). In some embodiments, the host cell will be an industrial *Zymomonas* species (e.g., *Z. mobilis, Z. lipolytica*), and the like.

The present disclosure is also suitable for use with a variety of animal cell types, including mammalian cells, for example, human (including 293, WI38, PER.C6 and Bowes melanoma cells), mouse (including 3T3, NS0, NS1, Sp2/0), hamster (CHO, BHK), monkey (COS, FRhL, Vero), and hybridoma cell lines.

In various embodiments, strains that may be used in the practice of the disclosure including both prokaryotic and eukaryotic strains, are readily accessible to the public from a number of culture collections such as American Type Culture Collection (ATCC), Deutsche Sammlung von Mikroorganismen and Zellkulturen GmbH (DSM), Centraalbureau Voor Schimmelcultures (CBS), and Agricultural Research Service Patent Culture Collection, Northern Regional Research Center (NRRL).

In some embodiments, the methods of the present disclosure are also applicable to multi-cellular organisms. For example, the platform could be used for improving the performance of crops. The organisms can comprise a plurality of plants such as *Gramineae, Fetucoideae, Poacoideae, Agrostis, Phleum, Dactylis, Sorgum, Setaria, Zea, Oryza, Triticum, Secale, Avena, Hordeum, Saccharum, Poa, Festuca, Stenotaphrum, Cynodon, Coix, Olyreae, Phareae, Compositae* or *Leguminosae*. For example, the plants can be corn, rice, soybean, cotton, wheat, rye, oats, barley, pea, beans, lentil, peanut, yam bean, cowpeas, velvet beans, clover, alfalfa, lupine, vetch, lotus, sweet clover, *wisteria*, sweet pea, sorghum, millet, sunflower, canola or the like. Similarly, the organisms can include a plurality of animals such as non-human mammals, fish, insects, or the like.

Generating Genetic Diversity Pools for Utilization in the Genetic Design & HTP Microbial Engineering Platform In some embodiments, the methods of the present disclosure are characterized as genetic design. As used herein, the term genetic design refers to the reconstruction or alteration of a host organism's genome through the identification and selection of the most optimum variants of a particular gene, portion of a gene, promoter, stop codon, 5'UTR, 3'UTR, or other DNA sequence to design and create new superior host cells.

In some embodiments, a first step in the genetic design methods of the present disclosure is to obtain an initial genetic diversity pool population with a plurality of sequence variations from which a new host genome may be reconstructed.

In some embodiments, a subsequent step in the genetic design methods taught herein is to use one or more of the aforementioned HTP molecular tool sets (e.g. SNP swapping or promoter swapping) to construct HTP genetic design libraries, which then function as drivers of the genomic engineering process, by providing libraries of particular genomic alterations for testing in a host cell.

Harnessing Diversity Pools from Existing Wild-Type Strains

In some embodiments, the present disclosure teaches methods for identifying the sequence diversity present among microbes of a given wild-type population. Therefore, a diversity pool can be a given number n of wild-type microbes utilized for analysis, with said microbes' genomes representing the "diversity pool."

In some embodiments, the diversity pools can be the result of existing diversity present in the natural genetic variation among said wild-type microbes. This variation may result from strain variants of a given host cell or may be the result of the microbes being different species entirely. Genetic variations can include any differences in the genetic sequence of the strains, whether naturally occurring or not. In some embodiments, genetic variations can include SNPs swaps, PRO swaps, Start/Stop Codon swaps, or STOP swaps, among others.

Harnessing Diversity Pools from Existing Industrial Strain Variants

In other embodiments of the present disclosure, diversity pools are strain variants created during traditional strain improvement processes (e.g., one or more host organism strains generated via random mutation and selected for improved yields over the years). Thus, in some embodiments, the diversity pool or host organisms can comprise a collection of historical production strains.

In particular aspects, a diversity pool may be an original parent microbial strain ($S_1$) with a "baseline" genetic sequence at a particular time point ($S_1Gen_1$) and then any number of subsequent offspring strains ($S_2$, $S_3$, $S_4$, $S_5$, etc., generalizable to $S_{2-n}$) that were derived/developed from said $S_1$ strain and that have a different genome ($S_{2-n}Gen_{2-n}$), in relation to the baseline genome of $S_1$.

For example, in some embodiments, the present disclosure teaches sequencing the microbial genomes in a diversity pool to identify the SNP's present in each strain. In one embodiment, the strains of the diversity pool are historical microbial production strains. Thus, a diversity pool of the present disclosure can include for example, an industrial base strain, and one or more mutated industrial strains produced via traditional strain improvement programs.

Once all SNPs in the diversity pool are identified, the present disclosure teaches methods of SNP swapping and screening methods to delineate (i.e. quantify and characterize) the effects (e.g. creation of a phenotype of interest) of SNPs individually and in groups. Thus, as aforementioned, an initial step in the taught platform can be to obtain an initial genetic diversity pool population with a plurality of sequence variations, e.g. SNPs. Then, a subsequent step in the taught platform can be to use one or more of the aforementioned HTP molecular tool sets (e.g. SNP swapping) to construct HTP genetic design libraries, which then function as drivers of the genomic engineering process, by providing libraries of particular genomic alterations for testing in a microbe.

In some embodiments, the SNP swapping methods of the present disclosure comprise the step of introducing one or more SNPs identified in a mutated strain (e.g., a strain from amongst $S_{2-n}Gen_{2-n}$) to a base strain ($S_1Gen_1$) or wild-type strain.

In other embodiments, the SNP swapping methods of the present disclosure comprise the step of removing one or more SNPs identified in a mutated strain (e.g., a strain from amongst $S_{2-n}Gen_{2-n}$).

Creating Diversity Pools Via Mutagenesis

In some embodiments, the mutations of interest in a given diversity pool population of cells can be artificially generated by any means for mutating strains, including mutagenic chemicals, or radiation. The term "mutagenizing" is used herein to refer to a method for inducing one or more genetic modifications in cellular nucleic acid material.

The term "genetic modification" refers to any alteration of DNA. Representative gene modifications include nucleotide insertions, deletions, substitutions, and combinations thereof, and can be as small as a single base or as large as tens of thousands of bases. Thus, the term "genetic modification" encompasses inversions of a nucleotide sequence and other chromosomal rearrangements, whereby the position or orientation of DNA comprising a region of a chromosome is altered. A chromosomal rearrangement can comprise an intrachromosomal rearrangement or an interchromosomal rearrangement.

In one embodiment, the mutagenizing methods employed in the presently claimed subject matter are substantially random such that a genetic modification can occur at any available nucleotide position within the nucleic acid material to be mutagenized. Stated another way, in one embodiment, the mutagenizing does not show a preference or increased frequency of occurrence at particular nucleotide sequences.

The methods of the disclosure can employ any mutagenic agent including, but not limited to: ultraviolet light, X-ray radiation, gamma radiation, N-ethyl-N-nitrosourea (ENU), methyinitrosourea (MNU), procarbazine (PRC), triethylene melamine (TEM), acrylamide monomer (AA), chlorambucil (CHL), melphalan (MLP), cyclophosphamide (CPP), diethyl sulfate (DES), ethyl methane sulfonate (EMS), methyl methane sulfonate (MMS), 6-mercaptopurine (6-MP), mitomycin-C(MMC), N-methyl-N'-nitro-N-nitrosoguanidine (MNNG), $^3H_2O$, and urethane (UR) (See e.g., Rinchik, 1991; Marker et al., 1997; and Russell, 1990). Additional mutagenic agents are well known to persons having skill in the art, including those described in http://www.iephb.nw.ru/~spirov/hazard/mutagen_1st. html.

The term "mutagenizing" also encompasses a method for altering (e.g., by targeted mutation) or modulating a cell function, to thereby enhance a rate, quality, or extent of mutagenesis. For example, a cell can be altered or modulated to thereby be dysfunctional or deficient in DNA repair, mutagen metabolism, mutagen sensitivity, genomic stability, or combinations thereof. Thus, disruption of gene functions that normally maintain genomic stability can be used to enhance mutagenesis. Representative targets of disruption include, but are not limited to DNA ligase I (Bentley et al., 2002) and casein kinase I (U.S. Pat. No. 6,060,296).

In some embodiments, site-specific mutagenesis (e.g., primer-directed mutagenesis using a commercially available kit such as the Transformer Site Directed mutagenesis kit (Clontech)) is used to make a plurality of changes throughout a nucleic acid sequence in order to generate nucleic acid encoding a cleavage enzyme of the present disclosure.

The frequency of genetic modification upon exposure to one or more mutagenic agents can be modulated by varying dose and/or repetition of treatment, and can be tailored for a particular application.

Thus, in some embodiments, "mutagenesis" as used herein comprises all techniques known in the art for inducing mutations, including error-prone PCR mutagenesis, oligonucleotide-directed mutagenesis, site-directed mutagenesis, and iterative sequence recombination by any of the techniques described herein.

Single Locus Mutations to Generate Diversity

In some embodiments, the present disclosure teaches mutating cell populations by introducing, deleting, or replacing selected portions of genomic DNA. Thus, in some embodiments, the present disclosure teaches methods for targeting mutations to a specific locus. In other embodiments, the present disclosure teaches the use of gene editing technologies such as ZFNs, TALENS, or CRISPR, to selectively edit target DNA regions.

In other embodiments, the present disclosure teaches mutating selected DNA regions outside of the host organism, and then inserting the mutated sequence back into the host organism. For example, in some embodiments, the present disclosure teaches mutating native or synthetic promoters to produce a range of promoter variants with various expression properties (see promoter ladder infra). In other embodiments, the present disclosure is compatible with single gene optimization techniques, such as ProSAR (Fox et al. 2007. "Improving catalytic function by ProSAR-driven enzyme evolution." Nature Biotechnology Vol 25 (3) 338-343, incorporated by reference herein).

In some embodiments, the selected regions of DNA are produced in vitro via gene shuffling of natural variants, or shuffling with synthetic oligos, plasmid-plasmid recombination, virus plasmid recombination, virus-virus recombination. In other embodiments, the genomic regions are produced via error-prone PCR (see e.g., FIG. 1).

In some embodiments, generating mutations in selected genetic regions is accomplished by "reassembly PCR." Briefly, oligonucleotide primers (oligos) are synthesized for PCR amplification of segments of a nucleic acid sequence of interest, such that the sequences of the oligonucleotides overlap the junctions of two segments. The overlap region is typically about 10 to 100 nucleotides in length. Each of the segments is amplified with a set of such primers. The PCR products are then "reassembled" according to assembly protocols. In brief, in an assembly protocol, the PCR products are first purified away from the primers, by, for example, gel electrophoresis or size exclusion chromatography. Purified products are mixed together and subjected to about 1-10 cycles of denaturing, reannealing, and extension in the presence of polymerase and deoxynucleoside triphosphates (dNTP's) and appropriate buffer salts in the absence of additional primers ("self-priming"). Subsequent PCR with primers flanking the gene are used to amplify the yield of the fully reassembled and shuffled genes.

In some embodiments of the disclosure, mutated DNA regions, such as those discussed above, are enriched for mutant sequences so that the multiple mutant spectrum, i.e. possible combinations of mutations, is more efficiently sampled. In some embodiments, mutated sequences are identified via a mutS protein affinity matrix (Wagner et al., Nucleic Acids Res. 23(19):3944-3948 (1995); Su et al., Proc. Natl. Acad. Sci. (U.S.A.), 83:5057-5061(1986)) with a preferred step of amplifying the affinity-purified material in vitro prior to an assembly reaction. This amplified material is then put into an assembly or reassembly PCR reaction as described in later portions of this application.

Promoter Ladders

Promoters regulate the rate at which genes are transcribed and can influence transcription in a variety of ways. Constitutive promoters, for example, direct the transcription of their associated genes at a constant rate regardless of the internal or external cellular conditions, while regulatable promoters increase or decrease the rate at which a gene is transcribed depending on the internal and/or the external cellular conditions, e.g. growth rate, temperature, responses to specific environmental chemicals, and the like. Promoters can be isolated from their normal cellular contexts and engineered to regulate the expression of virtually any gene, enabling the effective modification of cellular growth, product yield and/or other phenotypes of interest.

In some embodiments, the present disclosure teaches methods for producing promoter ladder libraries for use in downstream genetic design methods. For example, in some embodiments, the present disclosure teaches methods of identifying one or more promoters and/or generating variants of one or more promoters within a host cell, which exhibit a range of expression strengths, or superior regulatory properties. A particular combination of these identified and/or generated promoters can be grouped together as a promoter ladder, which is explained in more detail below.

In some embodiments, the present disclosure teaches the use of promoter ladders. In some embodiments, the promoter ladders of the present disclosure comprise promoters exhibiting a continuous range of expression profiles. For example, in some embodiments, promoter ladders are created by: identifying natural, native, or wild-type promoters that exhibit a range of expression strengths in response to a stimuli, or through constitutive expression (see e.g., FIG. 20 and FIGS. 28-30). These identified promoters can be grouped together as a promoter ladder.

In other embodiments, the present disclosure teaches the creation of promoter ladders exhibiting a range of expression profiles across different conditions. For example, in some embodiments, the present disclosure teaches creating a ladder of promoters with expression peaks spread throughout the different stages of a fermentation (see e.g., FIG. 28). In other embodiments, the present disclosure teaches creating a ladder of promoters with different expression peak dynamics in response to a specific stimulus (see e.g., FIG. 29). Persons skilled in the art will recognize that the regulatory promoter ladders of the present disclosure can be representative of any one or more regulatory profiles.

In some embodiments, the promoter ladders of the present disclosure are designed to perturb gene expression in a predictable manner across a continuous range of responses. In some embodiments, the continuous nature of a promoter ladder confers strain improvement programs with additional predictive power. For example, in some embodiments, swapping promoters or termination sequences of a selected metabolic pathway can produce a host cell performance curve, which identifies the most optimum expression ratio or profile; producing a strain in which the targeted gene is no longer a limiting factor for a particular reaction or genetic cascade, while also avoiding unnecessary over expression or misexpression under inappropriate circumstances. In some embodiments, promoter ladders are created by: identifying natural, native, or wild-type promoters exhibiting the desired profiles. In other embodiments, the promoter ladders are created by mutating naturally occurring promoters to derive multiple mutated promoter sequences. Each of these mutated promoters is tested for effect on target gene expression. In some embodiments, the edited promoters are tested for expression activity across a variety of conditions, such that each promoter variant's activity is documented/characterized/annotated and stored in a database. The resulting edited promoter variants are subsequently organized into promoter ladders arranged based on the strength of their expression (e.g., with highly expressing variants near the top, and attenuated expression near the bottom, therefore leading to the term "ladder").

In some embodiments, the present disclosure teaches promoter ladders that are a combination of identified naturally occurring promoters and mutated variant promoters.

In some embodiments, the present disclosure teaches methods of identifying natural, native, or wild-type promoters that satisfied both of the following criteria: 1) represented a ladder of constitutive promoters; and 2) could be encoded by short DNA sequences, ideally less than 100 base pairs. In some embodiments, constitutive promoters of the present disclosure exhibit constant gene expression across two selected growth conditions (typically compared among conditions experienced during industrial cultivation). In some embodiments, the promoters of the present disclosure will consist of a ~60 base pair core promoter, and a 5' UTR between 26- and 40 base pairs in length.

In some embodiments, one or more of the aforementioned identified naturally occurring promoter sequences are chosen for gene editing. In some embodiments, the natural promoters are edited via any of the mutation methods described supra. In other embodiments, the promoters of the present disclosure are edited by synthesizing new promoter variants with the desired sequence.

The entire disclosure of U.S. Patent Application No. 62/264,232, filed on Dec. 7, 2015, is hereby incorporated by reference in its entirety for all purposes A non-exhaustive list of the promoters of the present disclosure is provided in the below Table 1. Each of the promoter sequences can be referred to as a heterologous promoter or heterologous promoter polynucleotide.

TABLE 1

Selected promoter sequences of the present disclosure.

| SEQ ID No. | Promoter Short Name | Promoter Name |
| --- | --- | --- |
| 1 | P1 | Pcg0007_lib_39 |
| 2 | P2 | Pcg0007 |
| 3 | P3 | Pcg1860 |
| 4 | P4 | Pcg0755 |
| 5 | P5 | Pcg0007_265 |
| 6 | P6 | Pcg3381 |
| 7 | P7 | Pcg0007_119 |
| 8 | P8 | Pcg3121 |

In some embodiments, the promoters of the present disclosure exhibit at least 100%, 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, or 75% sequence identity with a promoter from the above table.

Terminator Ladders

In some embodiments, the present disclosure teaches methods of improving genetically engineered host strains by providing one or more transcriptional termination sequences at a position 3' to the end of the RNA encoding element. In some embodiments, the present disclosure teaches that the addition of termination sequences improves the efficiency of RNA transcription of a selected gene in the genetically engineered host. In other embodiments, the present disclosure teaches that the addition of termination sequences reduces the efficiency of RNA transcription of a selected gene in the genetically engineered host. Thus in some embodiments, the terminator ladders of the present disclosure comprises a series of terminator sequences exhibiting a range of transcription efficiencies (e.g., one weak terminator, one average terminator, and one strong promoter).

A transcriptional termination sequence may be any nucleotide sequence, which when placed transcriptionally downstream of a nucleotide sequence encoding an open reading frame, causes the end of transcription of the open reading frame. Such sequences are known in the art and may be of prokaryotic, eukaryotic or phage origin. Examples of terminator sequences include, but are not limited to, PTH-terminator, pET-T7 terminator, T3-Tφ terminator, pBR322-P4 terminator, vesicular stomatitis virus terminator, rrnB-T1 terminator, rrnC terminator, TTadc transcriptional terminator, and yeast-recognized termination sequences, such as Matα (α-factor) transcription terminator, native α-factor transcription termination sequence, ADR1transcription termination sequence, ADH2transcription termination sequence, and GAPD transcription termination sequence. A non-exhaustive listing of transcriptional terminator sequences may be found in the iGEM registry, which is available at: http://partsregistry.org/Terminators/Catalog.

In some embodiments, transcriptional termination sequences may be polymerase-specific or nonspecific, however, transcriptional terminators selected for use in the present embodiments should form a 'functional combination' with the selected promoter, meaning that the terminator sequence should be capable of terminating transcription by the type of RNA polymerase initiating at the promoter. For example, in some embodiments, the present disclosure teaches a eukaryotic RNA pol II promoter and eukaryotic RNA pol II terminators, a T7 promoter and T7 terminators, a T3 promoter and T3 terminators, a yeast-recognized promoter and yeast-recognized termination sequences, etc., would generally form a functional combination. The identity of the transcriptional termination sequences used may also be selected based on the efficiency with which transcription is terminated from a given promoter. For example, a heterologous transcriptional terminator sequence may be provided transcriptionally downstream of the RNA encoding element to achieve a termination efficiency of at least 60%, at least 70%, at least 75%, at least 80%, at least 85%, at least 90%, at least 91%, at least 92%, at least 93%, at least 94%, at least 95%, at least 96%, at least 97%, at least 98%, or at least 99% from a given promoter.

In some embodiments, efficiency of RNA transcription from the engineered expression construct can be improved by providing nucleic acid sequence forms a secondary structure comprising two or more hairpins at a position 3' to the end of the RNA encoding element. Not wishing to be bound by a particular theory, the secondary structure destabilizes the transcription elongation complex and leads to the polymerase becoming dissociated from the DNA template, thereby minimizing unproductive transcription of non-functional sequence and increasing transcription of the desired RNA. Accordingly, a termination sequence may be provided that forms a secondary structure comprising two or more adjacent hairpins. Generally, a hairpin can be formed by a palindromic nucleotide sequence that can fold back on itself to form a paired stem region whose arms are connected by a single stranded loop. In some embodiments, the termination sequence comprises 2, 3, 4, 5, 6, 7, 8, 9, 10 or more adjacent hairpins. In some embodiments, the adjacent hairpins are separated by 0, 1, 2, 3, 4, 5, 6, 7, 8, 9, 10, 11, 12, 13, 14, or 15 unpaired nucleotides. In some embodiments, a hairpin stem comprises 4, 5, 6, 7, 8, 9, 10, 11, 12, 13, 14, 15, 16, 17, 18, 19, 20, 21, 22, 23, 24, 25, 26, 27, 28, 29, 30 or more base pairs in length. In certain embodiments, a hairpin stem is 12 to 30 base pairs in length. In certain embodiments, the termination sequence comprises two or more medium-sized hairpins having stem region comprising about 9 to 25 base pairs. In some embodiments, the hairpin comprises a loop-forming region of 1, 2, 3, 4, 5, 6, 7, 8, 9, or 10 nucleotides. In some embodiments, the loop-forming region comprises 4-8 nucleotides. Not wishing to be bound by a particular theory, stability of the secondary structure can be correlated with termination efficiency. Hairpin stability is determined by its length, the number of mismatches or bulges it contains and the base composition of the paired region. Pairings between guanine and cytosine have three hydrogen bonds and are more stable compared to adenine-thymine pairings, which have only two. The G/C content of a hairpin-forming palindromic nucleotide sequence can be at least 60%, at least 65%, at least 70%, at least 75%, at least 80%, at least 85%, at least 90% or more. In some embodiments, the G/C content of a hairpin-forming palindromic nucleotide sequence is at least 80%. In some embodiments, the termination sequence is derived from one or more transcriptional terminator sequences of prokaryotic, eukaryotic or phage origin. In some embodiments, a nucleotide sequence encoding a series of 4, 5, 6, 7, 8, 9, 10 or more adenines (A) are provided 3' to the termination sequence.

In some embodiments, the present disclosure teaches the use of a series of tandem termination sequences. In some embodiments, the first transcriptional terminator sequence of a series of 2, 3, 4, 5, 6, 7, or more may be placed directly 3' to the final nucleotide of the dsRNA encoding element or at a distance of at least 1-5, 5-10, 10-15, 15-20, 20-25, 25-30, 30-35, 35-40, 40-45, 45-50, 50-100, 100-150, 150-200, 200-300, 300-400, 400-500, 500-1,000 or more nucleotides 3' to the final nucleotide of the dsRNA encoding element. The number of nucleotides between tandem transcriptional terminator sequences may be varied, for example, transcriptional terminator sequences may be separated by 0, 1, 2, 3, 4, 5, 6, 7, 8, 9, 10, 10-15, 15-20, 20-25, 25-30, 30-35, 35-40, 40-45, 45-50 or more nucleotides. In some embodiments, the transcriptional terminator sequences may be selected based on their predicted secondary structure as determined by a structure prediction algorithm. Structural prediction programs are well known in the art and include, for example, CLC Main Workbench.

Persons having skill in the art will recognize that the methods of the present disclosure are compatible with any termination sequence. In some embodiments, the present disclosure teaches use of annotated *Corynebacterium glutamicum* terminators as disclosed in from Pfeifer-Sancar et al. 2013. "Comprehensive analysis of the *Corynebacterium glutamicum* transcriptome using an improved RNAseq technique" Pfeifer-Sancar et al. BMC Genomics 2013, 14:888). In other embodiments, the present disclosure teaches use of transcriptional terminator sequences found in the iGEM registry, which is available at: http://partsregistry.org/Terminators/Catalog. A non-exhaustive listing of transcriptional terminator sequences of the present disclosure is provided in Table 1.1 below.

TABLE 1.1

Non-exhaustive list of termination sequences of the present disclosure.

| Name | Description | Direction | Length |
|---|---|---|---|
| *E. coli* | | | |
| BBa_B0010 | T1 from *E. coli* rrnB | Forward | 80 |
| BBa_B0012 | TE from coliphageT7 | Forward | 41 |
| BBa_B0013 | TE from coliphage T7 (+/−) | Forward | 47 |
| BBa_B0015 | double terminator (B0010-B0012) | Forward | 129 |
| BBa_B0017 | double terminator (B0010-B0010) | Forward | 168 |
| BBa_B0053 | Terminator (His) | Forward | 72 |
| BBa_B0055 | -- No description -- | | 78 |

TABLE 1.1-continued

Non-exhaustive list of termination sequences of the present disclosure.

| | | | |
|---|---|---|---|
| BBa_B1002 | Terminator (artificial, small, % T ~= 85%) | Forward | 34 |
| BBa_B1003 | Terminator (artificial, small, % T ~= 80) | Forward | 34 |
| BBa_B1004 | Terminator (artificial, small, % T ~= 55) | Forward | 34 |
| BBa_B1005 | Terminator (artificial, small, % T ~= 25% | Forward | 34 |
| BBa_B1006 | Terminator (artificial, large, % T ~>90) | Forward | 39 |
| BBa_B1010 | Terminator (artificial, large, % T ~<10) | Forward | 40 |
| BBa_I11013 | Modification of biobricks part BBa_B0015 | | 129 |
| BBa_I51003 | -- No description -- | | 110 |
| BBa_J61048 | [rnpB-T1] Terminator | Forward | 113 |
| BBa_K1392970 | Terminator + Tetr Promoter + T4 Endolysin | | 623 |
| BBa_K1486001 | Arabinose promoter + CpxR | Forward | 1924 |
| BBa_K1486005 | Arabinose promoter + sfGFP-CpxR [Cterm] | Forward | 2668 |
| BBa_K1486009 | CxpR & Split IFP1.4 [Nterm + Nterm] | Forward | 3726 |
| BBa_K780000 | Terminator for *Bacillus subtilis* | | 54 |
| BBa_K864501 | T22, P22 late terminator | Forward | 42 |
| BBa_K864600 | T0 (21 imm) transcriptional terminator | Forward | 52 |
| BBa_K864601 | Lambda t1 transcriptional terminator | Forward | |
| BBa_B0011 | LuxICDABEG (+/−) | Bidirectional | 46 |
| BBa_B0014 | double terminator (B0012-B0011) | Bidirectional | 95 |
| BBa_B0021 | LuxICDABEG (+/−), reversed | Bidirectional | 46 |
| BBa_B0024 | double terminator (B0012-B0011), reversed | Bidirectional | 95 |
| BBa_B0050 | Terminator (pBR322, +/−) | Bidirectional | 33 |
| BBa_B0051 | Terminator (yciA/tonA, +/−) | Bidirectional | 35 |
| BBa_B1001 | Terminator (artifical, small, % T ~= 90) | Bidirectional | 34 |
| BBa_B1007 | Terminator (artificial, large, % T ~= 80) | Bidirectional | 40 |
| BBa_B1008 | Terminator (artificial, large, % T ~= 70) | Bidirectional | 40 |
| BBa_B1009 | Terminator (artificial, large, % T ~= 40%) | Bidirectional | 40 |
| BBa_K187025 | terminator in pAB, BioBytes plasmid | | 60 |
| BBa_K259006 | GFP-Terminator | Bidirectional | 823 |
| BBa_B0020 | Terminator (Reverse B0010) | Reverse | 82 |
| BBa_B0022 | TE from coliphageT7, reversed | Reverse | 41 |
| BBa_B0023 | TE from coliphage T7, reversed | Reverse | 47 |
| BBa_B0025 | double terminator (B0015), reversed | Reverse | 129 |
| BBa_B0052 | Terminator (rrnC) | Forward | 41 |
| BBa_B0060 | Terminator (Reverse B0050) | Bidirectional | 33 |
| BBa_B0061 | Terminator (Reverse B0051) | Bidirectional | 35 |
| BBa_B0063 | Terminator (Reverse B0053) | Reverse | 72 |
| Yeast and other Eukaryotes | | | |
| BBa_J63002 | ADH1 terminator from *S. cerevisiae* | Forward | 225 |
| BBa_K110012 | STE2 terminator | Forward | 123 |
| BBa_K1462070 | cyc1 | | 250 |
| BBa_K1486025 | ADH1 Terminator | Forward | 188 |
| BBa_K392003 | yeast ADH1 terminator | | 129 |
| BBa_K801011 | TEF1 yeast terminator | | 507 |
| BBa_K801012 | ADH1 yeast terminator | | 349 |
| BBa_Y1015 | CycE1 | | 252 |
| BBa_J52016 | eukaryotic - derived from SV40 early poly A signal sequence | Forward | 238 |
| BBa_J63002 | ADH1 terminator from *S. cerevisiae* | Forward | 225 |
| BBa_K110012 | STE2 terminator | Forward | 123 |
| BBa_K1159307 | 35S Terminator of Cauliflower Mosaic Virus (CaMV) | | 217 |
| BBa_K1462070 | cyc1 | | 250 |
| BBa_K1484215 | nopaline synthase terminator | | 293 |
| BBa_K1486025 | ADH1 Terminator | Forward | 188 |
| BBa_K392003 | yeast ADH1 terminator | | 129 |
| BBa_K404108 | hGH terminator | | 481 |
| BBa_K404116 | hGH_[AAV2]-right-ITR | | 632 |
| BBa_K678012 | SV40 poly A, terminator for mammalian cells | | 139 |
| BBa_K678018 | hGH poly A, terminator for mammalian cells | | 635 |
| BBa_K678019 | BGH poly A, mammalian terminator | | 233 |
| BBa_K678036 | trpC terminator for *Aspergillus nidulans* | | 759 |
| BBa_K678037 | T1-motni, terminator for *Aspergillus niger* | | 1006 |
| BBa_K678038 | T2-motni, terminator for *Aspergillus niger* | | 990 |

TABLE 1.1-continued

Non-exhaustive list of termination sequences of the present disclosure.

| | | |
|---|---|---|
| BBa_K678039 | T3-motni, terminator for *Aspergillus niger* | 889 |
| BBa_K801011 | TEF1 yeast terminator | 507 |
| BBa_K801012 | ADH1 yeast terminator | 349 |
| BBa_Y1015 | CycE1 | 252 |

*Corynebacterium*

| Terminator | Terminator Start | Terminator End | strand | Transcript End | DNA Sequence |
|---|---|---|---|---|---|
| cg0001 T1 | 1628 | 1647 | + | loop | SEQ ID NO: 9 |
| cg0007 T2 | 7504 | 7529 | + | stem 1 | SEQ ID NO: 10 |
| cg0371 T3 | 322229 | 322252 | + | stem 1 | SEQ ID NO: 11 |
| cg0480 T4 | 421697 | 421720 | − | stem 1 | SEQ ID NO: 12 |
| cg0494 T5 | 436587 | 436608 | + | loop | SEQ ID NO: 13 |
| cg0564 T6 | 499895 | 499917 | + | stem 1 | SEQ ID NO: 14 |
| cg0610 T7 | 541016 | 541039 | + | stem 2 | SEQ ID NO: 15 |
| cg0695 T8 | 613847 | 613868 | − | loop | SEQ ID NO: 16 |

Hypothesis-Driven Diversity Pools and Hill Climbing

The present disclosure teaches that the HTP genomic engineering methods of the present disclosure do not require prior genetic knowledge in order to achieve significant gains in host cell performance. Indeed, the present disclosure teaches methods of generating diversity pools via several functionally agnostic approaches, including random mutagenesis, and identification of genetic diversity among pre-existing host cell variants (e.g., such as the comparison between a wild type host cell and an industrial variant).

In some embodiments however, the present disclosure also teaches hypothesis-driven methods of designing genetic diversity mutations that will be used for downstream HTP engineering. That is, in some embodiments, the present disclosure teaches the directed design of selected mutations. In some embodiments, the directed mutations are incorporated into the engineering libraries of the present disclosure (e.g., SNP swap, PRO swap, or STOP swap).

In some embodiments, the present disclosure teaches the creation of directed mutations based on gene annotation, hypothesized (or confirmed) gene function, or location within a genome. The diversity pools of the present disclosure may include mutations in genes hypothesized to be involved in a specific metabolic or genetic pathway associated in the literature with increased performance of a host cell. In other embodiments, the diversity pool of the present disclosure may also include mutations to genes present in an operon associated with improved host performance. In yet other embodiments, the diversity pool of the present disclosure may also include mutations to genes based on algorithmic predicted function, or other gene annotation.

In some embodiments, the present disclosure teaches a "shell" based approach for prioritizing the targets of hypothesis-driven mutations. The shell metaphor for target prioritization is based on the hypothesis that only a handful of primary genes are responsible for most of a particular aspect of a host cell's performance (e.g., production of a single biomolecule). These primary genes are located at the core of the shell, followed by secondary effect genes in the second layer, tertiary effects in the third shell, and . . . etc. For example, in one embodiment the core of the shell might comprise genes encoding critical biosynthetic enzymes within a selected metabolic pathway (e.g., production of citric acid). Genes located on the second shell might comprise genes encoding for other enzymes within the biosynthetic pathway responsible for product diversion or feedback signaling. Third tier genes under this illustrative metaphor would likely comprise regulatory genes responsible for modulating expression of the biosynthetic pathway, or for regulating general carbon flux within the host cell.

The present disclosure also teaches "hill climb" methods for optimizing performance gains from every identified mutation. In some embodiments, the present disclosure teaches that random, natural, or hypothesis-driven mutations in HTP diversity libraries can result in the identification of genes associated with host cell performance. For example, the present methods may identify one or more beneficial SNPs located on, or near, a gene coding sequence. This gene might be associated with host cell performance, and its identification can be analogized to the discovery of a performance "hill" in the combinatorial genetic mutation space of an organism.

In some embodiments, the present disclosure teaches methods of exploring the combinatorial space around the identified hill embodied in the SNP mutation. That is, in some embodiments, the present disclosure teaches the perturbation of the identified gene and associated regulatory sequences in order to optimize performance gains obtained from that gene node (i.e., hill climbing). Thus, according to the methods of the present disclosure, a gene might first be identified in a diversity library sourced from random mutagenesis, but might be later improved for use in the strain improvement program through the directed mutation of another sequence within the same gene.

The concept of hill climbing can also be expanded beyond the exploration of the combinatorial space surrounding a single gene sequence. In some embodiments, a mutation in a specific gene might reveal the importance of a particular metabolic or genetic pathway to host cell performance. For example, in some embodiments, the discovery that a mutation in a single RNA degradation gene resulted in significant host performance gains could be used as a basis for mutating related RNA degradation genes as a means for extracting additional performance gains from the host organism. Persons having skill in the art will recognize variants of the above describe shell and hill climb approaches to directed genetic design. High-throughput Screening.

Cell Culture and Fermentation

Cells of the present disclosure can be cultured in conventional nutrient media modified as appropriate for any desired biosynthetic reactions or selections. In some embodiments, the present disclosure teaches culture in inducing media for activating promoters. In some embodiments, the present disclosure teaches media with selection agents, including selection agents of transformants (e.g., antibiotics), or selection of organisms suited to grow under inhibiting conditions (e.g., high ethanol conditions). In some embodiments, the present disclosure teaches growing cell cultures in media optimized for cell growth. In other embodiments, the present disclosure teaches growing cell cultures in media optimized for product yield. In some embodiments, the present disclosure teaches growing cultures in media capable of inducing cell growth and also contains the necessary precursors for final product production (e.g., high levels of sugars for ethanol production).

Culture conditions, such as temperature, pH and the like, are those suitable for use with the host cell selected for expression, and will be apparent to those skilled in the art. As noted, many references are available for the culture and production of many cells, including cells of bacterial, plant, animal (including mammalian) and archaebacterial origin. See e.g., Sambrook, Ausubel (all supra), as well as Berger, *Guide to Molecular Cloning Techniques, Methods in Enzymology* volume 152 Academic Press, Inc., San Diego, Calif.; and Freshney (1994) *Culture of Animal Cells, a Manual of Basic Technique*, third edition, Wiley-Liss, New York and the references cited therein; Doyle and Griffiths (1997) *Mammalian Cell Culture: Essential Techniques* John Wiley and Sons, N.Y.; Humason (1979) *Animal Tissue Techniques*, fourth edition W.H. Freeman and Company; and Ricciardelle et al., (1989) *In Vitro Cell Dev. Biol.* 25:1016-1024, all of which are incorporated herein by reference. For plant cell culture and regeneration, Payne et al. (1992)*Plant Cell and Tissue Culture in Liquid Systems* John Wiley & Sons, Inc. New York, N.Y.; Gamborg and Phillips (eds) (1995) *Plant Cell, Tissue and Organ Culture*; Fundamental Methods Springer Lab Manual, Springer-Verlag (Berlin Heidelberg N.Y.); Jones, ed. (1984) *Plant Gene Transfer and Expression Protocols*, Humana Press, Totowa, N.J. and *Plant Molecular Biology* (1993) R. R. D. Croy, Ed. Bios Scientific Publishers, Oxford, U.K. ISBN 0 12 198370 6, all of which are incorporated herein by reference. Cell culture media in general are set forth in Atlas and Parks (eds.) *The Handbook of Microbiological Media* (1993) CRC Press, Boca Raton, Fla., which is incorporated herein by reference. Additional information for cell culture is found in available commercial literature such as the *Life Science Research Cell Culture Catalogue* from Sigma-Aldrich, Inc (St Louis, Mo.) ("Sigma-LSRCCC") and, for example, *The Plant Culture Catalogue* and supplement also from Sigma-Aldrich, Inc (St Louis, Mo.) ("Sigma-PCCS"), all of which are incorporated herein by reference.

The culture medium to be used must in a suitable manner satisfy the demands of the respective strains. Descriptions of culture media for various microorganisms are present in the "Manual of Methods for General Bacteriology" of the American Society for Bacteriology (Washington D.C., USA, 1981).

The present disclosure furthermore provides a process for fermentative preparation of a product of interest, comprising the steps of: a) culturing a microorganism according to the present disclosure in a suitable medium, resulting in a fermentation broth; and b) concentrating the product of interest in the fermentation broth of a) and/or in the cells of the microorganism.

In some embodiments, the present disclosure teaches that the microorganisms produced may be cultured continuously—as described, for example, in WO 05/021772—or discontinuously in a batch process (batch cultivation) or in a fed-batch or repeated fed-batch process for the purpose of producing the desired organic-chemical compound. A summary of a general nature about known cultivation methods is available in the textbook by Chmiel (Bioprozeßtechnik. 1: Einführung in die Bioverfahrenstechnik (Gustav Fischer Verlag, Stuttgart, 1991)) or in the textbook by Storhas (Bioreaktoren and periphere Einrichtungen (Vieweg Verlag, Braunschweig/Wiesbaden, 1994)).

In some embodiments, the cells of the present disclosure are grown under batch or continuous fermentations conditions.

Classical batch fermentation is a closed system, wherein the compositions of the medium is set at the beginning of the fermentation and is not subject to artificial alternations during the fermentation. A variation of the batch system is a fed-batch fermentation which also finds use in the present disclosure. In this variation, the substrate is added in increments as the fermentation progresses. Fed-batch systems are useful when catabolite repression is likely to inhibit the metabolism of the cells and where it is desirable to have limited amounts of substrate in the medium. Batch and fed-batch fermentations are common and well known in the art.

Continuous fermentation is a system where a defined fermentation medium is added continuously to a bioreactor and an equal amount of conditioned medium is removed simultaneously for processing and harvesting of desired biomolecule products of interest. In some embodiments, continuous fermentation generally maintains the cultures at a constant high density where cells are primarily in log phase growth. In some embodiments, continuous fermentation generally maintains the cultures at a stationary or late log/stationary, phase growth. Continuous fermentation systems strive to maintain steady state growth conditions.

Methods for modulating nutrients and growth factors for continuous fermentation processes as well as techniques for maximizing the rate of product formation are well known in the art of industrial microbiology.

For example, a non-limiting list of carbon sources for the cultures of the present disclosure include, sugars and carbohydrates such as, for example, glucose, sucrose, lactose, fructose, maltose, molasses, sucrose-containing solutions from sugar beet or sugar cane processing, starch, starch hydrolysate, and cellulose; oils and fats such as, for example, soybean oil, sunflower oil, groundnut oil and coconut fat; fatty acids such as, for example, palmitic acid, stearic acid, and linoleic acid; alcohols such as, for example, glycerol, methanol, and ethanol; and organic acids such as, for example, acetic acid or lactic acid.

A non-limiting list of the nitrogen sources for the cultures of the present disclosure include, organic nitrogen-containing compounds such as peptones, yeast extract, meat extract, malt extract, corn steep liquor, soybean flour, and urea; or inorganic compounds such as ammonium sulfate, ammonium chloride, ammonium phosphate, ammonium carbonate, and ammonium nitrate. The nitrogen sources can be used individually or as a mixture.

A non-limiting list of the possible phosphorus sources for the cultures of the present disclosure include, phosphoric acid, potassium dihydrogen phosphate or dipotassium hydrogen phosphate or the corresponding sodium-containing salts.

The culture medium may additionally comprise salts, for example in the form of chlorides or sulfates of metals such as, for example, sodium, potassium, magnesium, calcium and iron, such as, for example, magnesium sulfate or iron sulfate, which are necessary for growth.

Finally, essential growth factors such as amino acids, for example homoserine and vitamins, for example thiamine, biotin or pantothenic acid, may be employed in addition to the abovementioned substances.

In some embodiments, the pH of the culture can be controlled by any acid or base, or buffer salt, including, but not limited to sodium hydroxide, potassium hydroxide, ammonia, or aqueous ammonia; or acidic compounds such as phosphoric acid or sulfuric acid in a suitable manner. In some embodiments, the pH is generally adjusted to a value of from 6.0 to 8.5, preferably 6.5 to 8.

In some embodiments, the cultures of the present disclosure may include an anti-foaming agent such as, for example, fatty acid polyglycol esters. In some embodiments the cultures of the present disclosure are modified to stabilize the plasmids of the cultures by adding suitable selective substances such as, for example, antibiotics.

In some embodiments, the culture is carried out under aerobic conditions. In order to maintain these conditions, oxygen or oxygen-containing gas mixtures such as, for example, air are introduced into the culture. It is likewise possible to use liquids enriched with hydrogen peroxide. The fermentation is carried out, where appropriate, at elevated pressure, for example at an elevated pressure of from 0.03 to 0.2 MPa. The temperature of the culture is normally from 20° C. to 45° C. and preferably from 25° C. to 40° C., particularly preferably from 30° C. to 37° C. In batch or fed-batch processes, the cultivation is preferably continued until an amount of the desired product of interest (e.g. an organic-chemical compound) sufficient for being recovered has formed. This aim can normally be achieved within 10 hours to 160 hours. In continuous processes, longer cultivation times are possible. The activity of the microorganisms results in a concentration (accumulation) of the product of interest in the fermentation medium and/or in the cells of said microorganisms.

In some embodiments, the culture is carried out under anaerobic conditions.

Screening

In some embodiments, the present disclosure teaches high-throughput initial screenings. In other embodiments, the present disclosure also teaches robust tank-based validations of performance data (see FIG. 6B).

In some embodiments, the high-throughput screening process is designed to predict performance of strains in bioreactors. As previously described, culture conditions are selected to be suitable for the organism and reflective of bioreactor conditions. Individual colonies are picked and transferred into 96 well plates and incubated for a suitable amount of time. Cells are subsequently transferred to new 96 well plates for additional seed cultures, or to production cultures. Cultures are incubated for varying lengths of time, where multiple measurements may be made. These may include measurements of product, biomass or other characteristics that predict performance of strains in bioreactors. High-throughput culture results are used to predict bioreactor performance.

In some embodiments, the tank-based performance validation is used to confirm performance of strains isolated by high throughput screening. Fermentation processes/conditions are obtained from client sites. Candidate strains are screened using bench scale fermentation reactors (e.g., reactors disclosed in Table 5 of the present disclosure) for relevant strain performance characteristics such as productivity or yield.

Product Recovery and Quantification

Methods for screening for the production of products of interest are known to those of skill in the art and are discussed throughout the present specification. Such methods may be employed when screening the strains of the disclosure.

In some embodiments, the present disclosure teaches methods of improving strains designed to produce non-secreted intracellular products. For example, the present disclosure teaches methods of improving the robustness, yield, efficiency, or overall desirability of cell cultures producing intracellular enzymes, oils, pharmaceuticals, or other valuable small molecules or peptides. The recovery or isolation of non-secreted intracellular products can be achieved by lysis and recovery techniques that are well known in the art, including those described herein.

For example, in some embodiments, cells of the present disclosure can be harvested by centrifugation, filtration, settling, or other method. Harvested cells are then disrupted by any convenient method, including freeze-thaw cycling, sonication, mechanical disruption, or use of cell lysing agents, or other methods, which are well known to those skilled in the art.

The resulting product of interest, e.g. a polypeptide, may be recovered/isolated and optionally purified by any of a number of methods known in the art. For example, a product polypeptide may be isolated from the nutrient medium by conventional procedures including, but not limited to: centrifugation, filtration, extraction, spray-drying, evaporation, chromatography (e.g., ion exchange, affinity, hydrophobic interaction, chromatofocusing, and size exclusion), or precipitation. Finally, high performance liquid chromatography (HPLC) can be employed in the final purification steps. (See for example Purification of intracellular protein as described in Parry et al., 2001, *Biochem.* 1353:117, and Hong et al., 2007, *Appl. Microbiol. Biotechnol.* 73:1331, both incorporated herein by reference).

In addition to the references noted supra, a variety of purification methods are well known in the art, including, for example, those set forth in: Sandana (1997) *Bioseparation of Proteins*, Academic Press, Inc.; Bollag et al. (1996) *Protein Methods*, $2^{nd}$ Edition, Wiley-Liss, N.Y.; Walker (1996) *The Protein Protocols Handbook* Humana Press, N.J.; Harris and Angal (1990) *Protein Purification Applications: A Practical Approach*, IRL Press at Oxford, Oxford, England; Harris and Angal *Protein Purification Methods: A Practical Approach*, IRL Press at Oxford, Oxford, England; Scopes (1993) *Protein Purification: Principles and Practice* $3^{rd}$ Edition, Springer Verlag, N.Y.; Janson and Ryden (1998) *Protein Purification: Principles, High Resolution Methods and Applications*, Second Edition, Wiley-VCH, N.Y.; and Walker (1998) *Protein Protocols on CD-ROM*, Humana Press, N.J., all of which are incorporated herein by reference.

In some embodiments, the present disclosure teaches the methods of improving strains designed to produce secreted products. For example, the present disclosure teaches methods of improving the robustness, yield, efficiency, or overall desirability of cell cultures producing valuable small molecules or peptides.

In some embodiments, immunological methods may be used to detect and/or purify secreted or non-secreted products produced by the cells of the present disclosure. In one example approach, antibody raised against a product molecule (e.g., against an insulin polypeptide or an immunogenic fragment thereof) using conventional methods is immobilized on beads, mixed with cell culture media under conditions in which the endoglucanase is bound, and precipitated. In some embodiments, the present disclosure teaches the use of enzyme-linked immunosorbent assays (ELISA).

In other related embodiments, immunochromatography is used, as disclosed in U.S. Pat. Nos. 5,591,645, 4,855,240, 4,435,504, 4,980,298, and Se-Hwan Paek, et al., "Development of rapid One-Step Immunochromatographic assay, Methods", 22, 53-60, 2000), each of which are incorporated by reference herein. A general immunochromatography detects a specimen by using two antibodies. A first antibody exists in a test solution or at a portion at an end of a test piece in an approximately rectangular shape made from a porous membrane, where the test solution is dropped. This antibody is labeled with latex particles or gold colloidal particles (this antibody will be called as a labeled antibody hereinafter).

When the dropped test solution includes a specimen to be detected, the labeled antibody recognizes the specimen so as to be bonded with the specimen. A complex of the specimen and labeled antibody flows by capillarity toward an absorber, which is made from a filter paper and attached to an end opposite to the end having included the labeled antibody. During the flow, the complex of the specimen and labeled antibody is recognized and caught by a second antibody (it will be called as a tapping antibody hereinafter) existing at the middle of the porous membrane and, as a result of this, the complex appears at a detection part on the porous membrane as a visible signal and is detected.

In some embodiments, the screening methods of the present disclosure are based on photometric detection techniques (absorption, fluorescence). For example, in some embodiments, detection may be based on the presence of a fluorophore detector such as GFP bound to an antibody. In other embodiments, the photometric detection may be based on the accumulation on the desired product from the cell culture. In some embodiments, the product may be detectable via UV of the culture or extracts from said culture.

Persons having skill in the art will recognize that the methods of the present disclosure are compatible with host cells producing any desirable biomolecule product of interest. Table 2 below presents a non-limiting list of the product categories, biomolecules, and host cells, included within the scope of the present disclosure. These examples are provided for illustrative purposes, and are not meant to limit the applicability of the presently disclosed technology in any way.

TABLE 2

A non-limiting list of the host cells and products of interest of the present disclosure.

| Product category | Products | Host category | Hosts |
|---|---|---|---|
| Amino acids | Lysine | Bacteria | Corynebacterium glutamicum |
| Amino acids | Methionine | Bacteria | Escherichia coli |
| Amino acids | MSG | Bacteria | Corynebacterium glutamicum |
| Amino acids | Threonine | Bacteria | Escherichia coli |
| Amino acids | Threonine | Bacteria | Corynebacterium glutamicum |
| Amino acids | Tryptophan | Bacteria | Corynebacterium glutamicum |
| Enzymes | Enzymes (11) | Filamentous fungi | Trichoderma reesei |
| Enzymes | Enzymes (11) | Fungi | Myceliopthora thermophila (C1) |
| Enzymes | Enzymes (11) | Filamentous fungi | Aspergillus oryzae |
| Enzymes | Enzymes (11) | Filamentous fungi | Aspergillus niger |
| Enzymes | Enzymes (11) | Bacteria | Bacillus subtilis |
| Enzymes | Enzymes (11) | Bacteria | Bacillus licheniformis |
| Enzymes | Enzymes (11) | Bacteria | Bacillus clausii |
| Flavor & Fragrance | Agarwood | Yeast | Saccharomyces cerevisiae |
| Flavor & Fragrance | Ambrox | Yeast | Saccharomyces cerevisiae |
| Flavor & Fragrance | Nootkatone | Yeast | Saccharomyces cerevisiae |
| Flavor & Fragrance | Patchouli oil | Yeast | Saccharomyces cerevisiae |
| Flavor & Fragrance | Saffron | Yeast | Saccharomyces cerevisiae |
| Flavor & Fragrance | Sandalwood oil | Yeast | Saccharomyces cerevisiae |
| Flavor & Fragrance | Valencene | Yeast | Saccharomyces cerevisiae |
| Flavor & Fragrance | Vanillin | Yeast | Saccharomyces cerevisiae |
| Food | CoQ10/Ubiquinol | Yeast | Schizosaccharomyces pombe |
| Food | Omega 3 fatty acids | Microalgae | Schizochytrium |
| Food | Omega 6 fatty acids | Microalgae | Schizochytrium |

TABLE 2-continued

A non-limiting list of the host cells and products of interest of the present disclosure.

| Product category | Products | Host category | Hosts |
|---|---|---|---|
| Food | Vitamin B12 | Bacteria | *Propionibacterium freudenreichii* |
| Food | Vitamin B2 | Filamentous fungi | *Ashbya gossypii* |
| Food | Vitamin B2 | Bacteria | *Bacillus subtilis* |
| Food | Erythritol | Yeast-like fungi | *Torula coralline* |
| Food | Erythritol | Yeast-like fungi | *Pseudozyma tsukubaensis* |
| Food | Erythritol | Yeast-like fungi | *Moniliella pollinis* |
| Food | Steviol glycosides | Yeast | *Saccharomyces cerevisiae* |
| Hydrocolloids | Diutan gum | Bacteria | *Sphingomonas* sp |
| Hydrocolloids | Gellan gum | Bacteria | *Sphingomonas elodea* |
| Hydrocolloids | Xanthan gum | Bacteria | *Xanthomonas campestris* |
| Intermediates | 1,3-PDO | Bacteria | *Escherichia coli* |
| Intermediates | 1,4-BDO | Bacteria | *Escherichia coli* |
| Intermediates | Butadiene | Bacteria | *Cupriavidus necator* |
| Intermediates | n-butanol | Bacteria (obligate anaerobe) | *Clostridium acetobutylicum* |
| Organic acids | Citric acid | Filamentous fungi | *Aspergillus niger* |
| Organic acids | Citric acid | Yeast | *Pichia guilliermondii* |
| Organic acids | Gluconic acid | Filamentous fungi | *Aspergillus niger* |
| Organic acids | Itaconic acid | Filamentous fungi | *Aspergillus terreus* |
| Organic acids | Lactic acid | Bacteria | *Lactobacillus* |
| Organic acids | Lactic acid | Bacteria | *Geobacillus thermoglucosidasius* |
| Organic acids | LCDAs - DDDA | Yeast | *Candida* |
| Polyketides/Ag | Spinosad | Yeast | *Saccharopolyspora spinosa* |
| Polyketides/Ag | Spinetoram | Yeast | *Saccharopolyspora spinosa* |

Selection Criteria and Goals

The selection criteria applied to the methods of the present disclosure will vary with the specific goals of the strain improvement program. The present disclosure may be adapted to meet any program goals. For example, in some embodiments, the program goal may be to maximize single batch yields of reactions with no immediate time limits. In other embodiments, the program goal may be to rebalance biosynthetic yields to produce a specific product, or to produce a particular ratio of products. In other embodiments, the program goal may be to modify the chemical structure of a product, such as lengthening the carbon chain of a polymer. In some embodiments, the program goal may be to improve performance characteristics such as yield, titer, productivity, by-product elimination, tolerance to process excursions, optimal growth temperature and growth rate. In some embodiments, the program goal is improved host performance as measured by volumetric productivity, specific productivity, yield or titre, of a product of interest produced by a microbe.

In other embodiments, the program goal may be to optimize synthesis efficiency of a commercial strain in terms of final product yield per quantity of inputs (e.g., total amount of ethanol produced per pound of sucrose). In other embodiments, the program goal may be to optimize synthesis speed, as measured for example in terms of batch completion rates, or yield rates in continuous culturing systems. In other embodiments, the program goal may be to increase strain resistance to a particular phage, or otherwise increase strain vigor/robustness under culture conditions.

In some embodiments, strain improvement projects may be subject to more than one goal. In some embodiments, the goal of the strain project may hinge on quality, reliability, or overall profitability. In some embodiments, the present disclosure teaches methods of associated selected mutations or groups of mutations with one or more of the strain properties described above.

Persons having ordinary skill in the art will recognize how to tailor strain selection criteria to meet the particular project goal. For example, selections of a strain's single batch max yield at reaction saturation may be appropriate for identifying strains with high single batch yields. Selection based on consistency in yield across a range of temperatures and conditions may be appropriate for identifying strains with increased robustness and reliability.

In some embodiments, the selection criteria for the initial high-throughput phase and the tank-based validation will be identical. In other embodiments, tank-based selection may operate under additional and/or different selection criteria. For example, in some embodiments, high-throughput strain selection might be based on single batch reaction completion yields, while tank-based selection may be expanded to include selections based on yields for reaction speed.

Sequencing

In some embodiments, the present disclosure teaches whole-genome sequencing of the organisms described herein. In other embodiments, the present disclosure also teaches sequencing of plasmids, PCR products, and other oligos as quality controls to the methods of the present disclosure. Sequencing methods for large and small projects are well known to those in the art.

In some embodiments, any high-throughput technique for sequencing nucleic acids can be used in the methods of the disclosure. In some embodiments, the present disclosure teaches whole genome sequencing. In other embodiments, the present disclosure teaches amplicon sequencing ultra deep sequencing to identify genetic variations. In some embodiments, the present disclosure also teaches novel methods for library preparation, including tagmentation (see WO/2016/073690). DNA sequencing techniques include classic dideoxy sequencing reactions (Sanger method) using labeled terminators or primers and gel separation in slab or capillary; sequencing by synthesis using reversibly terminated labeled nucleotides, pyrosequencing; 454 sequencing; allele specific hybridization to a library of labeled oligonucleotide probes; sequencing by synthesis using allele specific hybridization to a library of labeled clones that is followed by ligation; real time monitoring of the incorporation of labeled nucleotides during a polymerization step; polony sequencing; and SOLiD sequencing.

In one aspect of the disclosure, high-throughput methods of sequencing are employed that comprise a step of spatially isolating individual molecules on a solid surface where they are sequenced in parallel. Such solid surfaces may include nonporous surfaces (such as in Solexa sequencing, e.g. Bentley et al, Nature, 456: 53-59 (2008) or Complete Genomics sequencing, e.g. Drmanac et al, Science, 327: 78-81 (2010)), arrays of wells, which may include bead- or particle-bound templates (such as with 454, e.g. Margulies et al, Nature, 437: 376-380 (2005) or Ion Torrent sequencing, U.S. patent publication 2010/0137143 or 2010/0304982), micromachined membranes (such as with SMRT sequencing, e.g. Eid et al, Science, 323: 133-138 (2009)), or bead arrays (as with SOLiD sequencing or polony sequencing, e.g. Kim et al, Science, 316: 1481-1414 (2007)).

In another embodiment, the methods of the present disclosure comprise amplifying the isolated molecules either before or after they are spatially isolated on a solid surface. Prior amplification may comprise emulsion-based amplification, such as emulsion PCR, or rolling circle amplification. Also taught is Solexa-based sequencing where individual template molecules are spatially isolated on a solid surface, after which they are amplified in parallel by bridge PCR to form separate clonal populations, or clusters, and then sequenced, as described in Bentley et al (cited above) and in manufacturer's instructions (e.g. TruSeq™ Sample Preparation Kit and Data Sheet, Illumina, Inc., San Diego, Calif., 2010); and further in the following references: U.S. Pat. Nos. 6,090,592; 6,300,070; 7,115,400; and EP0972081B1; which are incorporated by reference.

In one embodiment, individual molecules disposed and amplified on a solid surface form clusters in a density of at least $10^5$ clusters per my; or in a density of at least $5 \times 10^5$ per my; or in a density of at least $10^6$ clusters per $cm^2$. In one embodiment, sequencing chemistries are employed having relatively high error rates. In such embodiments, the average quality scores produced by such chemistries are monotonically declining functions of sequence read lengths. In one embodiment, such decline corresponds to 0.5 percent of sequence reads have at least one error in positions 1-75; 1 percent of sequence reads have at least one error in positions 76-100; and 2 percent of sequence reads have at least one error in positions 101-125.

Computational Analysis and Prediction of Effects of Genome-Wide Genetic Design Criteria In some embodiments, the present disclosure teaches methods of predicting the effects of particular genetic alterations being incorporated into a given host strain. In further aspects, the disclosure provides methods for generating proposed genetic alterations that should be incorporated into a given host strain, in order for said host to possess a particular phenotypic trait or strain parameter. In given aspects, the disclosure provides predictive models that can be utilized to design novel host strains.

In some embodiments, the present disclosure teaches methods of analyzing the performance results of each round of screening and methods for generating new proposed genome-wide sequence modifications predicted to enhance strain performance in the following round of screening.

In some embodiments, the present disclosure teaches that the system generates proposed sequence modifications to host strains based on previous screening results. In some embodiments, the recommendations of the present system are based on the results from the immediately preceding screening. In other embodiments, the recommendations of the present system are based on the cumulative results of one or more of the preceding screenings.

In some embodiments, the recommendations of the present system are based on previously developed HTP genetic design libraries. For example, in some embodiments, the present system is designed to save results from previous screenings, and apply those results to a different project, in the same or different host organisms.

In other embodiments, the recommendations of the present system are based on scientific insights. For example, in some embodiments, the recommendations are based on known properties of genes (from sources such as annotated gene databases and the relevant literature), codon optimization, transcriptional slippage, uORFs, or other hypothesis driven sequence and host optimizations.

In some embodiments, the proposed sequence modifications to a host strain recommended by the system, or predictive model, are carried out by the utilization of one or more of the disclosed molecular tools sets comprising: (1) Promoter swaps, (2) SNP swaps, (3) Start/Stop codon exchanges, (4) Sequence optimization, (5) Stop swaps, and (5) Epistasis mapping.

The HTP genetic engineering platform described herein is agnostic with respect to any particular microbe or phenotypic trait (e.g. production of a particular compound). That is, the platform and methods taught herein can be utilized with any host cell to engineer said host cell to have any desired phenotypic trait. Furthermore, the lessons learned from a given HTP genetic engineering process used to create one novel host cell, can be applied to any number of other host cells, as a result of the storage, characterization, and analysis of a myriad of process parameters that occurs during the taught methods.

As alluded to in the epistatic mapping section, it is possible to estimate the performance (a.k.a. score) of a hypothetical strain obtained by consolidating a collection of mutations from a HTP genetic design library into a particular background via some preferred predictive model. Given such a predictive model, it is possible to score and rank all hypothetical strains accessible to the mutation library via combinatorial consolidation. The below section outlines particular models utilized in the present HTP platform.

Predictive Strain Design

Described herein is an approach for predictive strain design, including: methods of describing genetic changes and strain performance, predicting strain performance based on the composition of changes in the strain, recommending candidate designs with high predicted performance, and filtering predictions to optimize for second-order considerations, e.g. similarity to existing strains, epistasis, or confidence in predictions.

Inputs to Strain Design Model

In one embodiment, for the sake of ease of illustration, input data may comprise two components: (1) sets of genetic changes and (2) relative strain performance. Those skilled in the art will recognize that this model can be readily extended to consider a wide variety of inputs, while keeping in mind the countervailing consideration of overfitting. In addition to genetic changes, some of the input parameters (independent variables) that can be adjusted are cell types (genus, species, strain, phylogenetic characterization, etc.) and process parameters (e.g., environmental conditions, handling equipment, modification techniques, etc.) under which fermentation is conducted with the cells.

The sets of genetic changes can come from the previously discussed collections of genetic perturbations termed HTP genetic design libraries. The relative strain performance can be assessed based upon any given parameter or phenotypic trait of interest (e.g. production of a compound, small molecule, or product of interest).

Cell types can be specified in general categories such as prokaryotic and eukaryotic systems, genus, species, strain, tissue cultures (vs. disperse cells), etc. Process parameters that can be adjusted include temperature, pressure, reactor configuration, and medium composition. Examples of reactor configuration include the volume of the reactor, whether the process is a batch or continuous, and, if continuous, the volumetric flow rate, etc. One can also specify the support structure, if any, on which the cells reside. Examples of medium composition include the concentrations of electrolytes, nutrients, waste products, acids, pH, and the like.

Sets of Genetic Changes from Selected HTP Genetic Design Libraries to be Utilized in the Initial Linear Regression Model that Subsequently is Used to Create the Predictive Strain Design Model An example set of entries from a table of genetic changes is shown below in Table 3. Each row indicates a genetic change in strain 7000051473, as well as metadata about the mechanism of change, e.g. promoter swap or SNP swap. aceE, zwf, and pyc are all related to the citric acid cycle.

In this case strain 7000051473 has a total of 7 changes. "Last change" means the change in this strain represents the most recent modification in this strain lineage. Thus, comparing this strain's performance to the performance of its parent represents a data point concerning the performance of the "last change" mutation.

above zero. Further, and more generally, of interest is whether any given strain outperforms its parent by some criteria. In practice, the criteria can be a product titer meeting or exceeding some threshold above the parent level, though having a statistically significant difference from the parent in the desired direction could also be used instead or in addition. The role of the base or "reference" strain is simply to serve as an added normalization factor for making comparisons within or between plates.

A concept to keep in mind is that of differences between: parent strain and reference strain. The parent strain is the background that was used for a current round of mutagenesis. The reference strain is a control strain run in every plate to facilitate comparisons, especially between plates, and is typically the "base strain" as referenced above. But since the base strain (e.g., the wild-type or industrial strain being used to benchmark overall performance) is not necessarily a "base" in the sense of being a mutagenesis target in a given round of strain improvement, a more descriptive term is "reference strain."

In summary, a base/reference strain is used to benchmark the performance of built strains, generally, while the parent strain is used to benchmark the performance of a specific genetic change in the relevant genetic background.

Ranking the Performance of Built Strains with Linear Regression

The goal of the disclosed model is to rank the performance of built strains, by describing relative strain performance, as a function of the composition of genetic changes introduced into the built strains. As discussed throughout the disclosure, the various HTP genetic design libraries provide the repertoire of possible genetic changes (e.g., genetic perturbations/alterations) that are introduced into the engineered strains. Linear regression is the basis for the currently described exemplary predictive model.

TABLE 3

Strain design entry table for strain 7000051473

| strain | name | library | change | from | to | last_change |
|---|---|---|---|---|---|---|
| 7000051473 | dlc19_42 | proswp | pcg3121 | cg1144 | pcg3121_cg1144 | 1 |
| 7000051473 | dlc19_42 | scswp | acee atg > ttg | ttg | acee_atg | 0 |
| 7000051473 | dlc19_42 | snpswp | dss_033 | NA | na | 0 |
| 7000051473 | dlc19_42 | snpswp | dss_084 | NA | t | 0 |
| 7000051473 | dlc19_42 | snpswp | dss_316 | NA | na | 0 |
| 7000051473 | dlc19_42 | proswp | pcg0007_39 | zwf | pcg0007_39_zwf | 0 |
| 7000051473 | dlc19_42 | proswp | pcg1860 | pyc | pcg1860_pyc | 0 |

Built Strain Performance Assessment

The goal of the taught model is to predict strain performance based on the composition of genetic changes introduced to the strain. To construct a standard for comparison, strain performance is computed relative to a common reference strain, by first calculating the median performance per strain, per assay plate. Relative performance is then computed as the difference in average performance between an engineered strain and the common reference strain within the same plate. Restricting the calculations to within-plate comparisons ensures that the samples under consideration all received the same experimental conditions.

Figure 23:
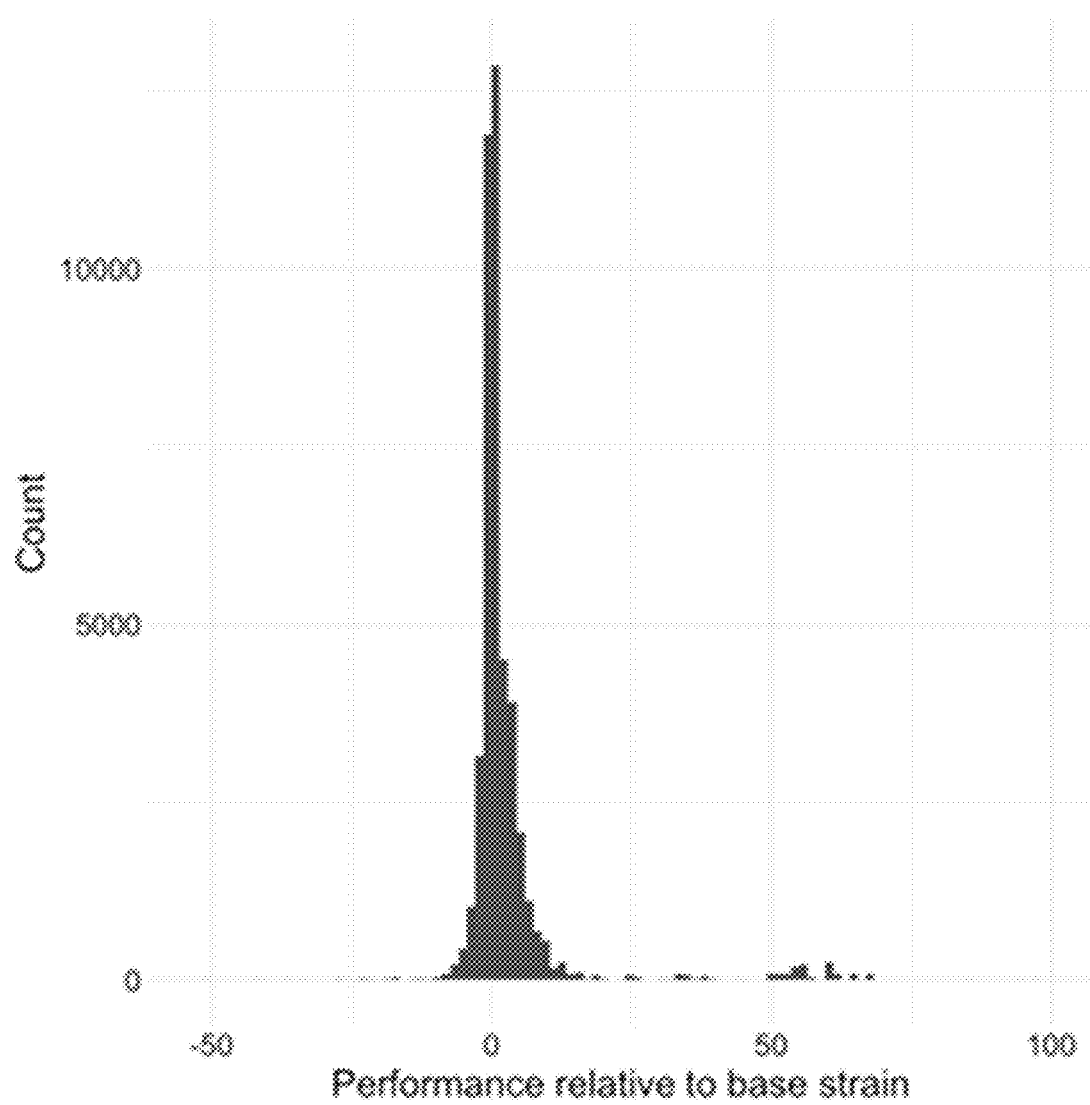
FIG. 23 illustrates the distribution of relative strain performances for the input data under consideration. A relative performance of zero indicates that the engineered strain performed equally well to the in-plate base strain. The processes described herein are designed to identify the strains that are likely to perform significantly above zero.

FIG. 23 shows the distribution of relative strain performances for the input data under consideration. A relative performance of zero indicates that the engineered strain performed equally well to the in-plate base or "reference" strain. Of interest is the ability of the predictive model to identify the strains that are likely to perform significantly The below table contains example input for regression-based modeling. The strain performances are ranked relative to a common base strain, as a function of the composition of the genetic changes contained in the strain.

Each column heading represents a genetic change, a "1" represents the presence of the change, whereas a "0" represents the absence of a change. "DSS" refers to SNP swaps from a particular library (first 3 columns after relative_perf). The last 3 columns are promoter swaps, where the pcgXXXX denotes the particular promoter, and the last 3 letters represent the gene the promoter is being applied to. The genes are related to central metabolism. The promoters are from *Corynebacterium glutamicum* (hence the "cg" notation). Further information on the utilized promoters can be found in Table 1, listing promoters P1-P8, and the sequence listing of the present application. Further, detailed information on each promoter P1-P8 can be found in U.S. Provisional Application No. 62/264,232, filed on Dec. 7, 2015, and entitled "Promoters from *Corynebacterium glutamicum*," which is incorporated herein by reference. For ease of reference, in the below table, pcg3121=P8; pcg0755=P4; and pcg1860=P3.

TABLE 4

Summary of genetic changes and their effect on relative performance.

| relative_perf | dss_033 | dss_034 | dss_056 | pcg3121_pgi | pcg0755_zwf | pcg1860_pyc |
|---|---|---|---|---|---|---|
| 0.1358908 | 0 | 0 | 0 | 0 | 0 | 1 |
| −1.8946985 | 1 | 0 | 0 | 1 | 0 | 1 |
| −0.0222045 | 0 | 0 | 0 | 1 | 0 | 0 |
| 0.6342183 | 1 | 0 | 1 | 0 | 0 | 0 |
| −0.0803285 | 1 | 1 | 0 | 0 | 0 | 0 |
| 2.6468117 | 0 | 0 | 0 | 1 | 0 | 0 |

Linear Regression to Characterize Built Strains

Linear regression is an attractive method for the described HTP genomic engineering platform, because of the ease of implementation and interpretation. The resulting regression coefficients can be interpreted as the average increase or decrease in relative strain performance attributable to the presence of each genetic change.

Figure 24:
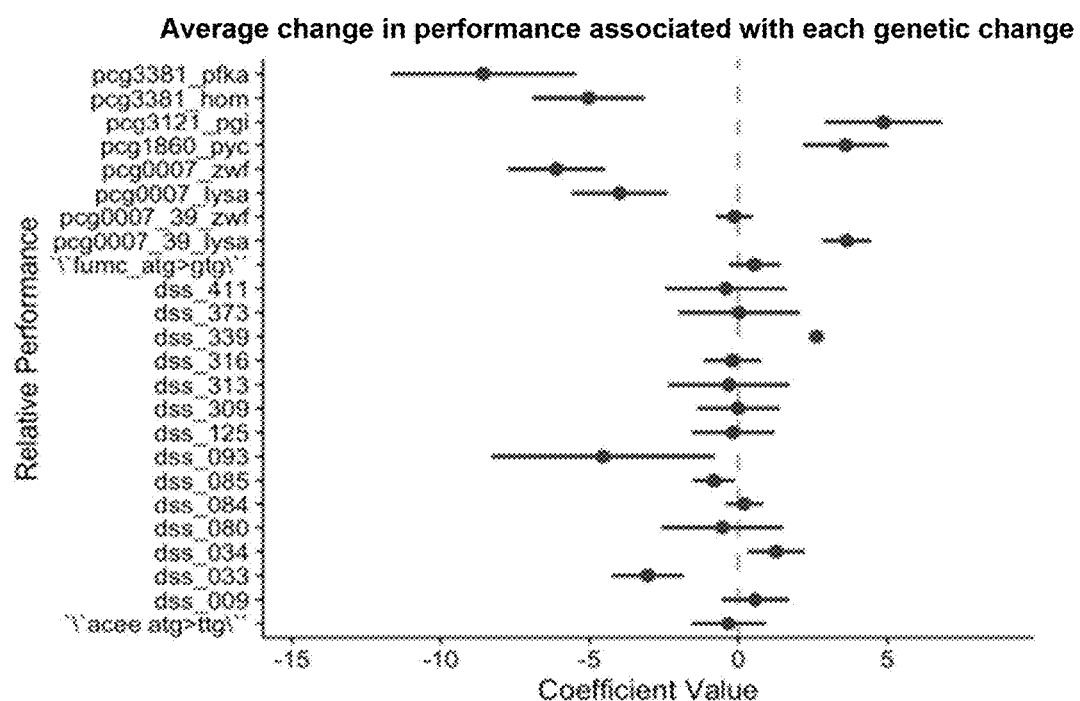
FIG. 24 illustrates the linear regression coefficient values, which depict the average change (increase or decrease) in relative strain performance associated with each genetic change incorporated into the depicted strains.

For example, as seen in FIG. 24, this technique allows us to conclude that changing the pgi promoter to pcg3121 improves relative strain performance by approximately 5 units on average and is thus a potentially highly desirable change, in the absence of any negative epistatic interactions (note: the input is a unit-less normalized value).

The taught method therefore uses linear regression models to describe/characterize and rank built strains, which have various genetic perturbations introduced into their genomes from the various taught libraries.

Predictive Design Modeling

The linear regression model described above, which utilized data from constructed strains, can be used to make performance predictions for strains that haven't yet been built.

The procedure can be summarized as follows: generate in silico all possible configurations of genetic changes→use the regression model to predict relative strain performance-→order the candidate strain designs by performance. Thus, by utilizing the regression model to predict the performance of as-yet-unbuilt strains, the method allows for the production of higher performing strains, while simultaneously conducting fewer experiments.

Generate Configurations

When constructing a model to predict performance of as-yet-unbuilt strains, the first step is to produce a sequence of design candidates. This is done by fixing the total number of genetic changes in the strain, and then defining all possible combinations of genetic changes. For example, one can set the total number of potential genetic changes/perturbations to 29 (e.g. 29 possible SNPs, or 29 different promoters, or any combination thereof as long as the universe of genetic perturbations is 29) and then decide to design all possible 3-member combinations of the 29 potential genetic changes, which will result in 3,654 candidate strain designs.

To provide context to the aforementioned 3,654 candidate strains, consider that one can calculate the number of non-redundant groupings of size r from n possible members using $n!/((n-r)!*r!)$. If $r=3$, $n=29$ gives 3,654. Thus, if one designs all possible 3-member combinations of 29 potential changes the results is 3,654 candidate strains. The 29 potential genetic changes are present in the x-axis of FIG. 25.

Predict Performance of New Strain Designs

Using the linear regression constructed above with the combinatorial configurations as input, one can then predict the expected relative performance of each candidate design.

Figure 25:
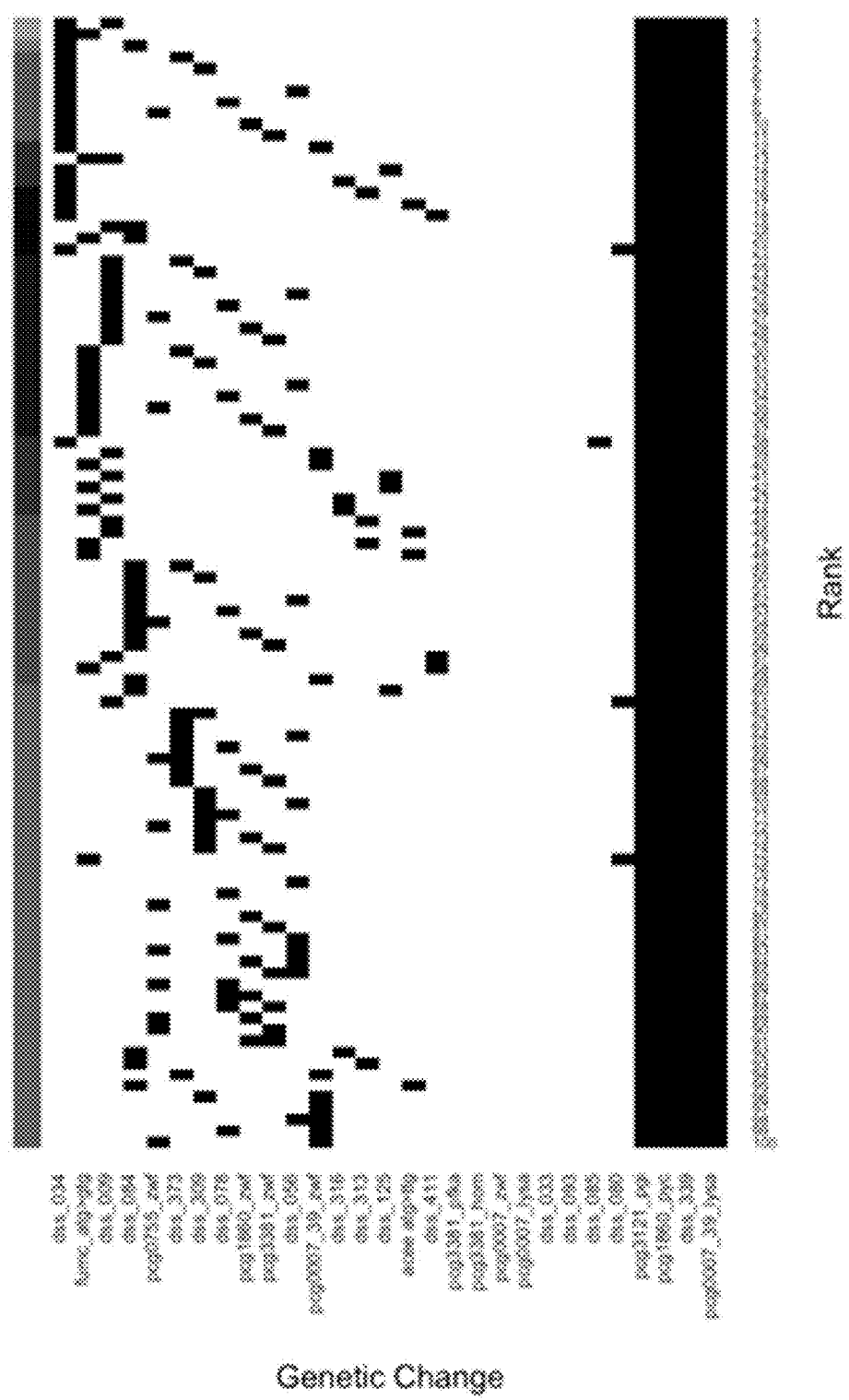
FIG. 25 illustrates the composition of changes for the top 100 predicted strain designs. The x-axis lists the pool of potential genetic changes (dss mutations are SNP swaps, and Pcg mutations are PRO swaps), and the y-axis shows the rank order. Black cells indicate the presence of a particular change in the candidate design, while white cells indicate the absence of that change. In this particular example, all of the top 100 designs contain the changes pcg3121_pgi, pcg1860_pyc, dss_339, and pcg0007_39_lysa. Additionally, the top candidate design contains the changes dss_034, dss_009.

FIG. 25 summarizes the composition of changes for the top 100 predicted strain designs. The x-axis lists the pool of potential genetic changes (29 possible genetic changes), and the y-axis shows the rank order. Black cells indicate the presence of a particular change in the candidate design, while white cells indicate the absence of that change. In this particular example, all of the top 100 designs contain the changes pcg3121_pgi, pcg1860_pyc, dss_339, and pcg0007_39_lysa. Additionally, the top candidate design contains the changes dss_034, dss_009.

Figure 47:
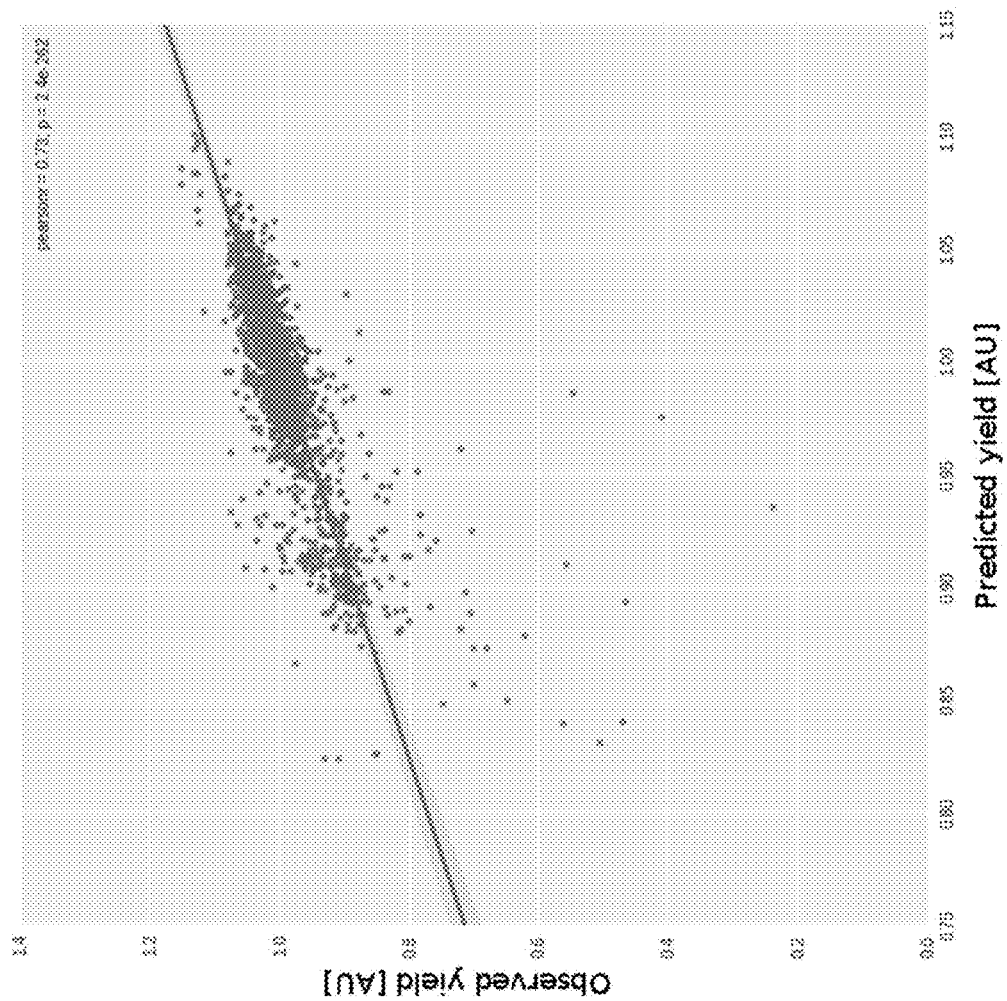
FIG. 47 is a dot plot for the predicted performance vs measured performance of training data for a yield model of the present disclosure. The underlying model is a Kernel Ridge Regression model (with 4th order polynomial kernel). The model is trained on 1864 unique genetic constructs and associated phenotypic performance. The fitted model has an r2 value of 0.52.

Predictive accuracy should increase over time as new observations are used to iteratively retrain and refit the model. Results from a study by the inventors illustrate the methods by which the predictive model can be iteratively retrained and improved. FIG. 47 compares model predictions with observed measurement values. The quality of model predictions can be assessed through several methods, including a correlation coefficient indicating the strength of association between the predicted and observed values, or the root-mean-square error, which is a measure of the average model error. Using a chosen metric for model evaluation, the system may define rules for when the model should be retrained.

A couple of unstated assumptions to the above model include: (1) there are no epistatic interactions; and (2) the genetic changes/perturbations utilized to build the predictive model (e.g. from built strain data as illustrated in FIG. 24, or whatever data set is used as the reference to construct the model) were all made in the same background, as the proposed combinations of genetic changes (e.g. as illustrated in FIG. 25).

Filtering for Second-Order Features

The above illustrative example focused on linear regression predictions based on predicted host cell performance. In some embodiments, the present linear regression methods can also be applied to non-biomolecule factors, such as saturation biomass, resistance, or other measurable host cell features. Thus the methods of the present disclosure also teach in considering other features outside of predicted performance when prioritizing the candidates to build. Assuming there is additional relevant data, nonlinear terms are also included in the regression model.

Closeness with Existing Strains

Predicted strains that are similar to ones that have already been built could result in time and cost savings despite not being a top predicted candidate Diversity of Changes When constructing the aforementioned models, one cannot be certain that genetic changes will truly be additive (as assumed by linear regression and mentioned as an assumption above) due to the presence of epistatic interactions. Therefore, knowledge of genetic change dissimilarity can be used to increase the likelihood of positive additivity. If one knows, for example, that the changes dss_034 and dss_009 (which are SNP swaps) from the top ranked strain above are on the same metabolic pathway and have similar performance characteristics, then that information could be used to select another top ranking strain with a dissimilar composition of changes. As described in the section above concerning epistasis mapping, the predicted best genetic changes may be filtered to restrict selection to mutations with sufficiently dissimilar response profiles. Alternatively, the linear regression may be a weighted least squares regression using the similarity matrix to weight predictions.

Diversity of Predicted Performance

Finally, one may choose to design strains with middling or poor predicted performance, in order to validate and subsequently improve the predictive models.

Iterative Strain Design Optimization

As described for the example above, all of the top 100 strain designs contain the changes pcg3121_pgi, pcg1860_pyc, dss_339, and pcg0007_39_lysa. Additionally, the top candidate strain design contains the changes dss_034, dss_009.

In embodiments, the order placement engine 208 places a factory order to the factory 210 to manufacture microbial strains incorporating the top candidate mutations. In feedback-loop fashion, the results may be analyzed by the analysis equipment 214 to determine which microbes exhibit desired phenotypic properties (314). During the analysis phase, the modified strain cultures are evaluated to determine their performance, i.e., their expression of desired phenotypic properties, including the ability to be produced at industrial scale. For example, the analysis phase uses, among other things, image data of plates to measure microbial colony growth as an indicator of colony health. The analysis equipment 214 is used to correlate genetic changes with phenotypic performance, and save the resulting genotype-phenotype correlation data in libraries, which may be stored in library 206, to inform future microbial production.

In particular, the candidate changes that actually result in sufficiently high measured performance may be added as rows in the database to tables such as Table 4 above. In this manner, the best performing mutations are added to the predictive strain design model in a supervised machine learning fashion.

LIMS iterates the design/build/test/analyze cycle based on the correlations developed from previous factory runs. During a subsequent cycle, the analysis equipment 214 alone, or in conjunction with human operators, may select the best candidates as base strains for input back into input interface 202, using the correlation data to fine tune genetic modifications to achieve better phenotypic performance with finer granularity. In this manner, the laboratory information management system of embodiments of the disclosure implements a quality improvement feedback loop.

Figure 33:
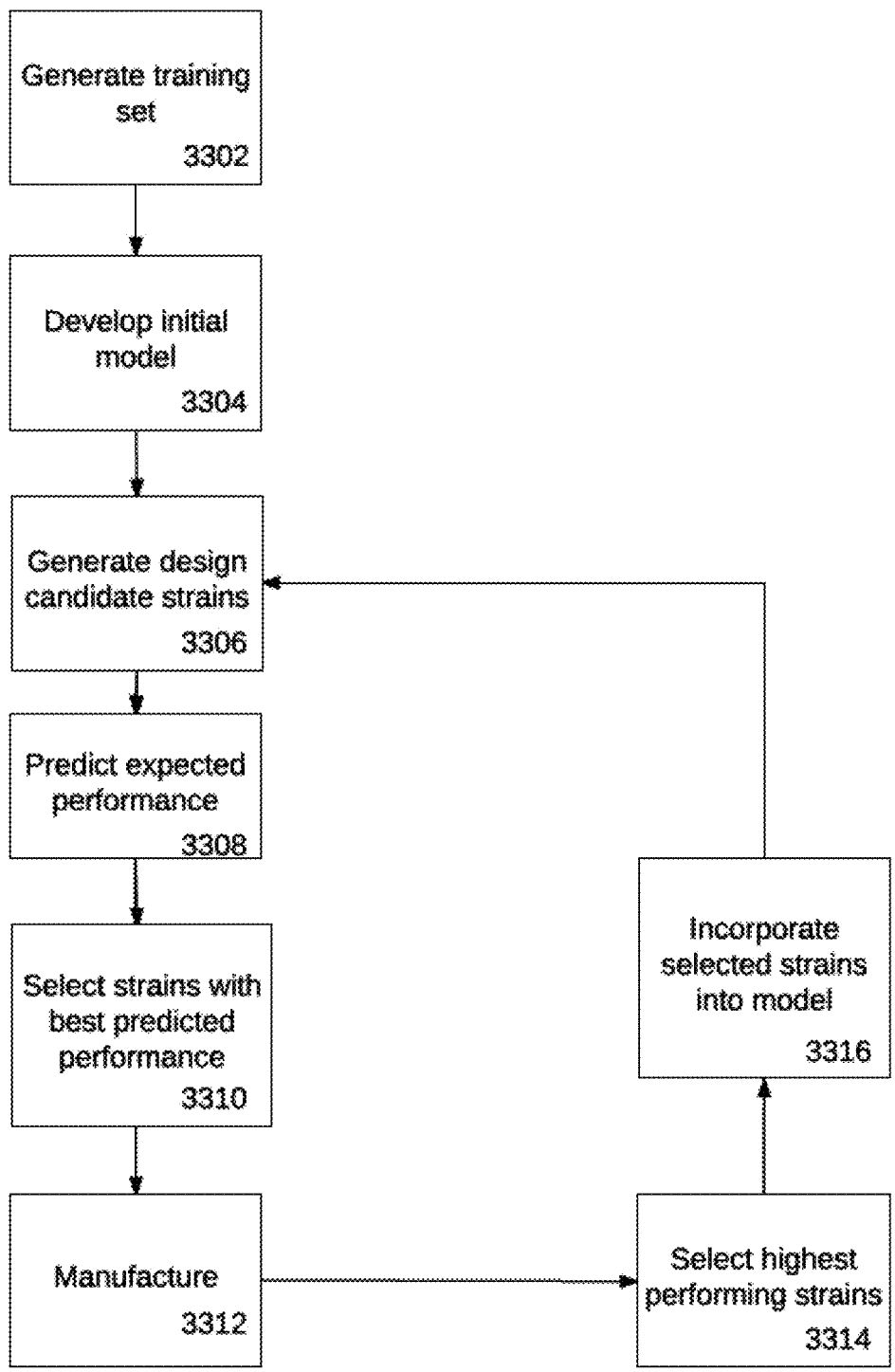
FIG. 33 depicts an embodiment of the iterative predictive strain design workflow of the present disclosure.

In sum, with reference to the flowchart of FIG. 33 the iterative predictive strain design workflow may be described as follows:

Generate a training set of input and output variables, e.g., genetic changes as inputs and performance features as outputs (3302). Generation may be performed by the analysis equipment 214 based upon previous genetic changes and the corresponding measured performance of the microbial strains incorporating those genetic changes.

Develop an initial model (e.g., linear regression model) based upon training set (3304). This may be performed by the analysis equipment 214.

Generate design candidate strains (3306)

In one embodiment, the analysis equipment 214 may fix the number of genetic changes to be made to a background strain, in the form of combinations of changes. To represent these changes, the analysis equipment 214 may provide to the interpreter 204 one or more DNA specification expressions representing those combinations of changes. (These genetic changes or the microbial strains incorporating those changes may be referred to as "test inputs.") The interpreter 204 interprets the one or more DNA specifications, and the execution engine 207 executes the DNA specifications to populate the DNA specification with resolved outputs representing the individual candidate design strains for those changes.

Based upon the model, the analysis equipment 214 predicts expected performance of each candidate design strain (3308).

The analysis equipment 214 selects a limited number of candidate designs, e.g., 100, with highest predicted performance (3310).

As described elsewhere herein with respect to epistasis mapping, the analysis equipment 214 may account for second-order effects such as epistasis, by, e.g., filtering top designs for epistatic effects, or factoring epistasis into the predictive model.

Build the filtered candidate strains (at the factory 210) based on the factory order generated by the order placement engine 208 (3312).

The analysis equipment 214 measures the actual performance of the selected strains, selects a limited number of those selected strains based upon their superior actual performance (3314), and adds the design changes and their resulting performance to the predictive model (3316). In the linear regression example, add the sets of design changes and their associated performance as new rows in Table 4.

The analysis equipment 214 then iterates back to generation of new design candidate strains (3306), and continues iterating until a stop condition is satisfied. The stop condition may comprise, for example, the measured performance of at least one microbial strain satisfying a performance metric, such as yield, growth rate, or titer.

In the example above, the iterative optimization of strain design employs feedback and linear regression to implement machine learning. In general, machine learning may be described as the optimization of performance criteria, e.g., parameters, techniques or other features, in the performance of an informational task (such as classification or regression) using a limited number of examples of labeled data, and then performing the same task on unknown data. In supervised machine learning such as that of the linear regression example above, the machine (e.g., a computing device) learns, for example, by identifying patterns, categories, statistical relationships, or other attributes, exhibited by training data. The result of the learning is then used to predict whether new data will exhibit the same patterns, categories, statistical relationships or other attributes.

Embodiments of the disclosure may employ other supervised machine learning techniques when training data is available. In the absence of training data, embodiments may employ unsupervised machine learning. Alternatively, embodiments may employ semi-supervised machine learning, using a small amount of labeled data and a large amount of unlabeled data. Embodiments may also employ feature selection to select the subset of the most relevant features to optimize performance of the machine learning model. Depending upon the type of machine learning approach selected, as alternatives or in addition to linear regression, embodiments may employ for example, logistic regression, neural networks, support vector machines (SVMs), decision trees, hidden Markov models, Bayesian networks, Gram Schmidt, reinforcement-based learning, cluster-based learning including hierarchical clustering, genetic algorithms, and any other suitable learning machines known in the art. In particular, embodiments may employ logistic regression to provide probabilities of classification (e.g., classification of genes into different functional groups) along with the classifications themselves. See, e.g., Shevade, A simple and efficient algorithm for gene selection using sparse logistic regression, Bioinformatics, Vol. 19, No. 17 2003, pp. 2246-2253, Leng, et al., Classification using functional data analysis for temporal gene expression data, Bioinformatics, Vol. 22, No. 1, Oxford University Press (2006), pp. 68-76, all of which are incorporated by reference in their entirety herein.

Embodiments may employ graphics processing unit (GPU) accelerated architectures that have found increasing popularity in performing machine learning tasks, particularly in the form known as deep neural networks (DNN). Embodiments of the disclosure may employ GPU-based machine learning, such as that described in GPU-Based Deep Learning Inference: A Performance and Power Analysis, NVidia Whitepaper, November 2015, Dahl, et al., Multi-task Neural Networks for QSAR Predictions, Dept. of Computer Science, Univ. of Toronto, June 2014 (arXiv: 1406.1231 [stat.ML]), all of which are incorporated by reference in their entirety herein. Machine learning techniques applicable to embodiments of the disclosure may also be found in, among other references, Libbrecht, et al., Machine learning applications in genetics and genomics, Nature Reviews: Genetics, Vol. 16, June 2015, Kashyap, et al., Big Data Analytics in Bioinformatics: A Machine Learning Perspective, Journal of Latex Class Files, Vol. 13, No. 9, September 2014, Prompramote, et al., Machine Learning in Bioinformatics, Chapter 5 of Bioinformatics Technologies, pp. 117-153, Springer Berlin Heidelberg 2005, all of which are incorporated by reference in their entirety herein.

Iterative Predictive Strain Design: Example

The following provides an example application of the iterative predictive strain design workflow outlined above.

An initial set of training inputs and output variables was prepared. This set comprised 1864 unique engineered strains with defined genetic composition. Each strain contained between 5 and 15 engineered changes. A total of 336 unique genetic changes were present in the training.

An initial predictive computer model was developed. The implementation used a generalized linear model (Kernel Ridge Regression with 4th order polynomial kernel). The implementation models two distinct phenotypes (yield and productivity). These phenotypes were combined as weighted sum to obtain a single score for ranking, as shown below. Various model parameters, e.g. regularization factor, were tuned via k-fold cross validation over the designated training data.

The implementation does not incorporate any explicit analysis of interaction effects as described in the Epistasis Mapping section above. However, as those skilled in the art would understand, the implemented generalized linear model may capture interaction effects implicitly through the second, third and fourth order terms of the kernel.

The model was trained against the training set. The fitted model has an $R^2$ value (coefficient of determination) of 0.52 with respect to yield and an $R^2$ value of 0.67 with respect to productivity. FIG. 47 demonstrates a significant quality fitting of the yield model to the training data.

Candidate strains were generated. This example includes a serial build constraint associated with the introduction of new genetic changes to a parent strain (in this example, only one new mutation was engineered into a strain at a time). Here, candidates are not considered simply as a function of the desired number of changes. Instead, the analysis equipment 214 selected, as a starting point, a collection of previously designed strains known to have high performance metrics ("seed strains"). The analysis equipment 214 individually applied genetic changes to each of the seed strains. The introduced genetic changes did not include those already present in the seed strain. For various technical, biological or other reasons, certain mutations were explicitly required, e.g., opca_4, or explicitly excluded, e.g., dss_422. Using 166 available seed strains and the 336 changes characterized by the model, 6239 novel candidate strains were designed.

Based upon the model, the analysis equipment 214 predicted the performance of candidate strain designs. The analysis equipment 214 ranked candidates from "best" to "worst" based on predicted performance with respect to two phenotypes of interest (yield and productivity). Specifically, the analysis equipment 214 used a weighted sum to score a candidate strain:

$$\text{Score}=0.8*\text{yield}/\max(\text{yields})+0.2*\text{prod}/\max(\text{prods}),$$

where yield represents predicted yield for the candidate strain, max(yields) represents the maximum yield over all candidate strains, prod represents productivity for the candidate strain, and max(prods) represents the maximum yield over all candidate strains.

The analysis equipment 214 generated a final set of recommendations from the ranked list of candidates by imposing both capacity constraints and operational constraints. In this example, the capacity limit was set at 48 computer-generated candidate design strains. Due to operational constraints, in this example only one seed strain was used per column of a 96-well plate. This means that after a seed strain was chosen, up to 8 changes to that strain could be built, but only 6 seed strains could be chosen in any given week.

Figure 48:
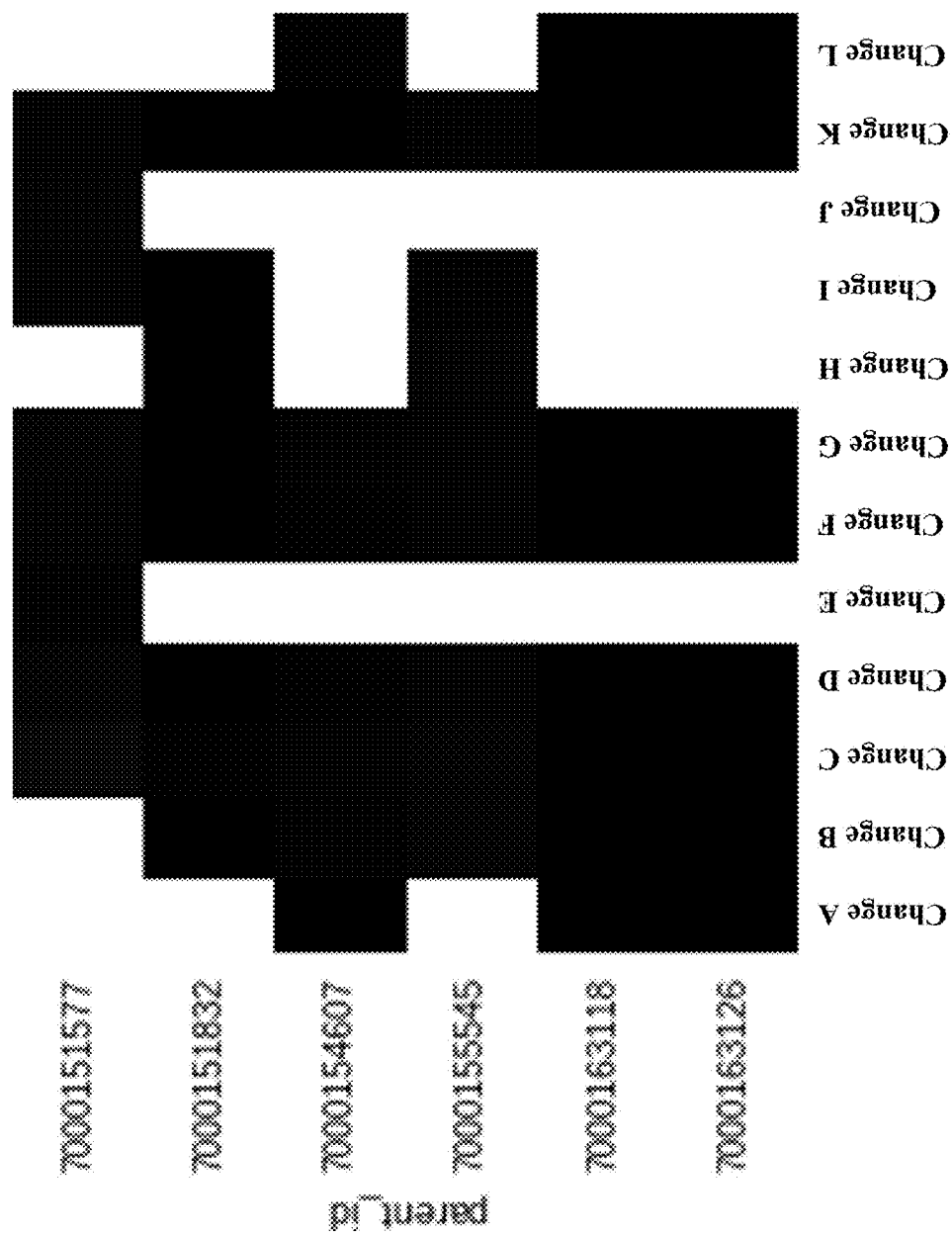
FIG. 48 Depicts the genetic makeup of candidate designs generated by the prediction algorithms of the present disclosure. These candidate designs were submitted for HTP build and analysis. Here the candidate design is defined as the combination of parent strain id and introduced mutation(s).

The trained model (described above) was used to predict the expected performance (for yield and productivity) of each candidate strain. The analysis equipment 214 ranked the candidate strains using the scoring function given above. Capacity and operational constraints were applied to yield a filtered set of 48 candidate strains. This set of filtered candidate strains is depicted in FIG. 48.

Filtered candidate strains were built (at the factory 210) based on a factory order generated by the order placement engine 208 (3312). The order was based upon DNA specifications corresponding to the candidate strains.

In practice, the build process has an expected failure rate whereby a random set of strains is not built. For this build cycle, roughly 20% of the candidate strains failed build, resulting in 37 built strains.

The analysis equipment 214 was used to measure the actual yield and productivity performance of the selected strains. The analysis equipment 214 evaluated the model and recommended strains based on three criteria: model accuracy; improvement in strain performance; and equivalence (or improvement) to human expert-generated designs.

Figure 49:
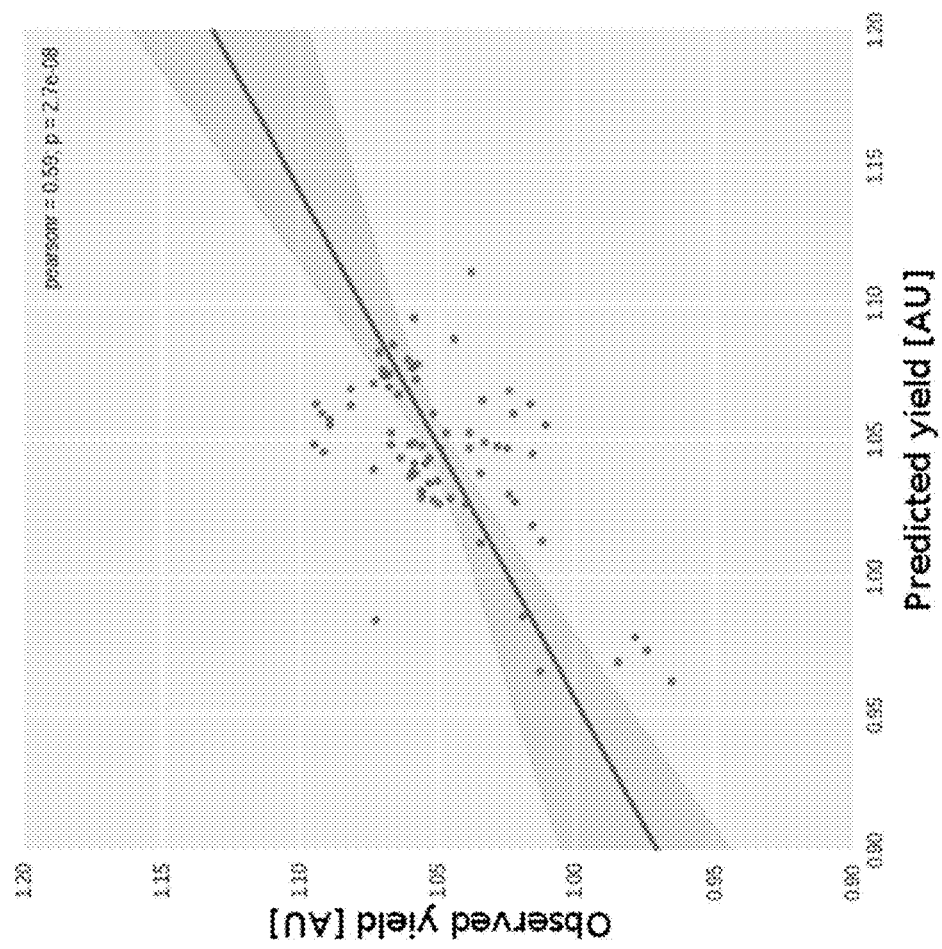
FIG. 49 is a dot plot of the predicted performance vs. measured performance of candidate designs generated by the prediction algorithms of the present disclosure, and built according to the HTP build methods of the present disclosure. This figure demonstrates that the model may predict candidate strain performance within an acceptable degree of accuracy.

The yield and productivity phenotypes were measured for recommended strains and compared to the values predicted by the model. As shown in FIG. 49, the model demonstrates useful predictive utility. In particular, the predicted yield values for the recommended strains have a Pearson-r correlation coefficient of 0.59 with the corresponding observations.

Figure 50:
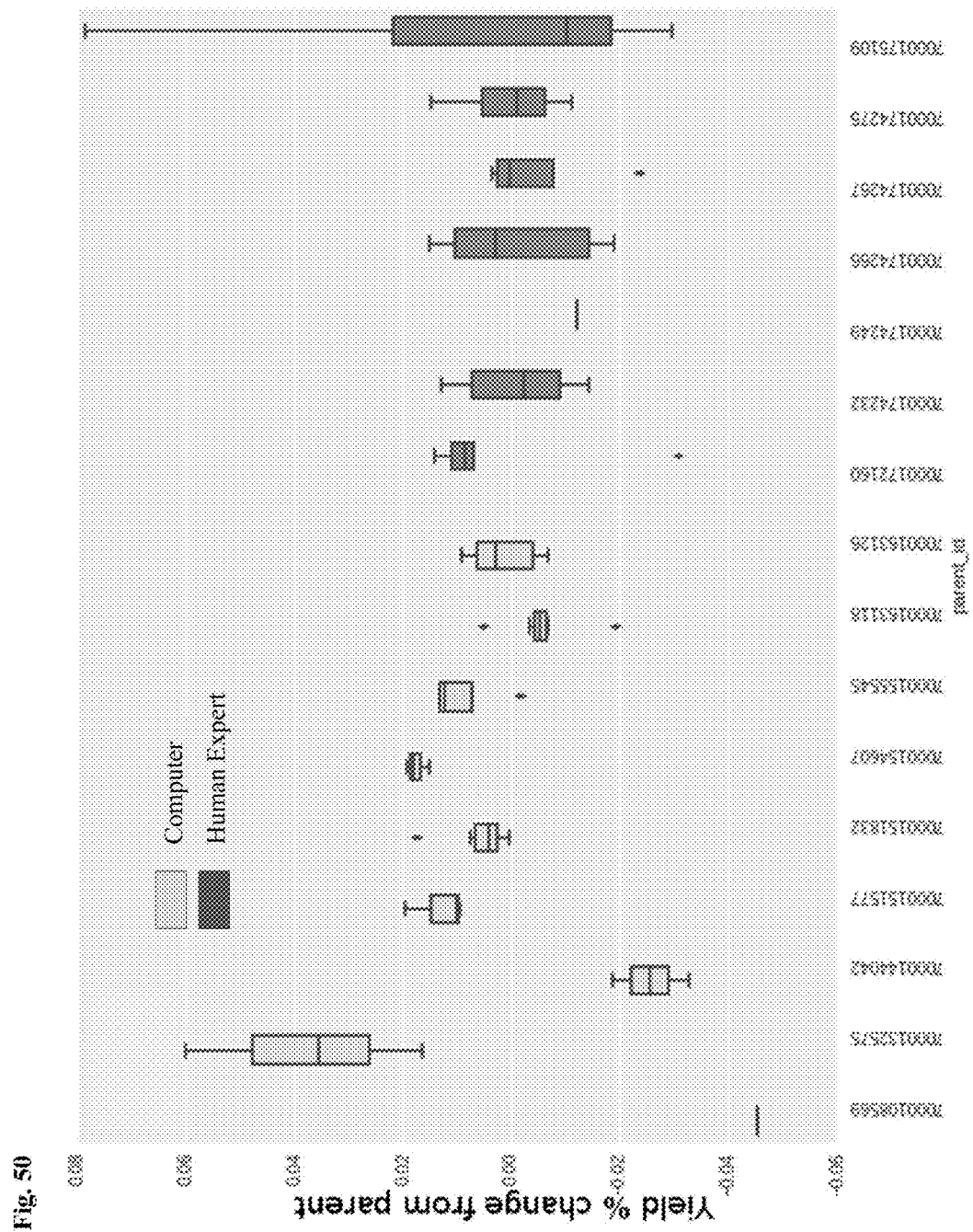
FIG. 50 is a box and whiskers plot depicting the yield percent change of candidate strains with respect to parent strains. On the y-axis, a value of 0.01 corresponds to 1%. This figure demonstrates that strains designed by a computer model (light gray) achieve measurable improvement over their corresponding parent strains. Additionally, the figure demonstrates that these model base strain improvements are comparable in magnitude to improvements achieved by human expert designed strains.

Next, the analysis equipment 214 computed percentage performance change from the parent strain for each of the recommended strains. This data is shown in FIG. 50 (in light gray). The inventors found that many of the predicted strains in fact exhibited the expected performance gains with respect to their immediate parents. In particular, the best predicted strain showed a 6% improvement in yield with respect to its immediate parent.

Figure 51:
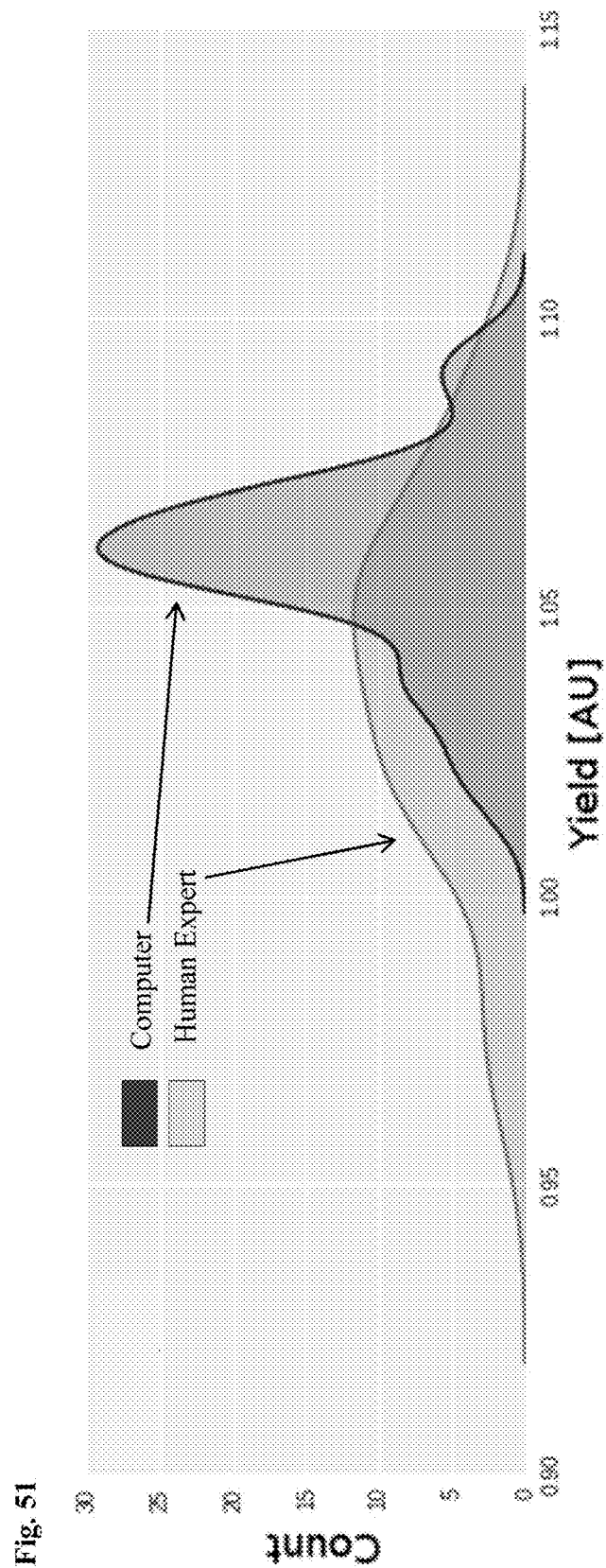
FIG. 51 illustrates the yield performance distribution for strains designed by the computer model (dark grey) and by a human expert (light grey). Computer-designed strains exhibited tighter distributions with higher median gains.

In parallel with the model-based strain design process described above, a collection of 48 strains was independently designed by a human expert. Of these strains, 37 were successfully built and tested. This data demonstrated that the model-based strain designs performed comparably to strains designed by human experts. These experts are highly-skilled (e.g., Ph.D.-level) scientists employed or otherwise engaged by the assignee of the present invention, and familiar with the embodiments of this disclosure. To compare the two methods, the inventors first inspected the performance distributions of each group (FIG. 51). In this experiment, the mean yield of model-based strains showed a 1% increase with respect to human expert generated designs.

Figure 52:
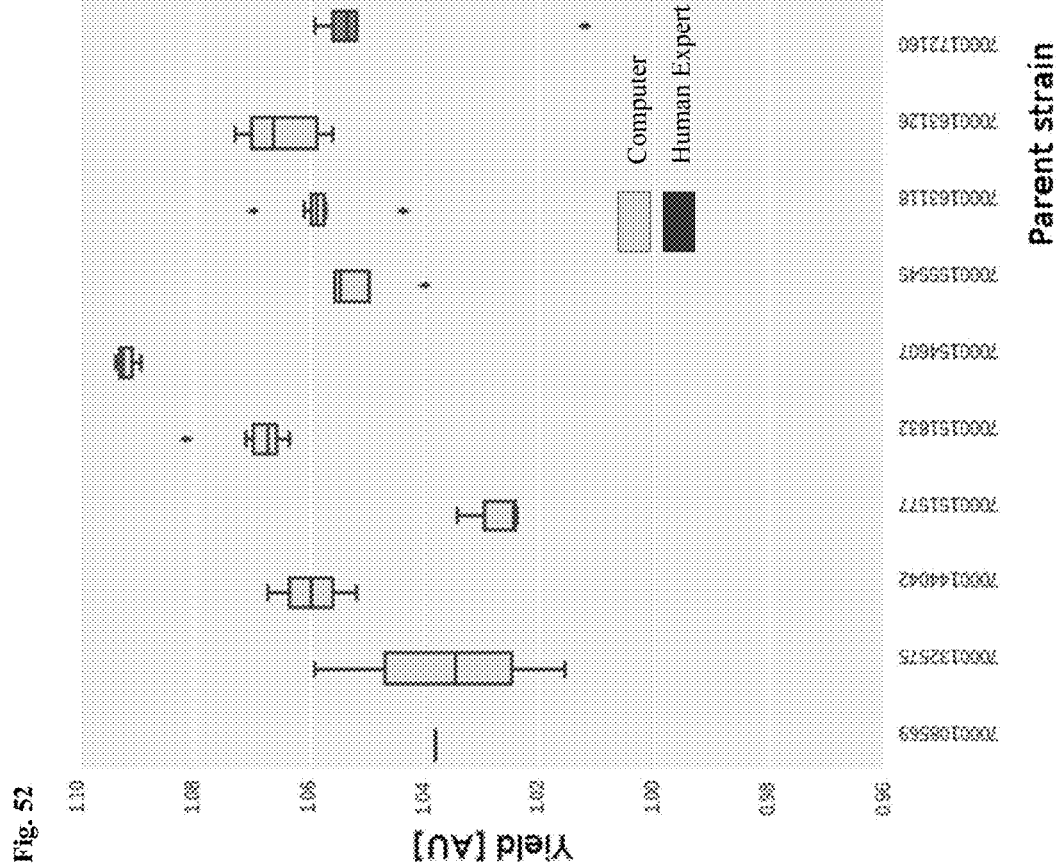
FIG. 52 is a box and whiskers plot depicting the absolute yield of candidate strains generated by the computer (light grey) or by a human expert (dark grey). Results are aggregated by parent strain.

The inventors then compared human expert-designed and computer-model-designed strains grouped by background, i.e., new strains with the same parent (FIG. 52). Again, the inventors found that computer-generated designs perform comparably to, and in some cases better than, the human expert-generated designs, and further tend to produce less variability. Finally, the inventors compared the percentage change with respect to the parent strains of the human expert and model-designed strains (FIG. 50). Again, these populations showed comparable gains.

See Table 4.1 for tabulated summary statistics.

TABLE 4.1

Measured performance statistics for strains designed by the predictive model and by a human expert reference.

| design method | | Yield [AU] | Yield change from parent [%] | Productivity [AU] | Productivity change from parent [%] |
|---|---|---|---|---|---|
| computer model | count | 37 | 37 | 37 | 37 |
| | mean | 1.058068108 | 0.3578340 | 0.737928919 | −2.5428848 |
| | std | 0.017811031 | 1.8293665 | 0.083619804 | 9.6743873 |
| | min | 1.015310000 | −4.5346677 | 0.572780000 | −23.3626353 |
| | median | 1.058710000 | 0.005007939 | 0.766870000 | −1.1824159 |
| | max | 1.093510000 | 6.0097309 | 0.872790000 | 26.6124119 |
| Human expert | count | 37 | 37 | 37 | 37 |
| | mean | 1.038804595 | −0.0005237 | 0.748320811 | −1.6126436 |
| | std | 0.032053625 | 1.9227716 | 0.120527468 | 9.8530758 |
| | min | 0.964910000 | −3.1043233 | 0.535980000 | −21.4589256 |
| | median | 1.045530000 | 0.0449168 | 0.760300000 | −1.9241048 |
| | max | 1.094790000 | 7.8487174 | 0.984110000 | 21.7335193 |

At the conclusion of each round of the prediction→build-→test cycle, the inventors were interested in evaluating the quality of the model predictions and iteratively incorporating new data into the previous model. For the former—model evaluation—the inventors focused on measuring predictive accuracy by comparing model predictions with experimental measurements. Predictive accuracy can be assessed through several methods, including a correlation coefficient indicating the strength of association between the predicted and observed values, or the root-mean-square error, which is a measure of the average model error.

Over many rounds of experimentation, model predictions may drift, and new genetic changes may be added to the training inputs to improve predictive accuracy. For this example, design changes and their resulting performance were added to the predictive model (3316).

Genomic Design and Engineering as a Service

Figure 31:
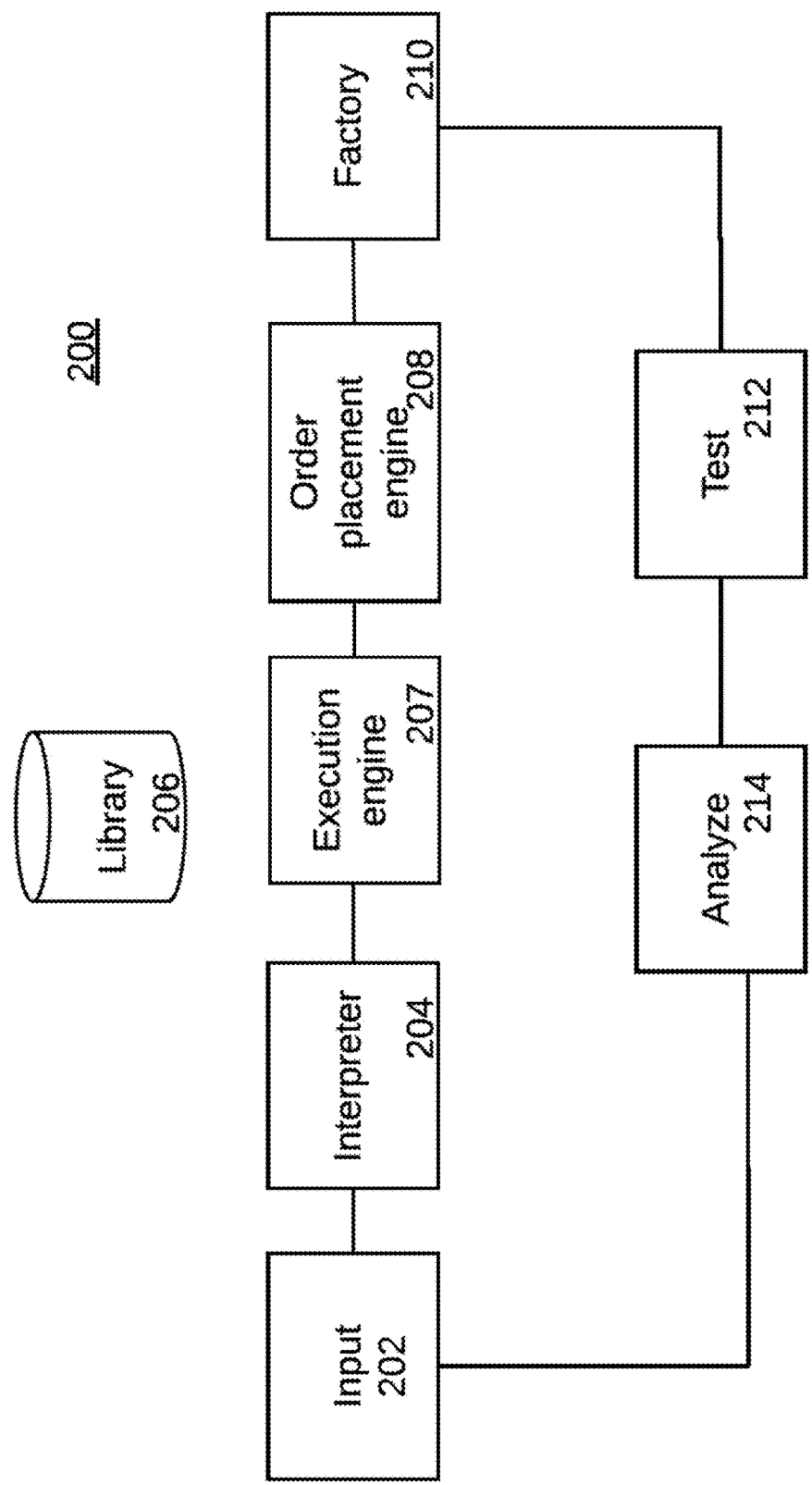
FIG. 31 diagrams an embodiment of LIMS system of the present disclosure for strain improvement.
Figure 32:
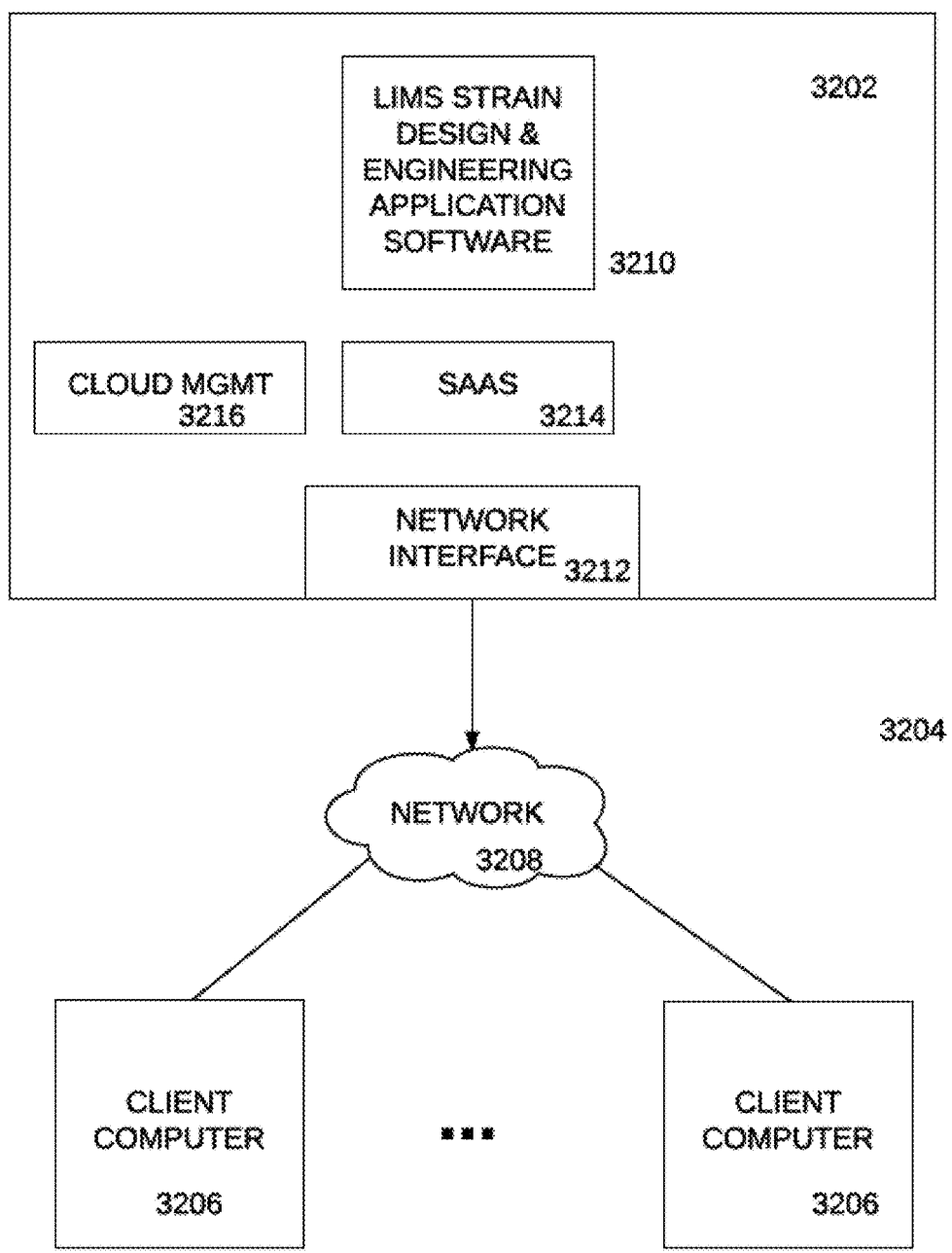
FIG. 32 diagrams a cloud computing implementation of embodiments of the LIMS system of the present disclosure.

In embodiments of the disclosure, the LIMS system software 3210 of FIG. 31 may be implemented in a cloud computing system 3202 of FIG. 32, to enable multiple users to design and build microbial strains according to embodiments of the present disclosure. FIG. 32 illustrates a cloud computing environment 3204 according to embodiments of the present disclosure. Client computers 3206, such as those illustrated in FIG. 34, access the LIMS system via a network 3208, such as the Internet. In embodiments, the LIMS system application software 3210 resides in the cloud computing system 3202. The LIMS system may employ one or more computing systems using one or more processors, of the type illustrated in FIG. 34. The cloud computing system itself includes a network interface 3212 to interface the LIMS system applications 3210 to the client computers 3206 via the network 3208. The network interface 3212 may include an application programming interface (API) to enable client applications at the client computers 3206 to access the LIMS system software 3210. In particular, through the API, client computers 3206 may access components of the LIMS system 200, including without limitation the software running the input interface 202, the interpreter 204, the execution engine 207, the order placement engine 208, the factory 210, as well as test equipment 212 and analysis equipment 214. A software as a service (SaaS) software module 3214 offers the LIMS system software 3210 as a service to the client computers 3206. A cloud management module 3216 manages access to the LIMS system 3210 by the client computers 3206. The cloud management module 3216 may enable a cloud architecture that employs multitenant applications, virtualization or other architectures known in the art to serve multiple users.

Genomic Automation

Automation of the methods of the present disclosure enables high-throughput phenotypic screening and identification of target products from multiple test strain variants simultaneously.

The aforementioned genomic engineering predictive modeling platform is premised upon the fact that hundreds and thousands of mutant strains are constructed in a high-throughput fashion. The robotic and computer systems described below are the structural mechanisms by which such a high-throughput process can be carried out.

In some embodiments, the present disclosure teaches methods of improving host cell productivities, or rehabilitating industrial strains. As part of this process, the present disclosure teaches methods of assembling DNA, building new strains, screening cultures in plates, and screening cultures in models for tank fermentation. In some embodiments, the present disclosure teaches that one or more of the aforementioned methods of creating and testing new host strains is aided by automated robotics.

In some embodiments, the present disclosure teaches a high-throughput strain engineering platform as depicted in FIG. 6.

HTP Robotic Systems

In some embodiments, the automated methods of the disclosure comprise a robotic system. The systems outlined herein are generally directed to the use of 96- or 384-well microtiter plates, but as will be appreciated by those in the art, any number of different plates or configurations may be used. In addition, any or all of the steps outlined herein may be automated; thus, for example, the systems may be completely or partially automated.

Figure 7:
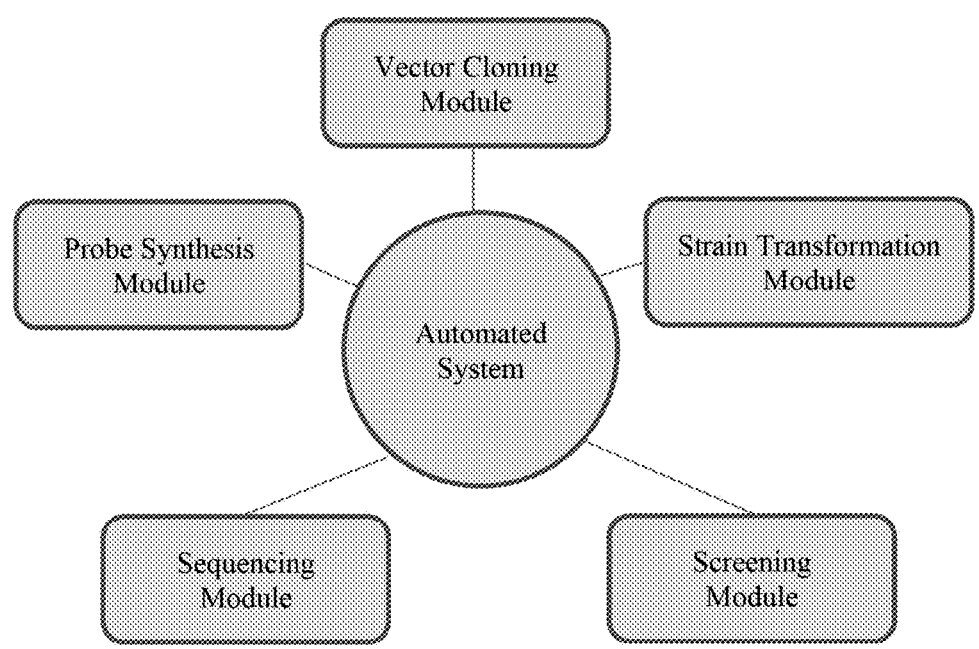
FIG. 7 depicts one embodiment of the automated system of the present disclosure. The present disclosure teaches use of automated robotic systems with various modules capable of cloning, transforming, culturing, screening and/or sequencing host organisms.
Figure 8:
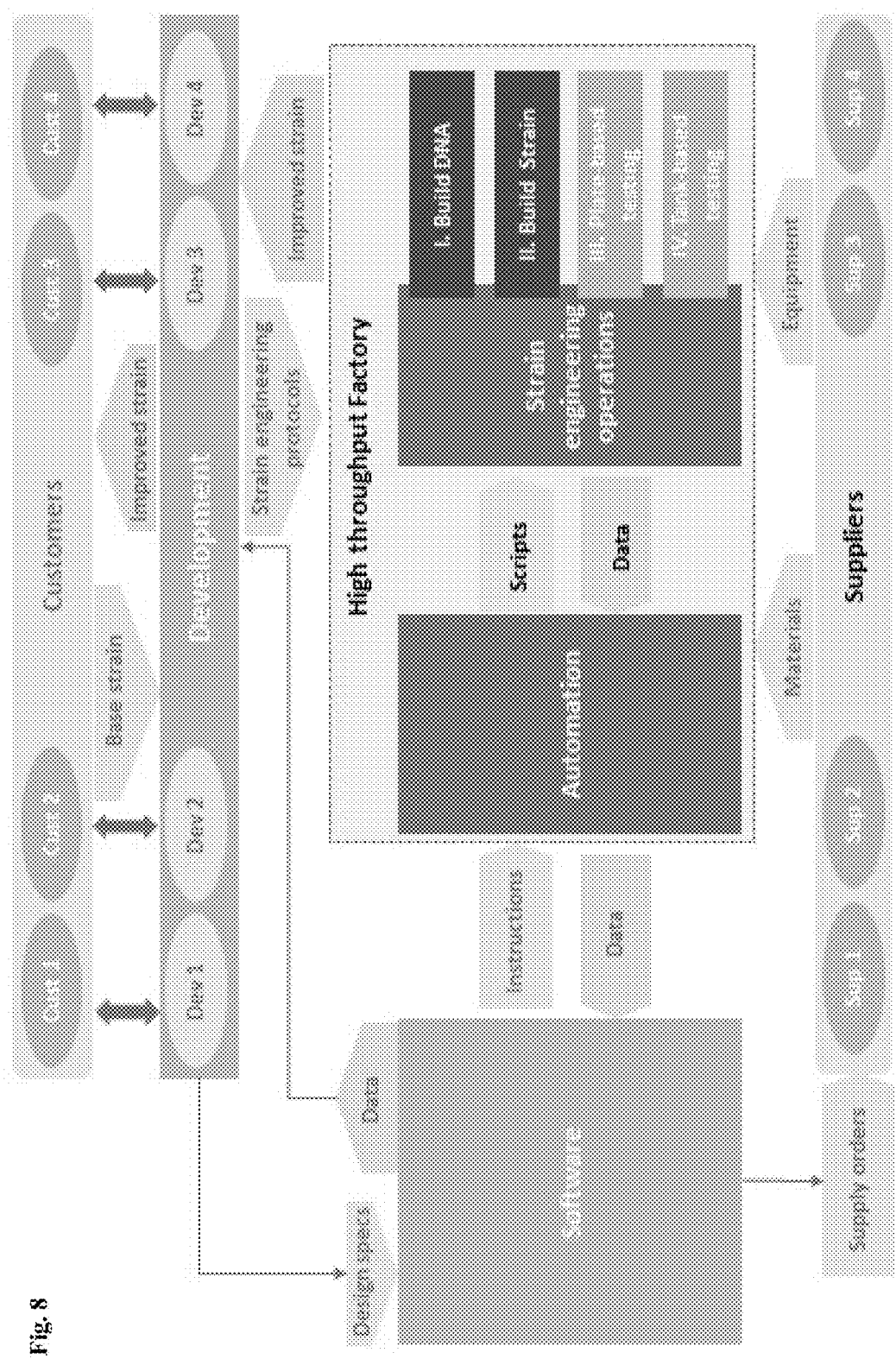
FIG. 8 depicts an overview of an embodiment of the host strain improvement program of the present disclosure.

In some embodiments, the automated systems of the present disclosure comprise one or more work modules. For example, in some embodiments, the automated system of the present disclosure comprises a DNA synthesis module, a vector cloning module, a strain transformation module, a screening module, and a sequencing module (see FIG. 7).

As will be appreciated by those in the art, an automated system can include a wide variety of components, including, but not limited to: liquid handlers; one or more robotic arms; plate handlers for the positioning of microplates; plate sealers, plate piercers, automated lid handlers to remove and replace lids for wells on non-cross contamination plates; disposable tip assemblies for sample distribution with disposable tips; washable tip assemblies for sample distribution; 96 well loading blocks; integrated thermal cyclers; cooled reagent racks; microtiter plate pipette positions (optionally cooled); stacking towers for plates and tips; magnetic bead processing stations; filtrations systems; plate shakers; barcode readers and applicators; and computer systems.

In some embodiments, the robotic systems of the present disclosure include automated liquid and particle handling enabling high-throughput pipetting to perform all the steps in the process of gene targeting and recombination applications. This includes liquid and particle manipulations such as aspiration, dispensing, mixing, diluting, washing, accurate volumetric transfers; retrieving and discarding of pipette tips; and repetitive pipetting of identical volumes for multiple deliveries from a single sample aspiration. These manipulations are cross-contamination-free liquid, particle, cell, and organism transfers. The instruments perform automated replication of microplate samples to filters, membranes, and/or daughter plates, high-density transfers, full-plate serial dilutions, and high capacity operation.

In some embodiments, the customized automated liquid handling system of the disclosure is a TECAN machine (e.g. a customized TECAN Freedom Evo).

In some embodiments, the automated systems of the present disclosure are compatible with platforms for multi-well plates, deep-well plates, square well plates, reagent troughs, test tubes, mini tubes, microfuge tubes, cryovials, filters, micro array chips, optic fibers, beads, agarose and acrylamide gels, and other solid-phase matrices or platforms are accommodated on an upgradeable modular deck. In some embodiments, the automated systems of the present disclosure contain at least one modular deck for multi-position work surfaces for placing source and output samples, reagents, sample and reagent dilution, assay plates, sample and reagent reservoirs, pipette tips, and an active tip-washing station.

In some embodiments, the automated systems of the present disclosure include high-throughput electroporation systems. In some embodiments, the high-throughput electroporation systems are capable of transforming cells in 96 or 384-well plates. In some embodiments, the high-throughput electroporation systems include VWR® High-throughput Electroporation Systems, BTX™, Bio-Rad® Gene Pulser MXcell™ or other multi-well electroporation system.

In some embodiments, the integrated thermal cycler and/or thermal regulators are used for stabilizing the temperature of heat exchangers such as controlled blocks or platforms to provide accurate temperature control of incubating samples from 0° C. to 100° C.

In some embodiments, the automated systems of the present disclosure are compatible with interchangeable machine-heads (single or multi-channel) with single or multiple magnetic probes, affinity probes, replicators or pipetters, capable of robotically manipulating liquid, particles, cells, and multi-cellular organisms. Multi-well or multi-tube magnetic separators and filtration stations manipulate liquid, particles, cells, and organisms in single or multiple sample formats.

In some embodiments, the automated systems of the present disclosure are compatible with camera vision and/or spectrometer systems. Thus, in some embodiments, the automated systems of the present disclosure are capable of detecting and logging color and absorption changes in ongoing cellular cultures.

In some embodiments, the automated system of the present disclosure is designed to be flexible and adaptable with multiple hardware add-ons to allow the system to carry out multiple applications. The software program modules allow creation, modification, and running of methods. The system's diagnostic modules allow setup, instrument alignment, and motor operations. The customized tools, labware, and liquid and particle transfer patterns allow different applications to be programmed and performed. The database allows method and parameter storage. Robotic and computer interfaces allow communication between instruments.

Figure 26:
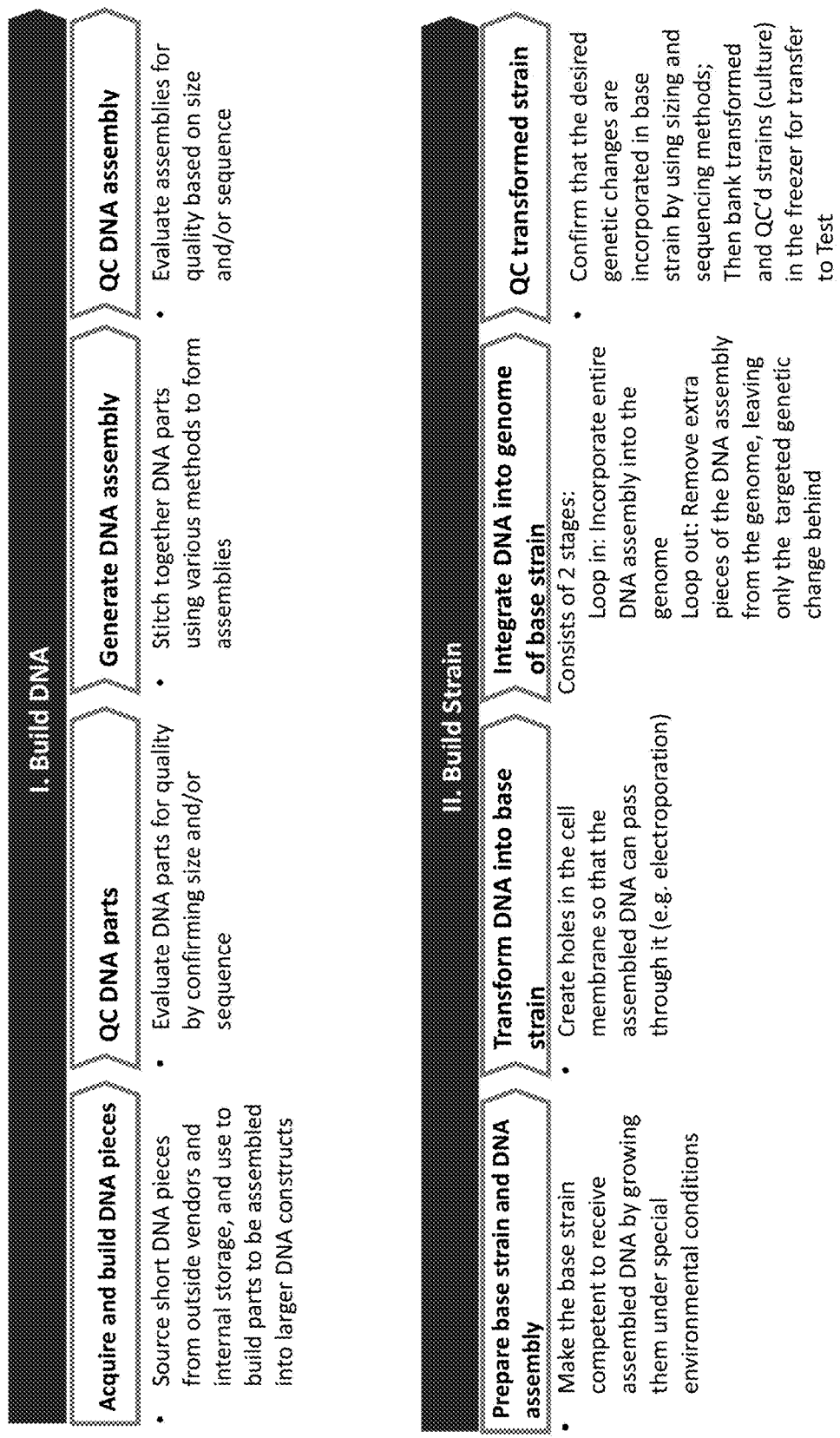
FIG. 26 depicts the DNA assembly and transformation steps of one of the embodiments of the present disclosure. The flow chart depicts the steps for building DNA fragments, cloning said DNA fragments into vectors, transforming said vectors into host strains, and looping out selection sequences through counter selection.
Figure 27:
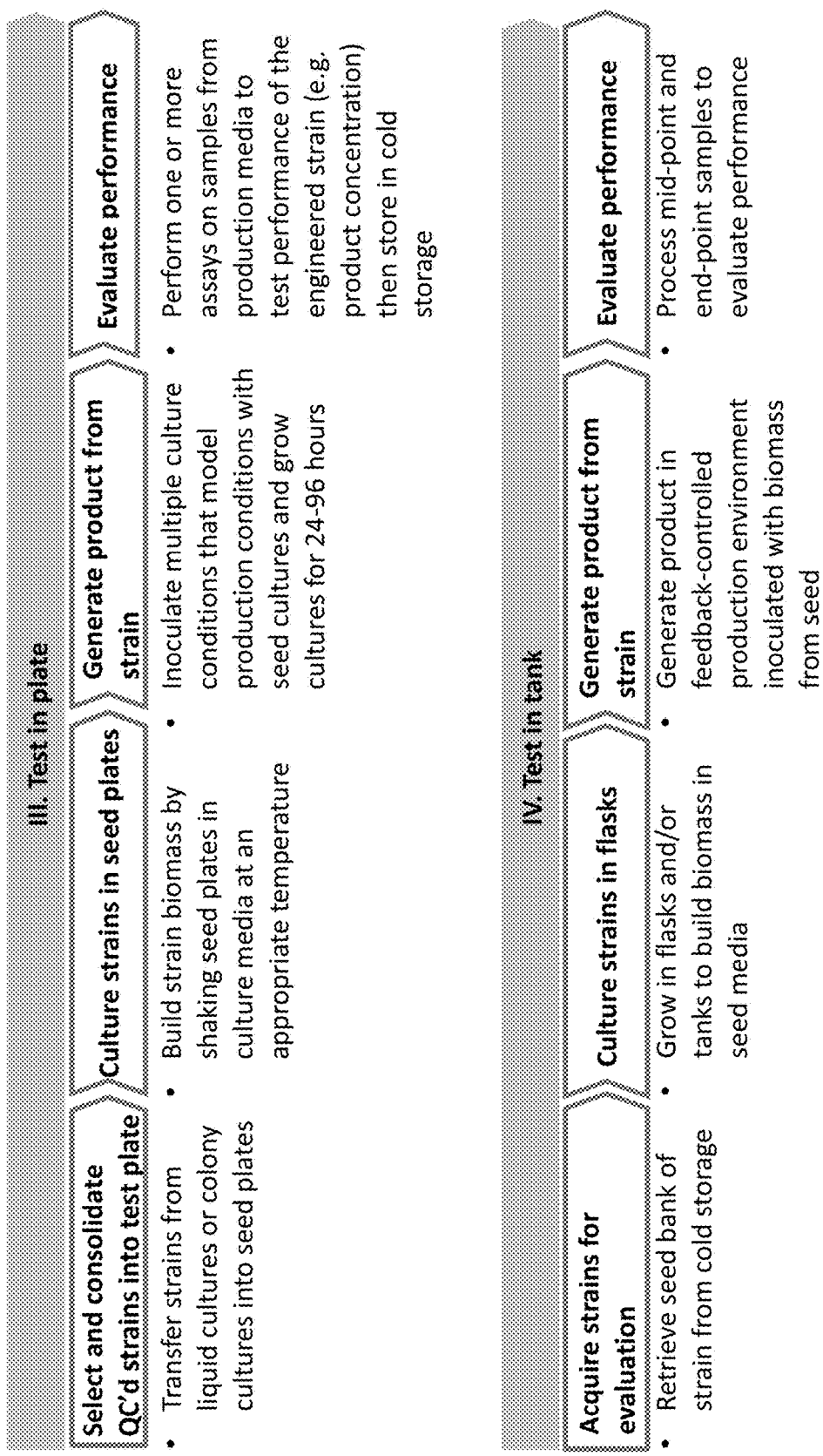
FIG. 27 depicts the steps for high-throughput culturing, screening, and evaluation of selected host strains. This figure also depicts the optional steps of culturing, screening, and evaluating selected strains in culture tanks.
Figure 28:
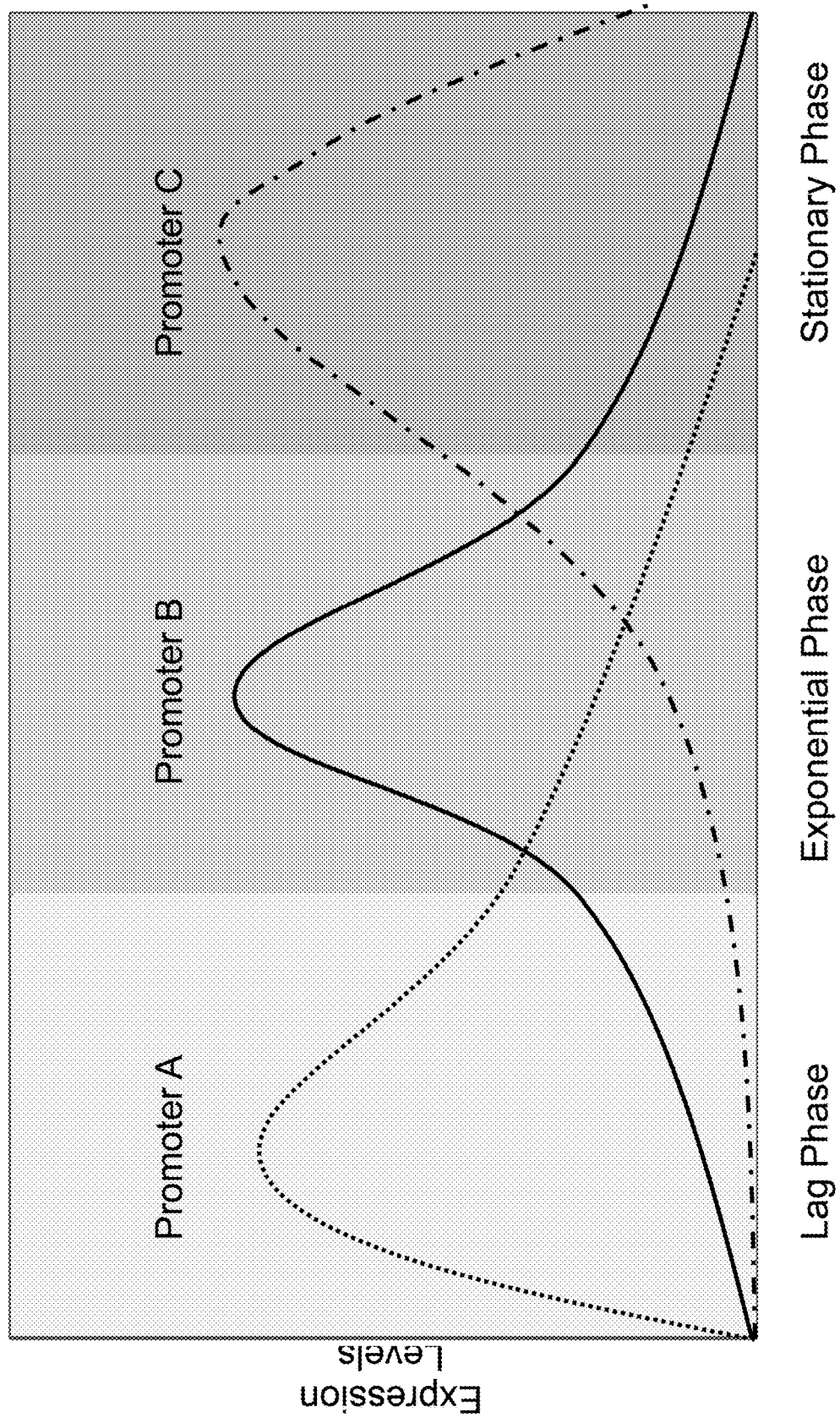
FIG. 28 depicts expression profiles of illustrative promoters exhibiting a range of regulatory expression, according to the promoter ladders of the present disclosure. Promoter A expression peaks at the lag phase of bacterial cultures, while promoter B and C peak at the exponential and stationary phase, respectively.
Figure 29:
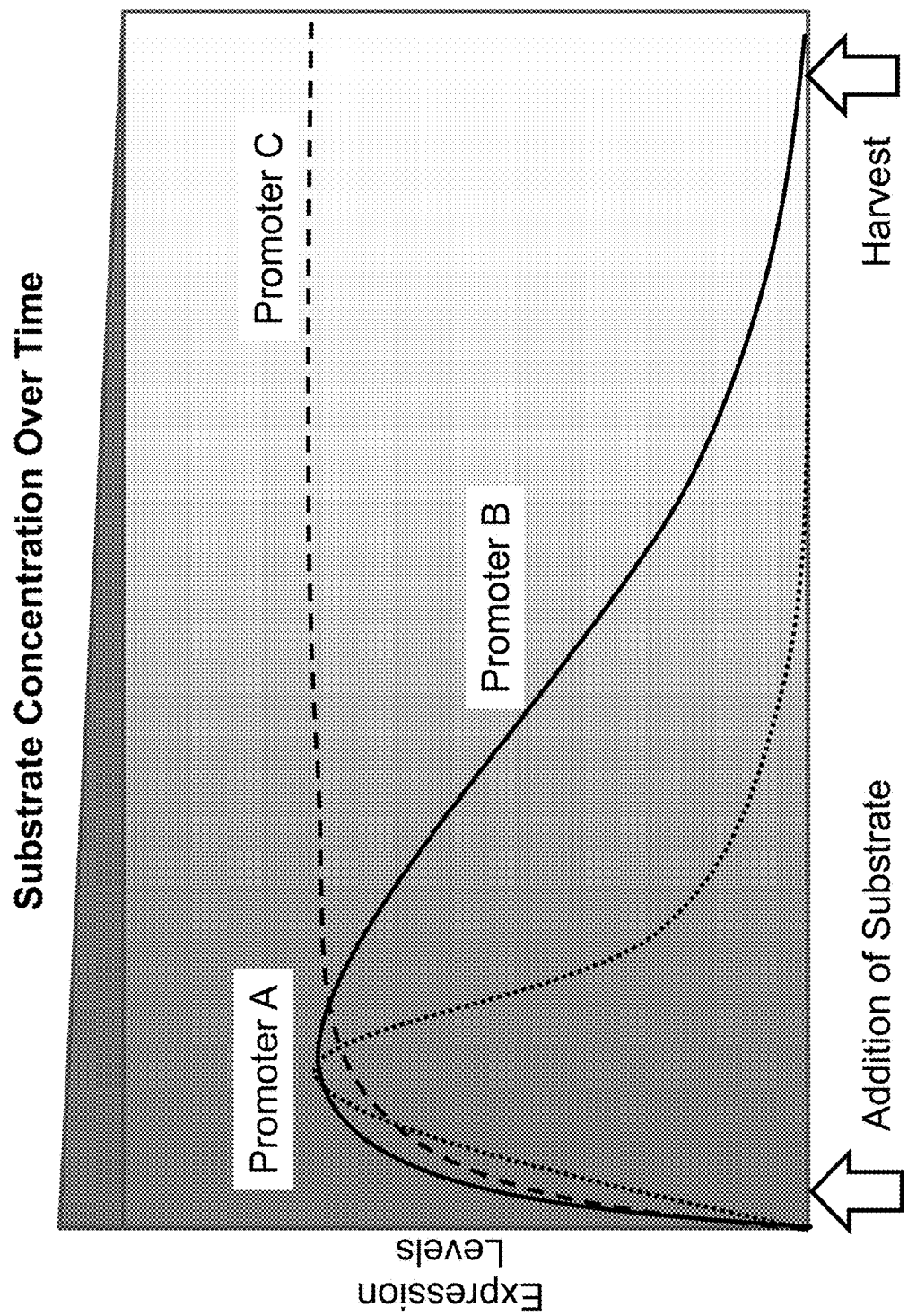
FIG. 29 depicts expression profiles of illustrative promoters exhibiting a range of regulatory expression, according to the promoter ladders of the present disclosure. Promoter A expression peaks immediately upon addition of a selected substrate, but quickly returns to undetectable levels as the concentration of the substrate is reduced. Promoter B expression peaks immediately upon addition of the selected substrate and lowers slowly back to undetectable levels together with the corresponding reduction in substrate. Promoter C expression peaks upon addition of the selected substrate, and remains highly expressed throughout the culture, even after the substrate has dissipated.
Figure 30:
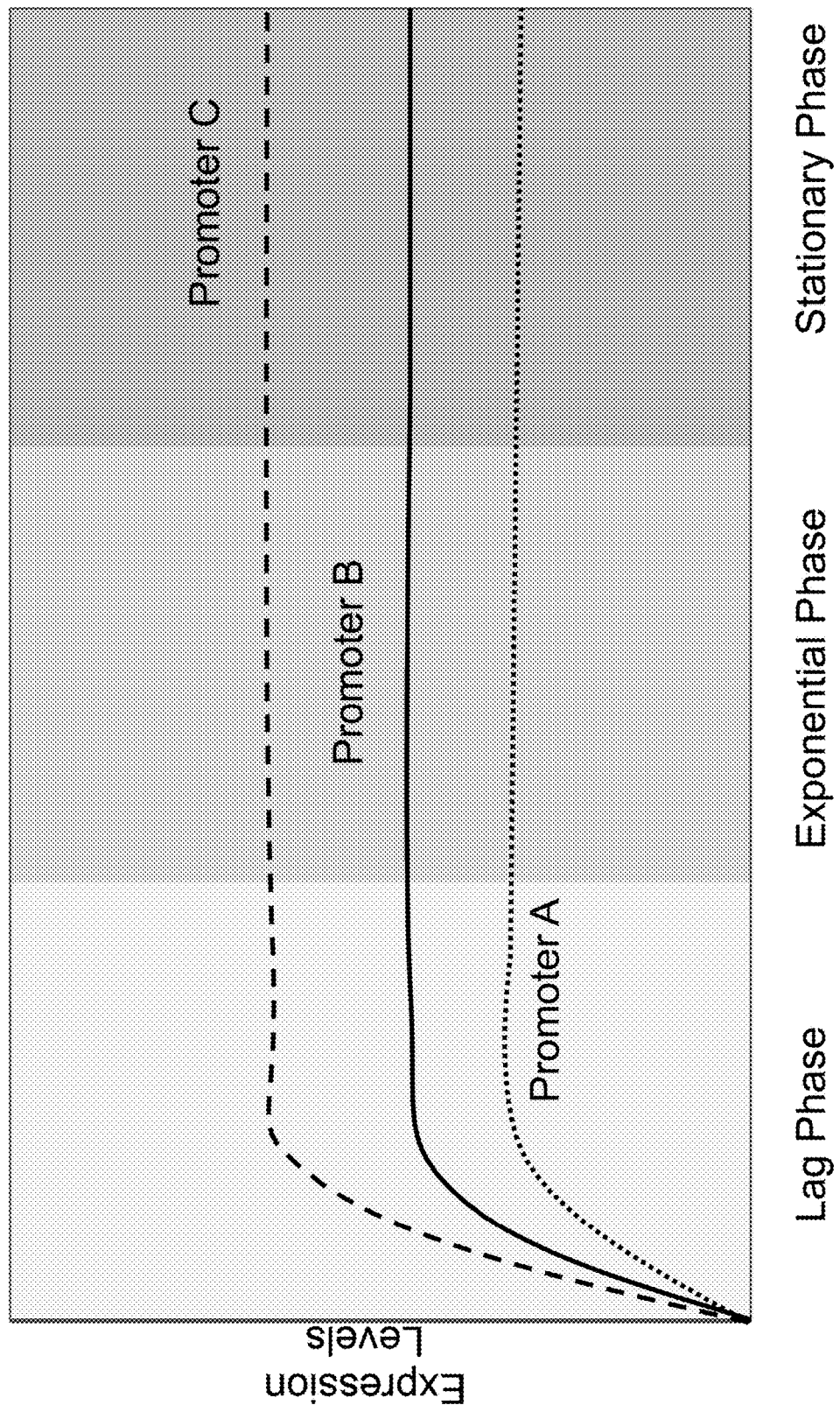
FIG. 30 depicts expression profiles of illustrative promoters exhibiting a range of constitutive expression levels, according to the promoter ladders of the present disclosure. Promoter A exhibits the lowest expression, followed by increasing expression levels promoter B and C, respectively.

Thus, in some embodiments, the present disclosure teaches a high-throughput strain engineering platform, as depicted in FIG. 26.

Persons having skill in the art will recognize the various robotic platforms capable of carrying out the HTP engineering methods of the present disclosure. Table 5 below provides a non-exclusive list of scientific equipment capable of carrying out each step of the HTP engineering steps of the present disclosure as described in FIG. 26.

TABLE 5

Non-exclusive list of Scientific Equipment Compatible with the HTP engineering methods of the present disclosure.

|  | Equipment Type | Operation(s) performed | Compatible Equipment Make/Model/Configuration |
|---|---|---|---|
| Acquire and build DNA pieces | liquid handlers | Hitpicking (combining by transferring) primers/templates for PCR amplification of DNA parts | Hamilton Microlab STAR, Labcyte Echo 550, Tecan EVO 200, Beckman Coulter Biomek FX, or equivalents |
|  | Thermal cyclers | PCR amplification of DNA parts | Inheco Cycler, ABI 2720, ABI Proflex 384, ABI Veriti, or equivalents |
| QC DNA parts | Fragment analyzers (capillary electrophoresis) | gel electrophoresis to confirm PCR products of appropriate size | Agilent Bioanalyzer, AATI Fragment Analyzer, or equivalents |
|  | Sequencer (sanger: Beckman) | Verifying sequence of parts/templates | Beckman Ceq-8000, Beckman GenomeLab ™, or equivalents |
|  | NGS (next generation sequencing) instrument | Verifying sequence of parts/templates | Illumina MiSeq series sequences, illumina Hi-Seq, Ion torrent, pac bio or other equivalents |
|  | nanodrop/plate reader | assessing concentration of DNA samples | Molecular Devices SpectraMax M5, Tecan M1000, or equivalents. |
| Generate DNA assembly | liquid handlers | Hitpicking (combining by transferring) DNA parts for assembly along with cloning vector, addition of reagents for assembly reaction/process | Hamilton Microlab STAR, Labcyte Echo 550, Tecan EVO 200, Beckman Coulter Biomek FX, or equivalents |
| QC DNA assembly | Colony pickers | for inoculating colonies in liquid media | Scirobotics Pickolo, Molecular Devices QPix 420 |
|  | liquid handlers | Hitpicking primers/templates, diluting samples | Hamilton Microlab STAR, Labcyte Echo 550, Tecan EVO 200, Beckman Coulter Biomek FX, or equivalents |
|  | Fragment analyzers (capillary electrophoresis) | gel electrophoresis to confirm assembled products of appropriate size | Agilent Bioanalyzer, AATI Fragment Analyzer |
|  | Sequencer (sanger: Beckman) | Verifying sequence of assembled plasmids | ABI3730 Thermo Fisher, Beckman Ceq-8000, Beckman GenomeLab ™, or equivalents |
|  | NGS (next generation sequencing) instrument | Verifying sequence of assembled plasmids | Illumina MiSeq series sequences, illumina Hi-Seq, Ion torrent, pac bio or other equivalents |
| Prepare base strain and DNA assembly | centrifuge | spinning/pelleting cells | Beckman Avanti floor centrifuge, Hettich Centrifuge |
| Transform DNA into base strain | Electroporators | electroporative transformation of cells | BTX Gemini X2, BIO-RAD MicroPulser Electroporator |
|  | Ballistic transformation | ballistic transformation of cells | BIO-RAD PDS1000 |
|  | Incubators, thermal cyclers | for chemical transformation/heat shock | Inheco Cycler, ABI 2720, ABI Proflex 384, ABI Veriti, or equivalents |
|  | Liquid handlers | for combining DNA, cells, buffer | Hamilton Microlab STAR, Labcyte Echo 550, Tecan EVO 200, Beckman Coulter Biomek FX, or equivalents |
| Integrate DNA into genome of base strain | Colony pickers | for inoculating colonies in liquid media | Scirobotics Pickolo, Molecular Devices QPix 420 |
|  | Liquid handlers | For transferring cells onto Agar, transferring from culture plates to different culture plates (inoculation into other selective media) | Hamilton Microlab STAR, Labcyte Echo 550, Tecan EVO 200, Beckman Coulter Biomek FX, or equivalents |
|  | Platform shaker-incubators | incubation with shaking of microtiter plate cultures | Kuhner Shaker ISF4-X, Inforsht Multitron Pro |
| QC transformed strain | Colony pickers | for inoculating colonies in liquid media | Scirobotics Pickolo, Molecular Devices QPix 420 |
|  | liquid handlers | Hitpicking primers/templates, diluting samples | Hamilton Microlab STAR, Labcyte Echo 550, Tecan EVO 200, Beckman Coulter Biomek FX, or equivalents |

TABLE 5-continued

Non-exclusive list of Scientific Equipment Compatible with the HTP engineering methods of the present disclosure.

| | Equipment Type | Operation(s) performed | Compatible Equipment Make/Model/Configuration |
|---|---|---|---|
| | Thermal cyclers | cPCR verification of strains | Inheco Cycler, ABI 2720, ABI Proflex 384, ABI Veriti, or equivalents |
| | Fragment analyzers (capillary electrophoresis) | gel electrophoresis to confirm cPCR products of appropriate size | Infors-ht Multitron Pro, Kuhner Shaker ISF4-X |
| | Sequencer (sanger: Beckman) | Sequence verification of introduced modification | Beckman Ceq-8000, Beckman GenomeLab ™, or equivalents |
| | NGS (next generation sequencing) instrument | Sequence verification of introduced modification | Illumina MiSeq series sequences, illumina Hi-Seq, Ion torrent, pac bio or other equivalents |
| Select and consolidate QC'd strains into test plate | Liquid handlers | For transferring from culture plates to different culture plates (inoculation into production media) | Hamilton Microlab STAR, Labcyte Echo 550, Tecan EVO 200, Beckman Coulter Biomek FX, or equivalents |
| | Colony pickers | for inoculating colonies in liquid media | Scirobotics Pickolo, Molecular Devices QPix 420 |
| | Platform shaker-incubators | incubation with shaking of microtiter plate cultures | Kuhner Shaker ISF4-X, Infors-ht Multitron Pro |
| Culture strains in seed plates | Liquid handlers | For transferring from culture plates to different culture plates (inoculation into production media) | Hamilton Microlab STAR, Labcyte Echo 550, Tecan EVO 200, Beckman Coulter Biomek FX, or equivalents |
| | Platform shaker-incubators | incubation with shaking of microtiter plate cultures | Kuhner Shaker ISF4-X, Infors-ht Multitron Pro |
| | liquid dispensers | Dispense liquid culture media into microtiter plates | Well mate (Thermo), Benchcel2R (velocity 11), plateloc (velocity 11) |
| | microplate labeler | apply barcoders to plates | Microplate labeler (a2+ cab - agilent), benchcell 6R (velocity11) |
| Generate product from strain | Liquid handlers | For transferring from culture plates to different culture plates (inoculation into production media) | Hamilton Microlab STAR, Labcyte Echo 550, Tecan EVO 200, Beckman Coulter Biomek FX, or equivalents |
| | Platform shaker-incubators | incubation with shaking of microtiter plate cultures | Kuhner Shaker ISF4-X, Infors-ht Multitron Pro |
| | liquid dispensers | Dispense liquid culture media into multiple microtiter plates and seal plates | well mate (Thermo), Benchcel2R (velocity 11), plateloc (velocity 11) |
| | microplate labeler | Apply barcodes to plates | microplate labeler (a2+ cab - agilent), benchcell 6R (velocity11) |
| Evaluate performance | Liquid handlers | For processing culture broth for downstream analytical | Hamilton Microlab STAR, Labcyte Echo 550, Tecan EVO 200, Beckman Coulter Biomek FX, or equivalents |
| | UHPLC, HPLC | quantitative analysis of precursor and target compounds | Agilent 1290 Series UHPLC and 1200 Series HPLC with UV and RI detectors, or equivalent; also any LC/MS |
| | LC/MS | highly specific analysis of precursor and target compounds as well as side and degradation products | Agilent 6490 QQQ and 6550 QTOF coupled to 1290 Series UHPLC |
| | Spectrophotometer | Quantification of different compounds using spectrophotometer based assays | Tecan M1000, spectramax M5, Genesys 10S |
| Culture strains in flasks | Fermenters: | incubation with shaking | Sartorius, DASGIPs (Eppendorf), BIO-FLOs (Sartorius-stedim). Applikon innova 4900, or any equivalent |
| | Platform shakers | | |
| Generate product from strain | Fermenters: DASGIPs (Eppendorf), BIO-FLOs (Sartorius-stedim) | | |
| Evaluate performance | Liquid handlers | For transferring from culture plates to different culture plates (inoculation into production media) | Hamilton Microlab STAR, Labcyte Echo 550, Tecan EVO 200, Beckman Coulter Biomek FX, or equivalents |

TABLE 5-continued

Non-exclusive list of Scientific Equipment Compatible with the HTP engineering methods of the present disclosure.

| Equipment Type | Operation(s) performed | Compatible Equipment Make/Model/Configuration |
|---|---|---|
| UHPLC, HPLC | quantitative analysis of precursor and target compounds | Agilent 1290 Series UHPLC and 1200 Series HPLC with UV and RI detectors, or equivalent; also any LC/MS |
| LC/MS | highly specific analysis of precursor and target compounds as well as side and degradation products | Agilent 6490 QQQ and 6550 QTOF coupled to 1290 Series UHPLC |
| Flow cytometer | Characterize strain performance (measure viability) | BD Accuri, Millipore Guava |
| Spectrophotometer | Characterize strain performance (measure biomass) | Tecan M1000, Spectramax M5, or other equivalents |

Computer System Hardware

Figure 34:
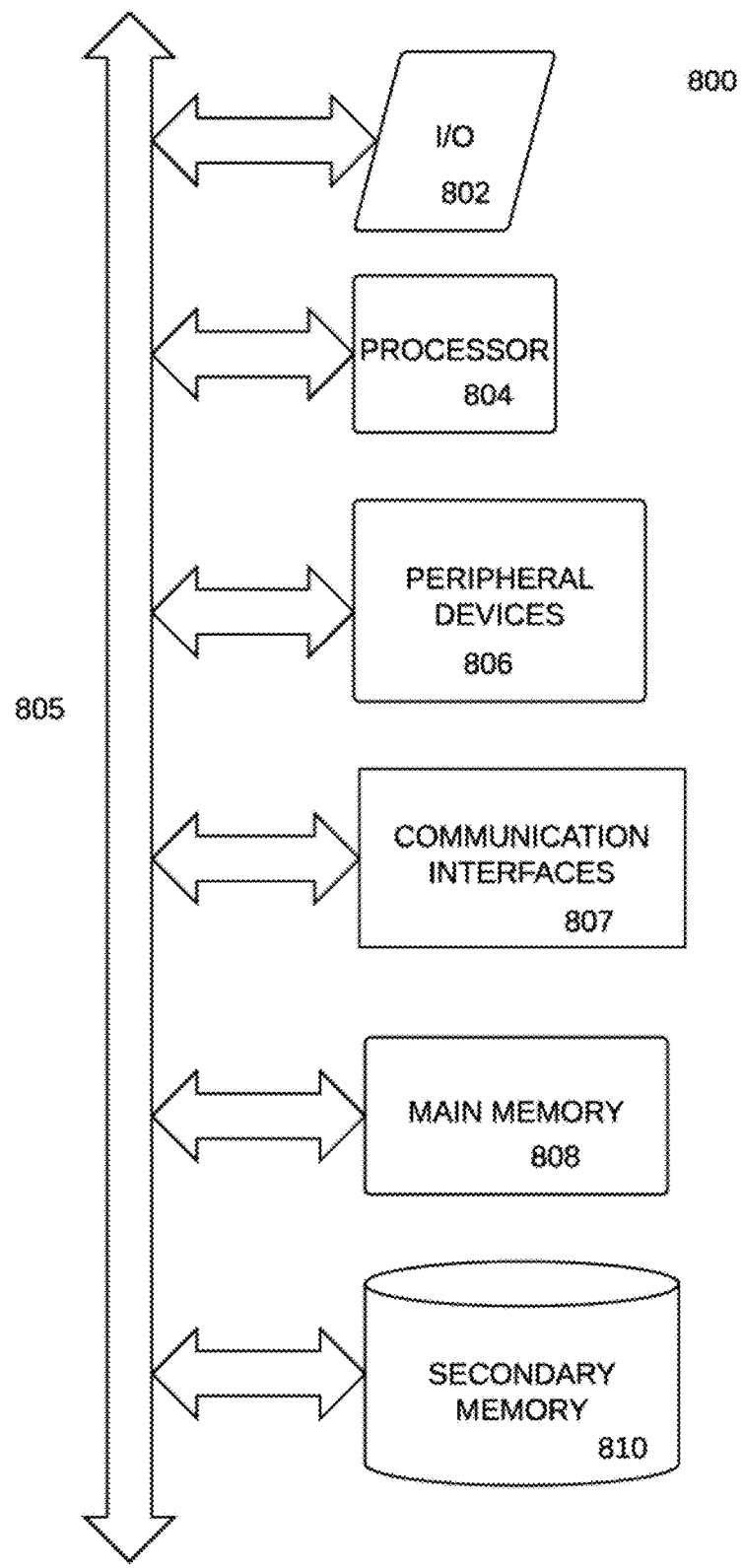
FIG. 34 diagrams an embodiment of a computer system, according to embodiments of the present disclosure.
Figure 35:
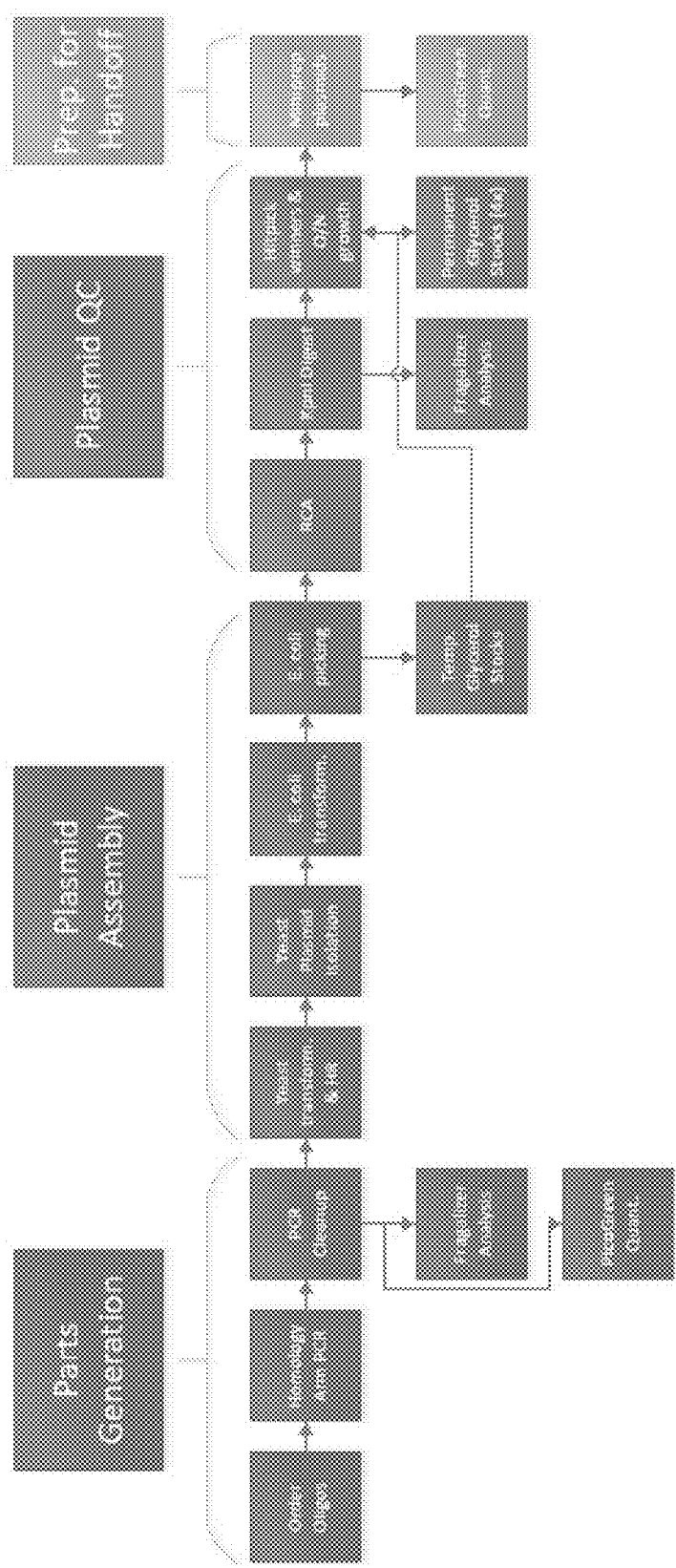
FIG. 35 depicts the workflow associated with the DNA assembly according to one embodiment of the present disclosure. This process is divided up into 4 stages: parts generation, plasmid assembly, plasmid QC, and plasmid preparation for transformation. During parts generation, oligos designed by Laboratory Information Management System (LIMS) are ordered from an oligo sequencing vendor and used to amplify the target sequences from the host organism via PCR. These PCR parts are cleaned to remove contaminants and assessed for success by fragment analysis, in silico quality control comparison of observed to theoretical fragment sizes, and DNA quantification. The parts are transformed into yeast along with an assembly vector and assembled into plasmids via homologous recombination. Assembled plasmids are isolated from yeast and transformed into E. coli for subsequent assembly quality control and amplification. During plasmid assembly quality control, several replicates of each plasmid are isolated, amplified using Rolling Circle Amplification (RCA), and assessed for correct assembly by enzymatic digest and fragment analysis. Correctly assembled plasmids identified during the QC process are hit picked to generate permanent stocks and the plasmid DNA extracted and quantified prior to transformation into the target host organism.

FIG. 34 illustrates an example of a computer system 800 that may be used to execute program code stored in a non-transitory computer readable medium (e.g., memory) in accordance with embodiments of the disclosure. The computer system includes an input/output subsystem 802, which may be used to interface with human users and/or other computer systems depending upon the application. The I/O subsystem 802 may include, e.g., a keyboard, mouse, graphical user interface, touchscreen, or other interfaces for input, and, e.g., an LED or other flat screen display, or other interfaces for output, including application program interfaces (APIs). Other elements of embodiments of the disclosure, such as the components of the LIMS system, may be implemented with a computer system like that of computer system 800.

Program code may be stored in non-transitory media such as persistent storage in secondary memory 810 or main memory 808 or both. Main memory 808 may include volatile memory such as random access memory (RAM) or non-volatile memory such as read only memory (ROM), as well as different levels of cache memory for faster access to instructions and data. Secondary memory may include persistent storage such as solid state drives, hard disk drives or optical disks. One or more processors 804 reads program code from one or more non-transitory media and executes the code to enable the computer system to accomplish the methods performed by the embodiments herein. Those skilled in the art will understand that the processor(s) may ingest source code, and interpret or compile the source code into machine code that is understandable at the hardware gate level of the processor(s) 804. The processor(s) 804 may include graphics processing units (GPUs) for handling computationally intensive tasks. Particularly in machine learning, one or more CPUs 804 may offload the processing of large quantities of data to one or more GPUs 804.

The processor(s) 804 may communicate with external networks via one or more communications interfaces 807, such as a network interface card, WiFi transceiver, etc. A bus 805 communicatively couples the I/O subsystem 802, the processor(s) 804, peripheral devices 806, communications interfaces 807, memory 808, and persistent storage 810. Embodiments of the disclosure are not limited to this representative architecture. Alternative embodiments may employ different arrangements and types of components, e.g., separate buses for input-output components and memory subsystems.

Those skilled in the art will understand that some or all of the elements of embodiments of the disclosure, and their accompanying operations, may be implemented wholly or partially by one or more computer systems including one or more processors and one or more memory systems like those of computer system 800. In particular, the elements of the LIMS system 200 and any robotics and other automated systems or devices described herein may be computer-implemented. Some elements and functionality may be implemented locally and others may be implemented in a distributed fashion over a network through different servers, e.g., in client-server fashion, for example. In particular, server-side operations may be made available to multiple clients in a software as a service (SaaS) fashion, as shown in FIG. 32.

The term component in this context refers broadly to software, hardware, or firmware (or any combination thereof) component. Components are typically functional components that can generate useful data or other output using specified input(s). A component may or may not be self-contained. An application program (also called an "application") may include one or more components, or a component can include one or more application programs.

Some embodiments include some, all, or none of the components along with other modules or application components. Still yet, various embodiments may incorporate two or more of these components into a single module and/or associate a portion of the functionality of one or more of these components with a different component.

The term "memory" can be any device or mechanism used for storing information. In accordance with some embodiments of the present disclosure, memory is intended to encompass any type of, but is not limited to: volatile memory, nonvolatile memory, and dynamic memory. For example, memory can be random access memory, memory storage devices, optical memory devices, magnetic media, floppy disks, magnetic tapes, hard drives, SIMMs, SDRAM, DIMMs, RDRAM, DDR RAM, SODIMMS, erasable programmable read-only memories (EPROMs), electrically erasable programmable read-only memories (EEPROMs), compact disks, DVDs, and/or the like. In accordance with some embodiments, memory may include one or more disk drives, flash drives, databases, local cache memories, processor cache memories, relational databases, flat databases, servers, cloud based platforms, and/or the like. In addition, those of ordinary skill in the art will appreciate many additional devices and techniques for storing information can be used as memory.

Memory may be used to store instructions for running one or more applications or modules on a processor. For example, memory could be used in some embodiments to house all or some of the instructions needed to execute the functionality of one or more of the modules and/or applications disclosed in this application.

HTP Microbial Strain Engineering Based Upon Genetic Design Predictions: An Example Workflow In some embodiments, the present disclosure teaches the directed engineering of new host organisms based on the recommendations of the computational analysis systems of the present disclosure.

In some embodiments, the present disclosure is compatible with all genetic design and cloning methods. That is, in some embodiments, the present disclosure teaches the use of traditional cloning techniques such as polymerase chain reaction, restriction enzyme digestions, ligation, homologous recombination, RT PCR, and others generally known in the art and are disclosed in for example: Sambrook et al. (2001) Molecular Cloning: A Laboratory Manual (3$^{rd}$ ed., Cold Spring Harbor Laboratory Press, Plainview, N.Y.), incorporated herein by reference.

In some embodiments, the cloned sequences can include possibilities from any of the HTP genetic design libraries taught herein, for example: promoters from a promoter swap library, SNPs from a SNP swap library, start or stop codons from a start/stop codon exchange library, terminators from a STOP swap library, or sequence optimizations from a sequence optimization library.

Further, the exact sequence combinations that should be included in a particular construct can be informed by the epistatic mapping function.

In other embodiments, the cloned sequences can also include sequences based on rational design (hypothesis-driven) and/or sequences based on other sources, such as scientific publications.

Figure 2:
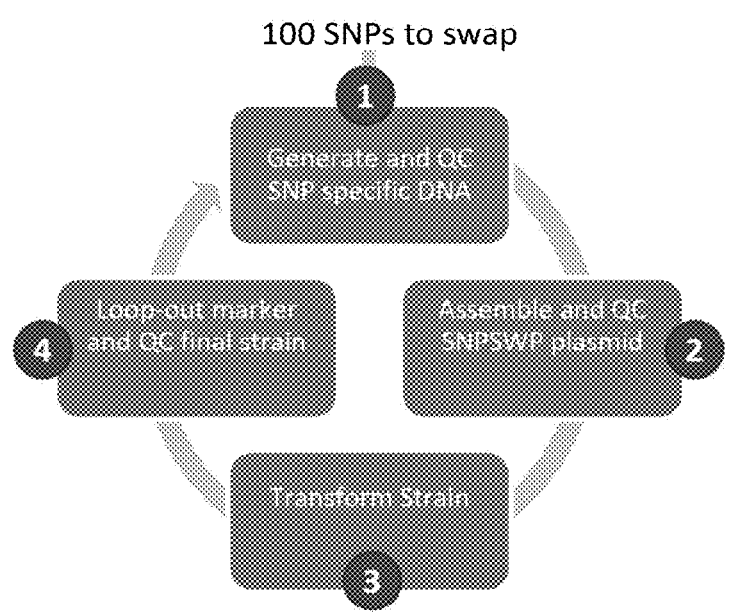
FIG. 2 outlines methods of the present disclosure for generating new host organisms with selected sequence modifications (e.g., 100 SNPs to swap). Briefly, the method comprises (1) desired DNA inserts are designed and generated by combining one or more synthesized oligos in an assembly reaction, (2) DNA inserts are cloned into transformation plasmids, (3) completed plasmids are transferred into desired production strains, where they are integrated into the host strain genome, and (4) selection markers and other unwanted DNA elements are looped out of the host strain. Each DNA assembly step may involve additional quality control (QC) steps, such as cloning plasmids into *E. coli* bacteria for amplification and sequencing.

In some embodiments, the present disclosure teaches methods of directed engineering, including the steps of i) generating custom-made SNP-specific DNA, ii) assembling SNP-specific plasmids, iii) transforming target host cells with SNP-specific DNA, and iv) looping out any selection markers (See FIG. 2).

Figure 6A:
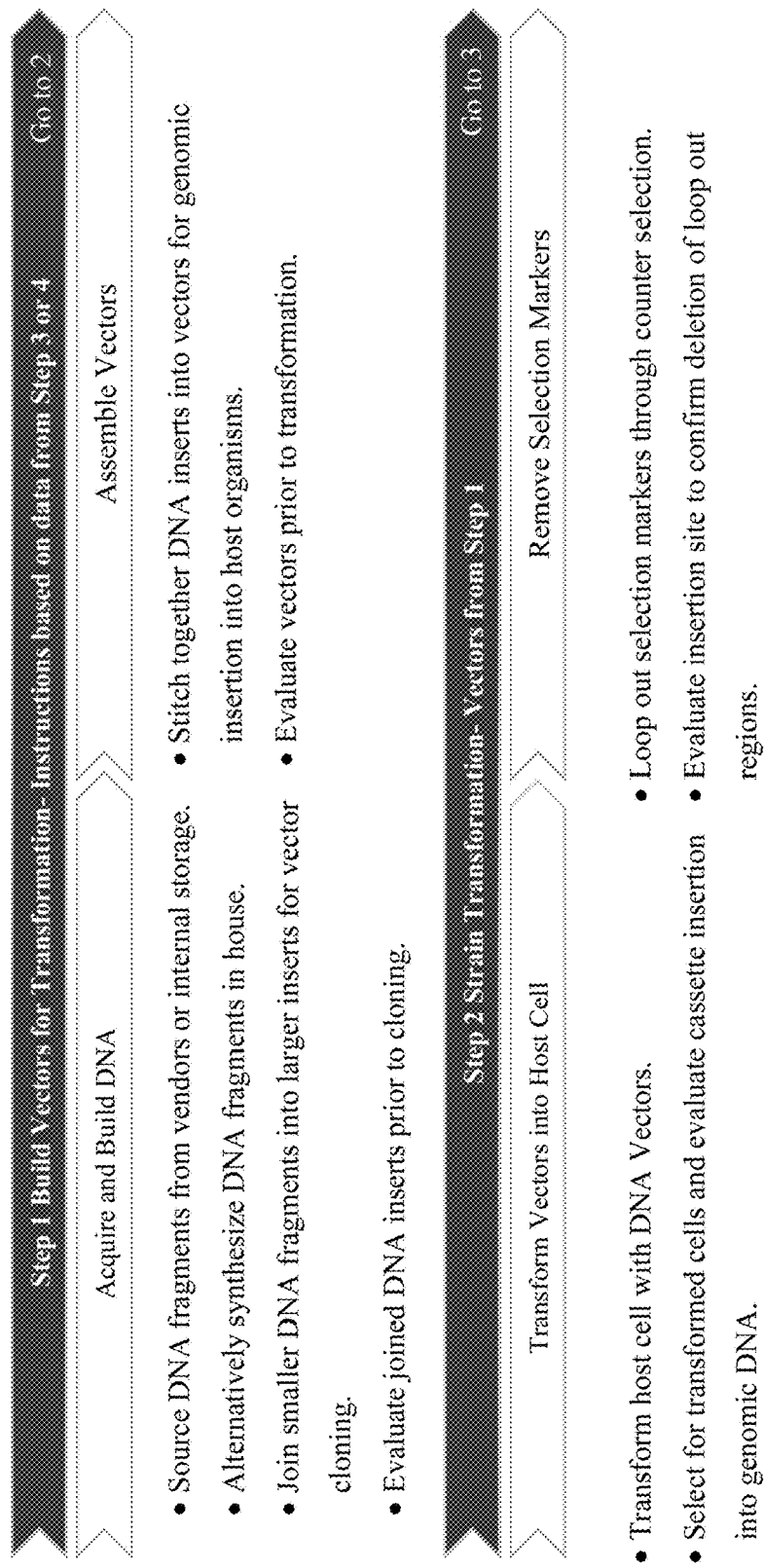
FIG. 6A-B depicts the DNA assembly, transformation, and strain screening steps of one of the embodiments of the present disclosure.
Figure 6B:

FIG. 6A depicts the general workflow of the strain engineering methods of the present disclosure, including acquiring and assembling DNA, assembling vectors, transforming host cells and removing selection markers.

Build Specific DNA Oligonucleotides

In some embodiments, the present disclosure teaches inserting and/or replacing and/or altering and/or deleting a DNA segment of the host cell organism. In some aspects, the methods taught herein involve building an oligonucleotide of interest (i.e. a target DNA segment), that will be incorporated into the genome of a host organism. In some embodiments, the target DNA segments of the present disclosure can be obtained via any method known in the art, including: copying or cutting from a known template, mutation, or DNA synthesis. In some embodiments, the present disclosure is compatible with commercially available gene synthesis products for producing target DNA sequences (e.g., GeneArt™, GeneMaker™, GenScript™, Anagen™, Blue Heron™, Entelechon™, GeNOsys, Inc., or Qiagen™).

In some embodiments, the target DNA segment is designed to incorporate a SNP into a selected DNA region of the host organism (e.g., adding a beneficial SNP). In other embodiments, the DNA segment is designed to remove a SNP from the DNA of the host organisms (e.g., removing a detrimental or neutral SNP).

In some embodiments, the oligonucleotides used in the inventive methods can be synthesized using any of the methods of enzymatic or chemical synthesis known in the art. The oligonucleotides may be synthesized on solid supports such as controlled pore glass (CPG), polystyrene beads, or membranes composed of thermoplastic polymers that may contain CPG. Oligonucleotides can also be synthesized on arrays, on a parallel microscale using microfluidics (Tian et al., Mol. BioSyst., 5, 714-722 (2009)), or known technologies that offer combinations of both (see Jacobsen et al., U.S. Pat. App. No. 2011/0172127).

Synthesis on arrays or through microfluidics offers an advantage over conventional solid support synthesis by reducing costs through lower reagent use. The scale required for gene synthesis is low, so the scale of oligonucleotide product synthesized from arrays or through microfluidics is acceptable. However, the synthesized oligonucleotides are of lesser quality than when using solid support synthesis (See Tian infra.; see also Staehler et al., U.S. Pat. App. No. 2010/0216648).

A great number of advances have been achieved in the traditional four-step phosphoramidite chemistry since it was first described in the 1980s (see for example, Sierzchala, et al. *J. Am. Chem. Soc.*, 125, 13427-13441 (2003) using peroxy anion deprotection; Hayakawa et al., U.S. Pat. No. 6,040,439 for alternative protecting groups; Azhayev et al, *Tetrahedron* 57, 4977-4986 (2001) for universal supports; Kozlov et al., Nucleosides, *Nucleotides, and Nucleic Acids*, 24 (5-7), 1037-1041 (2005) for improved synthesis of longer oligonucleotides through the use of large-pore CPG; and Damha et al., *NAR*, 18, 3813-3821 (1990) for improved derivatization).

Regardless of the type of synthesis, the resulting oligonucleotides may then form the smaller building blocks for longer oligonucleotides. In some embodiments, smaller oligonucleotides can be joined together using protocols known in the art, such as polymerase chain assembly (PCA), ligase chain reaction (LCR), and thermodynamically balanced inside-out synthesis (TBIO) (see Czar et al. Trends in Biotechnology, 27, 63-71 (2009)). In PCA, oligonucleotides spanning the entire length of the desired longer product are annealed and extended in multiple cycles (typically about 55 cycles) to eventually achieve full-length product. LCR uses ligase enzyme to join two oligonucleotides that are both annealed to a third oligonucleotide. TBIO synthesis starts at the center of the desired product and is progressively extended in both directions by using overlapping oligonucleotides that are homologous to the forward strand at the 5' end of the gene and against the reverse strand at the 3' end of the gene.

Another method of synthesizing a larger double stranded DNA fragment is to combine smaller oligonucleotides through top-strand PCR (TSP). In this method, a plurality of oligonucleotides spans the entire length of a desired product and contain overlapping regions to the adjacent oligonucleotide(s). Amplification can be performed with universal forward and reverse primers, and through multiple cycles of amplification a full-length double stranded DNA product is formed. This product can then undergo optional error correction and further amplification that results in the desired double stranded DNA fragment end product.

In one method of TSP, the set of smaller oligonucleotides that will be combined to form the full-length desired product are between 40-200 bases long and overlap each other by at least about 15-20 bases. For practical purposes, the overlap region should be at a minimum long enough to ensure specific annealing of oligonucleotides and have a high enough melting temperature ($T_m$) to anneal at the reaction temperature employed. The overlap can extend to the point where a given oligonucleotide is completely overlapped by adjacent oligonucleotides. The amount of overlap does not seem to have any effect on the quality of the final product. The first and last oligonucleotide building block in the assembly should contain binding sites for forward and reverse amplification primers. In one embodiment, the terminal end sequence of the first and last oligonucleotide contain the same sequence of complementarity to allow for the use of universal primers.

Assembling/Cloning Custom Plasmids

In some embodiments, the present disclosure teaches methods for constructing vectors capable of inserting desired target DNA sections (e.g. containing a particular SNP) into the genome of host organisms. In some embodiments, the present disclosure teaches methods of cloning vectors comprising the target DNA, homology arms, and at least one selection marker (see FIG. 3).

In some embodiments, the present disclosure is compatible with any vector suited for transformation into the host organism. In some embodiments, the present disclosure teaches use of shuttle vectors compatible with a host cell. In one embodiment, a shuttle vector for use in the methods provided herein is a shuttle vector compatible with an *E. coli* and/or *Corynebacterium* host cell. Shuttle vectors for use in the methods provided herein can comprise markers for selection and/or counter-selection as described herein. The markers can be any markers known in the art and/or provided herein. The shuttle vectors can further comprise any regulatory sequence(s) and/or sequences useful in the assembly of said shuttle vectors as known in the art. The shuttle vectors can further comprise any origins of replication that may be needed for propagation in a host cell as provided herein such as, for example, *E. coli* or *C. glutamicum*. The regulatory sequence can be any regulatory sequence known in the art or provided herein such as, for example, a promoter, start, stop, signal, secretion and/or termination sequence used by the genetic machinery of the host cell. In certain instances, the target DNA can be inserted into vectors, constructs or plasmids obtainable from any repository or catalogue product, such as a commercial vector (see e.g., DNA2.0 custom or GATEWAY® vectors). In certain instances, the target DNA can be inserted into vectors, constructs or plasmids obtainable from any repository or catalogue product, such as a commercial vector (see e.g., DNA2.0 custom or GATEWAY® vectors).

In some embodiments, the assembly/cloning methods of the present disclosure may employ at least one of the following assembly strategies: i) type II conventional cloning, ii) type II S-mediated or "Golden Gate" cloning (see, e.g., Engler, C., R. Kandzia, and S. Marillonnet. 2008 "A one pot, one step, precision cloning method with high-throughput capability". PLos One 3:e3647; Kotera, I., and T. Nagai. 2008 "A high-throughput and single-tube recombination of crude PCR products using a DNA polymerase inhibitor and type IIS restriction enzyme." J Biotechnol 137:1-7.; Weber, E., R. Gruetzner, S. Werner, C. Engler, and S. Marillonnet. 2011 Assembly of Designer TAL Effectors by Golden Gate Cloning. PloS One 6:e19722), iii) GATE-WAY® recombination, iv) TOPO® cloning, exonuclease-mediated assembly (Aslanidis and de Jong 1990. "Ligation-independent cloning of PCR products (LIC-PCR)." Nucleic Acids Research, Vol. 18, No. 20 6069), v) homologous recombination, vi) non-homologous end joining, vii) Gibson assembly (Gibson et al., 2009 "Enzymatic assembly of DNA molecules up to several hundred kilobases" Nature Methods 6, 343-345) or a combination thereof. Modular type IIS based assembly strategies are disclosed in PCT Publication WO 2011/154147, the disclosure of which is incorporated herein by reference.

In some embodiments, the present disclosure teaches cloning vectors with at least one selection marker. Various selection marker genes are known in the art often encoding antibiotic resistance function for selection in prokaryotic (e.g., against ampicillin, kanamycin, tetracycline, chloramphenicol, zeocin, spectinomycin/streptomycin) or eukaryotic cells (e.g. geneticin, neomycin, hygromycin, puromycin, blasticidin, zeocin) under selective pressure. Other marker systems allow for screening and identification of wanted or unwanted cells such as the well-known blue/white screening system used in bacteria to select positive clones in the presence of X-gal or fluorescent reporters such as green or red fluorescent proteins expressed in successfully transduced host cells. Another class of selection markers most of which are only functional in prokaryotic systems relates to counter selectable marker genes often also referred to as "death genes" which express toxic gene products that kill producer cells. Examples of such genes include sacB, rpsL (strA), tetAR, pheS, thyA, gata-1, or ccdB, the function of which is described in (Reyrat et al. 1998 "Counterselectable Markers: Untapped Tools for Bacterial Genetics and Pathogenesis." Infect Immun. 66(9): 4011-4017).

Protoplasting Methods

In one embodiment, the methods and systems provided herein make use of the generation of protoplasts from filamentous fungal cells. Suitable procedures for preparation of protoplasts can be any known in the art including, for example, those described in EP 238,023 and Yelton et al. (1984, Proc. Natl. Acad. Sci. USA 81:1470-1474). In one embodiment, protoplasts are generated by treating a culture of filamentous fungal cells with one or more lytic enzymes or a mixture thereof. The lytic enzymes can be a beta-glucanase and/or a polygalacturonase. In one embodiment, the enzyme mixture for generating protoplasts is VinoTaste concentrate. Following enzymatic treatment, the protoplasts can be isolated using methods known in the art such as, for example, centrifugation.

The pre-cultivation and the actual protoplasting step can be varied to optimize the number of protoplasts and the transformation efficiency. For example, there can be variations of inoculum size, inoculum method, pre-cultivation media, pre-cultivation times, pre-cultivation temperatures, mixing conditions, washing buffer composition, dilution ratios, buffer composition during lytic enzyme treatment, the type and/or concentration of lytic enzyme used, the time of incubation with lytic enzyme, the protoplast washing procedures and/or buffers, the concentration of protoplasts and/or polynucleotide and/or transformation reagents during the actual transformation, the physical parameters during the transformation, the procedures following the transformation up to the obtained transformants.

Protoplasts can be resuspended in an osmotic stabilizing buffer. The composition of such buffers can vary depending on the species, application and needs. However, typically these buffers contain either an organic component like sucrose, citrate, mannitol or sorbitol between 0.5 and 2 M. More preferably between 0.75 and 1.5 M; most preferred is 1 M. Otherwise these buffers contain an inorganic osmotic stabilizing component like KCl, $MgSO_4$, NaCl or $MgCl_2$ in concentrations between 0.1 and 1.5 M. Preferably between 0.2 and 0.8 M; more preferably between 0.3 and 0.6 M, most preferably 0.4 M. The most preferred stabilizing buffers are STC (sorbitol, 0.8 M; CaCl.sub.2, 25 mM; Tris, 25 mM; pH 8.0) or KCl-citrate (KCl, 0.3-0.6 M; citrate, 0.2% (w/v)). The protoplasts can be used in a concentration between $1 \times 10^5$ and $1 \times 10^{10}$ cells/ml. Preferably, the concentration is between $1 \times 10^6$ and $1 \times 10^9$; more preferably the concentration is between $1 \times 10^7$ and $5 \times 10^8$; most preferably the concentration is $1 \times 10^8$ cells/ml. DNA is used in a concentration between 0.01 and 10 ug; preferably between 0.1 and 5 ug, even more preferably between 0.25 and 2 ug; most preferably between 0.5 and 1 ug. To increase the efficiency of transfection carrier DNA (as salmon sperm DNA or non-coding vector DNA) may be added to the transformation mixture.

In one embodiment, following generation and subsequent isolation, the protoplasts are mixed with one or more cryoprotectants. The cryoprotectants can be glycols, dimethyl sulfoxide (DMSO), polyols, sugars, 2-Methyl-2,4-pentanediol (MPD), polyvinylpyrrolidone (PVP), methylcellulose, C-linked antifreeze glycoproteins (C-AFGP) or combinations thereof. Glycols for use as cryoprotectants in the methods and systems provided herein can be selected from ethylene glycol, propylene glycol, polypropylene glycol (PEG), glycerol, or combinations thereof. Polyols for use as cryoprotectants in the methods and systems provided herein can be selected from propane-1,2-diol, propane-1,3-diol, 1,1,1-tris-(hydroxymethyl)ethane (THME), and 2-ethyl-2-(hydroxymethyl)-propane-1,3-diol (EHMP), or combinations thereof. Sugars for use as cryoprotectants in the methods and systems provided herein can be selected from trehalose, sucrose, glucose, raffinose, dextrose or combinations thereof. In one embodiment, the protoplasts are mixed with DMSO. DMSO can be mixed with the protoplasts at a final concentration of at least, at most, less than, greater than, equal to, or about 1%, 2%, 3%, 4%, 5%, 6%, 7%, 8%, 9%, 10%, 12.5%, 15%, 20%, 25%, 30%, 35%, 40%, 45%, 50%, 55%, 60%, 65%, 70%, or 75% w/v or v/v. The protoplasts/cryoprotectant (e.g., DMSO) mixture can be distributed to microtiter plates prior to storage. The protoplast/cryoprotectant (e.g., DMSO) mixture can be stored at any temperature provided herein for long-term storage (e.g., several hours, day(s), week(s), month(s), year(s)) as provided herein such as, for example −20° C. or −80° C. In one embodiment, an additional cryoprotectant (e.g., PEG) is added to the protoplasts/DMSO mixture. In yet another embodiment, the additional cryoprotectant (e.g., PEG) is added to the protoplast/DMSO mixture prior to storage. The PEG can be any PEG provided herein and can be added at any concentration (e.g., w/v or v/v) as provided herein.

Protoplast Transformation Methods

In one embodiment, the methods and systems provided herein require the transfer of nucleic acids to protoplasts derived from filamentous fungal cells as described herein. In another embodiment, the transformation utilized by the methods and systems provided herein is high-throughput in nature and/or is partially or fully automated as described herein. Further to this embodiment, the transformation is performed by adding constructs or expression constructs as described herein to the wells of a microtiter plate followed by aliquoting protoplasts generated by the methods provided herein to each well of the microtiter plate. Suitable procedures for transformation/transfection of protoplasts can be any known in the art including, for example, those described in international patent applications PCT/NL99/00618, PCT/EP99/202516, Finkelstein and Ball (eds.), Biotechnology of filamentous fungi, technology and products, Butterworth-Heinemann (1992), Bennett and Lasure (eds.) More Gene Manipulations in fungi, Academic Press (1991), Turner, in: Puhler (ed), Biotechnology, second completely revised edition, VHC (1992) protoplast fusion, and the Ca-PEG mediated protoplast transformation as described in EP635574B. Alternatively, transformation of the filamentous fungal host cells or protoplasts derived therefrom can also be performed by electroporation such as, for example, the electroporation described by Chakraborty and Kapoor, Nucleic Acids Res. 18:6737 (1990), *Agrobacterium tumefaciens*-mediated transformation, biolistic introduction of DNA such as, for example, as described in Christiansen et al., Curr. Genet. 29:100 102 (1995); Durand et al., Curr. Genet. 31:158 161 (1997); and Barcellos et al., Can. J. Microbiol. 44:1137 1141 (1998) or "magneto-biolistic" transfection of cells such as, for example, described in U.S. Pat. Nos. 5,516,670 and 5,753,477. In one embodiment, the transformation procedure used in the methods and systems provided herein is one amendable to being high-throughput and/or automated as provided herein such as, for example, PEG mediated transformation.

Transformation of the protoplasts generated using the methods described herein can be facilitated through the use of any transformation reagent known in the art. Suitable transformation reagents can be selected from Polyethylene Glycol (PEG), FUGENE® HD (from Roche), Lipofectamine® or OLIGOFECTAMINE® (from Invitrogen), TRANSPASS® D1 (from New England Biolabs), LYPOVEC® or LIPOGEN® (from Invivogen). In one embodiment, PEG is the most preferred transformation/transfection reagent. PEG is available at different molecular weights and can be used at different concentrations. Preferably PEG 4000 is used between 10% and 60%, more preferably between 20% and 50%, most preferably at 30%. In one embodiment, the PEG is added to the protoplasts prior to storage as described herein.

Transformation of Host Cells

In some embodiments, the vectors of the present disclosure may be introduced into the host cells using any of a variety of techniques, including transformation, transfection, transduction, viral infection, gene guns, or Ti-mediated gene transfer (see Christie, P. J., and Gordon, J. E., 2014 "The *Agrobacterium* Ti Plasmids" Microbiol SPectr. 2014; 2(6); 10.1128). Particular methods include calcium phosphate transfection, DEAE-Dextran mediated transfection, lipofection, or electroporation (Davis, L., Dibner, M., Battey, I., 1986 "Basic Methods in Molecular Biology"). Other methods of transformation include for example, lithium acetate transformation and electroporation See, e.g., Gietz et al., Nucleic Acids Res. 27:69-74 (1992); Ito et al., J. Bacterol. 153:163-168 (1983); and Becker and Guarente, Methods in Enzymology 194:182-187 (1991). In some embodiments, transformed host cells are referred to as recombinant host strains.

In some embodiments, the present disclosure teaches high-throughput transformation of cells using the 96-well plate robotics platform and liquid handling machines of the present disclosure.

In some embodiments, the present disclosure teaches screening transformed cells with one or more selection markers as described above. In one such embodiment, cells transformed with a vector comprising a kanamycin resistance marker (KanR) are plated on media containing effective amounts of the kanamycin antibiotic. Colony forming units visible on kanamycin-laced media are presumed to have incorporated the vector cassette into their genome.

Insertion of the desired sequences can be confirmed via PCR, restriction enzyme analysis, and/or sequencing of the relevant insertion site.

Looping Out of Selected Sequences

In some embodiments, the present disclosure teaches methods of looping out selected regions of DNA from the host organisms. The looping out method can be as described in Nakashima et al. 2014 "Bacterial Cellular Engineering by Genome Editing and Gene Silencing." Int. J. Mol. Sci. 15(2), 2773-2793. In some embodiments, the present disclosure teaches looping out selection markers from positive transformants. Looping out deletion techniques are known in the art, and are described in (Tear et al. 2014 "Excision of Unstable Artificial Gene-Specific inverted Repeats Mediates Scar-Free Gene Deletions in *Escherichia coli*." Appl. Biochem. Biotech. 175:1858-1867). The looping out methods used in the methods provided herein can be performed using single-crossover homologous recombination or double-crossover homologous recombination. In one embodiment, looping out of selected regions as described herein can entail using single-crossover homologous recombination as described herein.

Figure 3:
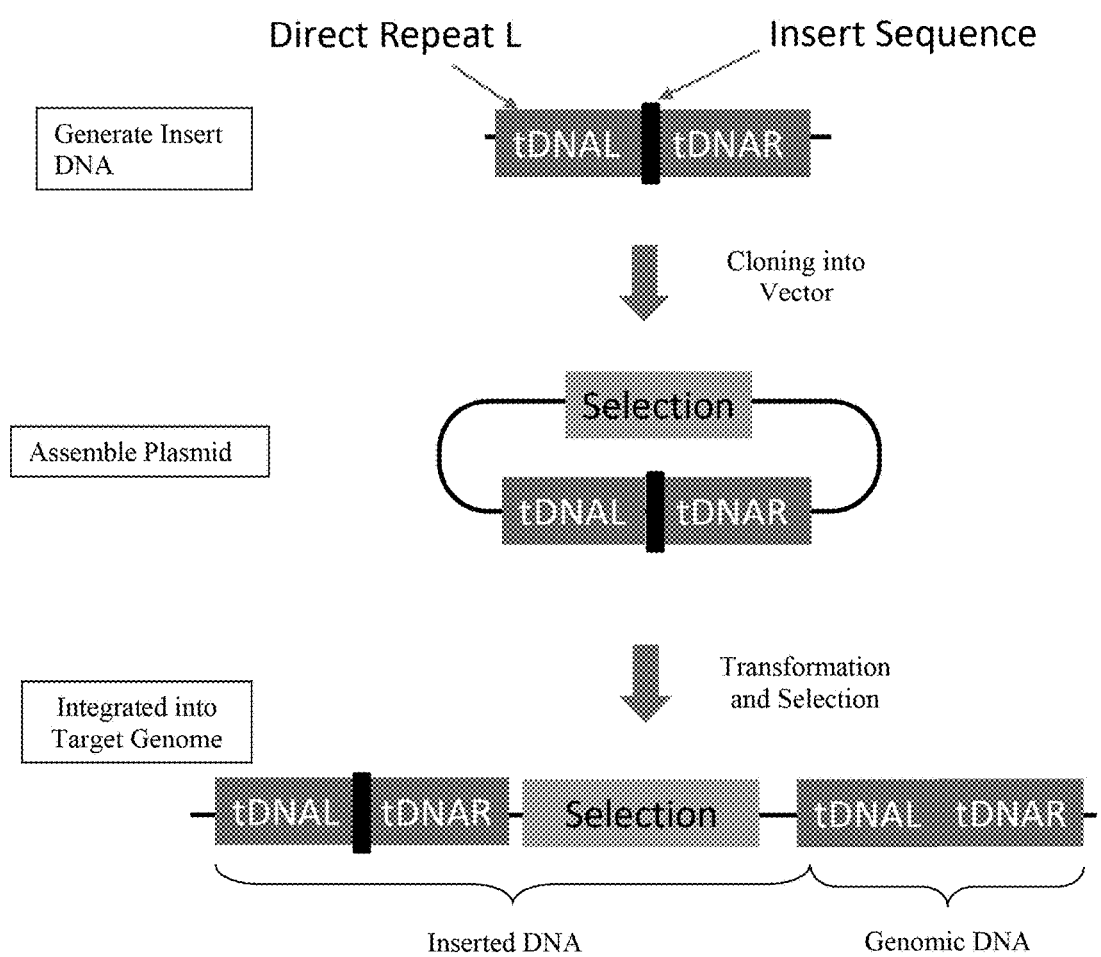
FIG. 3 depicts assembly of transformation plasmids of the present disclosure, and their integration into host organisms. The insert DNA is generated by combining one or more synthesized oligos in an assembly reaction. DNA inserts containing the desired sequence are flanked by regions of DNA homologous to the targeted region of the genome. These homologous regions facilitate genomic integration, and, once integrated, form direct repeat regions designed for looping out vector backbone DNA in subsequent steps. Assembled plasmids contain the insert DNA, and optionally, one or more selection markers.
Figure 4:
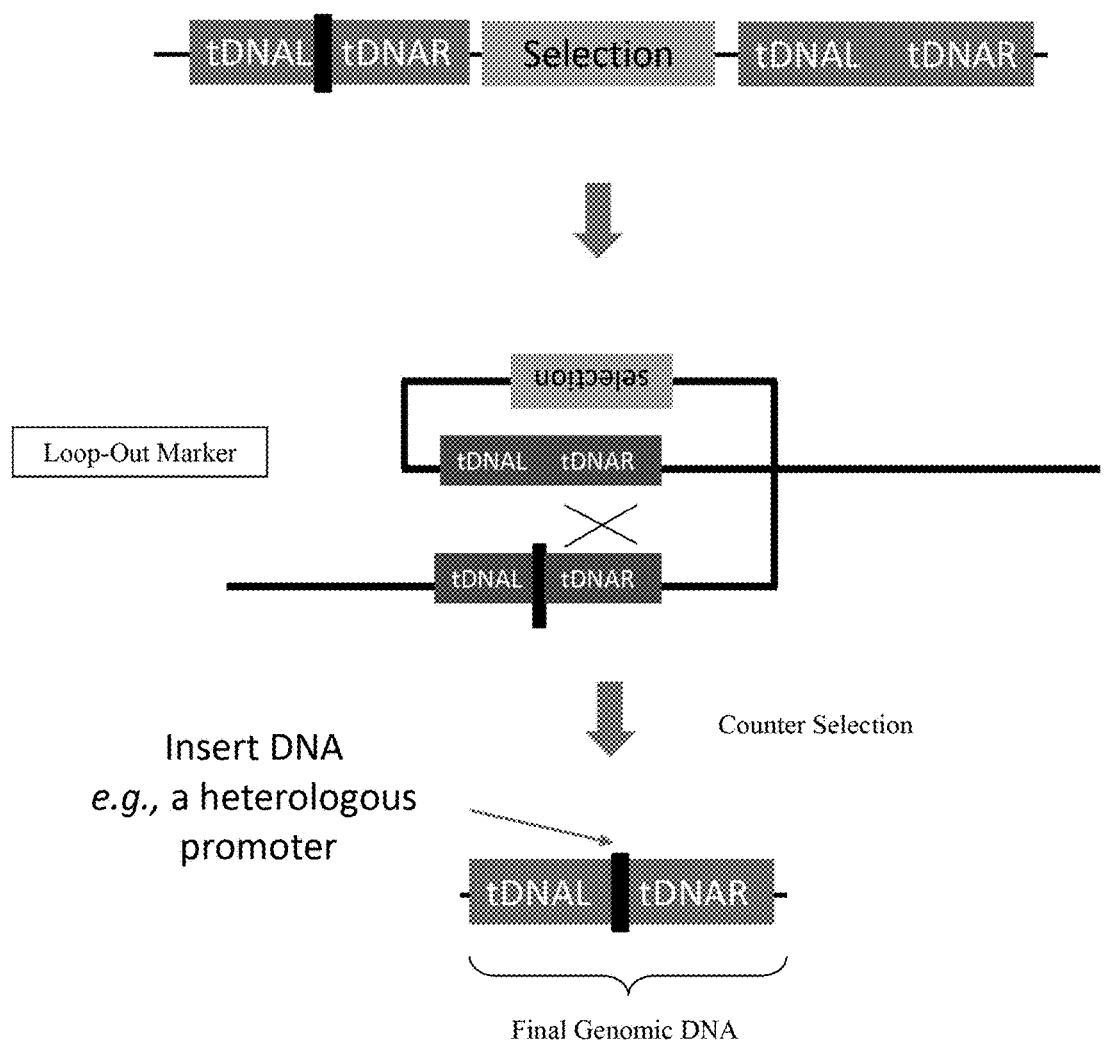
FIG. 4 depicts procedure for looping-out selected regions of DNA from host strains. Direct repeat regions of the inserted DNA and host genome can "loop out" in a recombination event. Cells counter selected for the selection marker contain deletions of the loop DNA flanked by the direct repeat regions.
Figure 5:
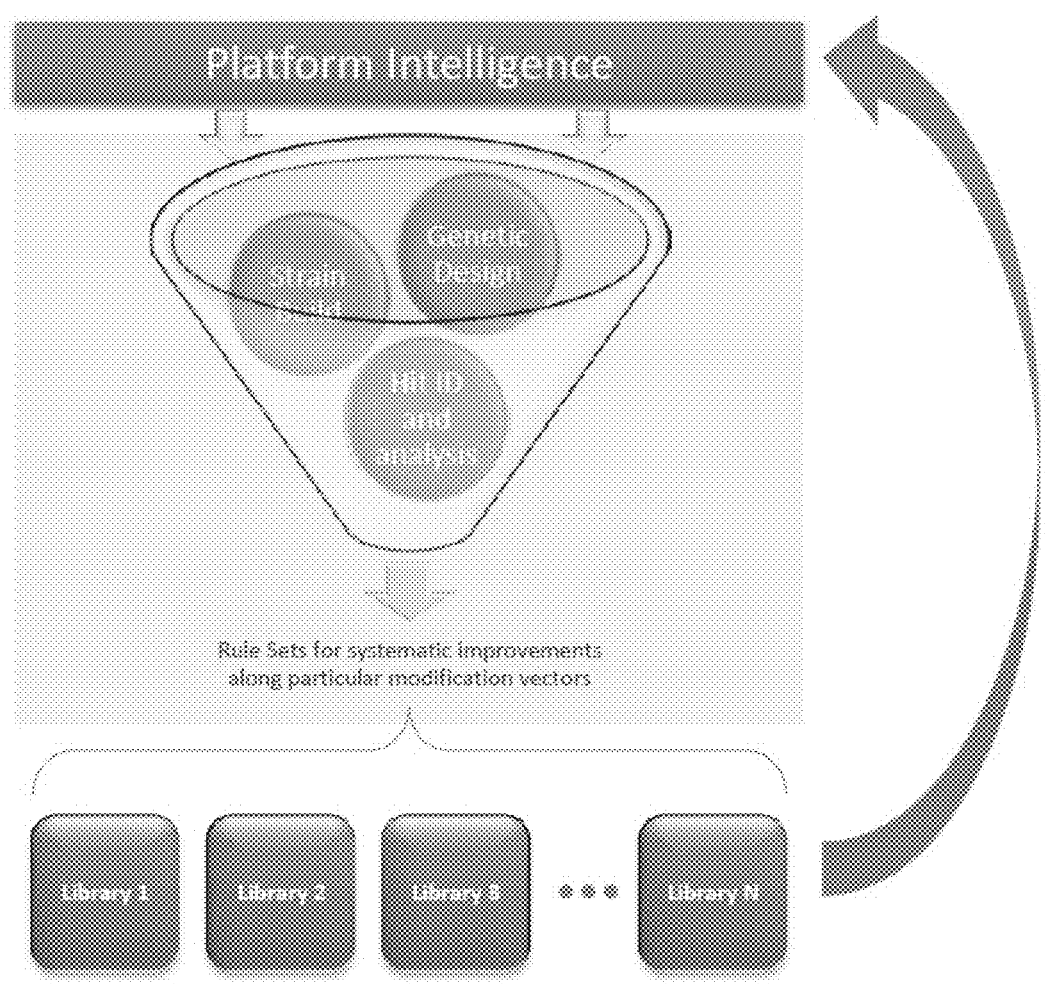
FIG. 5 depicts an embodiment of the strain improvement process of the present disclosure. Host strain sequences containing genetic modifications (Genetic Design) are tested for strain performance improvements in various strain backgrounds (Strain Build). Strains exhibiting beneficial mutations are analyzed (Hit ID and Analysis) and the data is stored in libraries for further analysis (e.g., SNP swap libraries, PRO swap libraries, and combinations thereof, among others). Selection rules of the present disclosure generate new proposed host strain sequences based on the predicted effect of combining elements from one or more libraries for additional iterative analysis.

First, loop out vectors are inserted into selected target regions within the genome of the host organism (e.g., via homologous recombination, CRISPR, or other gene editing technique). In one embodiment, single-crossover homologous recombination is used between a circular plasmid or vector and the host cell genome in order to loop-in the circular plasmid or vector such as depicted in FIG. 3. The inserted vector can be designed with a sequence which is a direct repeat of an existing or introduced nearby host sequence, such that the direct repeats flank the region of DNA slated for looping and deletion. Once inserted, cells containing the loop out plasmid or vector can be counter selected for deletion of the selection region (e.g., see FIG. 4; lack of resistance to the selection gene).

Persons having skill in the art will recognize that the description of the loopout procedure represents but one illustrative method for deleting unwanted regions from a genome. Indeed the methods of the present disclosure are compatible with any method for genome deletions, including but not limited to gene editing via CRISPR, TALENS, FOK, or other endonucleases. Persons skilled in the art will also recognize the ability to replace unwanted regions of the genome via homologous recombination techniques

EXAMPLES

The following examples are given for the Purpose of illustrating various embodiments of the disclosure and are not meant to limit the present disclosure in any fashion. Changes therein and other uses which are encompassed within the spirit of the disclosure, as defined by the scope of the claims, will be recognized by those skilled in the art.

A brief table of contents is provided below solely for the purpose of assisting the reader. Nothing in this table of contents is meant to limit the scope of the examples or disclosure of the application.

TABLE 5.1

Table of Contents For Example Section.

| Example # | Title | Brief Description |
|---|---|---|
| 1 | HTP Transformation of *Corynebacterium* & Demonstration of SNP Library Creation | Describes embodiments of the high throughput genetic engineering methods of the present disclosure. |
| 2 | HTP Genomic Engineering - Implementation of a SNP Library to Rehabilitate/Improve an Industrial Microbial Strain | Describes approaches for rehabilitating industrial organisms through SNP swap methods of the present disclosure. |
| 3 | HTP Genomic Engineering - Implementation of a SNP Swap Library to Improve Strain Performance in Lysine Production in *Corynebacterium*. | Describes an implementation of SNP swap techniques for improving the performance of *Corynebacterium* strain producing lysine. Also discloses selected second and third order mutation consolidations. |
| 4 | HTP Genomic Engineering - Implementation of a Promoter Swap Library to Improve an Industrial Microbial Strain | Describes methods for improving the strain performance of host organisms through PRO swap genetic design libraries of the present disclosure. |
| 5 | HTP Genomic Engineering - Implementation of a PRO Swap Library to Improve Strain Performance for Lysine Production | Describes an implementation of PRO swap techniques for improving the performance of *Corynebacterium* strain producing lysine. |
| 6 | Epistasis Mapping - An Algorithmic Tool for Predicting Beneficial Mutation Consolidations | Describes an embodiment of the automated tools/algorithms of the present disclosure for predicting beneficial gene mutation consolidations. |
| 7 | HTP Genomic Engineering - PRO Swap Mutation Consolidation and Multi-Factor Combinatorial Testing | Describes and illustrates the ability of the HTP methods of the present disclosure to effectively explore the large solution space created by the combinatorial consolidation of multiple gene/genetic design library combinations. |

TABLE 5.1-continued

Table of Contents For Example Section.

| Example # | Title | Brief Description |
|---|---|---|
| 8 | HTP Genomic Engineering - Implementation of a Terminator Library to Improve an Industrial Host Strain | Describes and illustrates an application of the STOP swap genetic design libraries of the present disclosure. |
| 9 | Comparing HTP Toolsets vs. Traditional UV Mutations. | Provides experimental results comparing the HTP genetic design methods of the present disclosure vs. traditional mutational strain improvement programs. |
| 10 | Application of HTP Engineering Methods in Eukaryotes | Describes embodiments of the high throughput genetic engineering methods of the present disclosure, as applied to eukaryotic host cells. |
| 11 | HTP Genomic Engineering - Implementation of an HTP SNP Library Strain Improvement Program to Improve Citric Acid production in Eukaryote *Aspergillus niger* ATCC11414 | Describes approaches for rehabilitating industrial eukaryotic organisms through SNP swap methods of the present disclosure. |

Example 1: HTP Transformation of *Corynebacterium* & Demonstration of SNP Library Creation This example illustrates embodiments of the HTP genetic engineering methods of the present disclosure. Host cells are transformed with a variety of SNP sequences of different sizes, all targeting different areas of the genome. The results demonstrate that the methods of the present disclosure are able to generate rapid genetic changes of any kind, across the entire genome of a host cell.

A. Cloning of Transformation Vectors

A variety of SNPs were chosen at random from *Corynebacterium glutamicum* (ATCC21300) and were cloned into *Corynebacterium* cloning vectors using yeast homologous recombination cloning techniques to assemble a vector in which each SNP was flanked by direct repeat regions, as described supra in the "Assembling/Cloning Custom Plasmids" section, and as illustrated in FIG. 3.

The SNP cassettes for this example were designed to include a range of homology direct repeat arm lengths ranging from 0.5 Kb, 1 Kb, 2 Kb, and 5 Kb. Moreover, SNP cassettes were designed for homologous recombination targeted to various distinct regions of the genome, as described in more detail below.

Figure 9:
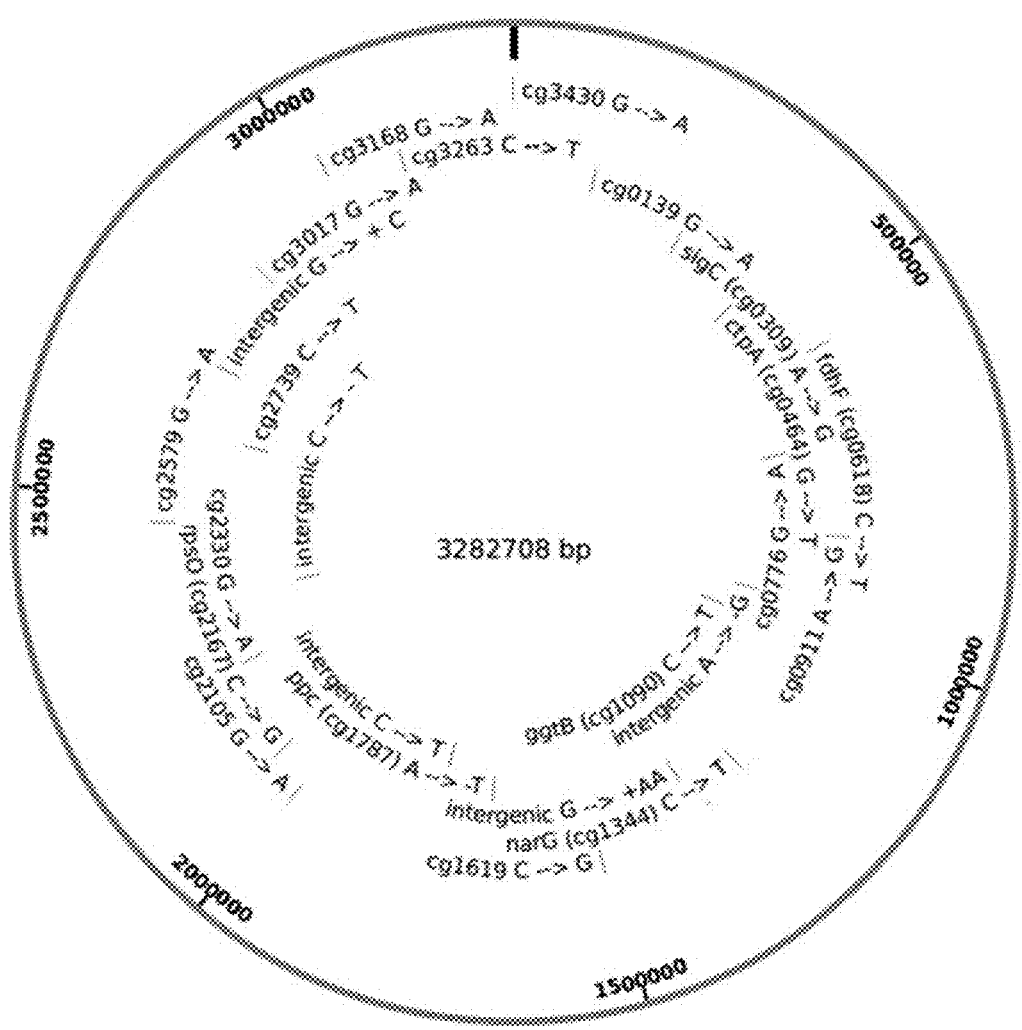
FIG. 9 is a representation of the genome of *Corynebacterium glutamicum*, comprising around 3.2 million base pairs.

The *C. glutamicum* genome is 3,282,708 bp in size (see FIG. 9). The genome was arbitrarily divided into 24 equal-sized genetic regions, and SNP cassettes were designed to target each of the 24 regions. Thus, a total of 96 distinct plasmids were cloned for this Example (4 different insert sizes×24 distinct genomic regions).

Each DNA insert was produced by PCR amplification of homologous regions using commercially sourced oligos and the host strain genomic DNA described above as template. The SNP to be introduced into the genome was encoded in the oligo tails. PCR fragments were assembled into the vector backbone using homologous recombination in yeast.

Cloning of each SNP and homology arm into the vector was conducted according to the HTP engineering workflow described in FIG. 6, FIG. 3, and Table 5.

B. Transformation of Assembled Clones into *E. coli*

Vectors were initially transformed into *E. coli* using standard heat shock transformation techniques in order to identify correctly assembled clones, and to amplify vector DNA for *Corynebacterium* transformation.

Figure 12:
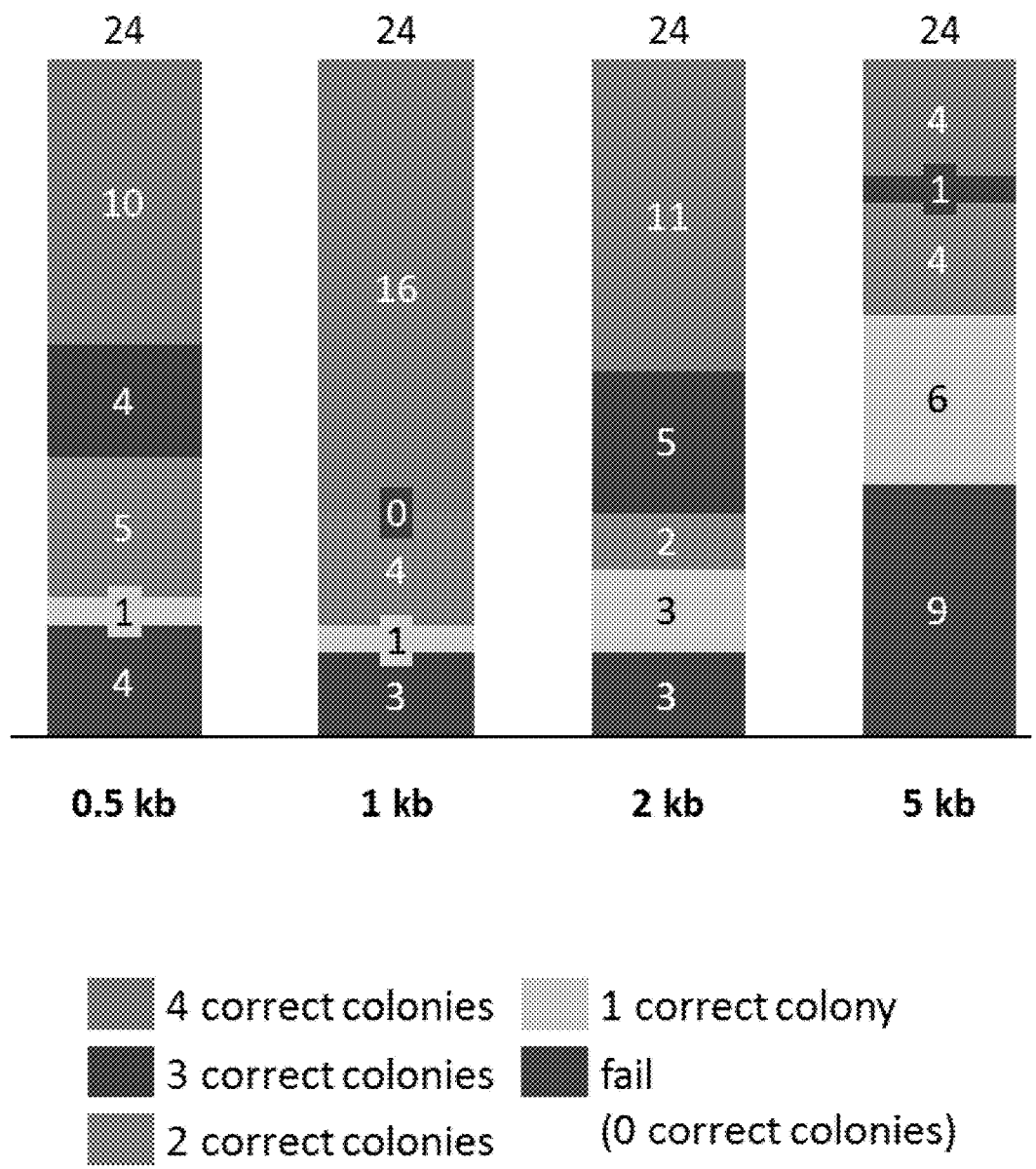
FIG. 12 depicts the results of an experiment testing successful plasmid assembly for plasmids transformed into *E. coli*. Picking four colonies is sufficient to achieve 13% failure rate for plasmids containing 1 and 2 kb insertion sequences. Larger insertions may require additional colony screening to achieve consistent results.

For example, transformed *E. coli* bacteria were tested for assembly success. Four colonies from each *E. coli* transformation plate were cultured and tested for correct assembly via PCR. This process was repeated for each of the 24 transformation locations and for each of the 4 different insert sizes (i.e., for all 96 transformants of this example). Results from this experiment were represented as the number of correct colonies identified out of the four colonies that were tested for each treatment (insert size and genomic location) (see FIG. 12). Longer 5 kb inserts exhibited a decrease in assembly efficiency compared to shorter counterparts (n=96).

C. Transformation of Assembled Clones into *Corynebacterium*

Figure 13:
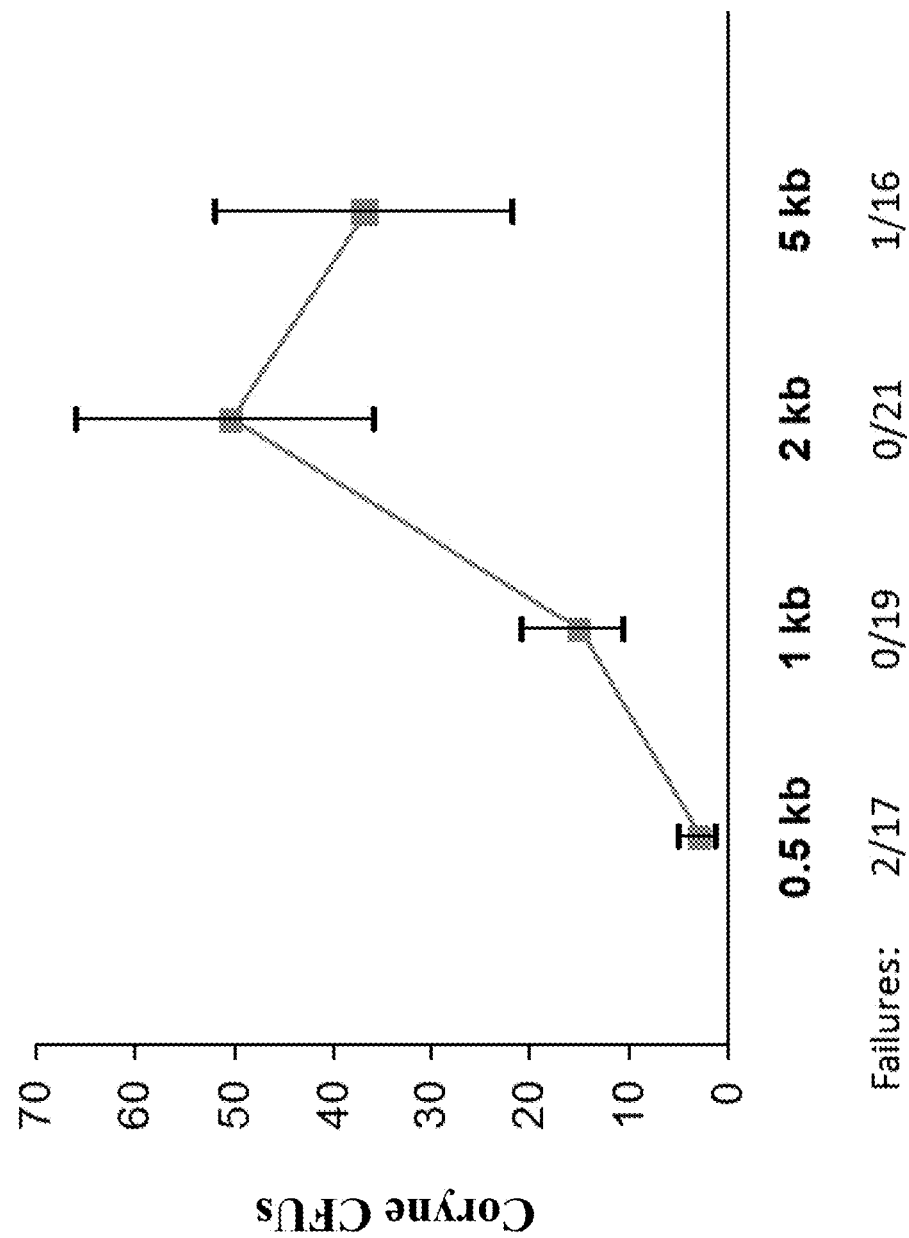
FIG. 13 depicts results of an experiment testing successful transformation of *Corynebacterium glutamicum* with insertion vectors. DNA insert sizes of 2 and 5 kb exhibited high transformation rates with low assembly failure rates.

Validated clones were transformed into *Corynebacterium glutamicum* host cells via electroporation. For each transformation, the number of Colony Forming Units (CFUs) per µg of DNA was determined as a function of the insert size (see FIG. 13). Coryne genome integration was also analyzed as a function of homology arm length, and the results showed that shorter arms had a lower efficiency (see FIG. 13).

Figure 10:
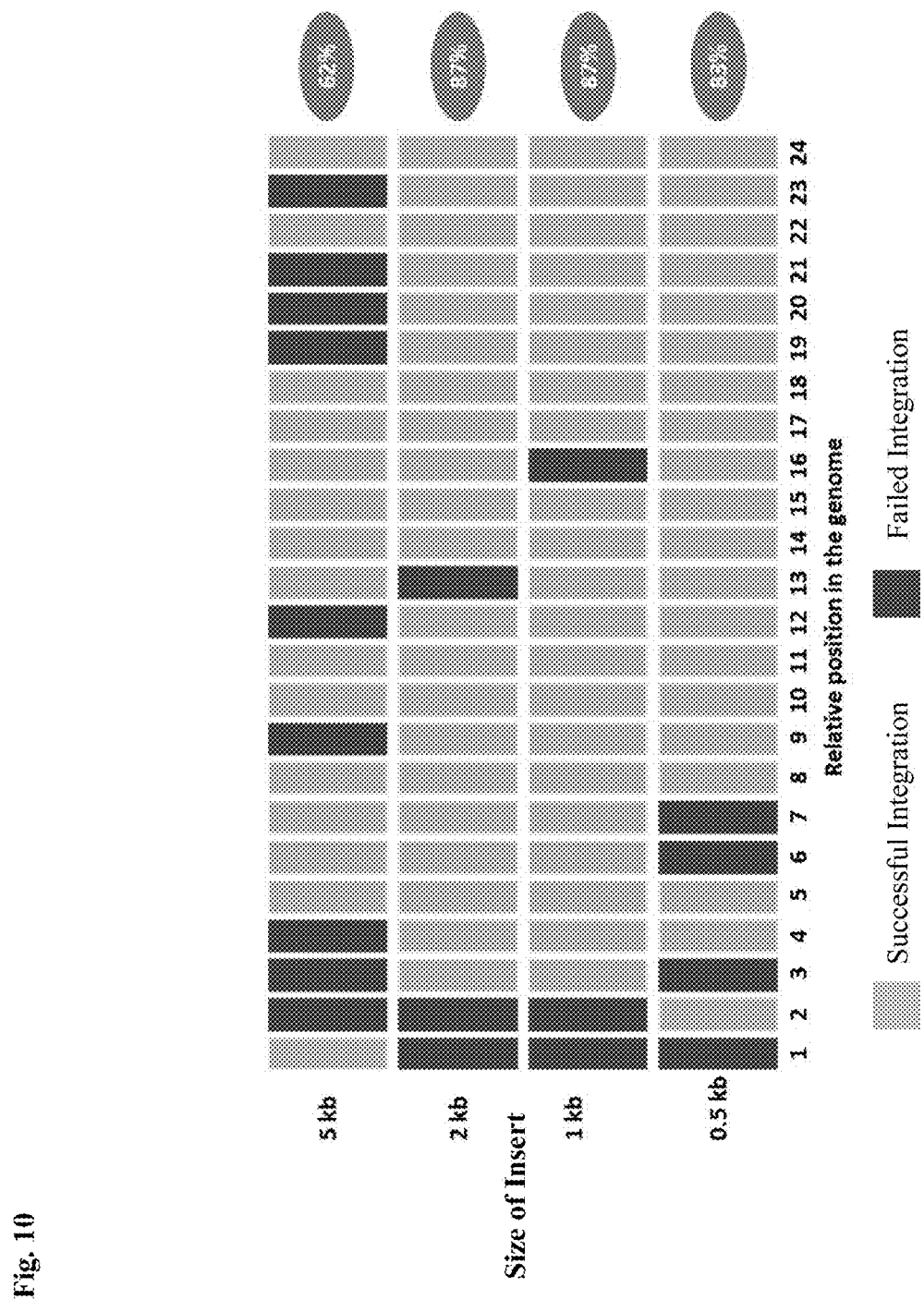
FIG. 10 depicts the results of a transformation experiment of the present disclosure. DNA inserts ranging from 0.5 kb to 5.0 kb were targeted for insertion into various regions (shown as relative positions 1-24) of the genome of *Corynebacterium glutamicum*. Light color indicates successful integration, while darker color indicates insertion failure.

Genomic integration efficiency was also analyzed with respect to the targeted genome location in *C. glutamicum* transformants. Genomic positions 1 and 2 exhibited slightly lowered integration efficiency compared to the rest of the genome (see FIG. 10).

D. Looping Out Selection Markers

Figure 14:
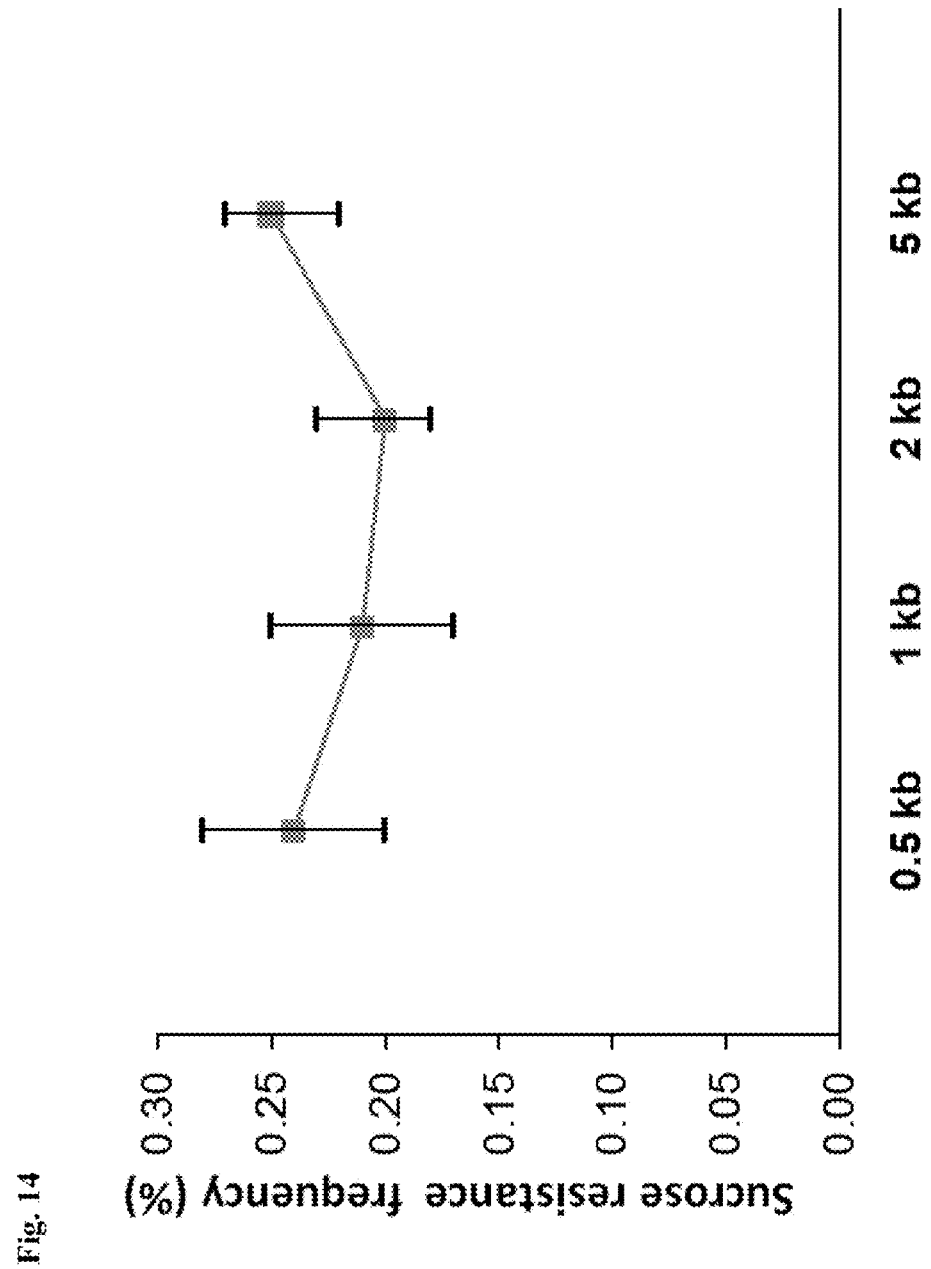
FIG. 14 depicts results of loop out selections in *Corynebacterium glutamicum*. Sucrose resistance of transformed bacteria indicates loop out of sacB selection marker. DNA insert size does not appear to impact loop out efficiency.

Cultures of *Corynebacterium* identified as having successful integrations of the insert cassette were cultured on media containing 5% sucrose to counter select for loop outs of the sacb selection gene. Sucrose resistance frequency for various homology direct repeat arms did not vary significantly with arm length (see FIG. 14). These results suggested that loopout efficiencies remained steady across homology arm lengths of 0.5 kb to 5 kb.

In order to further validate loop out events, colonies exhibiting sucrose resistance were cultured and analyzed via sequencing.

The results for the sequencing of the insert genomic regions are summarized in Table 6 below.

TABLE 6

Loop-out Validation Frequency

| Outcome | Frequency (sampling error 95% confidence) |
| --- | --- |
| Successful Loop out | 13% (9%/20%) |
| Loop Still present | 42% (34%/50%) |
| Mixed read | 44% (36%/52%) |

Sequencing results showed a 10-20% efficiency in loop outs. Actual loop-out probably is somewhat dependent on insert sequence. However, picking 10-20 sucrose-resistant colonies leads to high success rates.

E. Summary

Table 7 below provides a quantitative assessment of the efficiencies of the HTP genome engineering methods of the present invention. Construct assembly rates for yeast homology methodologies yielded expected DNA constructs in nearly 9 out of 10 tested colonies. Coryne transformations of SNP constructs with 2 kb homology arms yielded an average of 51 colony forming units per micro gram of DNA (CFU/µg), with 98% of said colonies exhibiting correctly integrated SNP inserts (targeting efficiency). Loop out efficiencies remained at 0.2% of cells becoming resistant when exposed to sucrose, with 13% of these exhibiting correctly looped out sequences.

TABLE 7

Summary Results for *Corynebacterium glutamicum* Strain Engineering

| QC Step | Results for 2 kb Homology Arms |
| --- | --- |
| Construct Assembly Success | 87% |
| Coryne Transformation efficiency | 51 CFU/µg DNA (+/−15) |
| Targeting efficiency | 98% |
| Loop out Efficiency | 0.2% (+/−0.03%) |

Example 2: HTP Genomic Engineering—Implementation of a SNP Library to Rehabilitate/Improve an Industrial Microbial Strain This example illustrates several aspects of the SNP swap libraries of the HTP strain improvement programs of the present disclosure. Specifically, the example illustrates several envisioned approaches for rehabilitating currently existing industrial strains. This example describes the wave up and wave down approaches to exploring the phenotypic solution space created by the multiple genetic differences that may be present between "base," "intermediate," and industrial strains.

A. Identification of SNPs in Diversity Pool

Figure 17:
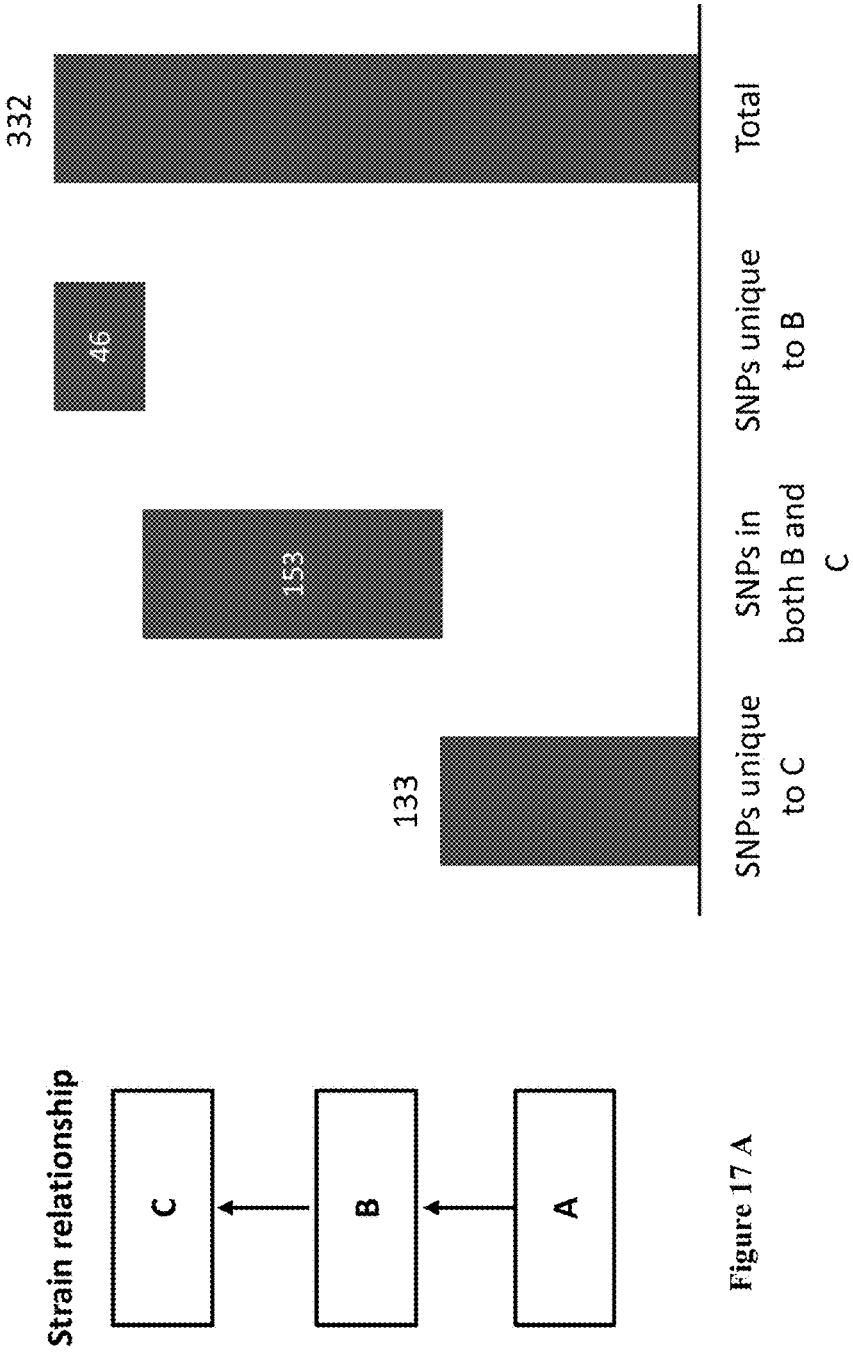
FIG. 17A-B depicts SNP differences among strain variants in the diversity pool.

An exemplary strain improvement program using the methods of the present disclosure was conducted on an industrial production microbial strain, herein referred to as "C." The diversity pool strains for this program are represented by A, B, and C. Strain A represented the original production host strain, prior to any mutagenesis. Strain C represented the current industrial strain, which has undergone many years of mutagenesis and selection via traditional strain improvement programs. Strain B represented a "middle ground" strain, which had undergone some mutagenesis, and had been the predecessor of strain C. (see FIG. 17A).

Strains A, B, and C were sequenced and their genomes were analyzed for genetic differences between strains. A total of 332 non-synonymous SNPs were identified. Of these, 133 SNPs were unique to C, 153 were additionally shared by B and C, and 46 were unique to strain B (see FIG. 17B). These SNPs will be used as the diversity pool for downstream strain improvement cycles.

B. SNP Swapping Analysis

Figure 18:
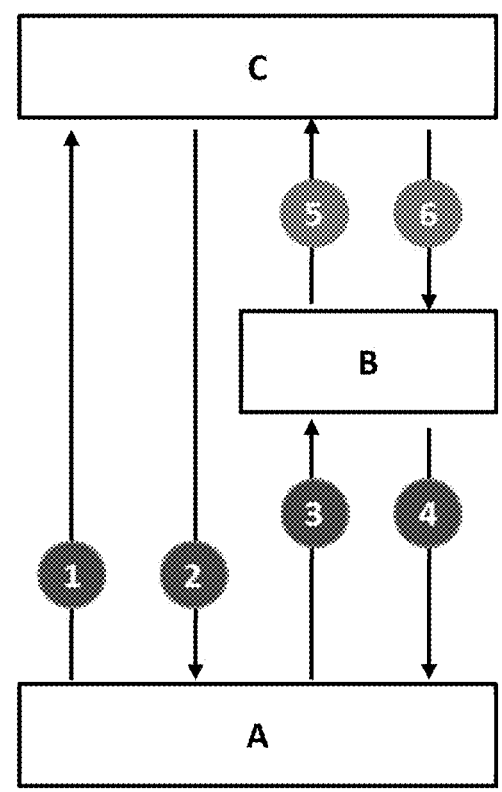
FIG. 18 depicts a first-round SNP swapping experiment according to the methods of the present disclosure. (1) all the SNPs from C will be individually and/or combinatorially cloned into the base A strain ("wave up" A to C). (2) all the SNPs from C will be individually and/or combinatorially removed from the commercial strain C ("wave down" C to A). (3) all the SNPs from B will be individually and/or combinatorially cloned into the base A strain (wave up A to B). (4) all the SNPs from B will be individually and/or combinatorially removed from the commercial strain B (wave down B to A). (5) all the SNPs unique to C will be individually and/or combinatorially cloned into the commercial B strain (wave up B to C). (6) all the SNPs unique to C will be individually and/or combinatorially removed from the commercial strain C (wave down C to B).

SNPs identified from the diversity pool in Part A of Example 2 will be analyzed to determine their effect on host cell performance. The initial "learning" round of the strain performance will be broken down into six steps as described below, and diagramed in FIG. 18.

First, all the SNPs from C will be individually and/or combinatorially cloned into the base A strain. This will represent a minimum of 286 individual transformants. The purpose of these transformants will be to identify beneficial SNPs.

Second, all the SNPs from C will be individually and/or combinatorially removed from the commercial strain C. This will represent a minimum of 286 individual transformants. The purpose of these transformants will be to identify neutral and detrimental SNPs. Additional optional steps 3-6 are also described below. The first and second steps of adding and subtracting SNPS from two genetic time points (base strain A, and industrial strain C) is herein referred to as "wave," which comprises a "wave up" (addition of SNPs to a base strain, first step), and a "wave down" (removal of SNPs from the industrial strain, second step). The wave concept extends to further additions/subtractions of SNPS.

Third, all the SNPs from B will be individually and/or combinatorially cloned into the base A strain. This will represent a minimum of 199 individual transformants. The purpose of these transformants will be to identify beneficial SNPs. Several of the transformants will also serve as validation data for transformants produced in the first step.

Fourth, all the SNPs from B will be individually and/or combinatorially removed from the commercial strain B. This will represent a minimum of 199 individual transformants. The purpose of these transformants will be to identify neutral and detrimental SNPs. Several of the transformants will also serve as validation data for transformants produced in the second step.

Fifth, all the SNPs unique to C (i.e., not also present in B) will be individually and/or combinatorially cloned into the commercial B strain. This will represent a minimum of 46 individual transformants. The purpose of these transformants will be to identify beneficial SNPs. Several of the transformants will also serve as validation data for transformants produced in the first and third steps.

Sixth, all the SNPs unique to C will be individually and/or combinatorially removed from the commercial strain C. This will represent a minimum of 46 individual transformants. The purpose of these transformants will be to identify neutral and detrimental SNPs. Several of the transformants will also serve as validation data for transformants produced in the second and fourth steps.

Data collected from each of these steps is used to classify each SNP as prima facie beneficial, neutral, or detrimental.

C. Utilization of Epistatic Mapping to Determine Beneficial SNP Combinations

Beneficial SNPs identified in Part B of Example 2 will be analyzed via the epistasis mapping methods of the present disclosure, in order to identify SNPs that are likely to improve host performance when combined.

New engineered strain variants will be created using the engineering methods of Example 1 to test SNP combinations according to epistasis mapping predictions. SNPs consolidation may take place sequentially, or may alternatively take place across multiple branches such that more than one improved strain may exist with a subset of beneficial SNPs. SNP consolidation will continue over multiple strain improvement rounds, until a final strain is produced containing the optimum combination of beneficial SNPs, without any of the neutral or detrimental SNP baggage Example 3: HTP Genomic Engineering—Implementation of a SNP Swap Library to Improve Strain Performance in Lysine Production in *Corynebacterium*

This example provides an illustrative implementation of a portion of the SNP Swap HTP design strain improvement program of Example 2 with the goal of producing yield and productivity improvements of lysine production in *Corynebacterium*.

Section B of this example further illustrates the mutation consolidation steps of the HTP strain improvement program of the present disclosure. The example thus provides experimental results for a first, second, and third round consolidation of the HTP strain improvement methods of the present disclosure.

Mutations for the second and third round consolidations are derived from separate genetic library swaps. These results thus also illustrate the ability for the HTP strain programs to be carried out multi-branch parallel tracks, and the "memory" of beneficial mutations that can be embedded into meta data associated with the various forms of the genetic design libraries of the present disclosure.

As described above, the genomes of a provided base reference strain (Strain A), and a second "engineered" strain (Strain C) were sequenced, and all genetic differences were identified. The base strain was a *Corynebacterium glutamicum* variant that had not undergone UV mutagenesis. The engineered strain was also a *C. glutamicum* strain that had been produced from the base strain after several rounds of traditional mutation improvement programs. This Example provides the SNP Swap results for 186 distinct non-synonymous SNP differences identified between strains A and C.

A. HTP Engineering and High Throughput Screening

Figure 38:
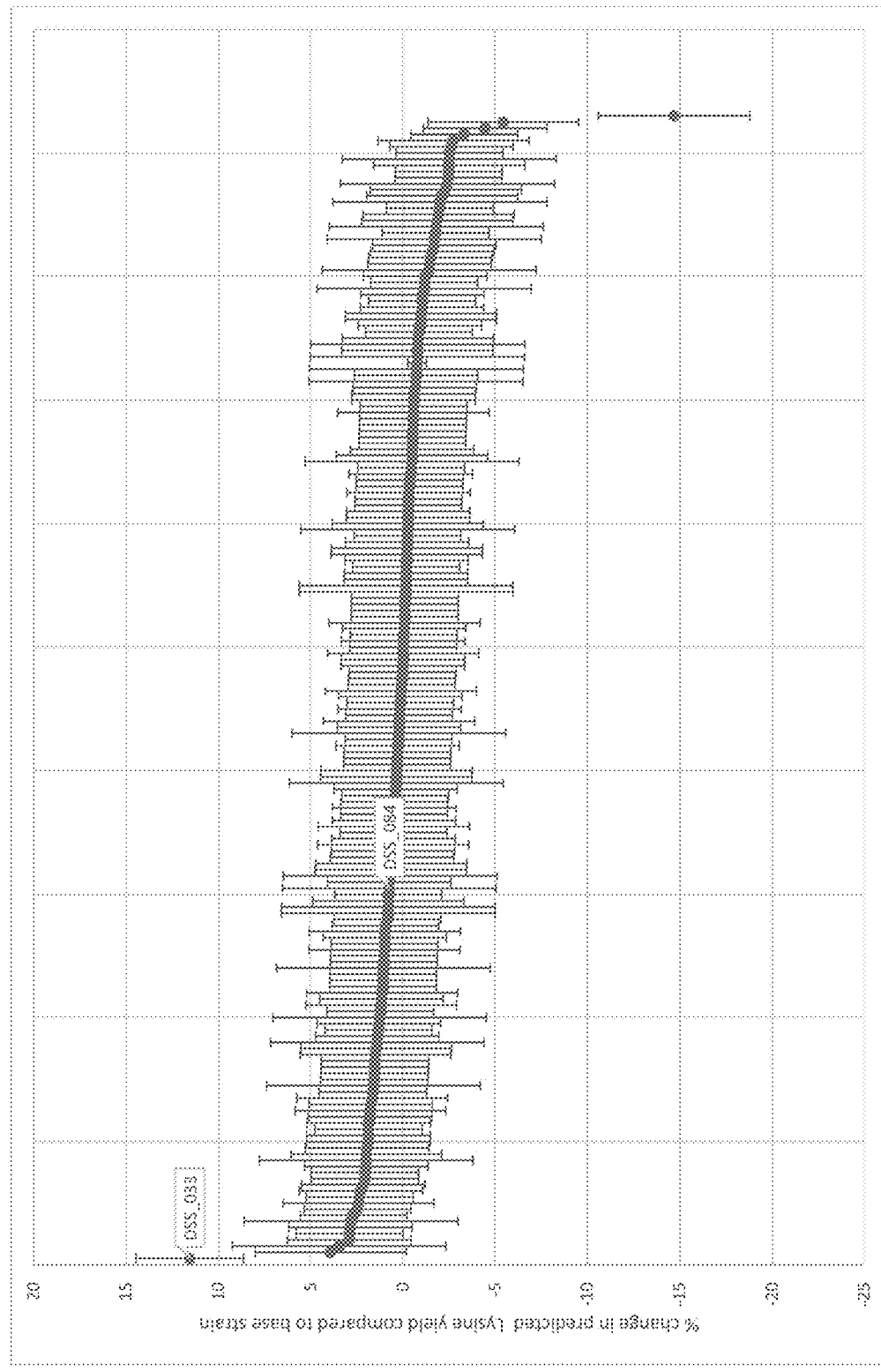
FIG. 38 depicts the results of a first round HTP engineering SNP swap program. 186 individual SNP mutations were identified and individually cloned onto a base strain. The resulting mutants were screened for differences in host cell yield of a selected biomolecule.

Each of the 186 identified SNPs were individually added back into the base strain, according to the cloning and transformation methods of the present disclosure. Each newly created strain comprising a single SNP was tested for lysine yield in small scale cultures designed to assess product titer performance. Small scale cultures were conducted using media from industrial scale cultures. Product titer was optically measured at carbon exhaustion (i.e., representative of single batch yield) with a standard colorimetric assay. Briefly, a concentrated assay mixture was prepared and was added to fermentation samples such that final concentrations of reagents were 160 mM sodium phosphate buffer, 0.2 mM Amplex Red, 0.2 U/mL Horseradish Peroxidase and 0.005 U/mL of lysine oxidase. Reactions were allowed to proceed to an end point and optical density measured using a Tecan M1000 plate spectrophotometer at a 560 nm wavelength. The results of the experiment are summarized in Table 8 below, and depicted in FIG. 38.

TABLE 8

Summary Results for SNP Swap Strain Engineering for Lysine Production

| SNP | N | Mean Lysine Yield (change in $A_{560}$ compared to reference strain) | Std Error | % Change over Reference | % Change error |
|---|---|---|---|---|---|
| DSS_033 | 4 | 0.1062 | 0.00888 | 11.54348 | 2.895652 |
| DSS_311 | 2 | 0.03603 | 0.01256 | 3.916304 | 4.095652 |
| DSS_350 | 1 | 0.03178 | 0.01777 | 3.454348 | 5.794565 |
| DSS_056 | 3 | 0.02684 | 0.01026 | 2.917391 | 3.345652 |
| DSS_014 | 4 | 0.02666 | 0.00888 | 2.897826 | 2.895652 |
| DSS_338 | 3 | 0.02631 | 0.01026 | 2.859783 | 3.345652 |
| DSS_128 | 1 | 0.02584 | 0.01777 | 2.808696 | 5.794565 |
| DSS_038 | 4 | 0.02467 | 0.00888 | 2.681522 | 2.895652 |
| DSS_066 | 4 | 0.02276 | 0.00888 | 2.473913 | 2.895652 |
| DSS_108 | 2 | 0.02216 | 0.01256 | 2.408696 | 4.095652 |
| DSS_078 | 4 | 0.02169 | 0.00888 | 2.357609 | 2.895652 |
| DSS_017 | 3 | 0.02102 | 0.01026 | 2.284783 | 3.345652 |
| DSS_120 | 3 | 0.01996 | 0.01026 | 2.169565 | 3.345652 |
| DSS_064 | 4 | 0.01889 | 0.00888 | 2.053261 | 2.895652 |
| DSS_380 | 4 | 0.01888 | 0.00888 | 2.052174 | 2.895652 |
| DSS_105 | 3 | 0.0184 | 0.01026 | 2 | 3.345652 |
| DSS_407 | 1 | 0.01831 | 0.01777 | 1.990217 | 5.794565 |
| DSS_018 | 2 | 0.01825 | 0.01256 | 1.983696 | 4.095652 |
| DSS_408 | 3 | 0.01792 | 0.01026 | 1.947826 | 3.345652 |
| DSS_417 | 3 | 0.01725 | 0.01026 | 1.875 | 3.345652 |
| DSS_130 | 3 | 0.01724 | 0.01026 | 1.873913 | 3.345652 |
| DSS_113 | 4 | 0.0172 | 0.00888 | 1.869565 | 2.895652 |
| DSS_355 | 3 | 0.01713 | 0.01026 | 1.861957 | 3.345652 |
| DSS_121 | 3 | 0.01635 | 0.01026 | 1.777174 | 3.345652 |
| DSS_097 | 2 | 0.0162 | 0.01256 | 1.76087 | 4.095652 |
| DSS_107 | 3 | 0.01604 | 0.01026 | 1.743478 | 3.345652 |
| DSS_110 | 2 | 0.01524 | 0.01256 | 1.656522 | 4.095652 |
| DSS_306 | 4 | 0.01501 | 0.00888 | 1.631522 | 2.895652 |
| DSS_316 | 1 | 0.01469 | 0.01777 | 1.596739 | 5.794565 |
| DSS_325 | 4 | 0.01436 | 0.00888 | 1.56087 | 2.895652 |
| DSS_016 | 4 | 0.01416 | 0.00888 | 1.53913 | 2.895652 |
| DSS_324 | 4 | 0.01402 | 0.00888 | 1.523913 | 2.895652 |
| DSS_297 | 4 | 0.01391 | 0.00888 | 1.511957 | 2.895652 |
| DSS_118 | 2 | 0.01371 | 0.01256 | 1.490217 | 4.095652 |
| DSS_100 | 2 | 0.01326 | 0.01256 | 1.441304 | 4.095652 |
| DSS_019 | 1 | 0.01277 | 0.01777 | 1.388043 | 5.794565 |
| DSS_131 | 3 | 0.01269 | 0.01026 | 1.379348 | 3.345652 |
| DSS_394 | 4 | 0.01219 | 0.00888 | 1.325 | 2.895652 |
| DSS_385 | 3 | 0.01192 | 0.01026 | 1.295652 | 3.345652 |
| DSS_395 | 1 | 0.01162 | 0.01777 | 1.263043 | 5.794565 |
| DSS_287 | 4 | 0.01117 | 0.00888 | 1.21413 | 2.895652 |
| DSS_418 | 2 | 0.01087 | 0.01256 | 1.181522 | 4.095652 |
| DSS_290 | 3 | 0.01059 | 0.01026 | 1.151087 | 3.345652 |
| DSS_314 | 2 | 0.01036 | 0.01256 | 1.126087 | 4.095652 |
| DSS_073 | 4 | 0.00986 | 0.00888 | 1.071739 | 2.895652 |
| DSS_040 | 4 | 0.00979 | 0.00888 | 1.06413 | 2.895652 |
| DSS_037 | 4 | 0.00977 | 0.00888 | 1.061957 | 2.895652 |
| DSS_341 | 1 | 0.00977 | 0.01777 | 1.061957 | 5.794565 |
| DSS_302 | 4 | 0.00939 | 0.00888 | 1.020652 | 2.895652 |
| DSS_104 | 4 | 0.00937 | 0.00888 | 1.018478 | 2.895652 |
| DSS_273 | 2 | 0.00915 | 0.01256 | 0.994565 | 4.095652 |
| DSS_322 | 4 | 0.00906 | 0.00888 | 0.984783 | 2.895652 |
| DSS_271 | 3 | 0.00901 | 0.01026 | 0.979348 | 3.345652 |
| DSS_334 | 2 | 0.00898 | 0.01256 | 0.976087 | 4.095652 |
| DSS_353 | 4 | 0.00864 | 0.00888 | 0.93913 | 2.895652 |
| DSS_391 | 4 | 0.00764 | 0.00888 | 0.830435 | 2.895652 |
| DSS_372 | 1 | 0.00737 | 0.01777 | 0.801087 | 5.794565 |
| DSS_007 | 1 | 0.00729 | 0.01777 | 0.792391 | 5.794565 |
| DSS_333 | 2 | 0.0072 | 0.01256 | 0.782609 | 4.095652 |
| DSS_402 | 4 | 0.00718 | 0.00888 | 0.780435 | 2.895652 |
| DSS_084 | 1 | 0.0069 | 0.01777 | 0.75 | 5.794565 |
| DSS_103 | 3 | 0.00676 | 0.01026 | 0.734783 | 3.345652 |
| DSS_362 | 1 | 0.00635 | 0.01777 | 0.690217 | 5.794565 |
| DSS_012 | 2 | 0.00595 | 0.01256 | 0.646739 | 4.095652 |
| DSS_396 | 2 | 0.00574 | 0.01256 | 0.623913 | 4.095652 |
| DSS_133 | 3 | 0.00534 | 0.01026 | 0.580435 | 3.345652 |
| DSS_065 | 3 | 0.00485 | 0.01026 | 0.527174 | 3.345652 |
| DSS_284 | 2 | 0.00478 | 0.01256 | 0.519565 | 4.095652 |
| DSS_301 | 3 | 0.00465 | 0.01026 | 0.505435 | 3.345652 |
| DSS_281 | 4 | 0.00461 | 0.00888 | 0.501087 | 2.895652 |
| DSS_405 | 2 | 0.00449 | 0.01256 | 0.488043 | 4.095652 |
| DSS_361 | 3 | 0.00438 | 0.01026 | 0.476087 | 3.345652 |
| DSS_342 | 4 | 0.00434 | 0.00888 | 0.471739 | 2.895652 |

TABLE 8-continued

Summary Results for SNP Swap Strain Engineering for Lysine Production

| SNP | N | Mean Lysine Yield (change in $A_{560}$ compared to reference strain) | Std Error | % Change over Reference | % Change error |
|---|---|---|---|---|---|
| DSS_053 | 3 | 0.00422 | 0.01026 | 0.458696 | 3.345652 |
| DSS_074 | 4 | 0.00422 | 0.00888 | 0.458696 | 2.895652 |
| DSS_079 | 4 | 0.00375 | 0.00888 | 0.407609 | 2.895652 |
| DSS_381 | 3 | 0.0036 | 0.01026 | 0.391304 | 3.345652 |
| DSS_294 | 1 | 0.00336 | 0.01777 | 0.365217 | 5.794565 |
| DSS_313 | 2 | 0.00332 | 0.01256 | 0.36087 | 4.095652 |
| DSS_388 | 2 | 0.00305 | 0.01256 | 0.331522 | 4.095652 |
| DSS_392 | 4 | 0.00287 | 0.00888 | 0.311957 | 2.895652 |
| DSS_319 | 4 | 0.00282 | 0.00888 | 0.306522 | 2.895652 |
| DSS_310 | 4 | 0.00263 | 0.00888 | 0.28587 | 2.895652 |
| DSS_344 | 3 | 0.00259 | 0.01026 | 0.281522 | 3.345652 |
| DSS_025 | 4 | 0.00219 | 0.00888 | 0.238043 | 2.895652 |
| DSS_412 | 1 | 0.00204 | 0.01777 | 0.221739 | 5.794565 |
| DSS_300 | 3 | 0.00188 | 0.01026 | 0.204348 | 3.345652 |
| DSS_299 | 2 | 0.00185 | 0.01256 | 0.201087 | 4.095652 |
| DSS_343 | 4 | 0.00184 | 0.00888 | 0.2 | 2.895652 |
| DSS_330 | 3 | 0.00153 | 0.01026 | 0.166304 | 3.345652 |
| DSS_416 | 4 | 0.00128 | 0.00888 | 0.13913 | 2.895652 |
| DSS_034 | 3 | 0.00128 | 0.01026 | 0.13913 | 3.345652 |
| DSS_291 | 2 | 0.00102 | 0.01256 | 0.11087 | 4.095652 |
| DSS_115 | 4 | 0.00063 | 0.00888 | 0.068478 | 2.895652 |
| DSS_288 | 4 | 0.00044 | 0.00888 | 0.047826 | 2.895652 |
| DSS_309 | 4 | 0.00008 | 0.00888 | 0.008696 | 2.895652 |
| DSS_125 | 3 | 0 | 0.01026 | 0 | 3.345652 |
| DSS_358 | 3 | −0.00015 | 0.01026 | −0.0163 | 3.345652 |
| DSS_099 | 2 | −0.00015 | 0.01256 | −0.0163 | 4.095652 |
| DSS_111 | 4 | −0.00017 | 0.00888 | −0.01848 | 2.895652 |
| DSS_359 | 3 | −0.00022 | 0.01026 | −0.02391 | 3.345652 |
| DSS_015 | 4 | −0.00043 | 0.00888 | −0.04674 | 2.895652 |
| DSS_060 | 3 | −0.0007 | 0.01026 | −0.07609 | 3.345652 |
| DSS_098 | 2 | −0.00088 | 0.01256 | −0.09565 | 4.095652 |
| DSS_379 | 4 | −0.00089 | 0.00888 | −0.09674 | 2.895652 |
| DSS_356 | 4 | −0.0009 | 0.00888 | −0.09783 | 2.895652 |
| DSS_278 | 4 | −0.00095 | 0.00888 | −0.10326 | 2.895652 |
| DSS_368 | 4 | −0.001 | 0.00888 | −0.1087 | 2.895652 |
| DSS_351 | 1 | −0.0015 | 0.01777 | −0.16304 | 5.794565 |
| DSS_296 | 1 | −0.0015 | 0.01777 | −0.16304 | 5.794565 |
| DSS_119 | 3 | −0.00156 | 0.01026 | −0.16957 | 3.345652 |
| DSS_307 | 3 | −0.00163 | 0.01026 | −0.17717 | 3.345652 |
| DSS_077 | 4 | −0.00167 | 0.00888 | −0.18152 | 2.895652 |
| DSS_030 | 3 | −0.00188 | 0.01026 | −0.20435 | 3.345652 |
| DSS_370 | 2 | −0.00189 | 0.01256 | −0.20543 | 4.095652 |
| DSS_375 | 2 | −0.00212 | 0.01256 | −0.23043 | 4.095652 |
| DSS_280 | 3 | −0.00215 | 0.01026 | −0.2337 | 3.345652 |
| DSS_345 | 4 | −0.00225 | 0.00888 | −0.24457 | 2.895652 |
| DSS_419 | 1 | −0.00234 | 0.01777 | −0.25435 | 5.794565 |
| DSS_298 | 2 | −0.00249 | 0.01256 | −0.27065 | 4.095652 |
| DSS_367 | 3 | −0.0026 | 0.01026 | −0.28261 | 3.345652 |
| DSS_072 | 3 | −0.00268 | 0.01026 | −0.2913 | 3.345652 |
| DSS_366 | 4 | −0.00272 | 0.00888 | −0.29565 | 2.895652 |
| DSS_063 | 4 | −0.00283 | 0.00888 | −0.30761 | 2.895652 |
| DSS_092 | 3 | −0.00292 | 0.01026 | −0.31739 | 3.345652 |
| DSS_347 | 4 | −0.0033 | 0.00888 | −0.3587 | 2.895652 |
| DSS_114 | 4 | −0.0034 | 0.00888 | −0.36957 | 2.895652 |
| DSS_303 | 3 | −0.00396 | 0.01026 | −0.43043 | 3.345652 |
| DSS_276 | 4 | −0.00418 | 0.00888 | −0.45435 | 2.895652 |
| DSS_083 | 1 | −0.00446 | 0.01777 | −0.48478 | 5.794565 |
| DSS_031 | 2 | −0.00456 | 0.01256 | −0.49565 | 4.095652 |
| DSS_328 | 3 | −0.00463 | 0.01026 | −0.50326 | 3.345652 |
| DSS_039 | 4 | −0.00475 | 0.00888 | −0.5163 | 2.895652 |
| DSS_331 | 4 | −0.00475 | 0.00888 | −0.5163 | 2.895652 |
| DSS_117 | 4 | −0.00485 | 0.00888 | −0.52717 | 2.895652 |
| DSS_382 | 4 | −0.00506 | 0.00888 | −0.55 | 2.895652 |
| DSS_323 | 4 | −0.00507 | 0.00888 | −0.55109 | 2.895652 |
| DSS_041 | 2 | −0.00527 | 0.01256 | −0.57283 | 4.095652 |
| DSS_069 | 4 | −0.00534 | 0.00888 | −0.58043 | 2.895652 |
| DSS_308 | 3 | −0.00534 | 0.01026 | −0.58043 | 3.345652 |
| DSS_365 | 3 | −0.00536 | 0.01026 | −0.58261 | 3.345652 |
| DSS_403 | 3 | −0.00594 | 0.01026 | −0.64565 | 3.345652 |
| DSS_376 | 1 | −0.00648 | 0.01777 | −0.70435 | 5.794565 |
| DSS_293 | 3 | −0.00652 | 0.01026 | −0.7087 | 3.345652 |
| DSS_286 | 1 | −0.00672 | 0.01777 | −0.73043 | 5.794565 |
| BS.2C | 139 | −0.00694 | 0.00151 | −0.75435 | 0.492391 |
| DSS_410 | 1 | −0.00724 | 0.01777 | −0.78696 | 5.794565 |
| DSS_312 | 2 | −0.00725 | 0.01256 | −0.78804 | 4.095652 |
| DSS_336 | 1 | −0.00747 | 0.01777 | −0.81196 | 5.794565 |
| DSS_327 | 2 | −0.00748 | 0.01256 | −0.81304 | 4.095652 |
| DSS_127 | 4 | −0.00801 | 0.00888 | −0.87065 | 2.895652 |
| DSS_332 | 3 | −0.0085 | 0.01026 | −0.92391 | 3.345652 |
| DSS_054 | 2 | −0.00887 | 0.01256 | −0.96413 | 4.095652 |
| DSS_024 | 2 | −0.00902 | 0.01256 | −0.98043 | 4.095652 |
| DSS_106 | 3 | −0.0096 | 0.01026 | −1.04348 | 3.345652 |
| DSS_400 | 4 | −0.00964 | 0.00888 | −1.04783 | 2.895652 |
| DSS_346 | 3 | −0.00976 | 0.01026 | −1.06087 | 3.345652 |
| DSS_320 | 1 | −0.01063 | 0.01777 | −1.15543 | 5.794565 |
| DSS_275 | 4 | −0.01066 | 0.00888 | −1.1587 | 2.895652 |
| DSS_371 | 3 | −0.01111 | 0.01026 | −1.20761 | 3.345652 |
| DSS_277 | 1 | −0.01315 | 0.01777 | −1.42935 | 5.794565 |
| DSS_282 | 3 | −0.01326 | 0.01026 | −1.4413 | 3.345652 |
| DSS_393 | 3 | −0.01379 | 0.01026 | −1.49891 | 3.345652 |
| DSS_378 | 3 | −0.01461 | 0.01026 | −1.58804 | 3.345652 |
| DSS_289 | 3 | −0.01563 | 0.01026 | −1.69891 | 3.345652 |
| DSS_317 | 1 | −0.01565 | 0.01777 | −1.70109 | 5.794565 |
| DSS_062 | 4 | −0.01626 | 0.00888 | −1.76739 | 2.895652 |
| DSS_340 | 1 | −0.01657 | 0.01777 | −1.80109 | 5.794565 |
| DSS_109 | 2 | −0.01706 | 0.01256 | −1.85435 | 4.095652 |
| DSS_011 | 2 | −0.0178 | 0.01256 | −1.93478 | 4.095652 |
| DSS_089 | 4 | −0.01844 | 0.00888 | −2.00435 | 2.895652 |
| DSS_059 | 1 | −0.01848 | 0.01777 | −2.0087 | 5.794565 |
| DSS_112 | 2 | −0.01959 | 0.01256 | −2.12935 | 4.095652 |
| DSS_043 | 2 | −0.0213 | 0.01256 | −2.31522 | 4.095652 |
| DSS_413 | 1 | −0.02217 | 0.01777 | −2.40978 | 5.794565 |
| DSS_305 | 4 | −0.0227 | 0.00888 | −2.46739 | 2.895652 |
| DSS_045 | 4 | −0.02289 | 0.00888 | −2.48804 | 2.895652 |
| DSS_082 | 2 | −0.0231 | 0.01256 | −2.51087 | 4.095652 |
| DSS_272 | 1 | −0.02311 | 0.01777 | −2.51196 | 5.794565 |
| DSS_390 | 4 | −0.02319 | 0.00888 | −2.52065 | 2.895652 |
| DSS_010 | 3 | −0.02424 | 0.01026 | −2.63478 | 3.345652 |
| DSS_357 | 2 | −0.02525 | 0.01256 | −2.74457 | 4.095652 |
| DSS_085 | 4 | −0.03062 | 0.00888 | −3.32826 | 2.895652 |
| DSS_044 | 3 | −0.04088 | 0.01026 | −4.44348 | 3.345652 |
| DSS_315 | 2 | −0.0501 | 0.01256 | −5.44565 | 4.095652 |
| DSS_080 | 2 | −0.13519 | 0.01256 | −14.6946 | 4.095652 |

Figure 22:
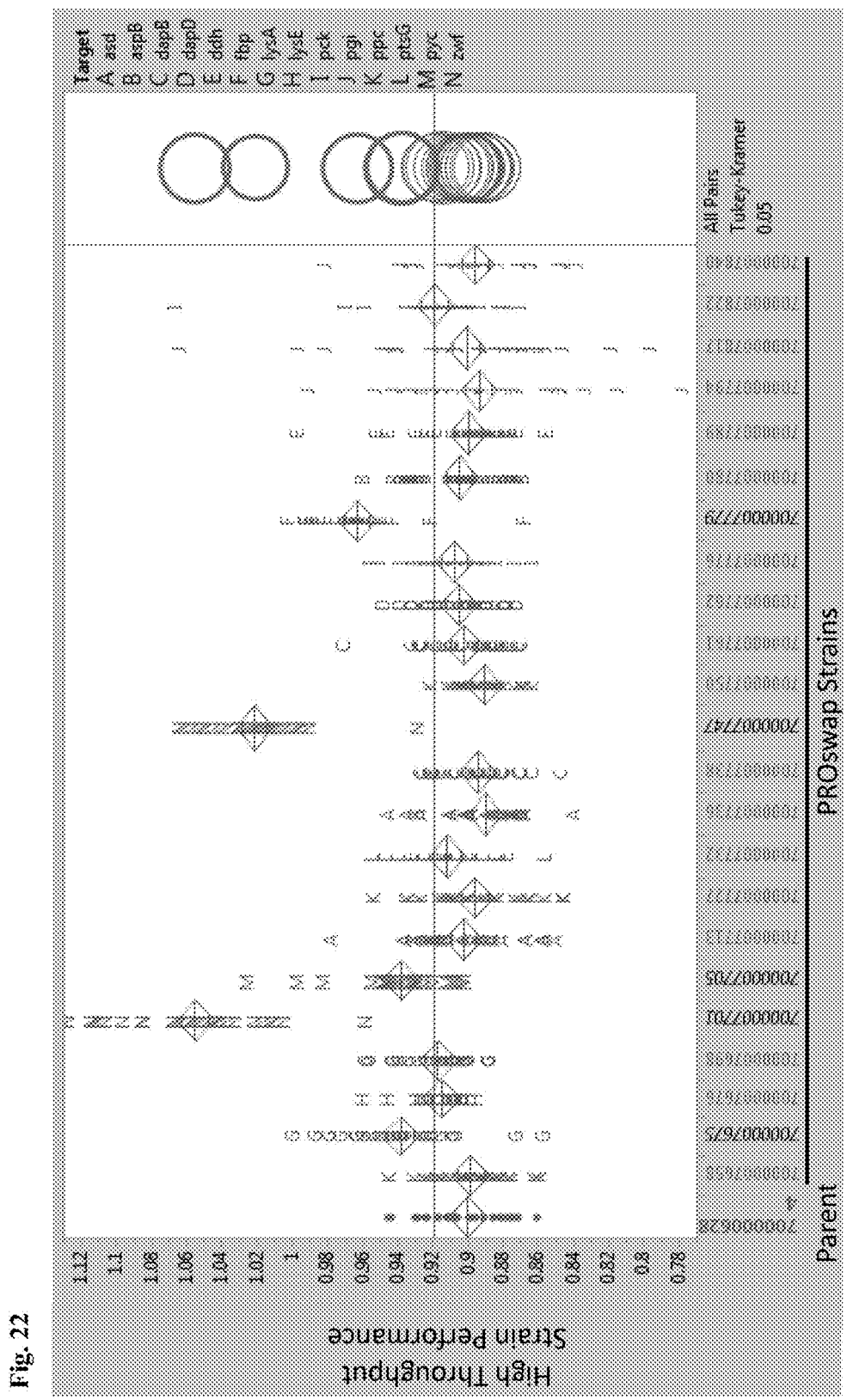
FIG. 22 depicts exemplary HTP promoter swapping data showing modifications that significantly affect performance on lysine yield. The X-axis represents different strains within the promoter swap genetic design microbial strain library, and the Y-axis includes relative lysine yield values for each strain. Each letter on the graph represents a PRO swap target gene. Each data point represents a replicate. The data demonstrates that a molecular tool adapted for HTP applications, as described herein (i.e. PRO swap), is able to efficiently create and optimize microbial strain performance for the production of a compound or molecule of interest. In this case, the compound of interest was lysine; however, the taught PRO swap molecular tool can be utilized to optimize and/or increase the production of any compound of interest. One of skill in the art would understand how to choose target genes, encoding the production of a desired compound, and then utilize the taught PRO swap procedure. One of skill in the art would readily appreciate that the demonstrated data exemplifying lysine yield increases taught herein, along with the detailed disclosure presented in the application, enables the PRO swap molecular tool to be a widely applicable advancement in HTP genomic engineering.

B. Second Round HTP Engineering and High Throughput Screening—Consolidation of SNP Swap Library with Selected PRO Swap Hits One of the strengths of the HTP methods of the present disclosure is their ability to store HTP genetic design libraries together with information associated with each SNP/Promoter/Terminator/Start Codon's effects on host cell phenotypes. The present inventors had previously conducted a promoter swap experiment that had identified several zwf promoter swaps in *C. glutamicum* with positive effects on biosynthetic yields (see e.g., results for target "N" in FIG. 22).

Figure 39:
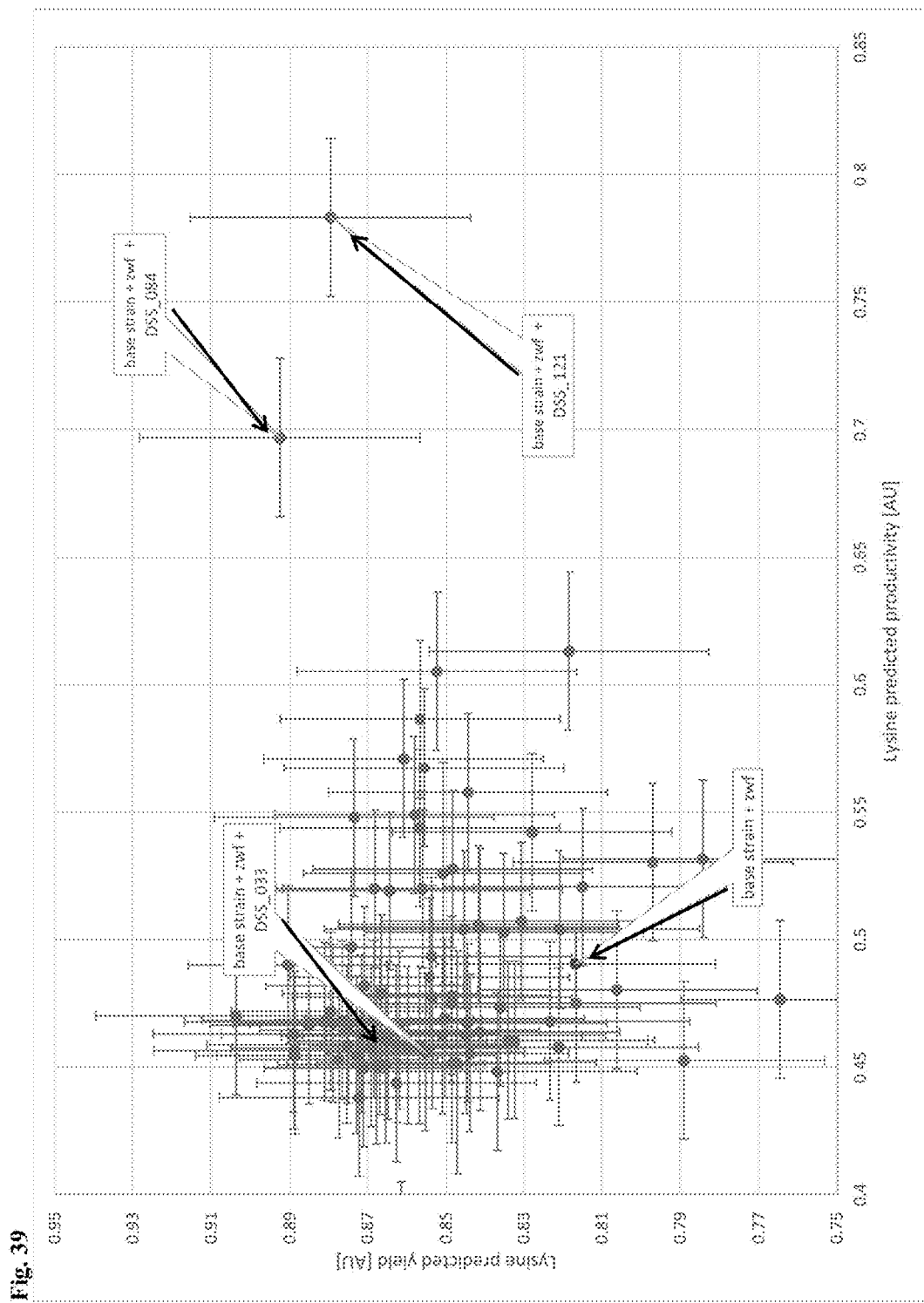
FIG. 39 depicts the results of a second round HTP engineering SNP swap program. 176 individual SNP mutations from a first round SNP swap program were individually cloned into a second round host cell strain containing a beneficial SNP identified during a first round SNP program. The resulting mutants thus represent the effect of two mutation combination pairs. Screening results for differences in host cell yield (Y-axis) and productivity (X-axis) for the selected biomolecule are shown.

The present inventors modified the base strain A of this Example to also include one of the previously identified zwf promoter swaps from Example 5. The top 176 SNPs identified from the initial screen described above in Table 8 were re-introduced into this new base strain to create a new SNP swap genetic design microbial library. As with the previous step, each newly created strain comprising a single SNP was tested for lysine yield. Selected SNP mutant strains were also tested for a productivity proxy, by measuring lysine production at 24 hours using the colorimetric method described supra. The results from this step are summarized in Table 9 below, and are depicted in FIG. 39.

TABLE 9

Second Round Screening for SNP Swap Strain Engineering for Lysine Production

| Strain ID | SNP | N for 24 hr | N for 96 hr | Mean 24 hr ($A_{560}$) | Mean 96 hr ($A_{560}$) | Std Error 24 hr | Std Error 96 hr |
|---|---|---|---|---|---|---|---|
| 7000006318 | BS2C_P0007_39zwf | 20 | 2 | 0.49 | 0.82 | 0.00 | 0.02 |
| 7000008538 | DSS_002 | 4 | 2 | 0.53 | 0.78 | 0.01 | 0.02 |
| 7000008539 | DSS_003 | 4 | | 0.56 | | 0.01 | |
| 7000008541 | DSS_005 | 4 | | 0.27 | | 0.01 | |
| 7000008542 | DSS_006 | 4 | | 0.49 | | 0.01 | |
| 7000008547 | DSS_011 | 4 | | 0.55 | | 0.01 | |
| 7000008548 | DSS_012 | 4 | | 0.58 | | 0.01 | |
| 7000008549 | DSS_013 | 4 | | 0.56 | | 0.01 | |
| 7000008550 | DSS_014 | 4 | | 0.52 | | 0.01 | |
| 7000008551 | DSS_015 | 4 | | 0.54 | | 0.01 | |
| 7000008552 | DSS_016 | 4 | 2 | 0.50 | 0.84 | 0.01 | 0.02 |
| 7000008553 | DSS_017 | 4 | | 0.44 | | 0.01 | |
| 7000008555 | DSS_019 | 4 | 4 | 0.46 | 0.84 | 0.01 | 0.01 |
| 7000008557 | DSS_021 | 4 | 4 | 0.46 | 0.86 | 0.01 | 0.01 |
| 7000008559 | DSS_023 | 4 | 2 | 0.55 | 0.86 | 0.01 | 0.02 |
| 7000008561 | DSS_025 | 4 | | 0.54 | | 0.01 | |
| 7000008562 | DSS_026 | 2 | | 0.46 | | 0.01 | |
| 7000008564 | DSS_028 | 4 | | 0.51 | | 0.01 | |
| 7000008565 | DSS_029 | 4 | 4 | 0.48 | 0.87 | 0.01 | 0.01 |
| 7000008566 | DSS_030 | 4 | 4 | 0.47 | 0.85 | 0.01 | 0.01 |
| 7000008567 | DSS_031 | 4 | | 0.56 | | 0.01 | |
| 7000008569 | DSS_033 | 4 | 4 | 0.46 | 0.86 | 0.01 | 0.01 |
| 7000008570 | DSS_034 | 2 | 2 | 0.53 | 0.85 | 0.01 | 0.02 |
| 7000008573 | DSS_037 | 4 | | 0.54 | | 0.01 | |
| 7000008574 | DSS_038 | 4 | | 0.53 | | 0.01 | |
| 7000008575 | DSS_039 | 4 | | 0.55 | | 0.01 | |
| 7000008576 | DSS_040 | 4 | | 0.57 | | 0.01 | |
| 7000008577 | DSS_041 | 4 | | 0.45 | | 0.01 | |
| 7000008578 | DSS_042 | 4 | 4 | 0.52 | 0.87 | 0.01 | 0.01 |
| 7000008579 | DSS_043 | 4 | 4 | 0.45 | 0.87 | 0.01 | 0.01 |
| 7000008580 | DSS_044 | 4 | 2 | 0.50 | 0.85 | 0.01 | 0.02 |
| 7000008581 | DSS_045 | 4 | | 0.47 | | 0.01 | |
| 7000008582 | DSS_046 | 4 | 2 | 0.61 | 0.85 | 0.01 | 0.02 |
| 7000008583 | DSS_047 | 4 | 2 | 0.61 | 0.82 | 0.01 | 0.02 |
| 7000008586 | DSS_050 | 4 | | 0.57 | | 0.01 | |
| 7000008587 | DSS_051 | 4 | | 0.56 | | 0.01 | |
| 7000008588 | DSS_052 | 4 | 2 | 0.49 | 0.85 | 0.01 | 0.02 |
| 7000008589 | DSS_053 | 4 | 4 | 0.45 | 0.85 | 0.01 | 0.01 |
| 7000008590 | DSS_054 | 4 | 4 | 0.45 | 0.88 | 0.01 | 0.01 |
| 7000008592 | DSS_056 | 4 | | 0.42 | | 0.01 | |
| 7000008596 | DSS_060 | 4 | 2 | 0.55 | 0.87 | 0.01 | 0.02 |
| 7000008597 | DSS_061 | 4 | 2 | 0.37 | 0.86 | 0.01 | 0.02 |
| 7000008598 | DSS_062 | 4 | 4 | 0.45 | 0.87 | 0.01 | 0.01 |
| 7000008601 | DSS_065 | 4 | 4 | 0.47 | 0.88 | 0.01 | 0.01 |
| 7000008602 | DSS_066 | 4 | | 0.47 | | 0.01 | |
| 7000008604 | DSS_068 | | 2 | | 0.51 | | 0.02 |
| 7000008605 | DSS_069 | 4 | 4 | 0.47 | 0.88 | 0.01 | 0.01 |
| 7000008606 | DSS_070 | 4 | | 0.55 | | 0.01 | |
| 7000008607 | DSS_071 | 4 | 2 | 0.56 | 0.84 | 0.01 | 0.02 |
| 7000008608 | DSS_072 | 4 | 2 | 0.54 | 0.83 | 0.01 | 0.02 |
| 7000008609 | DSS_073 | 4 | 2 | 0.47 | 0.84 | 0.01 | 0.02 |
| 7000008610 | DSS_074 | 4 | 2 | 0.51 | 0.83 | 0.01 | 0.02 |
| 7000008612 | DSS_076 | 4 | 4 | 0.48 | 0.76 | 0.01 | 0.01 |
| 7000008613 | DSS_077 | 4 | 4 | 0.46 | 0.87 | 0.01 | 0.01 |
| 7000008614 | DSS_078 | 4 | 2 | 0.44 | 0.87 | 0.01 | 0.02 |
| 7000008615 | DSS_079 | 4 | 2 | 0.47 | 0.90 | 0.01 | 0.02 |
| 7000008616 | DSS_080 | 4 | 2 | 0.48 | 0.81 | 0.01 | 0.02 |
| 7000008619 | DSS_083 | 4 | 2 | 0.59 | 0.86 | 0.01 | 0.02 |
| 7000008620 | DSS_084 | 4 | 2 | 0.70 | 0.89 | 0.01 | 0.02 |
| 7000008621 | DSS_085 | 4 | 4 | 0.49 | 0.89 | 0.01 | 0.01 |
| 7000008622 | DSS_086 | 4 | 2 | 0.48 | 0.82 | 0.01 | 0.02 |
| 7000008624 | DSS_088 | 4 | 2 | 0.47 | 0.88 | 0.01 | 0.02 |
| 7000008625 | DSS_089 | 4 | 4 | 0.45 | 0.89 | 0.01 | 0.01 |
| 7000008626 | DSS_090 | 4 | 4 | 0.47 | 0.87 | 0.01 | 0.01 |
| 7000008627 | DSS_091 | 4 | | 0.46 | | 0.01 | |
| 7000008629 | DSS_093 | 4 | 4 | 0.50 | 0.87 | 0.01 | 0.01 |
| 7000008630 | DSS_094 | 4 | 2 | 0.57 | 0.86 | 0.01 | 0.02 |
| 7000008634 | DSS_098 | 4 | 2 | 0.53 | 0.85 | 0.01 | 0.02 |
| 7000008636 | DSS_100 | 4 | | 0.52 | | 0.01 | |
| 7000008637 | DSS_101 | 4 | 2 | 0.49 | 0.85 | 0.01 | 0.02 |
| 7000008640 | DSS_104 | 4 | 2 | 0.51 | 0.84 | 0.01 | 0.02 |
| 7000008645 | DSS_109 | 4 | | 0.51 | | 0.01 | |
| 7000008646 | DSS_110 | 4 | 2 | 0.57 | 0.86 | 0.01 | 0.02 |
| 7000008648 | DSS_112 | 4 | 2 | 0.54 | 0.86 | 0.01 | 0.02 |

TABLE 9-continued

Second Round Screening for SNP Swap Strain Engineering for Lysine Production

| Strain ID | SNP | N for 24 hr | N for 96 hr | Mean 24 hr ($A_{560}$) | Mean 96 hr ($A_{560}$) | Std Error 24 hr | Std Error 96 hr |
|---|---|---|---|---|---|---|---|
| 7000008651 | DSS_115 | 4 | | 0.49 | | 0.01 | |
| 7000008652 | DSS_116 | 4 | 2 | 0.52 | 0.82 | 0.01 | 0.02 |
| 7000008653 | DSS_117 | 4 | 2 | 0.50 | 0.84 | 0.01 | 0.02 |
| 7000008657 | DSS_121 | 4 | 2 | 0.78 | 0.88 | 0.01 | 0.02 |
| 7000008659 | DSS_123 | 4 | | 0.54 | | 0.01 | |
| 7000008663 | DSS_127 | 4 | | 0.58 | | 0.01 | |
| 7000008665 | DSS_129 | 4 | | 0.48 | | 0.01 | |
| 7000008666 | DSS_130 | 4 | | 0.56 | | 0.01 | |
| 7000008669 | DSS_133 | 4 | | 0.50 | | 0.01 | |
| 7000008670 | DSS_271 | 4 | 2 | 0.52 | 0.86 | 0.01 | 0.02 |
| 7000008672 | DSS_273 | 4 | | 0.56 | | 0.01 | |
| 7000008677 | DSS_278 | 2 | | 0.46 | | 0.01 | |
| 7000008678 | DSS_279 | 4 | | 0.55 | | 0.01 | |
| 7000008681 | DSS_282 | 4 | | 0.51 | | 0.01 | |
| 7000008683 | DSS_284 | 4 | | 0.59 | | 0.01 | |
| 7000008684 | DSS_285 | 4 | | 0.51 | | 0.01 | |
| 7000008685 | DSS_286 | 4 | | 0.56 | | 0.01 | |
| 7000008687 | DSS_288 | 4 | | 0.46 | | 0.01 | |
| 7000008688 | DSS_289 | 4 | | 0.57 | | 0.01 | |
| 7000008689 | DSS_290 | 4 | | 0.47 | | 0.01 | |
| 7000008693 | DSS_294 | 4 | 2 | 0.52 | 0.63 | 0.01 | 0.02 |
| 7000008696 | DSS_297 | 4 | 2 | 0.52 | 0.86 | 0.01 | 0.02 |
| 7000008697 | DSS_298 | 4 | | 0.58 | | 0.01 | |
| 7000008699 | DSS_300 | 4 | | 0.48 | | 0.01 | |
| 7000008700 | DSS_301 | 4 | | 0.58 | | 0.01 | |
| 7000008701 | DSS_302 | 4 | | 0.47 | | 0.01 | |
| 7000008702 | DSS_303 | 3 | | 0.46 | | 0.01 | |
| 7000008703 | DSS_304 | 3 | | 0.48 | | 0.01 | |
| 7000008705 | DSS_306 | 4 | 2 | 0.53 | 0.80 | 0.01 | 0.02 |
| 7000008708 | DSS_309 | 4 | | 0.56 | | 0.01 | |
| 7000008709 | DSS_310 | 4 | | 0.56 | | 0.01 | |
| 7000008711 | DSS_312 | 4 | | 0.55 | | 0.01 | |
| 7000008712 | DSS_313 | 4 | | 0.51 | | 0.01 | |
| 7000008718 | DSS_319 | 4 | 2 | 0.50 | 0.82 | 0.01 | 0.02 |
| 7000008720 | DSS_321 | 4 | | 0.56 | | 0.01 | |
| 7000008722 | DSS_323 | 2 | 2 | 0.48 | 0.85 | 0.01 | 0.02 |
| 7000008723 | DSS_324 | 4 | | 0.55 | | 0.01 | |
| 7000008724 | DSS_325 | 4 | | 0.50 | | 0.01 | |
| 7000008725 | DSS_326 | 3 | | 0.46 | | 0.01 | |
| 7000008726 | DSS_327 | 3 | | 0.47 | | 0.01 | |
| 7000008730 | DSS_331 | 4 | | 0.56 | | 0.01 | |
| 7000008731 | DSS_332 | 4 | 4 | 0.47 | 0.89 | 0.01 | 0.01 |
| 7000008732 | DSS_333 | 4 | 4 | 0.47 | 0.87 | 0.01 | 0.01 |
| 7000008733 | DSS_334 | 4 | | 0.45 | | 0.01 | |
| 7000008734 | DSS_335 | 2 | | 0.47 | | 0.01 | |
| 7000008735 | DSS_336 | 4 | | 0.47 | | 0.01 | |
| 7000008739 | DSS_340 | 4 | | 0.46 | | 0.01 | |
| 7000008740 | DSS_341 | 4 | 2 | 0.46 | 0.89 | 0.01 | 0.02 |
| 7000008741 | DSS_342 | 4 | | 0.56 | | 0.01 | |
| 7000008742 | DSS_343 | 4 | | 0.55 | | 0.01 | |
| 7000008743 | DSS_344 | 4 | 4 | 0.48 | 0.87 | 0.01 | 0.01 |
| 7000008746 | DSS_347 | 4 | 4 | 0.48 | 0.85 | 0.01 | 0.01 |
| 7000008747 | DSS_348 | 4 | 4 | 0.46 | 0.86 | 0.01 | 0.01 |
| 7000008749 | DSS_350 | 4 | 2 | 0.29 | 0.74 | 0.01 | 0.02 |
| 7000008752 | DSS_353 | 4 | 2 | 0.46 | 0.85 | 0.01 | 0.02 |
| 7000008753 | DSS_354 | 4 | 4 | 0.45 | 0.87 | 0.01 | 0.01 |
| 7000008755 | DSS_356 | 4 | 4 | 0.46 | 0.86 | 0.01 | 0.01 |
| 7000008756 | DSS_357 | 4 | 4 | 0.46 | 0.86 | 0.01 | 0.01 |
| 7000008758 | DSS_359 | 2 | 2 | 0.45 | 0.85 | 0.01 | 0.02 |
| 7000008760 | DSS_361 | 4 | 2 | 0.46 | 0.84 | 0.01 | 0.02 |
| 7000008761 | DSS_362 | 4 | | 0.44 | | 0.01 | |
| 7000008763 | DSS_364 | 4 | | 0.44 | | 0.01 | |
| 7000008764 | DSS_365 | 4 | | 0.46 | | 0.01 | |
| 7000008765 | DSS_366 | 4 | | 0.55 | | 0.01 | |
| 7000008766 | DSS_367 | 4 | | 0.55 | | 0.01 | |
| 7000008767 | DSS_368 | 4 | 2 | 0.44 | 0.86 | 0.01 | 0.02 |
| 7000008770 | DSS_371 | 4 | 2 | 0.47 | 0.88 | 0.01 | 0.02 |
| 7000008771 | DSS_372 | 4 | 2 | 0.46 | 0.83 | 0.01 | 0.02 |
| 7000008772 | DSS_373 | 4 | 2 | 0.46 | 0.88 | 0.01 | 0.02 |
| 7000008774 | DSS_375 | 4 | | 0.45 | | 0.01 | |
| 7000008776 | DSS_377 | 4 | | 0.45 | | 0.01 | |
| 7000008777 | DSS_378 | 4 | | 0.57 | | 0.01 | |
| 7000008778 | DSS_379 | 4 | | 0.54 | | 0.01 | |
| 7000008779 | DSS_380 | 4 | 2 | 0.46 | 0.87 | 0.01 | 0.02 |

TABLE 9-continued

Second Round Screening for SNP Swap Strain Engineering for Lysine Production

| Strain ID | SNP | N for 24 hr | N for 96 hr | Mean 24 hr ($A_{560}$) | Mean 96 hr ($A_{560}$) | Std Error 24 hr | Std Error 96 hr |
|---|---|---|---|---|---|---|---|
| 7000008781 | DSS_382 | 4 | 2 | 0.46 | 0.84 | 0.01 | 0.02 |
| 7000008782 | DSS_383 | 4 | | 0.48 | | 0.01 | |
| 7000008783 | DSS_384 | 4 | 2 | 0.47 | 0.82 | 0.01 | 0.02 |
| 7000008784 | DSS_385 | 4 | 2 | 0.46 | 0.83 | 0.01 | 0.02 |
| 7000008786 | DSS_387 | 3 | | 0.43 | | 0.01 | |
| 7000008787 | DSS_388 | 3 | | 0.47 | | 0.01 | |
| 7000008788 | DSS_389 | 4 | 2 | 0.46 | 0.89 | 0.01 | 0.02 |
| 7000008790 | DSS_391 | 4 | | 0.57 | | 0.01 | |
| 7000008791 | DSS_392 | 4 | | 0.44 | | 0.01 | |
| 7000008795 | DSS_396 | 4 | 2 | 0.46 | 0.82 | 0.01 | 0.02 |
| 7000008799 | DSS_400 | 4 | | 0.47 | | 0.01 | |
| 7000008800 | DSS_401 | 4 | 2 | 0.46 | 0.86 | 0.01 | 0.02 |
| 7000008801 | DSS_402 | 4 | | 0.54 | | 0.01 | |
| 7000008805 | DSS_406 | 4 | 2 | 0.47 | 0.85 | 0.01 | 0.02 |
| 7000008807 | DSS_408 | 4 | | 0.45 | | 0.01 | |
| 7000008810 | DSS_411 | 4 | 2 | 0.46 | 0.87 | 0.01 | 0.02 |
| 7000008812 | DSS_413 | 3 | | 0.47 | | 0.01 | |
| 7000008813 | DSS_414 | 4 | 2 | 0.45 | 0.84 | 0.01 | 0.02 |
| 7000008815 | DSS_416 | 4 | 2 | 0.45 | 0.87 | 0.01 | 0.02 |
| 7000008816 | DSS_417 | 4 | | 0.46 | | 0.01 | |
| 7000008818 | DSS_419 | 4 | 2 | 0.47 | 0.84 | 0.01 | 0.02 |
| 7000008820 | DSS_421 | 4 | 2 | 0.45 | 0.79 | 0.01 | 0.02 |
| 7000008821 | DSS_422 | 4 | | 0.44 | | 0.01 | |

The results from this second round of SNP swap identified several SNPs capable of increasing base strain yield and productivity of lysine in a base strain comprising the zwf promoter swap mutation (see e.g., SNP 084 and SNP 121 on the upper right hand corner of FIG. 39).

C. Tank Culture Validation

Strains containing top SNPs identified during the HTP steps above were cultured into medium sized test fermentation tanks. Briefly, small 100 ml cultures of each strain were grown over night, and were then used to inoculate 5 liter cultures in the test fermentation tanks with equal amounts of inoculate. The inoculate was normalized to contain the same cellular density following an OD600 measurement.

Figure 40:
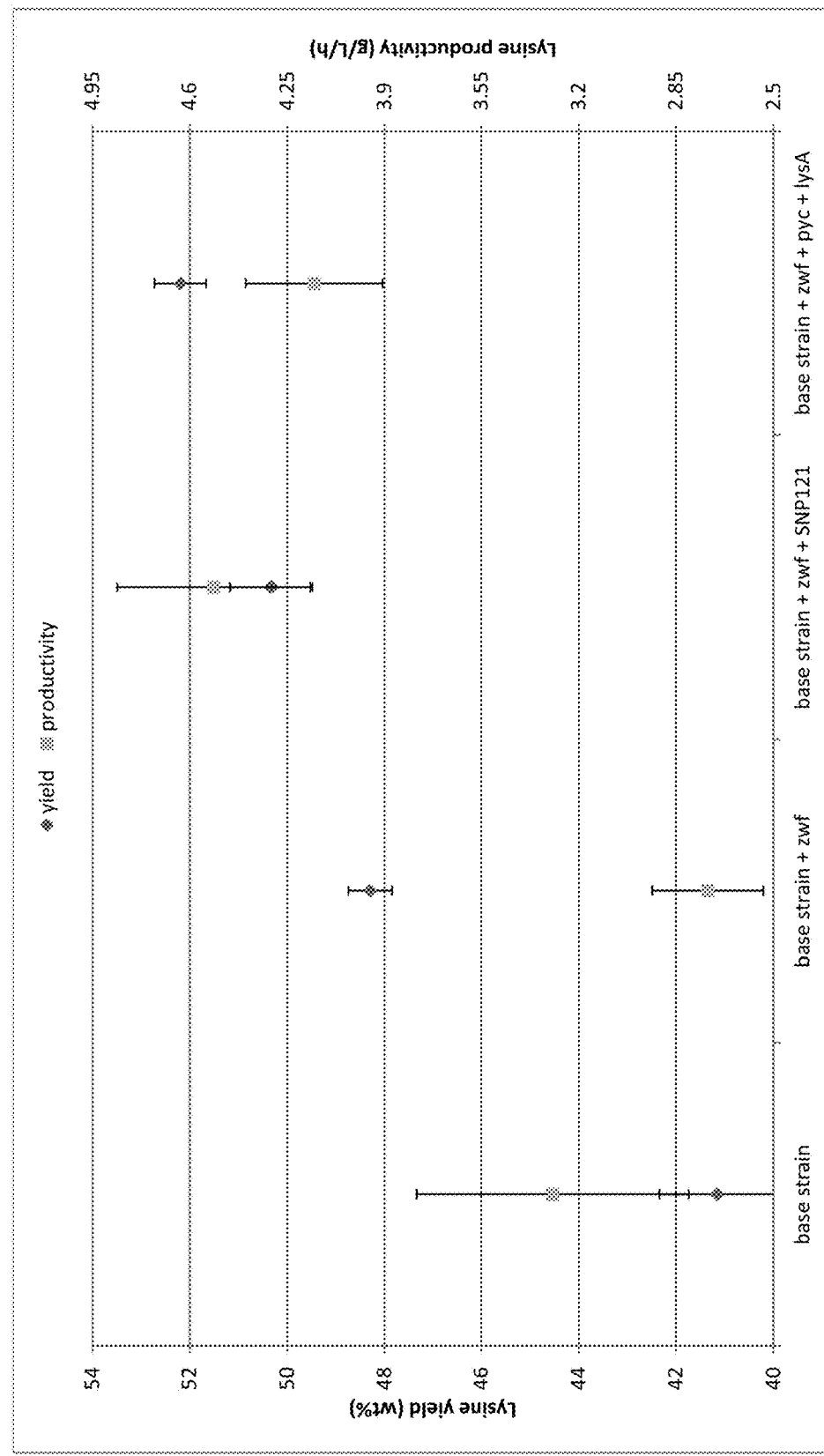
FIG. 40 depicts the results of a tank fermentation validation experiment. The top mutation pairs from the second round of HTP SNP swap were cultured in fermentation tanks. Results for host cell yield and productivity for the selected biomolecule (i.e. lysine) are shown. As can be seen, in one round of genomic engineering the inventors utilized the PRO swap procedure to determine that a particular PRO swap mutant (zwf) exhibited increased yield of a selected biomolecule compared to base strain (i.e. compare base strain to base strain+zwf). Then, the inventors performed another round of genomic engineering, wherein a SNP swap procedure was used to determine beneficial SNP mutations that could affect yield of the biomolecule, when combined with said PRO swap mutant. The combination of the PRO swap procedure and SNP swap procedure created mutants with even higher yields than the previous PRO swap only mutants (i.e. compare base strain+zwf+SNP121 to the previously discussed base strain+zwf). This figure illustrates the dramatic improvements in yield that can be achieved by combining the PRO swap and SNP swap procedures of the disclosure. In aspects, combining a PRO swap genomic engineering campaign with a SNP swap genomic engineering campaign can lead to increased yield and/or productivity of a biomolecule/product of interest by a factor of 1%, 2%, 3%, 4%, 5%, 6%, 7%, 8%, 9% 10%, 15%, 20%, 25%, 30%, 40%, 45%, 50%, or more, relative to a base strain.

The resulting tank cultures were allowed to proceed for 3 days before harvest. Yield and productivity measurements were calculated from substrate and product titers in samples taken from the tank at various points throughout the fermentation. Samples were analyzed for particular small molecule concentrations by high pressure liquid chromatography using the appropriate standards. Results for this experiment are summarized in Table 10 below, and depicted in FIG. 40.

TABLE 10

Tank Validation of SNP Swap Microbes

| Strain | N | Mean Yield (%)(g lysine produced/g glucose consumed) | Std Error | Mean Productivity (g/L/h) | Std Error |
|---|---|---|---|---|---|
| base strain | 1 | 41.1502 | 0.59401 | 3.29377 | 0.24508 |
| base strain + zwf | 7 | 48.2952 | 0.22451 | 2.73474 | 0.10005 |
| base strain + zwf + SNP121 | 2 | 50.325 | 0.42003 | 4.51397 | 0.1733 |
| base strain + zwf + pyc + lysA | 5 | 52.191 | 0.26565 | 4.15269 | 0.12254 |

As predicted by the small scale high throughput cultures, larger tank cultures for strains comprising the combined zwf promoter swap and SNP 121 exhibited significant increases in yield and productivity over the base reference strain. Productivity of this strain for example, jumped to 4.5 g/L/h compared to the 3.29 g/L/h productivity of the base strain (a 37.0% increase in productivity in only 2 rounds of SNP Swap).

Example 4: HTP Genomic Engineering—Implementation of a Promoter Swap Library to Improve an Industrial Microbial Strain Previous examples have demonstrated the power of the HTP strain improvement programs of the present disclosure for rehabilitating industrial strains. Examples 2 and 3 described the implementation of SNP swap techniques and libraries exploring the existing genetic diversity within various base, intermediate, and industrial strains This example illustrates embodiments of the HTP strain improvement programs using the PRO swap techniques of the present disclosure. Unlike Example 3, this example teaches methods for the de-novo generation of mutations via PRO swap library generation.

A. Identification of a Target for Promoter Swapping

As aforementioned, promoter swapping is a multi-step process that comprises a step of: Selecting a set of "n" genes to target.

In this example, the inventors have identified a group of 23 potential pathway genes to modulate via the promoter ladder methods of the present disclosure (19 genes to overexpress and 4+ diverting genes to downregulate, in an exemplary metabolic pathway producing the molecule lysine). (See, FIG. 19).

B. Creation of Promoter Ladder

Another step in the implementation of a promoter swap process is the selection of a set of "x" promoters to act as a "ladder". Ideally these promoters have been shown to lead to highly variable expression across multiple genomic loci, but the only requirement is that they perturb gene expression in some way.

These promoter ladders, in particular embodiments, are created by: identifying natural, native, or wild-type promoters associated with the target gene of interest and then mutating said promoter to derive multiple mutated promoter sequences. Each of these mutated promoters is tested for effect on target gene expression. In some embodiments, the edited promoters are tested for expression activity across a variety of conditions, such that each promoter variant's activity is documented/characterized/annotated and stored in a database. The resulting edited promoter variants are subsequently organized into "ladders" arranged based on the strength of their expression (e.g., with highly expressing variants near the top, and attenuated expression near the bottom, therefore leading to the term "ladder").

Figure 19:
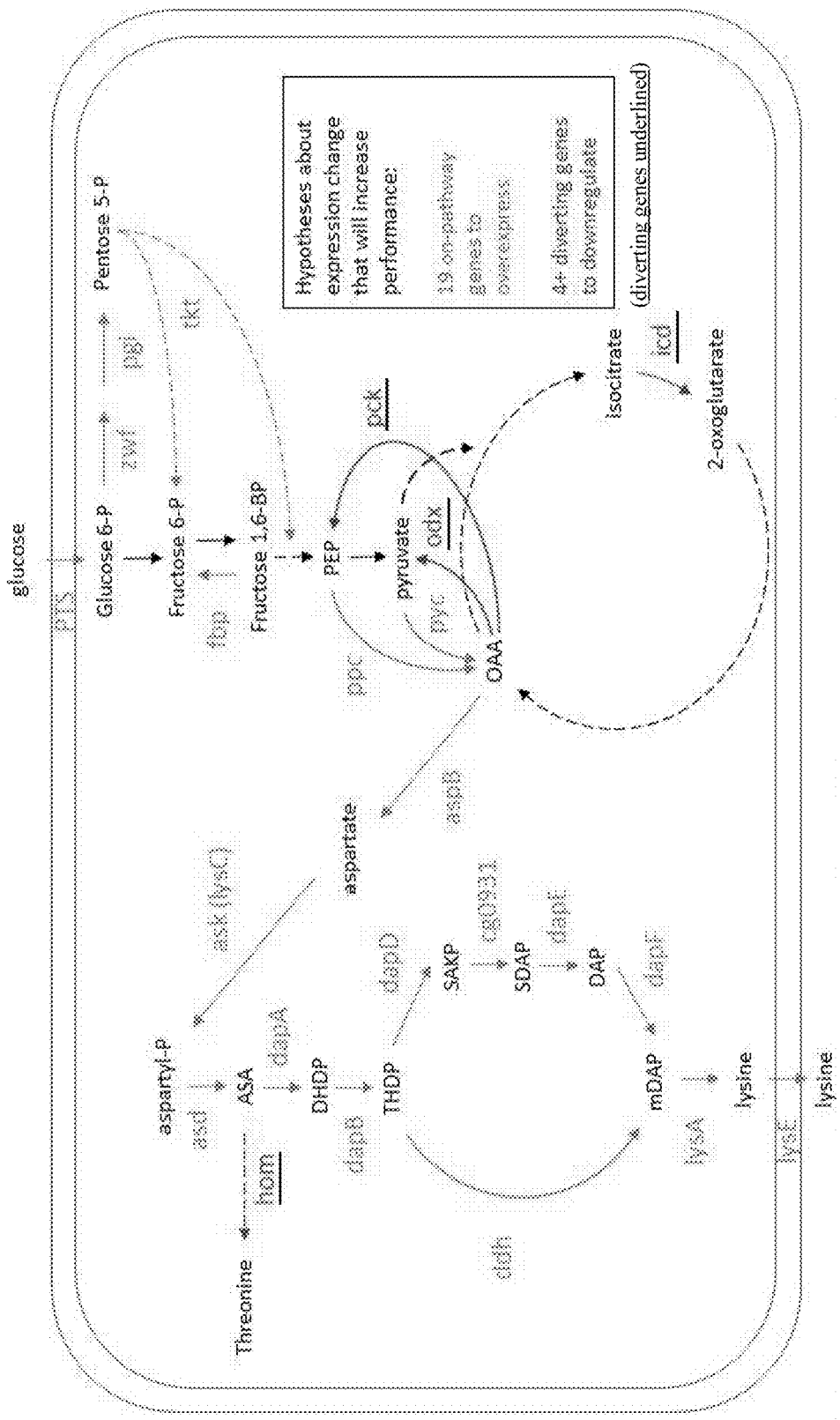
FIG. 19 illustrates example gene targets to be utilized in a promoter swap process.

In the present exemplary embodiment, the inventors have created promoter ladder:ORF combinations for each of the target genes identified in FIG. 19.

C. Associating Promoters from the Ladder with Target Genes

Another step in the implementation of a promoter swap process is the HTP engineering of various strains that comprise a given promoter from the promoter ladder associated with a particular target gene.

If a native promoter exists in front of target gene n and its sequence is known, then replacement of the native promoter with each of the x promoters in the ladder can be carried out. When the native promoter does not exist or its sequence is unknown, then insertion of each of the x promoters in the ladder in front of gene n can be carried out. In this way a library of strains is constructed, wherein each member of the library is an instance of x promoter operably linked to n target, in an otherwise identical genetic context (see e.g., FIG. 20).

D. HTP Screening of the Strains

A final step in the promoter swap process is the HTP screening of the strains in the aforementioned library. Each of the derived strains represents an instance of x promoter linked to n target, in an otherwise identical genetic background.

By implementing a HTP screening of each strain, in a scenario where their performance against one or more metrics is characterized, the inventors are able to determine what promoter/target gene association is most beneficial for a given metric (e.g. optimization of production of a molecule of interest). See, FIG. 20 (promoters P1-P8 effect on gene of interest).

In the exemplary embodiment illustrated in FIGS. 19-22, the inventors have utilized the promoter swap process to optimize the production of lysine. An application of the Pro SWAP methods described above is described in Example 5, below.

Example 5: HTP Genomic Engineering—Implementation of a PRO Swap Library to Improve Strain Performance for Lysine Production The section below provides an illustrative implementation of the PRO swap HTP design strain improvement program tools of the present disclosure, as described in Example 4. In this example, a *Corynebacterium* strain was subjected to the PRO swap methods of the present disclosure in order to increase host cell yield of lysine.

A. Promoter Swap

Promoter Swaps were conducted as described in Example 4. Selected genes from the Lysine biosynthetic pathway in FIG. 19 were targeted for promoter swaps using promoters P1-P8.

B. HTP Engineering and High Throughput Screening

Figure 41:
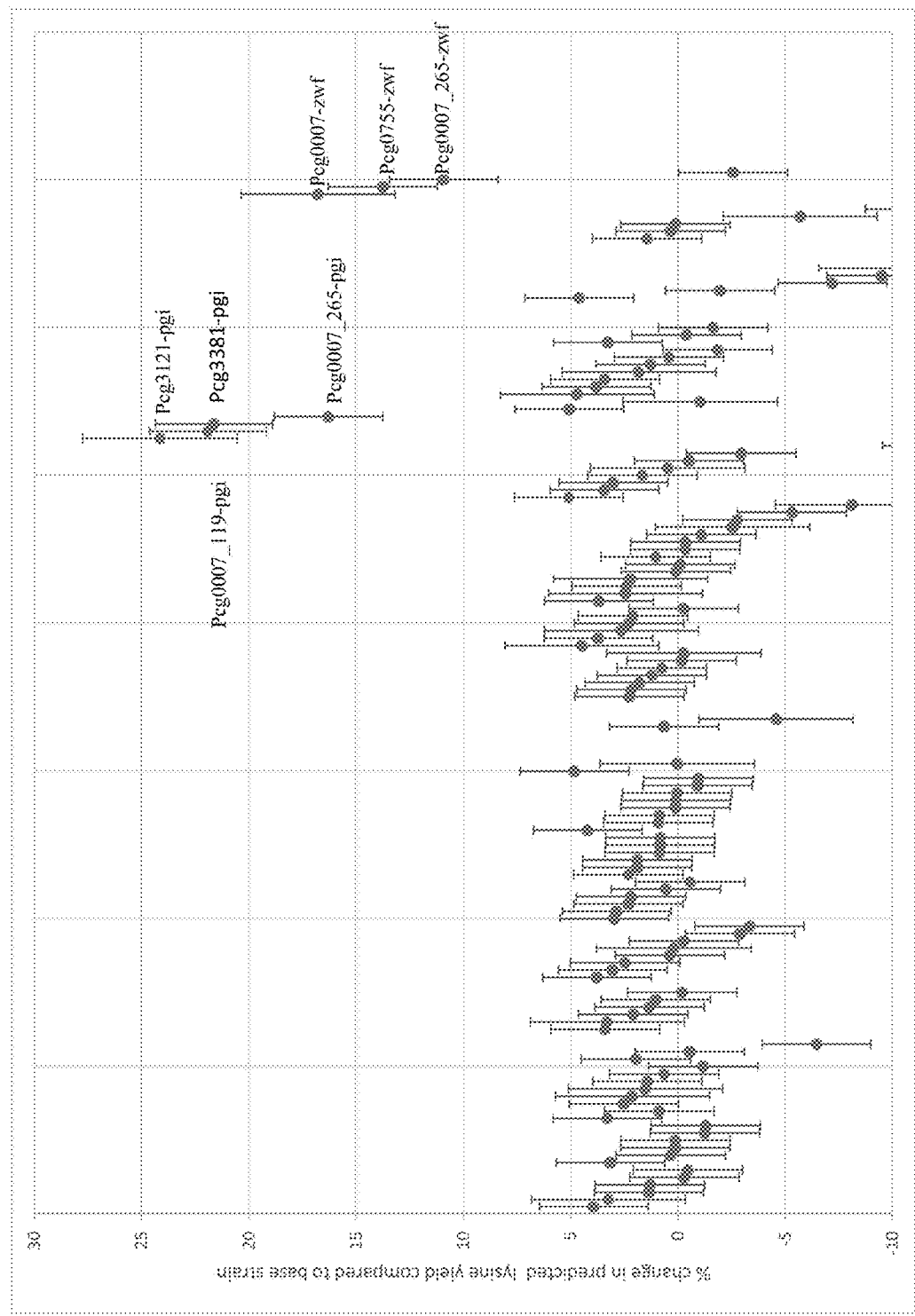
FIG. 41 depicts the results of a first round HTP engineering PRO swap program. Selected genes believed to be associated with host performance were combined with a promoter ladder to create a first round PRO swap library, according to the methods of the present disclosure. The resulting mutants were screened for differences in host cell yield of a selected biomolecule (i.e. lysine).

HTP engineering of the promoter swaps was conducted as described in Example 1 and 3. HTP screening of the resulting promoter swap strains was conducted as described in Example 3. In total 145 PRO swaps were conducted. The results of the experiment are summarized in Table 11 below, and are depicted in FIG. 41.

TABLE 11

HTP Screening of Lysine PRO Swap Libraries

| Strain | promoter-target | N | Mean ($A_{560}$) | Std Error | % Yield Change From Base |
|---|---|---|---|---|---|
| 7000007713 | Pcg1860-asd | 8 | 0.84595 | 0.00689 | 3.927615 |
| 7000007736 | Pcg0755-asd | 4 | 0.84036 | 0.00974 | 3.240866 |
| 7000007805 | Pcg0007_119-asd | 8 | 0.82493 | 0.00689 | 1.345242 |
| 7000007828 | Pcg3121-asd | 8 | 0.8246 | 0.00689 | 1.3047 |
| 7000007759 | Pcg0007_265-asd | 8 | 0.81155 | 0.00689 | −0.29853 |
| 7000007782 | Pcg3381-asd | 8 | 0.8102 | 0.00689 | −0.46438 |
| 7000007712 | Pcg1860-ask | 8 | 0.83958 | 0.00689 | 3.14504 |
| 7000007735 | Pcg0755-ask | 8 | 0.81673 | 0.00689 | 0.337846 |
| 7000007827 | Pcg3121-ask | 8 | 0.81498 | 0.00689 | 0.122853 |
| 7000007804 | Pcg0007_119-ask | 8 | 0.81492 | 0.00689 | 0.115482 |
| 7000007758 | Pcg0007_265-ask | 8 | 0.80381 | 0.00689 | −1.24942 |
| 7000007781 | Pcg3381-ask | 8 | 0.80343 | 0.00689 | −1.2961 |
| 7000007780 | Pcg3381-aspB | 8 | 0.84072 | 0.00689 | 3.285093 |
| 7000007803 | Pcg0007_119-aspB | 8 | 0.82106 | 0.00689 | 0.8698 |
| 7000007809 | Pcg0007_119-cg0931 | 8 | 0.83446 | 0.00689 | 2.516032 |
| 7000007717 | Pcg1860-cg0931 | 4 | 0.83129 | 0.00974 | 2.126588 |
| 7000007763 | Pcg0007_265-cg0931 | 4 | 0.82628 | 0.00974 | 1.511094 |
| 7000007671 | Pcg0007_39-cg0931 | 8 | 0.82554 | 0.00689 | 1.420182 |
| 7000007740 | Pcg0755-cg0931 | 8 | 0.81921 | 0.00689 | 0.642522 |
| 7000007694 | Pcg0007-cg0931 | 8 | 0.80444 | 0.00689 | −1.17202 |
| 7000007691 | Pcg0007-dapA | 8 | 0.8299 | 0.00689 | 1.955822 |
| 7000007783 | Pcg3381-dapA | 8 | 0.80951 | 0.00689 | −0.54915 |
| 7000007760 | Pcg0007_265-dapA | 8 | 0.76147 | 0.00689 | −6.45102 |
| 7000007806 | Pcg0007_119-dapA | 8 | 0.35394 | 0.00689 | −56.5174 |
| 7000007761 | Pcg0007_265-dapB | 8 | 0.84157 | 0.00689 | 3.389518 |

TABLE 11-continued

HTP Screening of Lysine PRO Swap Libraries

| Strain | promoter-target | N | Mean ($A_{560}$) | Std Error | % Yield Change From Base |
|---|---|---|---|---|---|
| 7000007738 | Pcg0755-dapB | 4 | 0.84082 | 0.00974 | 3.297378 |
| 7000007692 | Pcg0007-dapB | 8 | 0.83088 | 0.00689 | 2.076218 |
| 7000007784 | Pcg3381-dapB | 8 | 0.82474 | 0.00689 | 1.3219 |
| 7000007715 | Pcg1860-dapB | 8 | 0.82232 | 0.00689 | 1.024595 |
| 7000007830 | Pcg3121-dapB | 8 | 0.81236 | 0.00689 | −0.19902 |
| 7000007807 | Pcg0007_119-dapB | 4 | 0.69622 | 0.00974 | −14.4672 |
| 7000007762 | Pcg0007_265-dapD | 8 | 0.84468 | 0.00689 | 3.771591 |
| 7000007808 | Pcg0007_119-dapD | 8 | 0.83869 | 0.00689 | 3.035701 |
| 7000007785 | Pcg3381-dapD | 8 | 0.83397 | 0.00689 | 2.455834 |
| 7000007670 | Pcg0007_39-dapD | 8 | 0.81698 | 0.00689 | 0.368559 |
| 7000007831 | Pcg3121-dapD | 4 | 0.8155 | 0.00974 | 0.186737 |
| 7000007693 | Pcg0007-dapD | 8 | 0.8117 | 0.00689 | −0.28011 |
| 7000007716 | Pcg1860-dapD | 8 | 0.79044 | 0.00689 | −2.89196 |
| 7000007739 | Pcg0755-dapD | 8 | 0.78694 | 0.00689 | −3.32195 |
| 7000007787 | Pcg3381-dapE | 8 | 0.83814 | 0.00689 | 2.968132 |
| 7000007833 | Pcg3121-dapE | 8 | 0.83721 | 0.00689 | 2.853878 |
| 7000007741 | Pcg0755-dapE | 8 | 0.83263 | 0.00689 | 2.291211 |
| 7000007810 | Pcg0007_119-dapE | 8 | 0.83169 | 0.00689 | 2.175729 |
| 7000007718 | Pcg1860-dapE | 8 | 0.81855 | 0.00689 | 0.561439 |
| 7000007672 | Pcg0007_39-dapE | 8 | 0.80932 | 0.00689 | −0.5725 |
| 7000007765 | Pcg0007_265-dapF | 8 | 0.8327 | 0.00689 | 2.299811 |
| 7000007788 | Pcg3381-dapF | 8 | 0.82942 | 0.00689 | 1.896853 |
| 7000007811 | Pcg0007_119-dapF | 8 | 0.82926 | 0.00689 | 1.877196 |
| 7000007696 | Pcg0007-dapF | 8 | 0.82099 | 0.00689 | 0.861201 |
| 7000007719 | Pcg1860-dapF | 8 | 0.82067 | 0.00689 | 0.821888 |
| 7000007673 | Pcg0007_39-dapF | 8 | 0.82062 | 0.00689 | 0.815745 |
| 7000007789 | Pcg3381-ddh | 8 | 0.84817 | 0.00689 | 4.200349 |
| 7000007835 | Pcg3121-ddh | 8 | 0.82141 | 0.00689 | 0.912799 |
| 7000007812 | Pcg0007_119-ddh | 8 | 0.82093 | 0.00689 | 0.853829 |
| 7000007674 | Pcg0007_39-ddh | 8 | 0.81494 | 0.00689 | 0.117939 |
| 7000007720 | Pcg1860-ddh | 8 | 0.81473 | 0.00689 | 0.09214 |
| 7000007766 | Pcg0007_265-ddh | 8 | 0.81427 | 0.00689 | 0.035627 |
| 7000007743 | Pcg0755-ddh | 8 | 0.80655 | 0.00689 | −0.9128 |
| 7000007697 | Pcg0007-ddh | 8 | 0.80621 | 0.00689 | −0.95457 |
| 7000007779 | Pcg3381-fbp | 8 | 0.85321 | 0.00689 | 4.819529 |
| 7000007802 | Pcg0007_119-fbp | 4 | 0.81425 | 0.00974 | 0.03317 |
| 7000007710 | Pcg1860-fbp | 4 | 0.40253 | 0.00974 | −50.5479 |
| 7000007687 | Pcg0007-fbp | 8 | 0.14881 | 0.00689 | −81.7182 |
| 7000007825 | Pcg3121-fbp | 4 | 0.12471 | 0.00974 | −84.679 |
| 7000007733 | Pcg0755-fbp | 4 | 0.08217 | 0.00974 | −89.9052 |
| 7000007746 | Pcg0755-hom | 8 | 0.81925 | 0.00689 | 0.647436 |
| 7000007792 | Pcg3381-hom | 4 | 0.77674 | 0.00974 | −4.57505 |
| 7000007723 | Pcg1860-hom | 8 | 0.71034 | 0.00689 | −12.7325 |
| 7000007838 | Pcg3121-hom | 8 | 0.559 | 0.00689 | −31.3251 |
| 7000007800 | Pcg0007_119-icd | 8 | 0.83236 | 0.00689 | 2.258041 |
| 7000007823 | Pcg3121-icd | 8 | 0.83155 | 0.00689 | 2.15853 |
| 7000007777 | Pcg3381-icd | 8 | 0.82844 | 0.00689 | 1.776456 |
| 7000007708 | Pcg1860-icd | 8 | 0.82384 | 0.00689 | 1.211332 |
| 7000007662 | Pcg0007_39-icd | 12 | 0.82008 | 0.00562 | 0.749404 |
| 7000007685 | Pcg0007-icd | 8 | 0.81257 | 0.00689 | −0.17322 |
| 7000007754 | Pcg0007_265-icd | 4 | 0.81172 | 0.00974 | −0.27765 |
| 7000007698 | Pcg0007-lysA | 4 | 0.8504 | 0.00974 | 4.474311 |
| 7000007675 | Pcg0007_39-lysA | 8 | 0.84414 | 0.00689 | 3.705251 |
| 7000007836 | Pcg3121-lysA | 4 | 0.83545 | 0.00974 | 2.637657 |
| 7000007767 | Pcg0007_265-lysA | 8 | 0.83249 | 0.00689 | 2.274012 |
| 7000007813 | Pcg0007_119-lysA | 8 | 0.83096 | 0.00689 | 2.086046 |
| 7000007790 | Pcg3381-lysA | 8 | 0.8118 | 0.00689 | −0.26782 |
| 7000007676 | Pcg0007_39-lysE | 8 | 0.84394 | 0.00689 | 3.68068 |
| 7000007699 | Pcg0007-lysE | 4 | 0.83393 | 0.00974 | 2.45092 |
| 7000007768 | Pcg0007_265-lysE | 8 | 0.83338 | 0.00689 | 2.383351 |
| 7000007837 | Pcg3121-lysE | 4 | 0.83199 | 0.00974 | 2.212585 |
| 7000007791 | Pcg3381-lysE | 8 | 0.81476 | 0.00689 | 0.095825 |
| 7000007814 | Pcg0007_119-lysE | 8 | 0.81315 | 0.00689 | −0.10197 |
| 7000007775 | Pcg3381-odx | 8 | 0.82237 | 0.00689 | 1.030738 |
| 7000007752 | Pcg0007_265-odx | 8 | 0.81118 | 0.00689 | −0.34399 |
| 7000007729 | Pcg0755-odx | 8 | 0.81103 | 0.00689 | −0.36242 |
| 7000007683 | Pcg0007-odx | 8 | 0.80507 | 0.00689 | −1.09462 |
| 7000007706 | Pcg1860-odx | 4 | 0.79332 | 0.00974 | −2.53815 |
| 7000007660 | Pcg0007_39-odx | 8 | 0.79149 | 0.00689 | −2.76297 |
| 7000007798 | Pcg0007_119-odx | 8 | 0.77075 | 0.00689 | −5.31094 |
| 7000007821 | Pcg3121-odx | 4 | 0.74788 | 0.00974 | −8.12059 |
| 7000007822 | Pcg3121-pck | 8 | 0.85544 | 0.00689 | 5.093491 |
| 7000007776 | Pcg3381-pck | 8 | 0.8419 | 0.00689 | 3.43006 |
| 7000007799 | Pcg0007_119-pck | 8 | 0.83851 | 0.00689 | 3.013588 |
| 7000007753 | Pcg0007_265-pck | 8 | 0.82738 | 0.00689 | 1.646232 |

TABLE 11-continued

HTP Screening of Lysine PRO Swap Libraries

| Strain | promoter-target | N | Mean ($A_{560}$) | Std Error | % Yield Change From Base |
|---|---|---|---|---|---|
| 7000007730 | Pcg0755-pck | 4 | 0.81785 | 0.00974 | 0.475442 |
| 7000007661 | Pcg0007_39-pck | 8 | 0.80976 | 0.00689 | −0.51844 |
| 7000007684 | Pcg0007-pck | 8 | 0.79007 | 0.00689 | −2.93742 |
| 7000007707 | Pcg1860-pck | 8 | 0.71566 | 0.00689 | −12.0789 |
| 7000007840 | Pcg3121-pgi | 4 | 1.01046 | 0.00974 | 24.13819 |
| 7000007817 | Pcg0007_119-pgi | 7 | 0.99238 | 0.00736 | 21.917 |
| 7000007794 | Pcg3381-pgi | 7 | 0.99008 | 0.00736 | 21.63444 |
| 7000007771 | Pcg0007_265-pgi | 8 | 0.94665 | 0.00689 | 16.29893 |
| 7000007725 | Pcg1860-pgi | 8 | 0.85515 | 0.00689 | 5.057864 |
| 7000007702 | Pcg0007-pgi | 4 | 0.8056 | 0.00974 | −1.02951 |
| 7000007658 | Pcg0007_39-ppc | 4 | 0.85221 | 0.00974 | 4.696676 |
| 7000007750 | Pcg0007_265-ppc | 8 | 0.84486 | 0.00689 | 3.793705 |
| 7000007727 | Pcg0755-ppc | 8 | 0.84166 | 0.00689 | 3.400575 |
| 7000007773 | Pcg3381-ppc | 4 | 0.82883 | 0.00974 | 1.824369 |
| 7000007796 | Pcg0007_119-ppc | 8 | 0.82433 | 0.00689 | 1.27153 |
| 7000007704 | Pcg1860-ppc | 8 | 0.81736 | 0.00689 | 0.415244 |
| 7000007819 | Pcg3121-ppc | 8 | 0.79898 | 0.00689 | −1.8428 |
| 7000007732 | Pcg0755-ptsG | 8 | 0.84055 | 0.00689 | 3.264208 |
| 7000007709 | Pcg1860-ptsG | 8 | 0.81075 | 0.00689 | −0.39682 |
| 7000007663 | Pcg0007_39-ptsG | 8 | 0.80065 | 0.00689 | −1.63763 |
| 7000007778 | Pcg3381-ptsG | 8 | 0.23419 | 0.00689 | −71.229 |
| 7000007801 | Pcg0007_119-ptsG | 8 | 0.17295 | 0.00689 | −78.7525 |
| 7000007824 | Pcg3121-ptsG | 8 | 0.16035 | 0.00689 | −80.3005 |
| 7000007705 | Pcg1860-pyc | 8 | 0.85143 | 0.00689 | 4.60085 |
| 7000007728 | Pcg0755-pyc | 8 | 0.79803 | 0.00689 | −1.95951 |
| 7000007659 | Pcg0007_39-pyc | 8 | 0.75539 | 0.00689 | −7.19797 |
| 7000007751 | Pcg0007_265-pyc | 8 | 0.73664 | 0.00689 | −9.50146 |
| 7000007682 | Pcg0007-pyc | 4 | 0.73142 | 0.00974 | −10.1428 |
| 7000007774 | Pcg3381-pyc | 4 | 0.66667 | 0.00974 | −18.0975 |
| 7000007797 | Pcg0007_119-pyc | 4 | 0.52498 | 0.00974 | −35.5046 |
| 7000007820 | Pcg3121-pyc | 8 | 0.52235 | 0.00689 | −35.8277 |
| 7000007841 | Pcg3121-tkt | 8 | 0.82565 | 0.00689 | 1.433696 |
| 7000007818 | Pcg0007_119-tkt | 8 | 0.81674 | 0.00689 | 0.339075 |
| 7000007749 | Pcg0755-tkt | 8 | 0.81496 | 0.00689 | 0.120396 |
| 7000007703 | Pcg0007-tkt | 4 | 0.76763 | 0.00974 | −5.69424 |
| 7000007795 | Pcg3381-tkt | 8 | 0.72213 | 0.00689 | −11.2841 |
| 7000007772 | Pcg0007_265-tkt | 8 | 0.68884 | 0.00689 | −15.3738 |
| 7000007701 | Pcg0007-zwf | 4 | 0.95061 | 0.00974 | 16.78542 |
| 7000007747 | Pcg0755-zwf | 8 | 0.92595 | 0.00689 | 13.75587 |
| 7000007770 | Pcg0007_265-zwf | 8 | 0.9029 | 0.00689 | 10.9241 |
| 7000007724 | Pcg1860-zwf | 8 | 0.79309 | 0.00689 | −2.5664 |
| 7000007839 | Pcg3121-zwf | 4 | 0.13379 | 0.00974 | −83.5635 |
| 7000000017 | — | 116 | 0.92115 | 0.00181 | 13.16617 |
| 7000006284 | — | 128 | 0.81398 | 0.00172 | 0 |
| 7000005754 | — | 64 | 0.79489 | 0.00243 | −2.34527 |

When visualized, the results of the promoter swap library screening serve to identify gene targets that are most closely correlated with the performance metric being measured. In this case, gene targets pgi, zwf, ppc, pck, fbp, and ddh were identified as genes for which promoter swaps produce large gains in yield over base strains.

Selected strains from Table 11 were re-cultured in small plates and tested for lysine yield as describe above. The results from this secondary screening are provided in FIG. 22.

Example 6: Epistasis Mapping—an Algorithmic Tool for Predicting Beneficial Mutation Consolidations This example describes an embodiment of the predictive modeling techniques utilized as part of the HTP strain improvement program of the present disclosure. After an initial identification of potentially beneficial mutations (through the use of genetic design libraries as described above), the present disclosure teaches methods of consolidating beneficial mutations in second, third, fourth, and additional subsequent rounds of HTP strain improvement. In some embodiments, the present disclosure teaches that mutation consolidations may be based on the individual performance of each of said mutations. In other embodiments, the present disclosure teaches methods for predicting the likelihood that two or more mutations will exhibit additive or synergistic effects if consolidated into a single host cell. The example below illustrates an embodiment of the predicting tools of the present disclosure.

Selected mutations from the SNP swap and promoter swapping (PRO swap) libraries of Examples 3 and 5 were analyzed to identify SNP/PRO swap combinations that would be most likely to lead to strain host performance improvements.

SNP swapping library sequences were compared to each other using a cosine similarity matrix, as described in the "Epistasis Mapping" section of the present disclosure. The results of the analysis yielded functional similarity scores for each SNP/PRO swap combination. A visual representation of the functional similarities among all SNPs/PRO swaps is depicted in a heat map in FIG. 15. The resulting functional similarity scores were also used to develop a dendrogram depicting the similarity distance between each of the SNPs/PRO swaps (FIG. 16A).

Mutations from the same or similar functional group (i.e., SNPs/PRO swaps with high functional similarity) are more likely to operate by the same mechanism, and are thus more likely to exhibit negative or neutral epistasis on overall host performance when combined. In contrast, mutations from different functional groups would be more likely to operate by independent mechanisms, and thus more likely to produce beneficial additive or combinatorial effects on host performance.

In order to illustrate the effects of biological pathways on epistasis, SNPs and PRO swaps exhibiting various functional similarities were combined and tested on host strains. Three SNP/PRO swap combinations were engineered into the genome of *Corynebacterium glutamicum* as described in Example 1: i) Pcg0007::zwf PRO swap+Pcg1860::pyc PRO swap, ii) Pcg0007::zwf PRO swap+SNP 309, and iv) Pcg0007::zwf PRO swap+Pcg0007::lysA PRO swap (see FIGS. 15 and 16A for functional similarity relationships).

The performance of each of the host cells containing the SNP/PRO swap combinations was tested as described in Example 3, and was compared to that of a control host cell containing only zwf PRO swap. Tables 12 and 13 below summarize the results of host cell yield (96 hr measurements) and productivity (24 hr measurements) of each of the strains.

TABLE 12

Lysine Accumulation for Epistasis Mapping Experiment at 24 hours.

| SNP/PRO swap | Mean Lysine ($A_{560}$) | StDev |
|---|---|---|
| 6318 (zwf) | 0.51 | 0.03 |
| 8126 (zwf + lysA) | 0.88 | 0.06 |
| 8156 (zwf + pyc) | 0.53 | 0.01 |
| 8708 (zwf + SNP 309) | 0.56 | 0.00 |

TABLE 13

Lysine Accumulation for Epistasis Mapping Experiment at 96 hours.

| SNP/PRO swap | Mean Lysine ($A_{560}$) | StDev |
|---|---|---|
| 6318 (zwf) | 0.83 | 0.01 |
| 8126 (zwf + lysA) | 0.94 | 0.02 |
| 8156 (zwf + pyc) | 0.83 | 0.06 |

Host yield performance results for each SNP/PRO swap combination are also depicted in FIG. 16B. Host strains combining SNPs/PRO swaps exhibiting lower functional similarity outperformed strains in which the combined SNPs had exhibited higher functional similarity at both 24, and 96 hour measurements.

Thus, the epistatic mapping procedure is useful for predicting/programming/informing effective and/or positive consolidations of designed genetic changes. The analytical insight from the epistatic mapping procedure allows for the creation of predictive rule sets that can guide subsequent rounds of microbial strain development. The predictive insight gained from the epistatic library may be used across microbial types and target molecule types.

Example 7: HTP Genomic Engineering—Pro Swap Mutation Consolidation and Multi-Factor Combinatorial Testing Previous examples have illustrated methods for consolidating a small number of pre-selected PRO swap mutations with SNP swap libraries (Example 3). Other examples have illustrated the epistatic methods for selecting mutation consolidations that are most likely to yield additive or synergistic beneficial host cell properties (Example 6). This example illustrates the ability of the HTP methods of the present disclosure to effectively explore the large solution space created by the combinatorial consolidation of multiple gene/genetic design library combinations (e.g., PRO swap library x SNP Library or combinations within a PRO swap library).

In this illustrative application of the HTP strain improvement methods of the present disclosure, promoter swaps identified as having a positive effect on host performance in Example 5 are consolidated in second order combinations with the original PRO swap library. The decision to consolidate PRO swap mutations was based on each mutation's overall effect on yield or productivity, and the likelihood that the combination of the two mutations would produce an additive or synergistic effect.

For example, applicants refer to their choice of combining Pcg0007::zwf and Pcg0007::lysA, based on the epistasis mapping results of Example 6.

A. Consolidation Round for PRO Swap Strain Engineering

Strains were transformed as described in previous Example 1. Briefly, strains already containing one desired PRO swap mutation were once again transformed with the second desired PRO swap mutation. In total, the 145 tested PRO swaps from Example 5 were consolidated into 53 second round consolidation strains, each comprising two PRO swap mutations expected to exhibit beneficial additive or synergistic effects.

The resulting second round strains were once again screened as described in Example 3. Results from this experiment are summarized in Table 14 below, and depicted in FIG. 11.

TABLE 14

HTP Screening of Second Round Consolidated Lysine PRO Swap Libraries

| Strain ID | Number | PRO Swap 1 | PRO Swap 2 | Mean Yield ($A_{560}$) | Std Dev |
|---|---|---|---|---|---|
| 7000008489 | 4 | Pcg0007-lysA | Pcg3121-pgi | 1.17333 | 0.020121 |
| 7000008530 | 8 | Pcg1860-pyc | Pcg0007-zwf | 1.13144 | 0.030023 |
| 7000008491 | 7 | Pcg0007-lysA | Pcg0007-zwf | 1.09836 | 0.028609 |
| 7000008504 | 8 | Pcg3121-pck | Pcg0007-zwf | 1.09832 | 0.021939 |

TABLE 14-continued

HTP Screening of Second Round Consolidated Lysine PRO Swap Libraries

| Strain ID | Number | PRO Swap 1 | PRO Swap 2 | Mean Yield ($A_{560}$) | Std Dev |
|---|---|---|---|---|---|
| 7000008517 | 8 | Pcg0007_39-ppc | Pcg0007-zwf | 1.09502 | 0.030777 |
| 7000008502 | 4 | Pcg3121-pck | Pcg3121-pgi | 1.09366 | 0.075854 |
| 7000008478 | 4 | Pcg3381-ddh | Pcg0007-zwf | 1.08893 | 0.025505 |
| 7000008465 | 4 | Pcg0007_265-dapB | Pcg0007-zwf | 1.08617 | 0.025231 |
| 7000008535 | 8 | Pcg0007-zwf | Pcg3121-pgi | 1.06261 | 0.019757 |
| 7000008476 | 6 | Pcg3381-ddh | Pcg3121-pgi | 1.04808 | 0.084307 |
| 7000008510 | 8 | Pcg3121-pgi | Pcg1860-pyc | 1.04112 | 0.021087 |
| 7000008525 | 8 | Pcg1860-pyc | Pcg0007_265-dapB | 1.0319 | 0.034045 |
| 7000008527 | 8 | Pcg1860-pyc | Pcg0007-lysA | 1.02278 | 0.043549 |
| 7000008452 | 5 | Pcg1860-asd | Pcg0007-zwf | 1.02029 | 0.051663 |
| 7000008463 | 4 | Pcg0007_265-dapB | Pcg3121-pgi | 1.00511 | 0.031604 |
| 7000008524 | 8 | Pcg1860-pyc | Pcg1860-asd | 1.00092 | 0.026355 |
| 7000008458 | 4 | Pcg3381-aspB | Pcg1860-pyc | 1.00043 | 0.020083 |
| 7000008484 | 8 | Pcg3381-fbp | Pcg1860-pyc | 0.99686 | 0.061364 |
| 7000008474 | 8 | Pcg3381-ddh | Pcg3381-fbp | 0.99628 | 0.019733 |
| 7000008522 | 8 | Pcg0755-ptsG | Pcg3121-pgi | 0.99298 | 0.066021 |
| 7000008528 | 8 | Pcg1860-pyc | Pcg3121-pck | 0.99129 | 0.021561 |
| 7000008450 | 4 | Pcg1860-asd | Pcg3121-pgi | 0.98262 | 0.003107 |
| 7000008448 | 8 | Pcg1860-asd | Pcg3381-fbp | 0.97814 | 0.022285 |
| 7000008494 | 8 | Pcg0007_39-lysE | Pcg3381-fbp | 0.97407 | 0.027018 |
| 7000008481 | 8 | Pcg3381-fbp | Pcg0007-lysA | 0.9694 | 0.029315 |
| 7000008497 | 8 | Pcg0007_39-lysE | Pcg1860-pyc | 0.9678 | 0.028569 |
| 7000008507 | 8 | Pcg3121-pgi | Pcg3381-fbp | 0.96358 | 0.035078 |
| 7000008501 | 8 | Pcg3121-pck | Pcg0007-lysA | 0.96144 | 0.018665 |
| 7000008486 | 8 | Pcg0007-lysA | Pcg0007_265-dapB | 0.94523 | 0.017578 |
| 7000008459 | 8 | Pcg0007_265-dapB | Pcg1860-asd | 0.94462 | 0.023847 |
| 7000008506 | 2 | Pcg3121-pgi | Pcg0007_265-dapD | 0.94345 | 0.014014 |
| 7000008487 | 8 | Pcg0007-lysA | Pcg3381-ddh | 0.94249 | 0.009684 |
| 7000008498 | 8 | Pcg3121-pck | Pcg1860-asd | 0.94154 | 0.016802 |
| 7000008485 | 8 | Pcg0007-lysA | Pcg1860-asd | 0.94135 | 0.013578 |
| 7000008499 | 8 | Pcg3121-pck | Pcg0007_265-dapB | 0.93805 | 0.013317 |
| 7000008472 | 8 | Pcg3381-ddh | Pcg1860-asd | 0.93716 | 0.012472 |
| 7000008511 | 8 | Pcg0007_39-ppc | Pcg1860-asd | 0.93673 | 0.015697 |
| 7000008514 | 8 | Pcg0007_39-ppc | Pcg0007-lysA | 0.93668 | 0.027204 |
| 7000008473 | 8 | Pcg3381-ddh | Pcg0007_265-dapB | 0.93582 | 0.030377 |
| 7000008461 | 7 | Pcg0007_265-dapB | Pcg3381-fbp | 0.93498 | 0.037862 |
| 7000008512 | 8 | Pcg0007_39-ppc | Pcg0007_265-dapB | 0.93033 | 0.017521 |
| 7000008456 | 8 | Pcg3381-aspB | Pcg3121-pck | 0.92544 | 0.020075 |
| 7000008460 | 8 | Pcg0007_265-dapB | Pcg0007_265-dapD | 0.91723 | 0.009508 |
| 7000008492 | 8 | Pcg0007_39-lysE | Pcg3381-aspB | 0.91165 | 0.012988 |
| 7000008493 | 8 | Pcg0007_39-lysE | Pcg0007_265-dapD | 0.90609 | 0.031968 |
| 7000008453 | 8 | Pcg3381-aspB | Pcg0007_265-dapB | 0.90338 | 0.013228 |
| 7000008447 | 8 | Pcg1860-asd | Pcg0007_265-dapD | 0.89886 | 0.028896 |
| 7000008455 | 8 | Pcg3381-aspB | Pcg0007-lysA | 0.89531 | 0.027108 |
| 7000008454 | 6 | Pcg3381-aspB | Pcg3381-ddh | 0.87816 | 0.025807 |
| 7000008523 | 8 | Pcg0755-ptsG | Pcg1860-pyc | 0.87693 | 0.030322 |
| 7000008520 | 8 | Pcg0755-ptsG | Pcg3381-fbp | 0.87656 | 0.018452 |
| 7000008533 | 4 | Pcg0007-zwf | Pcg3381-fbp | 0.84584 | 0.017012 |
| 7000008519 | 8 | Pcg0755-ptsG | Pcg0007_265-dapD | 0.84196 | 0.025747 |

Figure 11:
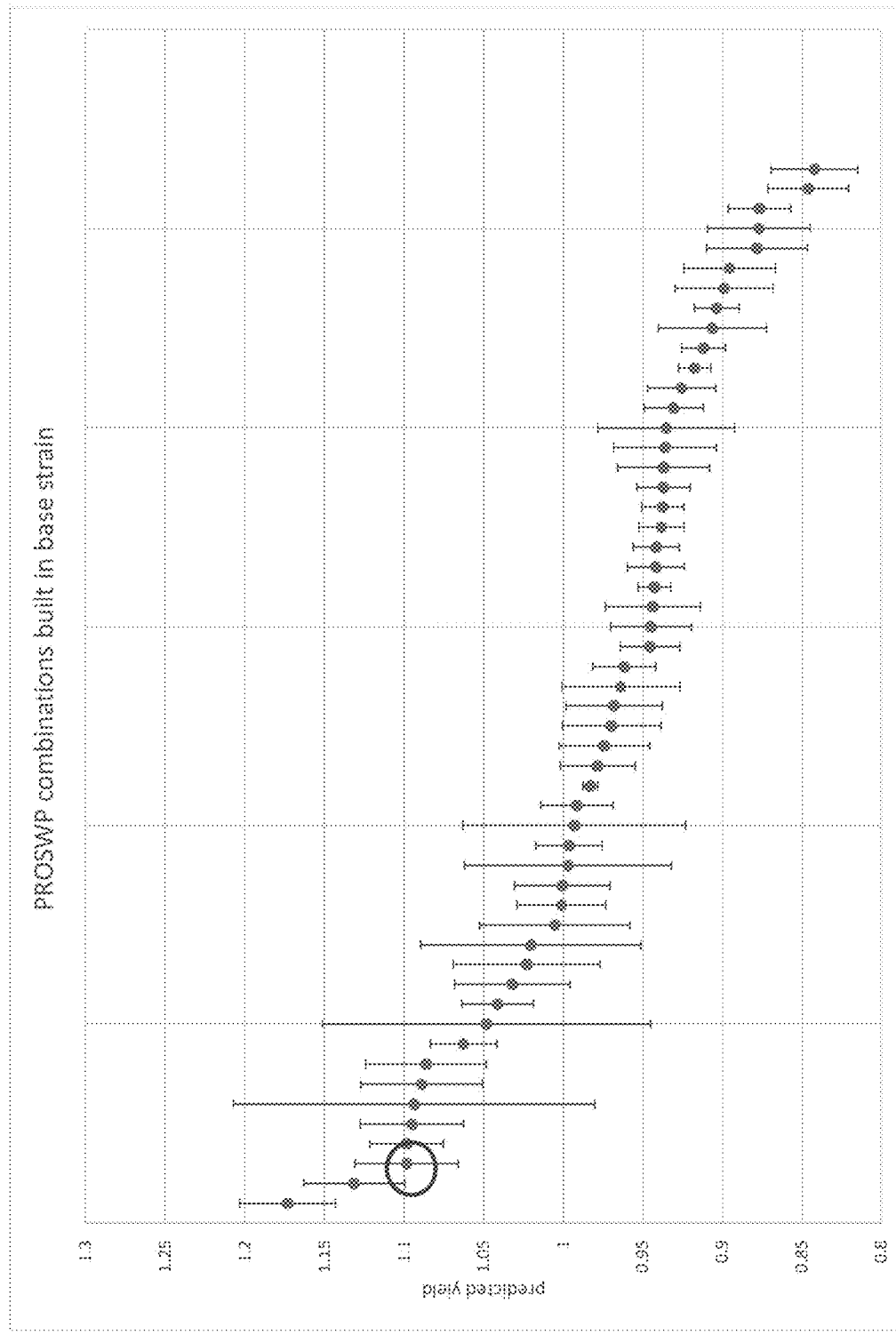
FIG. 11 depicts the results of a second round HTP engineering PRO swap program. Top promoter::gene combinations identified during the first PRO swap round were analyzed according to the methods of the present disclosure to identify combinations of said mutations that would be likely to exhibit additive or combinatorial beneficial effects on host performance. Second round PRO swap mutants thus comprised pair combinations of various promoter::gene mutations. The resulting second round mutants were screened for differences in host cell yield of a selected biomolecule. A combination pair of mutations that had been predicted to exhibit beneficial effects is emphasized with a circle.

As predicted by the epistasis model, the second round PRO swap strain comprising the Pcg0007::zwf and Pcg0007::lysA mutations exhibited one of the highest yield improvements, with a nearly 30% improvement in yield over Pcg0007::lysA alone, and a 35.5% improvement over the base strain (see circled data point on FIG. 11).

The HTP methods for exploring solution space of single and double consolidated mutations, can also be applied to third, fourth, and subsequent mutation consolidations. Attention is also drawn, for example, to the disclosed 3-change consolidation strain corresponding to zwf, pyc, and lysa that was made from amongst the top hits of identified in the 2 change consolidations as shown in Table 14 above, and as identified by the epistatic methods of the present disclosure. This 3-change consolidation strain was further validated in tanks as being significantly improved as compared to the parent or parent+zwf (see Table 10 supra, and FIG. 40).

Example 8: HTP Genomic Engineering—Implementation of a Terminator Library to Improve an Industrial Host Strain The present example applies the HTP methods of the present disclosure to additional HTP genetic design libraries, including STOP swap. The example further illustrates the ability of the present disclosure to combine elements from basic genetic design libraries (e.g., PRO swap, SNP swap, STOP swap, etc.,) to create more complex genetic design libraries (e.g., PRO-STOP swap libraries, incorporating both a promoter and a terminator). In some embodiments, the present disclosure teaches any and all possible genetic design libraries, including those derived from combining any of the previously disclosed genetic design libraries.

In this example, a small scale experiment was conducted to demonstrate the effect of the STOP swap methods of the present invention on gene expression. Terminators T1-T8 of the present disclosure were paired with one of two native *Corynebacterium glutamicum* promoters as described below, and were analyzed for their ability to impact expression of a fluorescent protein.

A. Assembly of DNA Constructs

Terminators T1-T8 were paired with one of two native *Corynebacterium glutamicum* promoters (e.g., Pcg0007 or Pcg0047) expressing a yellow fluorescence protein (YFP). To facilitate DNA amplification and assembly, the final promoter-YFP-terminator sequence was synthesized in two portions; the first portion encoded (from 5' to 3') i) the vector homology arm, ii) the selected promoter, iii) and ⅔ of the YFP gene. The second portion encoded (from 5' to 3') iv) the next ⅔ of the YFP gene, v) the selected terminator, and vi) the second vector homology arm. Each portion was amplified using synthetic oligonucleotides and gel purified. Gel purified amplicons were assembled with a vector backbone using yeast homologous recombination.

B. Transformation of Assembled Clones into *E. coli*

Vectors containing the Promoter-YFP-terminator sequences were each individually transformed into *E. coli* in order to identify correctly assembled clones, and to amplify vector DNA for *Corynebacterium* transformation. Correctly assembled vectors were confirmed by restriction enzyme digest and Sanger sequencing. Positive clones were stored at −20° C. for future use.

C. Transformation of Assembled Clones into *Corynebacterium*

Verified vector clones were individually transformed into *Corynebacterium glutamicum* host cells via electroporation. Each vector was designed to integrate into a neutral integration site within the *Corynebacterium glutamicum* genome that was empirically determined to permit expression of heterologous yellow fluorescence protein but not be detrimental to the host cell. To facilitate integration, the expression vector further comprised about 2 kbp of sequence homologous (i.e., homology arm) to the desired integration site whereby each gene cassette described above was inserted downstream of the homology am. Integration into the genome occurred by single-crossover integration. Transformed *Corynebacterium* were then tested for correct integration via PCR. This process was repeated for each of the transformations conducted for each gene construct.

D. Evaluation of Individual Terminator Constructs in *Corynebacterium*

The phenotype of each *Corynebacterium* transformant containing promoter-YFP-terminator constructs was then tested in two media types (brain heart infusion-BHI and HTP test media) at two time points in order to evaluate expression. Briefly, between four and six PCR-confirmed transformants were chosen and cultivated in selective media in a 96-well format. The initial cultures were then split into selective BHI media or selective seed media. At 48 hours, cultures in seed media were inoculated into selective HTP test media or BHI media and analyzed at two time points representing different portions of the growth curve. Time points for HTP test media cultures were 48 and 96 hours after inoculation. Cultures in the selective BHI media were analyzed at 48 and 72 hours after inoculation.

Figure 36:
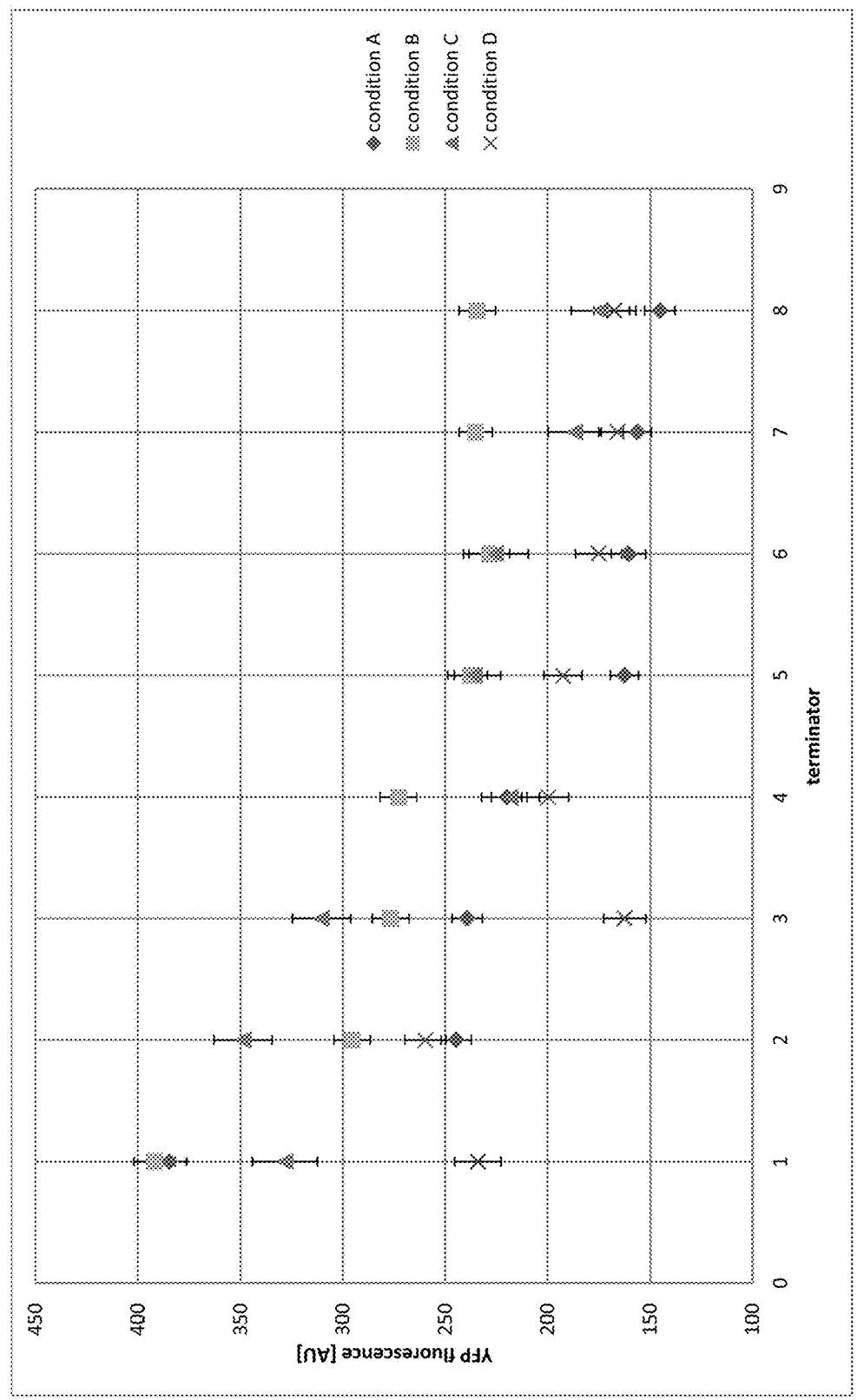
FIG. 36 depicts the results of an experiment characterizing the effects of Terminators T1-T8 in two media over two time points. Conditions A and C represent the two time points for the BHI media, while the B and D points represent the two time points for the HTP test media.

Analysis of the cultures was performed using a benchtop flow cytometer. Briefly, cultures were diluted 1:100 in 200 μl of phosphate buffered saline (PBS). For each culture, between 3000 and 5000 individual events (i.e., cells) were analyzed for yellow fluorescence. The benchtop flow cytometer plots a histogram of yellow fluorescence of each "event" and calculates the median fluorescence within each well. FIG. 36 depicts the mean of the median fluorescence for each construct (across the 4-6 biological replicates). Error bars indicate the 95% confidence interval of each data point. Conditions A-D each refer to a single media and a single time point. Thus conditions A and B represent the two time points for the BHI media, while the C and D points represent the two time points for the HTP test media. Note that the arbitrary units (e.g., AU) represent the median fluorescence recorded by the benchtop flow cytometer.

The results show that terminators 1-8 of the STOP swap genetic design library result in a continuous range of YFP expression. These terminators thus form a terminator ladder that can be implemented into future genetic design libraries, according to the HTP methods of the present disclosure.

Example 9: Comparing HTP Toolsets Vs. Traditional UV Mutations

This example demonstrates the benefits of the HTP genetic design libraries of the present disclosure over traditional mutational strain improvement programs. The experiments in this portion of the specification quantify the improved magnitude and speed of the phenotypical improvements achieved through the HTP methods of the present disclosure over traditional UV mutagenesis.

The present disclosure teaches new methods for accelerating the strain improvement programs of host cells. In some embodiments, the HTP strain improvement program of the present disclosure relies on the ability of the HTP toolsets to generate and identify genetic perturbations. The present inventors attempted to quantify the benefits of the HTP tool sets by conducting a small parallel track strain improvement program comparing the promoter swap techniques of the present disclosure against traditional UV mutations approaches.

A base reference strain producing a biochemical metabolite of interest was chosen as the starting point for both UV and promoter swap genetic perturbations.

A. UV Mutations

Cultures of the base strain were grown in BHI medium in cultures that were OD normalized to $OD_{600}$ of 10. This culture was aliquoted into a sterile petri dish and agitated using a small magnetic stirrer bar. A UV trans illuminator at 254 nm wavelength was then inverted over the culture and aliquots taken at 5 and 9 minutes of UV exposure. These samples were serially diluted 10-fold and each dilution plated onto BHI medium Q-trays. From these Q-trays, approximately 2500 colonies from each UV exposure point were picked using an automated colony picking apparatus and the performance evaluated as below.

B. Promoter Swap

PRO swap constructs were generated in the base strain for 15 gene targets using either all or a subset of promoters selected from P1, P3, P4 and P8 described in Table 1. The final step in the biosynthesis of the product of interest is catalyzed by an O-methyltransferase enzyme that utilizes the potentially rate limiting cofactor S-adenosylmethionine. Gene targets for PRO swaps were therefore selected on the basis that they are directly involved in the biosynthesis of this cofactor or upstream metabolites.

C. UV and Promoter Swap Library Evaluation

The phenotype of each *Corynebacterium* strain developed for this example was tested for its ability to produce a selected biomolecule. Briefly, between four and six sequence confirmed colonies from each PRO swap strain, and single colonies for each UV strain were chosen and propagated in selective media in a 96-well format in production liquid media.

After biomass propagation in 96-well microwell plates, cell mass was added to fermentation media containing substrate in 96-well microwell plates and bioconversion was allowed to proceed for 24 hrs. Titers of product were determined for each strain using high-performance liquid chromatography from samples taken at 24 hrs. The titer results for each genetic perturbation (UV and PRO swap) was analyzed. Results for each replicate was averaged and assigned to represent the overall performance of said strain. Strains were then binned into categories based on each mutation's effect on measured yield expressed as a ratio over the yield of the base strain.

Figure 37:
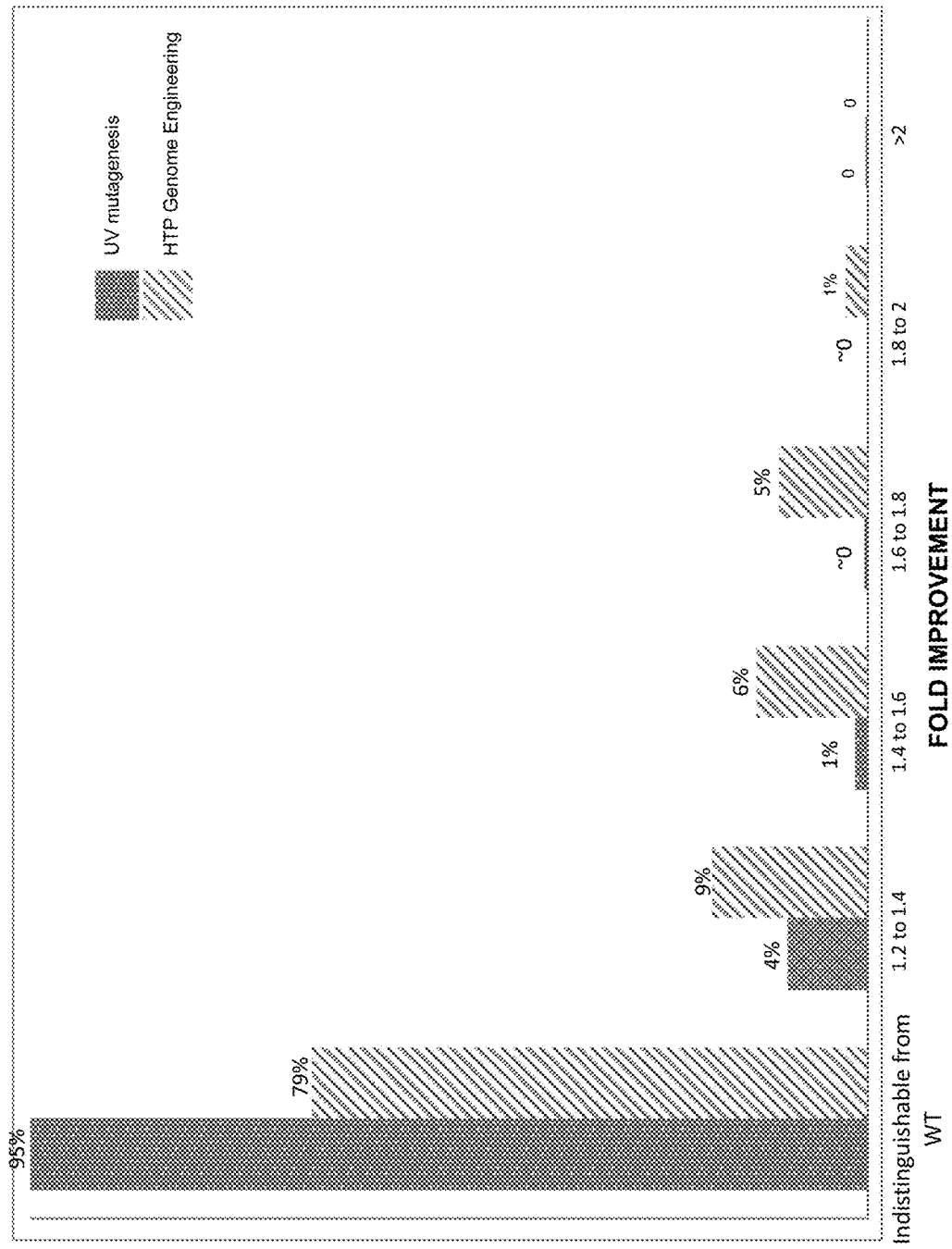
FIG. 37 depicts the results of an experiment comparing the effectiveness of traditional strain improvement approaches such as UV mutagenesis against the HTP engineering methodologies of the present disclosure. The vast majority of UV mutations produced no noticeable increase in host cell performance. In contrast, PRO swap methodologies of the present disclosure produced a high proportion of mutants exhibiting 1.2 to 2 fold increases in host cell performance.

FIG. 37 summarizes the results of this experiment, which are presented as the number of strains for each strain improvement technique that produced: i) no change in yield, ii) a 1.2 to 1.4 fold improvement to yield, iii) a 1.4 to 1.6 fold improvement to yield, iv) a 1.6 to 1.8 fold improvement to yield, or v) a 1.8 to 2 fold improvement to yield.

The results are illustrative of the benefits of the HTP toolsets of the present disclosure over traditional UV mutagenesis approaches. For example, the results of FIG. 37 demonstrate that the PRO swap strains exhibited a higher rate of positive changes in yield, and were therefore more likely to provide mutations that could significantly improve the strain. Most striking, was the high incidence of high improvement strains showing 1.6, 1.8 and 2 fold increases in the PRO swap library, with little to no identified improvements in the UV library.

The results are also important because they highlight the accelerated rate of improvement of the PRO swap methods of the present disclosure. Indeed, results for the PRO swap library were based on less than 100 promoter::gene perturbations, whereas UV mutation results included the screening of over 4,000 distinct mutant strains. Thus the methods of the present disclosure drastically reduce the number of mutants that must be screened before identifying genetic perturbations capable of conferring strains with high gains in performance.

Example 10: Application of HTP Engineering Methods in Eukaryotes

Previous examples illustrate applications of HTP strain improvement programs on prokaryotic cells. This example demonstrates the applicability of the same techniques to eukaryotic cells. Specifically, Examples 10 and 11 describe a SNP swap strain improvement program for *Aspergillus niger* for the industrial production of citric acid.

A. *Aspergillus Niger* Protoplast Formation and Transformation

A large volume (500 ml) of protoplasts of a eukaryotic fungal strain of *Aspergillus niger*, ATCC 1015, was generated using a commercially available enzyme mixture which contains beta-glucanase activity. The protoplasts were isolated from the enzyme mixture by centrifugation and were ultimately re-suspended in a buffer containing calcium chloride.

The protoplasts were aliquoted and frozen at negative 80 degrees Celsius in containers containing a suspension of dimethyl sulfoxide and polyethylene glycol (PEG). In some embodiments, the present disclosure teaches that a stock of 96-well microtiter plates containing 25-50 microliters of protoplasts in each well can be prepared and frozen in large batches for large scale genome editing campaigns using this technique.

Traditional PEG Calcium mediated transformations were carried out by automated liquid handlers, which combined the DNA with the protoplast-PEG mixtures in the 96 wells. An additional automated liquid handling step was used to plate the transformation on to selective media after transformation.

B. Automated Screening of Transformants

As discussed in more detail below, the *A. niger* cells had been transformed with a functional pyrG gene, which permitted transformed cells to grow in the absence of Uracil. The pyrG gene of this example was further designed to incorporate into the location of *A. niger*'s wild type aygA gene, thus incorporating a mutation into to the naturally occurring aygA gene. Disruption the aygA gene further results in a yellow spore color, providing a secondary screening method for identifying transformants.

Transformants grown on the selective media without Uracil were isolated and placed into individual wells of a second microtiter plate. The transformants in the second microtiter plate were allowed to grow and sporulate for 2-3 days, before being resuspended in a liquid consisting of water and a small amount of detergent to generate a spore stock suitable for storage and downstream automated screening.

A small aliquot of each of the aforementioned spore stocks was then used to inoculate liquid media in a third 96 well PCR plate. These small cultures are allowed to grow over night in a stationary incubator so that the yellow-pigment containing spores germinate and form hyphae that are more amenable to selection, and downstream steps.

Following the culturing step, the hyphae of the third PCR plate were lysed by adding a commercially available buffer and heating the cultures to 99 degrees Celsius for 20 minutes. The plates were then centrifuged to separate the DNA suspension supernatant from the cell/organelle pellets. The DNA extractions were then used for PCR analysis to identify cell lines comprising the desired DNA modifications.

C. Co-Transformation for Integration of SNPs-Design of SNPs

The DNA sequence of the *Aspergillus niger* gene aygA was obtained and the proper reading frame was determined. Four distinct types of mutations were designed, which if integrated would result in a null mutation.

The mutations included a single base pair change that incorporates an in-frame stop codon, a small two base pair deletion, a three-base pair integration, and a larger 100 base pair deletion all of which if properly integrated will eliminate aygA activity. Strains lacking aygA activity have a yellow spore phenotype. The designs were generated as in silico constructs that predicted a set of oligomers that were used to build the constructs using Gibson assembly.

D. Integration of SNPs by Co-Transformation

Using the transformation approach described above, amplicons containing the small changes were incorporated into the genome of an *Aspergillus niger* strain 1015. As previously discussed, this strain of *Aspergillus niger* comprised a non functional pyrG gene, and was therefore unable to grow in the absence of exogenous uracil. Cells that had successfully integrated the pyrG gene were now capable of growth in the absence of uracil. Of these pyrG+ transformants, isolates that also integrated the small mutations in the aygA gene exhibited the yellow spore phenotype. (FIG. 43A). The presence of the mutation is also detected through Sequencing of small amplicons that contain the region targeted for the SNP exchange (FIG. 43B).

Example 11: HTP Genomic
Engineering—Implementation of an HTP SNP
Library Strain Improvement Program to Improve
Citric Acid Production in Eukaryote *Aspergillus
niger* ATCC11414

Example 10 above described the techniques for automating the genetic engineering techniques of the present disclosure in a high throughput manner. This example applies the techniques described above to the specific HTP strain improvement of *Aspergillus niger* strain ATCC11414.

*Aspergillus niger* is a species of filamentous fungi used for the large scale production of citric acid through fermentation. Multiple strains of this species have been isolated and shown to have varying capacity for production of citric and other organic acids. The HTP strain engineering methods of the present disclosure can be used to combine causative alleles and eliminate detrimental alleles to improve citric acid production.

A. Identification of a Library of Genetic Design Library for SNPs from Natural *A. niger* Strain Variants.

*A. niger* strain ATCC 1015 was identified as a producer of citric acid in the early twentieth century. An isolate of this strain named ATCC 11414, was later found to exhibit increased citric acid yield over its parent. For example, *A. niger* strain ATCC 1015 on average produces 7 grams of citric acid from 140 grams of glucose in media containing ammonium nitrate, but lacking both iron and manganese cations. Isolate strain ATCC 11414 on the other hand, exhibits a 10-fold yield increase (70 grams of citric acid) under the same conditions. Moreover, strain ATCC 11414 spores germinate and grow better in citric acid production media than do spores of strain 1015.

In order to identify potential genetic sources for these phenotypic differences, the genomes of both the ATCC 1015 and ATCC 11414 strains were sequenced and analyzed. The resulting analysis identified 42 SNPs distinguishing the 1015 and 11414 strains.

B. Exchanging Causative Alleles

Protoplasts were prepared from strain ATCC 1015 ("base strain") for transformation. Each of the above-identified 42 SNPs were then individually introduced into the base strain via the gene editing techniques of the present disclosure ("wave up" FIG. 44A). Each SNP was co-transformed with the functional pyrG and aygA gene mutation as described above. Transformants that had successful gene targeting to the aygA locus produced yellow spores (FIG. 44B).

C. Screening for Successful Integration

Transformants containing putative SNPs were isolated and a spore stock was propagated as stated above. Amplicons that contain the region of DNA containing the putative SNP were analyzed by next generation sequencing. Using this approach it is possible to determine successful integration events within each transformant even in the presence of the parental DNA. This capability is essential to determine targeting in fungi which can grow as heterokaryons which contain nuclei with differing genotype in the same cell.

Figure 45:
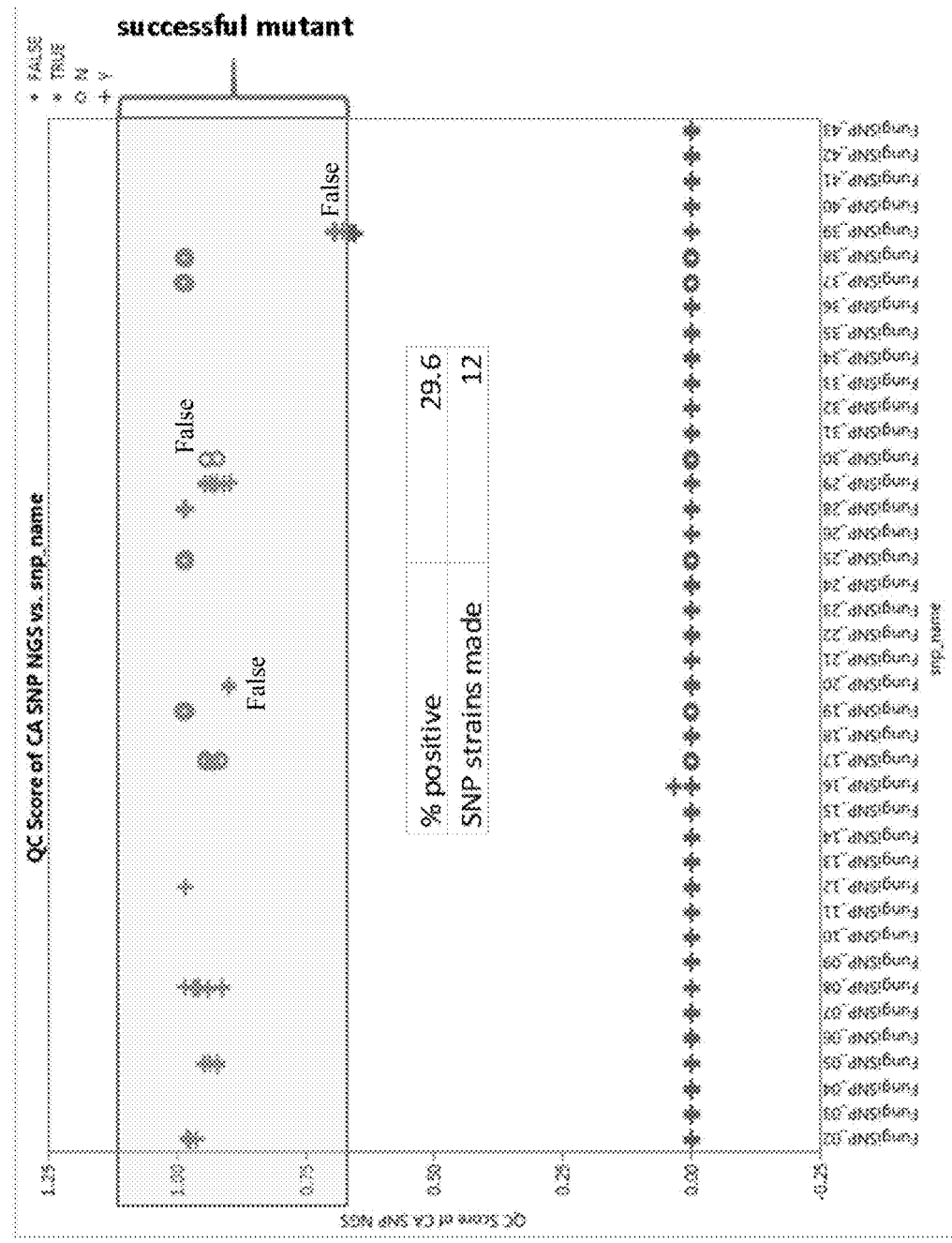
FIG. 45 depicts a quality control (QC) chart identifying successful A. niger mutant transformants (top box) based on next generation sequencing results. Overall 29.2% of yellow colonies selected from the culture plates exhibit the expected SNP genetic change.
Figure 46:
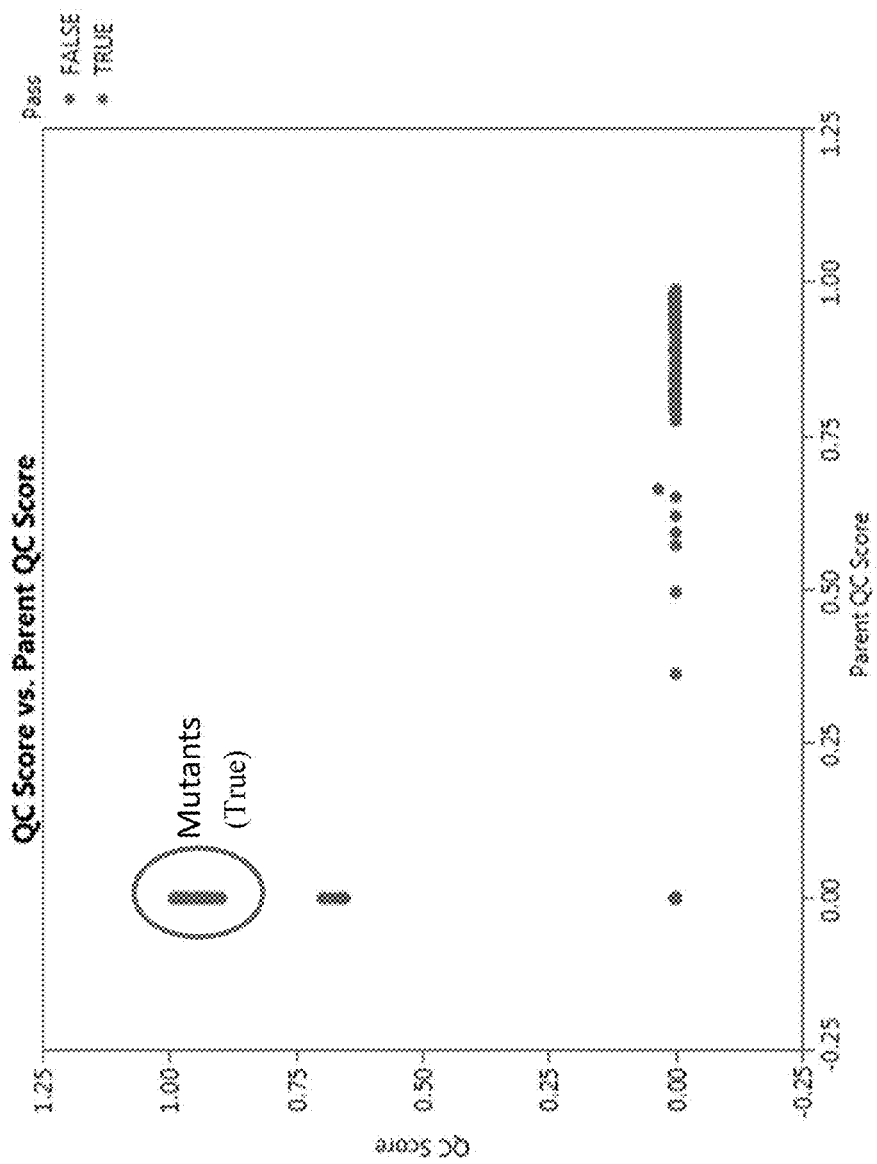
FIG. 46 Depicts the results of next generation sequencing of transformed A. niger mutants. The X-axis represents the target DNA's sequence identity with the untransformed parent strain. The Y-axis represents the target DNA's sequence identity with the expected mutation. Data points towards the bottom right of the chart exhibit high similarity with the parent strain, and low similarity with the expected transformed sequences. Data points towards the top left of the chart exhibit high similarity to expected transformed sequences and low identity with parent strain. Data points in the middle likely represent heterokaryons with multiple nuclei.

Transformants were further validated for presence of the desired SNP change. The co-transformants that had the yellow spore phenotype also contained proper integration of the citric acid SNP in approximately 30% of the isolates (FIGS. 45 and 46).

The inventors expect to phenotypically screen the created SNP swap microbial strain library, in order to identify SNPs beneficial to the production of citric acid. The inventors will utilize this information, in the context of the HTP methods of genomic engineering described herein, to derive an *A. niger* strain with increased citric acid production.

Further Embodiments of the Invention

Other subject matter contemplated by the present disclosure is set out in the following numbered embodiments:
1. A high-throughput (HTP) method of genomic engineering to evolve a microbe to acquire a desired phenotype, comprising:
   a. perturbing the genomes of an initial plurality of microbes having the same microbial strain background, to thereby create an initial HTP genetic design microbial strain library comprising individual microbial strains with unique genetic variations;
   b. screening and selecting individual microbial strains of the initial HTP genetic design microbial strain library for the desired phenotype;
   c. providing a subsequent plurality of microbes that each comprise a unique combination of genetic variation, said genetic variation selected from the genetic variation present in at least two individual microbial strains screened in the preceding step, to thereby create a subsequent HTP genetic design microbial strain library;
   d. screening and selecting individual microbial strains of the subsequent HTP genetic design microbial strain library for the desired phenotype; and
   e. repeating steps c)-d) one or more times, in a linear or non-linear fashion, until a microbe has acquired the desired phenotype, wherein each subsequent iteration creates a new HTP genetic design microbial strain library comprising individual microbial strains harboring unique genetic variations that are a combination of genetic variation selected from amongst at least two individual microbial strains of a preceding HTP genetic design microbial strain library.
2. The HTP method of genomic engineering according to embodiment 1, wherein the initial HTP genetic design microbial strain library comprises at least one selected from the group consisting of a promoter swap microbial strain library, SNP swap microbial strain library, start/stop codon microbial strain library, optimized sequence microbial strain library, a terminator swap microbial strain library, and any combination thereof
3. The HTP method of genomic engineering according to any one of embodiments 1-2, wherein the subsequent HTP genetic design microbial strain library is a full combinatorial microbial strain library of the initial HTP genetic design microbial strain library.
4. The HTP method of genomic engineering according to any one of embodiments 1-2, wherein the subsequent HTP genetic design microbial strain library is a subset of a full combinatorial microbial strain library of the initial HTP genetic design microbial strain library.
5. The HTP method of genomic engineering according to any one of embodiments 1-2, wherein the subsequent HTP genetic design microbial strain library is a full combinatorial microbial strain library of a preceding HTP genetic design microbial strain library.
6. The HTP method of genomic engineering according to any one of embodiments 1-5, wherein the subsequent HTP genetic design microbial strain library is a subset of a full combinatorial microbial strain library of a preceding HTP genetic design microbial strain library.
7. The HTP method of genomic engineering according to any one of embodiments 1-5, wherein perturbing the genome comprises utilizing at least one method selected from the group consisting of: random mutagenesis, targeted sequence insertions, targeted sequence deletions, targeted sequence replacements, and any combination thereof.

8. The HTP method of genomic engineering according to any one of embodiments 1-6, wherein the initial plurality of microbes comprises unique genetic variations derived from an industrial production strain microbe.

9. The HTP method of genomic engineering according to any one of embodiments 1-6, wherein the initial plurality of microbes comprises industrial production strain microbes denoted $S_1Gen_1$ and any number of subsequent microbial generations derived therefrom denoted $S_nGen_n$.

10. A method for generating a SNP swap microbial strain library, comprising the steps of:
   a. providing a reference microbial strain and a second microbial strain, wherein the second microbial strain comprises a plurality of identified genetic variations selected from single nucleotide polymorphisms, DNA insertions, and DNA deletions, which are not present in the reference microbial strain; and
   b. perturbing the genome of either the reference microbial strain, or the second microbial strain, to thereby create an initial SNP swap microbial strain library comprising a plurality of individual microbial strains with unique genetic variations found within each strain of said plurality of individual microbial strains, wherein each of said unique genetic variations corresponds to a single genetic variation selected from the plurality of identified genetic variations between the reference microbial strain and the second microbial strain.

11. The method for generating a SNP swap microbial strain library according to embodiment 10, wherein the genome of the reference microbial strain is perturbed to add one or more of the identified single nucleotide polymorphisms, DNA insertions, or DNA deletions, which are found in the second microbial strain.

12. The method for generating a SNP swap microbial strain library according to embodiment 10, wherein the genome of the second microbial strain is perturbed to remove one or more of the identified single nucleotide polymorphisms, DNA insertions, or DNA deletions, which are not found in the reference microbial strain.

13. The method for generating a SNP swap microbial strain library according to any one of embodiments 10-12, wherein the resultant plurality of individual microbial strains with unique genetic variations, together comprise a full combinatorial library of all the identified genetic variations between the reference microbial strain and the second microbial strain.

14. The method for generating a SNP swap microbial strain library according to any one of embodiments 10-12, wherein the resultant plurality of individual microbial strains with unique genetic variations, together comprise a subset of a full combinatorial library of all the identified genetic variations between the reference microbial strain and the second microbial strain.

15. A method for rehabilitating and improving the phenotypic performance of an industrial microbial strain, comprising the steps of:
   a. providing a parental lineage microbial strain and an industrial microbial strain derived therefrom, wherein the industrial microbial strain comprises a plurality of identified genetic variations selected from single nucleotide polymorphisms, DNA insertions, and DNA deletions, not present in the parental lineage microbial strain;
   b. perturbing the genome of either the parental lineage microbial strain, or the industrial microbial strain, to thereby create an initial SNP swap microbial strain library comprising a plurality of individual microbial strains with unique genetic variations found within each strain of said plurality of individual microbial strains, wherein each of said unique genetic variations corresponds to a single genetic variation selected from the plurality of identified genetic variations between the parental lineage microbial strain and the industrial microbial strain;
   c. screening and selecting individual microbial strains of the initial SNP swap microbial strain library for phenotype performance improvements over a reference microbial strain, thereby identifying unique genetic variations that confer said individual microbial strains with phenotype performance improvements;
   d. providing a subsequent plurality of microbes that each comprise a unique combination of genetic variation, said genetic variation selected from the genetic variation present in at least two individual microbial strains screened in the preceding step, to thereby create a subsequent SNP swap microbial strain library;
   e. screening and selecting individual microbial strains of the subsequent SNP swap microbial strain library for phenotype performance improvements over the reference microbial strain, thereby identifying unique combinations of genetic variation that confer said microbial strains with additional phenotype performance improvements; and
   f. repeating steps d)-e) one or more times, in a linear or non-linear fashion, until a microbial strain exhibits a desired level of improved phenotype performance compared to the phenotype performance of the industrial microbial strain, wherein each subsequent iteration creates a new SNP swap microbial strain library comprising individual microbial strains harboring unique genetic variations that are a combination of genetic variation selected from amongst at least two individual microbial strains of a preceding SNP swap microbial strain library.

15.1. The method for rehabilitating and improving the phenotypic performance of an industrial microbial strain according to embodiment 15, wherein the identified genetic variations further comprise artificial promoter swap genetic variations from a promoter swap library.

16. The method for rehabilitating and improving the phenotypic performance of an industrial microbial strain according to any one of embodiments 15-15.1, wherein the resultant plurality of individual microbial strains with unique genetic variations, together comprise a full combinatorial library of all the identified genetic variations between the reference microbial strain and the second microbial strain.

17. The method for rehabilitating and improving the phenotypic performance of an industrial microbial strain according to any one of embodiments 15-15.1, wherein the resultant plurality of individual microbial strains with unique genetic variations, together comprise a subset of a full combinatorial library of all the identified genetic variations between the reference microbial strain and the second microbial strain.

18. The method for rehabilitating and improving the phenotypic performance of an industrial microbial strain according to any one of embodiments 15-17, wherein the resultant subsequent plurality of individual microbial strains with unique combinations of genetic variations, together comprise a subset of a full combinatorial library of all the genetic variations present in the individual microbial strains screened in the preceding step.

19. The method for rehabilitating and improving the phenotypic performance of an industrial microbial strain according to any one of embodiments 15-18, wherein the genome of the parental lineage microbial strain is perturbed to add one or more of the identified single nucleotide polymorphisms, DNA insertions, or DNA deletions, which are found in the industrial microbial strain.

20. The method for rehabilitating and improving the phenotypic performance of an industrial microbial strain according to any one of embodiments 15-18, wherein the genome of the industrial microbial strain is perturbed to remove one or more of the identified single nucleotide polymorphisms, DNA insertions, or DNA deletions, which are not found in the parental lineage microbial strain.

21. A method for generating a promoter swap microbial strain library, said method comprising the steps of:
    a. providing a plurality of target genes endogenous to a base microbial strain, and a promoter ladder, wherein said promoter ladder comprises a plurality of promoters exhibiting different expression profiles in the base microbial strain; and
    b. engineering the genome of the base microbial strain, to thereby create an initial promoter swap microbial strain library comprising a plurality of individual microbial strains with unique genetic variations found within each strain of said plurality of individual microbial strains, wherein each of said unique genetic variations comprises one or more of the promoters from the promoter ladder operably linked to one of the target genes endogenous to the base microbial strain.

22. A promoter swap method of genomic engineering to evolve a microbe to acquire a desired phenotype, said method comprising the steps of:
    a. providing a plurality of target genes endogenous to a base microbial strain, and a promoter ladder, wherein said promoter ladder comprises a plurality of promoters exhibiting different expression profiles in the base microbial strain;
    b. engineering the genome of the base microbial strain, to thereby create an initial promoter swap microbial strain library comprising a plurality of individual microbial strains with unique genetic variations found within each strain of said plurality of individual microbial strains, wherein each of said unique genetic variations comprises one or more of the promoters from the promoter ladder operably linked to one of the target genes endogenous to the base microbial strain;
    c. screening and selecting individual microbial strains of the initial promoter swap microbial strain library for the desired phenotype;
    d. providing a subsequent plurality of microbes that each comprise a unique combination of genetic variation, said genetic variation selected from the genetic variation present in at least two individual microbial strains screened in the preceding step, to thereby create a subsequent promoter swap microbial strain library;
    e. screening and selecting individual microbial strains of the subsequent promoter swap microbial strain library for the desired phenotype; and
    f. repeating steps d)-e) one or more times, in a linear or non-linear fashion, until a microbe has acquired the desired phenotype, wherein each subsequent iteration creates a new promoter swap microbial strain library comprising individual microbial strains harboring unique genetic variations that are a combination of genetic variation selected from amongst at least two individual microbial strains of a preceding promoter swap microbial strain library.

23. The promoter swap method of genomic engineering to evolve a microbe to acquire a desired phenotype according to embodiment 22, wherein the resultant subsequent plurality of individual microbial strains with unique combinations of genetic variations, together comprise a subset of a full combinatorial library of all the genetic variations present in the individual microbial strains screened in the preceding step.

23.1. The promoter swap method of genomic engineering to evolve a microbe to acquire a desired phenotype according to embodiment 22, wherein the resultant subsequent plurality of individual microbial strains with unique combinations of genetic variations, together comprise a full combinatorial library of all the genetic variations present in the individual microbial strains screened in the preceding step.

24. A method for generating a terminator swap microbial strain library, said method comprising the steps of:
    a. providing a plurality of target genes endogenous to a base microbial strain, and a terminator ladder, wherein said terminator ladder comprises a plurality of terminators exhibiting different expression profiles in the base microbial strain; and
    b. engineering the genome of the base microbial strain, to thereby create an initial terminator swap microbial strain library comprising a plurality of individual microbial strains with unique genetic variations found within each strain of said plurality of individual microbial strains, wherein each of said unique genetic variations comprises one of the target genes endogenous to the base microbial strain operably linked to one or more of the terminators from the terminator ladder.

25. A terminator swap method of genomic engineering to evolve a microbe to acquire a desired phenotype, said method comprising the steps of:
    a. providing a plurality of target genes endogenous to a base microbial strain, and a terminator ladder, wherein said terminator ladder comprises a plurality of terminators exhibiting different expression profiles in the base microbial strain;
    b. engineering the genome of the base microbial strain, to thereby create an initial terminator swap microbial strain library comprising a plurality of individual microbial strains with unique genetic variations found within each strain of said plurality of individual microbial strains, wherein each of said unique genetic variations comprises one of the target genes endogenous to the base microbial strain operably linked to one or more of the terminators from the terminator ladder;

c. screening and selecting individual microbial strains of the initial terminator swap microbial strain library for the desired phenotype;

d. providing a subsequent plurality of microbes that each comprise a unique combination of genetic variation, said genetic variation selected from the genetic variation present in at least two individual microbial strains screened in the preceding step, to thereby create a subsequent terminator swap microbial strain library;

e. screening and selecting individual microbial strains of the subsequent terminator swap microbial strain library for the desired phenotype; and f. repeating steps d)-e) one or more times, in a linear or non-linear fashion, until a microbe has acquired the desired phenotype, wherein each subsequent iteration creates a new terminator swap microbial strain library comprising individual microbial strains harboring unique genetic variations that are a combination of genetic variation selected from amongst at least two individual microbial strains of a preceding terminator swap microbial strain library.

26. The terminator swap method of genomic engineering to evolve a microbe to acquire a desired phenotype according to embodiment 25, wherein the resultant subsequent plurality of individual microbial strains with unique combinations of genetic variations, together comprise a subset of a full combinatorial library of all the genetic variations present in the individual microbial strains screened in the preceding step.

26.1. The terminator swap method of genomic engineering to evolve a microbe to acquire a desired phenotype according to embodiment 25, wherein the resultant subsequent plurality of individual microbial strains with unique combinations of genetic variations, together comprise a full combinatorial library of all the genetic variations present in the individual microbial strains screened in the preceding step.

27. A high-throughput (HTP) genomic engineering system for evolving a microbe to acquire a desired phenotype, the system comprising:
  one or more processors; and
  one or more memories operatively coupled to at least one of the one or more processors and having instructions stored thereon that, when executed by at least one of the one or more processors, cause the system to:
  a. perturb the genomes of an initial plurality of microbes having the same microbial strain background, to thereby create an initial HTP genetic design microbial strain library comprising individual microbial strains with unique genetic variations;
  b. screen and select individual microbial strains of the initial HTP genetic design microbial strain library for the desired phenotype;
  c. provide a subsequent plurality of microbes that each comprise a unique combination of genetic variation, said genetic variation selected from the genetic variation present in at least two individual microbial strains screened in the preceding step, to thereby create a subsequent HTP genetic design microbial strain library;
  d. screen and select individual microbial strains of the subsequent HTP genetic design microbial strain library for the desired phenotype; and
  e. repeat steps c)-d) one or more times, in a linear or non-linear fashion, until a microbe has acquired the desired phenotype, wherein each subsequent iteration creates a new HTP genetic design microbial strain library comprising individual microbial strains harboring unique genetic variations that are a combination of genetic variation selected from amongst at least two individual microbial strains of a preceding HTP genetic design microbial strain library.

28. One or more non-transitory computer readable media storing instructions for evolving a microbe to acquire a desired phenotype, wherein the instructions, when executed by one or more computing devices, cause at least one of the one or more computing devices to:
  a. perturb the genomes of an initial plurality of microbes having the same microbial strain background, to thereby create an initial HTP genetic design microbial strain library comprising individual microbial strains with unique genetic variations;
  b. screen and select individual microbial strains of the initial HTP genetic design microbial strain library for the desired phenotype;
  c. provide a subsequent plurality of microbes that each comprise a unique combination of genetic variation, said genetic variation selected from the genetic variation present in at least two individual microbial strains screened in the preceding step, to thereby create a subsequent HTP genetic design microbial strain library;
  d. screen and select individual microbial strains of the subsequent HTP genetic design microbial strain library for the desired phenotype; and
  e. repeat steps c)-d) one or more times, in a linear or non-linear fashion, until a microbe has acquired the desired phenotype, wherein each subsequent iteration creates a new HTP genetic design microbial strain library comprising individual microbial strains harboring unique genetic variations that are a combination of genetic variation selected from amongst at least two individual microbial strains of a preceding HTP genetic design microbial strain library.

29. A system for generating a SNP swap microbial strain library, the system comprising:
  one or more processors; and
  one or more memories operatively coupled to at least one of the one or more processors and having instructions stored thereon that, when executed by at least one of the one or more processors, cause the system to:
  a. provide a reference microbial strain and a second microbial strain, wherein the second microbial strain comprises a plurality of identified genetic variations selected from single nucleotide polymorphisms, DNA insertions, and DNA deletions, which are not present in the reference microbial strain; and
  b. perturb the genome of either the reference microbial strain, or the second microbial strain, to thereby create an initial SNP swap microbial strain library comprising a plurality of individual microbial strains with unique genetic variations found within each strain of said plurality of individual microbial strains, wherein each of said unique genetic variations corresponds to a single genetic variation selected from the plurality of identified genetic variations between the reference microbial strain and the second microbial strain.

30. One or more non-transitory computer readable media storing instructions for generating a SNP swap microbial strain library, wherein the instructions, when executed by one or more computing devices, cause at least one of the one or more computing devices to:
   a. provide a reference microbial strain and a second microbial strain, wherein the second microbial strain comprises a plurality of identified genetic variations selected from single nucleotide polymorphisms, DNA insertions, and DNA deletions, which are not present in the reference microbial strain; and
   b. perturb the genome of either the reference microbial strain, or the second microbial strain, to thereby create an initial SNP swap microbial strain library comprising a plurality of individual microbial strains with unique genetic variations found within each strain of said plurality of individual microbial strains, wherein each of said unique genetic variations corresponds to a single genetic variation selected from the plurality of identified genetic variations between the reference microbial strain and the second microbial strain.

31. A system for rehabilitating and improving the phenotypic performance of an industrial microbial strain, the system comprising:
   one or more processors; and
   one or more memories operatively coupled to at least one of the one or more processors and having instructions stored thereon that, when executed by at least one of the one or more processors, cause the system to:
   a. provide a parental lineage microbial strain and an industrial microbial strain derived therefrom, wherein the industrial microbial strain comprises a plurality of identified genetic variations selected from single nucleotide polymorphisms, DNA insertions, and DNA deletions, not present in the parental lineage microbial strain;
   b. perturb the genome of either the parental lineage microbial strain, or the industrial microbial strain, to thereby create an initial SNP swap microbial strain library comprising a plurality of individual microbial strains with unique genetic variations found within each strain of said plurality of individual microbial strains, wherein each of said unique genetic variations corresponds to a single genetic variation selected from the plurality of identified genetic variations between the parental lineage microbial strain and the industrial microbial strain;
   c. screen and select individual microbial strains of the initial SNP swap microbial strain library for phenotype performance improvements over a reference microbial strain, thereby identifying unique genetic variations that confer said microbial strains with phenotype performance improvements;
   d. provide a subsequent plurality of microbes that each comprise a unique combination of genetic variation, said genetic variation selected from the genetic variation present in at least two individual microbial strains screened in the preceding step, to thereby create a subsequent SNP swap microbial strain library;
   e. screen and select individual microbial strains of the subsequent SNP swap microbial strain library for phenotype performance improvements over the reference microbial strain, thereby identifying unique combinations of genetic variation that confer said microbial strains with additional phenotype performance improvements; and
   f. repeat steps d)-e) one or more times, in a linear or non-linear fashion, until a microbial strain exhibits a desired level of improved phenotype performance compared to the phenotype performance of the industrial microbial strain, wherein each subsequent iteration creates a new SNP swap microbial strain library comprising individual microbial strains harboring unique genetic variations that are a combination of genetic variation selected from amongst at least two individual microbial strains of a preceding SNP swap microbial strain library.

32. One or more non-transitory computer readable media storing instructions for rehabilitating and improving the phenotypic performance of an industrial microbial strain, wherein the instructions, when executed by one or more computing devices, cause at least one of the one or more computing devices to:
   a. provide a parental lineage microbial strain and an industrial microbial strain derived therefrom, wherein the industrial microbial strain comprises a plurality of identified genetic variations selected from single nucleotide polymorphisms, DNA insertions, and DNA deletions, not present in the parental lineage microbial strain;
   b. perturb the genome of either the parental lineage microbial strain, or the industrial microbial strain, to thereby create an initial SNP swap microbial strain library comprising a plurality of individual microbial strains with unique genetic variations found within each strain of said plurality of individual microbial strains, wherein each of said unique genetic variations corresponds to a single genetic variation selected from the plurality of identified genetic variations between the parental lineage microbial strain and the industrial microbial strain;
   c. screen and select individual microbial strains of the initial SNP swap microbial strain library for phenotype performance improvements over a reference microbial strain, thereby identifying unique genetic variations that confer said microbial strains with phenotype performance improvements;
   d. provide a subsequent plurality of microbes that each comprise a unique combination of genetic variation, said genetic variation selected from the genetic variation present in at least two individual microbial strains screened in the preceding step, to thereby create a subsequent SNP swap microbial strain library;
   e. screen and select individual microbial strains of the subsequent SNP swap microbial strain library for phenotype performance improvements over the reference microbial strain, thereby identifying unique combinations of genetic variation that confer said microbial strains with additional phenotype performance improvements; and
   f. repeat steps d)-e) one or more times, in a linear or non-linear fashion, until a microbial strain exhibits a desired level of improved phenotype performance compared to the phenotype performance of the industrial microbial strain, wherein each subsequent iteration creates a new SNP swap microbial strain library comprising individual microbial strains harboring unique genetic variations that are a combination of genetic variation selected from amongst at least two individual microbial strains of a preceding SNP swap microbial strain library.

33. A system for generating a promoter swap microbial strain library, the system comprising:
one or more processors; and
one or more memories operatively coupled to at least one of the one or more processors and having instructions stored thereon that, when executed by at least one of the one or more processors, cause the system to:
a. provide a plurality of target genes endogenous to a base microbial strain, and a promoter ladder, wherein said promoter ladder comprises a plurality of promoters exhibiting different expression profiles in the base microbial strain; and
b. engineer the genome of the base microbial strain, to thereby create an initial promoter swap microbial strain library comprising a plurality of individual microbial strains with unique genetic variations found within each strain of said plurality of individual microbial strains, wherein each of said unique genetic variations comprises one or more of the promoters from the promoter ladder operably linked to one of the target genes endogenous to the base microbial strain.

34. One or more non-transitory computer readable media storing instructions for generating a promoter swap microbial strain library, wherein the instructions, when executed by one or more computing devices, cause at least one of the one or more computing devices to:
a. provide a plurality of target genes endogenous to a base microbial strain, and a promoter ladder, wherein said promoter ladder comprises a plurality of promoters exhibiting different expression profiles in the base microbial strain; and
b. engineer the genome of the base microbial strain, to thereby create an initial promoter swap microbial strain library comprising a plurality of individual microbial strains with unique genetic variations found within each strain of said plurality of individual microbial strains, wherein each of said unique genetic variations comprises one or more of the promoters from the promoter ladder operably linked to one of the target genes endogenous to the base microbial strain.

35. A genomic engineering system to evolve a microbe through promoter swapping to acquire a desired phenotype, the system comprising:
one or more processors; and
one or more memories operatively coupled to at least one of the one or more processors and having instructions stored thereon that, when executed by at least one of the one or more processors, cause the system to:
a. provide a plurality of target genes endogenous to a base microbial strain, and a promoter ladder, wherein said promoter ladder comprises a plurality of promoters exhibiting different expression profiles in the base microbial strain;
b. engineer the genome of the base microbial strain, to thereby create an initial promoter swap microbial strain library comprising a plurality of individual microbial strains with unique genetic variations found within each strain of said plurality of individual microbial strains, wherein each of said unique genetic variations comprises one or more of the promoters from the promoter ladder operably linked to one of the target genes endogenous to the base microbial strain;
c. screen and select individual microbial strains of the initial promoter swap microbial strain library for the desired phenotype;
d. provide a subsequent plurality of microbes that each comprise a unique combination of genetic variation, said genetic variation selected from the genetic variation present in at least two individual microbial strains screened in the preceding step, to thereby create a subsequent promoter swap microbial strain library;
e. screen and select individual microbial strains of the subsequent promoter swap microbial strain library for the desired phenotype; and
f. repeat steps d)-e) one or more times, in a linear or non-linear fashion, until a microbe has acquired the desired phenotype, wherein each subsequent iteration creates a new promoter swap microbial strain library comprising individual microbial strains harboring unique genetic variations that are a combination of genetic variation selected from amongst at least two individual microbial strains of a preceding promoter swap microbial strain library.

36. One or more non-transitory computer readable media storing instructions for evolving a microbe through promoter swapping to acquire a desired phenotype, wherein the instructions, when executed by one or more computing devices, cause at least one of the one or more computing devices to:
a. provide a plurality of target genes endogenous to a base microbial strain, and a promoter ladder, wherein said promoter ladder comprises a plurality of promoters exhibiting different expression profiles in the base microbial strain;
b. engineer the genome of the base microbial strain, to thereby create an initial promoter swap microbial strain library comprising a plurality of individual microbial strains with unique genetic variations found within each strain of said plurality of individual microbial strains, wherein each of said unique genetic variations comprises one or more of the promoters from the promoter ladder operably linked to one of the target genes endogenous to the base microbial strain;
c. screen and select individual microbial strains of the initial promoter swap microbial strain library for the desired phenotype;
d. provide a subsequent plurality of microbes that each comprise a unique combination of genetic variation, said genetic variation selected from the genetic variation present in at least two individual microbial strains screened in the preceding step, to thereby create a subsequent promoter swap microbial strain library;
e. screen and select individual microbial strains of the subsequent promoter swap microbial strain library for the desired phenotype; and
f. repeat steps d)-e) one or more times, in a linear or non-linear fashion, until a microbe has acquired the desired phenotype, wherein each subsequent iteration creates a new promoter swap microbial strain library comprising individual microbial strains harboring unique genetic variations that are a combination of genetic variation selected from amongst at least two individual microbial strains of a preceding promoter swap microbial strain library.

37. A system for generating a terminator swap microbial strain library, the system comprising:
   one or more processors; and
   one or more memories operatively coupled to at least one of the one or more processors and having instructions stored thereon that, when executed by at least one of the one or more processors, cause the system to:
   a. provide a plurality of target genes endogenous to a base microbial strain, and a terminator ladder, wherein said terminator ladder comprises a plurality of terminators exhibiting different expression profiles in the base microbial strain; and
   b. engineer the genome of the base microbial strain, to thereby create an initial terminator swap microbial strain library comprising a plurality of individual microbial strains with unique genetic variations found within each strain of said plurality of individual microbial strains, wherein each of said unique genetic variations comprises one of the target genes endogenous to the base microbial strain operably linked to one or more of the terminators from the terminator ladder.

38. One or more non-transitory computer readable media storing instructions for generating a terminator swap microbial strain library, wherein the instructions, when executed by one or more computing devices, cause at least one of the one or more computing devices to:
   a. provide a plurality of target genes endogenous to a base microbial strain, and a terminator ladder, wherein said terminator ladder comprises a plurality of terminators exhibiting different expression profiles in the base microbial strain; and
   b. engineer the genome of the base microbial strain, to thereby create an initial terminator swap microbial strain library comprising a plurality of individual microbial strains with unique genetic variations found within each strain of said plurality of individual microbial strains, wherein each of said unique genetic variations comprises one of the target genes endogenous to the base microbial strain operably linked to one or more of the terminators from the terminator ladder.

39. A genomic engineering system to evolve through terminator swapping a microbe to acquire a desired phenotype, the system comprising:
   one or more processors; and
   one or more memories operatively coupled to at least one of the one or more processors and having instructions stored thereon that, when executed by at least one of the one or more processors, cause the system to:
   a. provide a plurality of target genes endogenous to a base microbial strain, and a terminator ladder, wherein said terminator ladder comprises a plurality of terminators exhibiting different expression profiles in the base microbial strain;
   b. engineer the genome of the base microbial strain, to thereby create an initial terminator swap microbial strain library comprising a plurality of individual microbial strains with unique genetic variations found within each strain of said plurality of individual microbial strains, wherein each of said unique genetic variations comprises one of the target genes endogenous to the base microbial strain operably linked to one or more of the terminators from the terminator ladder;
   c. screen and select individual microbial strains of the initial terminator swap microbial strain library for the desired phenotype;
   d. provide a subsequent plurality of microbes that each comprise a unique combination of genetic variation, said genetic variation selected from the genetic variation present in at least two individual microbial strains screened in the preceding step, to thereby create a subsequent terminator swap microbial strain library;
   e. screen and select individual microbial strains of the subsequent terminator swap microbial strain library for the desired phenotype; and
   f. repeat steps d)-e) one or more times, in a linear or non-linear fashion, until a microbe has acquired the desired phenotype, wherein each subsequent iteration creates a new terminator swap microbial strain library comprising individual microbial strains harboring unique genetic variations that are a combination of genetic variation selected from amongst at least two individual microbial strains of a preceding terminator swap microbial strain library.

40. One or more non-transitory computer readable media storing instructions for evolving through terminator swapping a microbe to acquire a desired phenotype, wherein the instructions, when executed by one or more computing devices, cause at least one of the one or more computing devices to:
   a. provide a plurality of target genes endogenous to a base microbial strain, and a terminator ladder, wherein said terminator ladder comprises a plurality of terminators exhibiting different expression profiles in the base microbial strain;
   b. engineer the genome of the base microbial strain, to thereby create an initial terminator swap microbial strain library comprising a plurality of individual microbial strains with unique genetic variations found within each strain of said plurality of individual microbial strains, wherein each of said unique genetic variations comprises one of the target genes endogenous to the base microbial strain operably linked to one or more of the terminators from the terminator ladder;
   c. screen and select individual microbial strains of the initial terminator swap microbial strain library for the desired phenotype;
   d. provide a subsequent plurality of microbes that each comprise a unique combination of genetic variation, said genetic variation selected from the genetic variation present in at least two individual microbial strains screened in the preceding step, to thereby create a subsequent terminator swap microbial strain library;
   e. screen and select individual microbial strains of the subsequent terminator swap microbial strain library for the desired phenotype; and
   f. repeat steps d)-e) one or more times, in a linear or non-linear fashion, until a microbe has acquired the desired phenotype, wherein each subsequent iteration creates a new terminator swap microbial strain library comprising individual microbial strains harboring unique genetic variations that are a combination of genetic variation selected from amongst at least two individual microbial strains of a preceding terminator swap microbial strain library.

41. A computer-implemented method for iteratively improving the design of candidate microbial strains, the method comprising:
   a. accessing a predictive model populated with a training set comprising (1) inputs representing genetic changes to one or more background microbial strains and (2) corresponding performance measures;
   b. applying test inputs to the predictive model that represent genetic changes, the test inputs corresponding to candidate microbial strains incorporating those genetic changes;
   c. predicting phenotypic performance of the candidate microbial strains based at least in part upon the predictive model;
   d. selecting a first subset of the candidate microbial strains based at least in part upon their predicted performance;
   e. obtaining measured phenotypic performance of the first subset of the candidate microbial strains;
   f. obtaining a selection of a second subset of the candidate microbial strains based at least in part upon their measured phenotypic performance;
   g. adding to the training set of the predictive model (1) inputs corresponding to the selected second subset of candidate microbial strains, along with (2) corresponding measured performance of the selected second subset of candidate microbial strains; and
   h. repeating (b)-(g).

42. The method of embodiment 41, wherein repeating (b)-(g) comprises repeating (b)-(g) until measured phenotypic performance of at least one candidate microbial strain satisfies a performance metric.

43. The method of embodiment 41, wherein:
   during a first application of test inputs to the predictive model, the genetic changes represented by the test inputs comprise genetic changes to the one or more background microbial strains; and
   during subsequent applications of test inputs, the genetic changes represented by the test inputs comprise genetic changes to candidate microbial strains within a previously selected second subset of candidate microbial strains.

44. The method of embodiment 41, wherein the selection of the first subset of the candidate microbial strains is based at least in part upon epistatic effects.

45. The method of embodiment 44, wherein the selection of the first subset based at least in part upon epistatic effects comprises:
   during a first selection of the first subset:
   determining degrees of dissimilarity between performance measures of the one or more background microbial strains in response to application of a plurality of respective inputs representing genetic changes to the one or more background microbial strains; and
   selecting for inclusion in the first subset at least two candidate microbial strains based at least in part upon the degrees of dissimilarity in the performance measures of the one or more background microbial strains in response to application of genetic changes incorporated into the at least two candidate microbial strains.

46. The method of embodiment 45, further comprising:
   during subsequent selections of the first subset:
   determining degrees of dissimilarity between performance measures of previous first subset candidate microbial strains in response to application of a plurality of respective inputs representing genetic changes, wherein the previous first subset candidate microbial strains are strains that were selected during a previous selection of the first subset; and
   selecting for inclusion into the first subset at least two candidate microbial strains based at least in part upon the degrees of dissimilarity in the performance measures of the previous first subset candidate microbial strains in response to application of the genetic changes incorporated into the at least two candidate microbial strains.

47. A system for iteratively improving the design of candidate microbial strains, the system comprising:
   one or more processors; and
   one or more memories operatively coupled to at least one of the one or more processors and having instructions stored thereon that, when executed by at least one of the one or more processors, cause the system to:
   a. access a predictive model populated with a training set comprising (1) inputs representing genetic changes to one or more background microbial strains and (2) corresponding performance measures;
   b. apply test inputs to the predictive model that represent genetic changes, the test inputs corresponding to candidate microbial strains incorporating those genetic changes;
   c. predict phenotypic performance of the candidate microbial strains based at least in part upon the predictive model;
   d. select a first subset of the candidate microbial strains based at least in part upon their predicted performance;
   e. obtain measured phenotypic performance of the first subset of the candidate microbial strains;
   f. obtain a selection of a second subset of the candidate microbial strains based at least in part upon their measured phenotypic performance;
   g. add to the training set of the predictive model (1) inputs corresponding to the selected second subset of candidate microbial strains, along with (2) corresponding measured performance of the selected second subset of candidate microbial strains; and
   h. repeat (b)-(g).

48. The system of embodiment 47, wherein the instructions, when executed by at least one of the one or more processors, cause the system to repeat (b)-(g) until measured phenotypic performance of at least one candidate microbial strain satisfies a performance metric.

49. The system of embodiment 47, wherein:
   during a first application of test inputs to the predictive model, the genetic changes represented by the test inputs comprise genetic changes to the one or more background microbial strains; and
   during subsequent applications of test inputs, the genetic changes represented by the test inputs comprise genetic changes to candidate microbial strains within a previously selected second subset of candidate microbial strains.

50. The system of embodiment 47, wherein the selection of the first subset of the candidate microbial strains is based at least in part upon epistatic effects.

51. The system of embodiment 50, wherein the instructions, when executed by at least one of the one or more processors, cause the system, during a first selection of the first subset, to:
  determine degrees of dissimilarity between performance measures of the one or more background microbial strains in response to application of a plurality of respective inputs representing genetic changes to the one or more background microbial strains; and
  select for inclusion in the first subset at least two candidate microbial strains based at least in part upon the degrees of dissimilarity in the performance measures of the one or more background microbial strains in response to application of genetic changes incorporated into the at least two candidate microbial strains.

52. The system of embodiment 51, wherein the instructions, when executed by at least one of the one or more processors, cause the system, during subsequent selections of the first subset, to:
  determine degrees of dissimilarity between performance measures of previous first subset candidate microbial strains in response to application of a plurality of respective inputs representing genetic changes, wherein the previous first subset candidate microbial strains are strains that were selected during a previous selection of the first subset; and
  select for inclusion into the first subset at least two candidate microbial strains based at least in part upon the degrees of dissimilarity in the performance measures of the previous first subset candidate microbial strains in response to application of the genetic changes incorporated into the at least two candidate microbial strains.

53. One or more non-transitory computer readable media storing instructions for iteratively improving the design of candidate microbial strains, wherein the instructions, when executed by one or more computing devices, cause at least one of the one or more computing devices to:
  a. access a predictive model populated with a training set comprising (1) inputs representing genetic changes to one or more background microbial strains and (2) corresponding performance measures;
  b. apply test inputs to the predictive model that represent genetic changes, the test inputs corresponding to candidate microbial strains incorporating those genetic changes;
  c. predict phenotypic performance of the candidate microbial strains based at least in part upon the predictive model;
  d. select a first subset of the candidate microbial strains based at least in part upon their predicted performance;
  e. obtain measured phenotypic performance of the first subset of the candidate microbial strains;
  f. obtain a selection of a second subset of the candidate microbial strains based at least in part upon their measured phenotypic performance;
  g. add to the training set of the predictive model (1) inputs corresponding to the selected second subset of candidate microbial strains, along with (2) corresponding measured performance of the selected second subset of candidate microbial strains; and
  h. repeat (b)-(g).

54. The computer readable media of embodiment 53, wherein the instructions, when executed, cause at least one of the one or more computing devices to repeat (b)-(g) until measured phenotypic performance of at least one candidate microbial strain satisfies a performance metric.

55. The computer readable media of embodiment 53, wherein:
  during a first application of test inputs to the predictive model, the genetic changes represented by the test inputs comprise genetic changes to the one or more background microbial strains; and
  during subsequent applications of test inputs, the genetic changes represented by the test inputs comprise genetic changes to candidate microbial strains within a previously selected second subset of candidate microbial strains.

56. The computer readable media of embodiment 53, wherein the selection of the first subset of the candidate microbial strains is based at least in part upon epistatic effects.

57. The computer readable media of embodiment 56, wherein the instructions, when executed, cause at least one of the one or more computing devices, during a first selection of the first subset, to:
  determine degrees of dissimilarity between performance measures of the one or more background microbial strains in response to application of a plurality of respective inputs representing genetic changes to the one or more background microbial strains; and
  select for inclusion in the first subset at least two candidate microbial strains based at least in part upon the degrees of dissimilarity in the performance measures of the one or more background microbial strains in response to application of genetic changes incorporated into the at least two candidate microbial strains.

58. The computer readable media of embodiment 53, wherein the instructions, when executed, cause at least one of the one or more computing devices, during subsequent selections of the first subset, to:
  determine degrees of dissimilarity between performance measures of previous first subset candidate microbial strains in response to application of a plurality of respective inputs representing genetic changes, wherein the previous first subset candidate microbial strains are strains that were selected during a previous selection of the first subset; and
  select for inclusion into the first subset at least two candidate microbial strains based at least in part upon the degrees of dissimilarity in the performance measures of the previous first subset candidate microbial strains in response to application of the genetic changes incorporated into the at least two candidate microbial strains.

59. A computer-implemented method for applying epistatic effects in the iterative improvement of candidate microbial strains, the method comprising:
  obtaining data representing measured performance in response to corresponding genetic changes made to at least one microbial background strain;
  obtaining a selection of at least two genetic changes based at least in part upon a degree of dissimilarity between the corresponding responsive performance measures of the at least two genetic changes, wherein the degree of dissimilarity relates to the degree to which the at least two genetic changes affect their corresponding responsive performance measures through different biological pathways; and designing genetic changes to a microbial background strain that include the selected genetic changes.

60. The method of embodiment 59, wherein the microbial background strain for which the at least two selected genetic changes are designed is the same as the at least one microbial background strain for which data representing measured responsive performance was obtained.

61. A system for applying epistatic effects in the iterative improvement of candidate microbial strains, the system comprising:

one or more processors; and one or more memories operatively coupled to at least one of the one or more processors and having instructions stored thereon that, when executed by at least one of the one or more processors, cause the system to:

obtain data representing measured performance in response to corresponding genetic changes made to at least one microbial background strain;

obtain a selection of at least two genetic changes based at least in part upon a degree of dissimilarity between the corresponding responsive performance measures of the at least two genetic changes, wherein the degree of dissimilarity relates to the degree to which the at least two genetic changes affect their corresponding responsive performance measures through different biological pathways; and design genetic changes to a microbial background strain that include the selected genetic changes.

62. The system of embodiment 61, wherein the microbial background strain for which the at least two selected genetic changes are designed is the same as the at least one microbial background strain for which data representing measured responsive performance was obtained.

63. One or more non-transitory computer readable media storing instructions for applying epistatic effects in the iterative improvement of candidate microbial strains, wherein the instructions, when executed by one or more computing devices, cause at least one of the one or more computing devices to:

obtain data representing measured performance in response to corresponding genetic changes made to at least one microbial background strain;

obtain a selection of at least two genetic changes based at least in part upon a degree of dissimilarity between the corresponding responsive performance measures of the at least two genetic changes, wherein the degree of dissimilarity relates to the degree to which the at least two genetic changes affect their corresponding responsive performance measures through different biological pathways; and design genetic changes to a microbial background strain that include the selected genetic changes.

64. The computer readable media of embodiment 63, wherein the microbial background strain for which the at least two selected genetic changes are designed is the same as the at least one microbial background strain for which data representing measured responsive performance was obtained.

INCORPORATION BY REFERENCE

All references, articles, publications, patents, patent publications, and patent applications cited herein are incorporated by reference in their entireties for all purposes. However, mention of any reference, article, publication, patent, patent publication, and patent application cited herein is not, and should not be taken as an acknowledgment or any form of suggestion that they constitute valid prior art or form part of the common general knowledge in any country in the world.

What is claimed is:

1. A high-throughput method for engineering a host cell to have improved phenotypic performance, comprising:
   a. accessing a training data set containing one or more genetic alteration input variables and one or more measured phenotypic performance output variables,
      i. wherein the one or more genetic alteration input variables represent one or more genetic alterations that have been introduced into a host cell, and
      ii. wherein the one or more measured phenotypic performance output variables represent one or more phenotypic performance measurements that are associated with the one or more introduced genetic alterations;
   b. developing a predictive machine learning model that is populated with the training data set;
   c. generating, in silico, a pool of design candidate host cells incorporating the one or more genetic alterations;
   d. utilizing the predictive machine learning model to predict the expected phenotypic performance of each member of the pool of design candidate host cells,
      i. wherein at least one design candidate host cell comprises a consolidated combination of genetic alterations from among the genetic alterations of step (a), in a genomic sequence, said combination being uncharacterized for improving the phenotypic performance at the time that step (d) is carried out;
      ii. wherein the expected phenotypic performance predicted by the machine learning model is based upon the introduced genetic alterations and their associated phenotypic performance measurements of step (a);
   e. selecting a subset of the design candidate host cells based upon their predicted phenotypic performance;
   f. manufacturing host cells from the subset of the design candidate host cells to thereby create engineered host cells;
   g. measuring, in an in vitro assay, the phenotypic performance of the engineered host cells; and
   h. adding to the training data set of (a):
      i. one or more genetic alteration input variables representing one or more genetic alterations that were introduced into the engineered host cells, and
      ii. one or more measured phenotypic performance output variables representing the phenotypic performance measurements of the engineered host cells.

2. The method of claim 1, wherein (a)-(h) are repeated until an engineered host cell exhibits a desired level of improved phenotypic performance.

3. The method of claim 1, wherein the predictive machine learning model incorporates epistatic effects.

4. The method of claim 1, wherein the predictive machine learning model incorporates at least one of the following: linear regression, kernel ridge regression, logistic regression, neural networks, support vector machines (SVMs), decision trees, hidden Markov models, Bayesian networks, a Gram-Schmidt process, reinforcement-based learning, cluster-based learning, hierarchical clustering, genetic algorithms, and combinations thereof.

5. The method of claim 1, wherein the predictive machine learning model is supervised, semi-supervised, or unsupervised.

6. The method of claim 1, wherein the one or more genetic alterations comprise at least one genetic alteration selected from the group consisting of: a single nucleotide polymorphism, nucleotide sequence insertion, nucleotide sequence deletion, and nucleotide sequence replacements.

7. The method of claim 1, wherein the one or more genetic alterations comprise one or more heterologous promoters from a promoter ladder operably linked to an endogenous target gene.

8. The method of claim 1, wherein the improved phenotypic performance is increased or more efficient production of a product of interest, said product of interest selected from the group consisting of: a small molecule, enzyme, protein, peptide, amino acid, organic acid, synthetic compound, fuel, alcohol, primary extracellular metabolite, secondary extracellular metabolite, intracellular component molecule, and combinations thereof.

9. A high-throughput method for engineering a microbial strain to have improved phenotypic performance, comprising:
   a. accessing a training data set containing one or more genetic alteration input variables and one or more measured phenotypic performance output variables,
      i. wherein the one or more genetic alteration input variables represent one or more genetic alterations that have been introduced into a microbial strain, and
      ii. wherein the one or more measured phenotypic performance output variables represent one or more phenotypic performance measurements that are associated with the one or more introduced genetic alterations;

b. developing a predictive machine learning model that is populated with the training data set;
c. generating, in silico, a pool of design candidate microbial strains incorporating the one or more genetic alterations;
d. utilizing the predictive machine learning model to predict the expected phenotypic performance of each member of the pool of design candidate microbial strains,
 i. wherein at least one design candidate microbial strain comprises a consolidated combination of genetic alterations from among the genetic alterations of step (a), in a genomic sequence, said combination being uncharacterized for improving the phenotypic performance at the time that step (d) is carried out;
 ii. wherein the expected phenotypic performance predicted by the machine learning model is based upon the introduced genetic alterations and their associated phenotypic performance measurements of step (a);
e. selecting a subset of the design candidate microbial strains based upon their predicted phenotypic performance;
f. manufacturing microbial strains from the subset of design candidate microbial strains to thereby create engineered microbial strains;
g. measuring, in an in vitro assay, the phenotypic performance of the engineered microbial strains;
h. selecting a subset of the engineered microbial strains based upon their measured phenotypic performance;
i. adding to the training data set of (a):
 i. one or more genetic alteration input variables representing one or more genetic alterations that were introduced into the subset of the engineered microbial strains, and
 ii. one or more measured phenotypic performance output variables representing the phenotypic performance measurements of the subset of the engineered microbial strains; and
j. repeating steps (a)-(i) until an engineered microbial strain exhibits a desired level of improved phenotypic performance.

10. The method of claim 9, wherein the improved phenotypic performance is increased or more efficient production of a product of interest, said product of interest selected from the group consisting of: a small molecule, enzyme, protein, peptide, amino acid, organic acid, synthetic compound, fuel, alcohol, primary extracellular metabolite, secondary extracellular metabolite, intracellular component molecule, and combinations thereof.

11. The method of claim 9, wherein the improved phenotypic performance is increased or more efficient production of lysine or citric acid.

12. A high-throughput method for engineering a host cell to have improved phenotypic performance, comprising:
a. accessing a training data set containing one or more genetic alteration input variables and one or more measured phenotypic performance output variables,
 i. wherein the one or more genetic alteration input variables represent one or more genetic alterations that have been introduced into a host cell through application of one or more libraries, and
 ii. wherein the one or more measured phenotypic performance output variables represent one or more phenotypic performance measurements that are associated with the introduced genetic alterations;
b. developing a predictive machine learning model that is populated with the training data set;
c. generating, in silico, a pool of design candidate host cells incorporating the one or more genetic alterations;
d. utilizing the predictive machine learning model to predict the expected phenotypic performance of each member of the pool of design candidate host cells,
 i. wherein at least one design candidate host cell comprises a consolidated combination of genetic alterations from among the genetic alterations of step (a), in a genomic sequence, said combination being uncharacterized for improving the phenotypic performance at the time that step (d) is carried out;
 ii. wherein the expected phenotypic performance predicted by the machine learning model is based upon the introduced genetic alterations and their associated phenotypic performance measurements of step (a);
e. providing a subset of the design candidate host cells for use in creating engineered host cells; and
f. manufacturing the engineered host cells of step (e).

13. The method of claim 12, wherein the one or more libraries are selected from the group consisting of: a promoter swap library, a SNP swap library, a start/stop codon library, an optimized sequence library, a terminator swap library, and combinations thereof.

14. The method of claim 12, wherein the predictive machine learning model incorporates epistatic effects.

15. The method of claim 12, wherein the predictive machine learning model incorporates at least one of the following: linear regression, kernel ridge regression, logistic regression, neural networks, support vector machines (SVMs), decision trees, hidden Markov models, Bayesian networks, a Gram-Schmidt process, reinforcement-based learning, cluster-based learning, hierarchical clustering, genetic algorithms, or combinations thereof.

16. The method of claim 12, wherein the predictive machine learning model is supervised, semi-supervised, or unsupervised.

17. The method of claim 12, wherein the one or more genetic alterations comprise at least one genetic alteration selected from the group consisting of: a single nucleotide polymorphism, nucleotide sequence insertion, nucleotide sequence deletion, and nucleotide sequence replacements.

18. The method of claim 12, wherein the one or more genetic alterations comprise one or more heterologous promoters from a promoter ladder operably linked to an endogenous target gene.

19. The method of claim 12, wherein the improved phenotypic performance is increased or more efficient production of a product of interest, said product of interest selected from the group consisting of: a small molecule, enzyme, protein, peptide, amino acid, organic acid, synthetic compound, fuel, alcohol, primary extracellular metabolite, secondary extracellular metabolite, intracellular component molecule, and combinations thereof.

* * * * *